US011072663B2

(12) United States Patent
Goldberg et al.

(10) Patent No.: US 11,072,663 B2
(45) Date of Patent: *Jul. 27, 2021

(54) CYSTEINE ENGINEERED FIBRONECTIN TYPE III DOMAIN BINDING MOLECULES

(71) Applicant: Janssen Biotech, Inc., Horsham, PA (US)

(72) Inventors: Shalom Goldberg, Spring House, PA (US); Steven Jacobs, Spring House, PA (US); Tricia Lin, Spring House, PA (US); Karyn O'Neil, Spring House, PA (US)

(73) Assignee: Janssen Biotech, Inc., Horsham, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/227,597

(22) Filed: Dec. 20, 2018

(65) Prior Publication Data
US 2019/0263915 A1 Aug. 29, 2019

Related U.S. Application Data

(63) Continuation of application No. 14/512,801, filed on Oct. 13, 2014, now Pat. No. 10,196,446.

(60) Provisional application No. 61/890,539, filed on Oct. 14, 2013.

(51) Int. Cl.
C07K 16/28 (2006.01)
G01N 33/74 (2006.01)
C07K 14/78 (2006.01)
A61K 39/00 (2006.01)

(52) U.S. Cl.
CPC .......... C07K 16/2863 (2013.01); C07K 14/78 (2013.01); G01N 33/74 (2013.01); A61K 2039/505 (2013.01); C07K 2317/31 (2013.01); C07K 2317/73 (2013.01); C07K 2317/76 (2013.01); C07K 2317/92 (2013.01); C07K 2318/20 (2013.01); C07K 2319/00 (2013.01); C07K 2319/30 (2013.01); C07K 2319/31 (2013.01)

(58) Field of Classification Search
None
See application file for complete search history.

(56) References Cited

U.S. PATENT DOCUMENTS

| 5,223,409 | A | 6/1993 | Ladner et al. |
| 5,643,763 | A | 7/1997 | Dunn et al. |
| 5,643,768 | A | 7/1997 | Kawasaki |
| 5,846,456 | A | 12/1998 | Liu |
| 5,856,456 | A | 1/1999 | Whitlow et al. |
| 6,172,197 | B1 | 1/2001 | McCafferty et al. |
| 6,472,147 | B1 | 10/2002 | Janda et al. |
| 6,582,915 | B1 | 6/2003 | Griffiths et al. |
| 6,673,901 | B2 | 1/2004 | Koide |
| 6,969,108 | B2 | 11/2005 | Fukumoto et al. |
| 7,842,476 | B2 | 11/2010 | McGregor et al. |
| 10,196,446 | B2 | 2/2019 | Goldberg et al. |
| 2004/0197332 | A1 | 10/2004 | Ullrich et al. |
| 2005/0004029 | A1 | 1/2005 | Garcia |
| 2005/0272083 | A1 | 12/2005 | Seshagiri |
| 2008/0241159 | A1 | 10/2008 | Gerritsen et al. |
| 2009/0042906 | A1 | 2/2009 | Huang et al. |
| 2009/0274693 | A1 | 11/2009 | Gilmer et al. |
| 2009/0299040 | A1 | 12/2009 | Camphausen et al. |
| 2009/0311803 | A1 | 12/2009 | Way et al. |
| 2010/0179094 | A1 | 7/2010 | Emanuel et al. |
| 2010/0216708 | A1 | 8/2010 | Jacobs et al. |
| 2010/0254989 | A1 | 10/2010 | Bossenmaier et al. |
| 2011/0038866 | A1 | 2/2011 | Hastewell et al. |
| 2011/0053842 | A1 | 3/2011 | Camphausen et al. |
| 2011/0118144 | A1 | 5/2011 | Hyun et al. |
| 2011/0274623 | A1 | 11/2011 | Jacobs |
| 2011/0287009 | A1 | 11/2011 | Scheer et al. |
| 2012/0225870 | A1 | 9/2012 | Janne et al. |
| 2012/0244164 | A1 | 9/2012 | Beste et al. |
| 2012/0263723 | A1 | 10/2012 | Davies et al. |
| 2013/0012435 | A1 | 1/2013 | Camphausen et al. |
| 2013/0039927 | A1 | 2/2013 | Dewhurst et al. |

(Continued)

FOREIGN PATENT DOCUMENTS

| CN | 102076713 A | 5/2011 |
| JP | 2010518115 A | 5/2010 |

(Continued)

OTHER PUBLICATIONS

Mamluk et al., "Anti-tumor effect of CT-322 as an Adnectin inhibitor of vascular endothelial growth factor receptor-2", mAbs, 2(2), pp. 199-208, 2010.
Klein et al. "Abstract LB-312: Bispecific Centyrin Simultaneously targeting EGFR and c-Met demonstrates improved activity compared to the mixture of single agents", Cancer Research, 73 (8 Supplement), Abstract LB-312, Apr. 2013.
Diem et al., "Selection of high-affinity Centyrin FN3 domains from a simple library diversified at a combination of strand and loop positions", Protein Engineering, Design & Selection, vol. 27, No. 10, pp. 419-429, 2014.

(Continued)

Primary Examiner — Paul J Holland
(74) Attorney, Agent, or Firm — Ice Miller LLP

(57) ABSTRACT

Cysteine engineered monospecific and bispecific EGFR and/or c-Met FN3 domain containing molecules comprising one or more free cysteine amino acids are prepared by mutagenizing a nucleic acid sequence of a parent molecule and replacing one or more amino acid residues by cysteine to encode the cysteine engineered FN3 domain containing monospecific or bispecific molecules; expressing the cysteine engineered FN3 domain containing molecules; and recovering the cysteine engineered FN3 domain containing molecule. Isolated cysteine engineered monospecific or bispecific FN3 domain containing molecules may be covalently attached to a detection label or a drug moiety and used therapeutically.

8 Claims, 13 Drawing Sheets

Specification includes a Sequence Listing.

(56) References Cited

U.S. PATENT DOCUMENTS

| | | |
|---|---|---|
| 2013/0184212 A1 | 7/2013 | Camphausen et al. |
| 2013/0226834 A1 | 8/2013 | Gannalo, II |
| 2014/0141000 A1 | 5/2014 | Chiu et al. |
| 2014/0155325 A1 | 6/2014 | Mark et al. |
| 2014/0155326 A1 | 6/2014 | Mark et al. |
| 2014/0255408 A1 | 9/2014 | Chiu et al. |
| 2014/0349929 A1 | 11/2014 | Camphausen et al. |
| 2015/0104808 A1 | 4/2015 | Goldberg et al. |
| 2017/0348397 A1 | 12/2017 | Diem et al. |

FOREIGN PATENT DOCUMENTS

| | | |
|---|---|---|
| JP | 2010535032 A | 11/2010 |
| JP | 2011507543 A | 3/2011 |
| JP | 2011517314 A | 6/2011 |
| JP | 2011520961 A | 7/2011 |
| JP | 2011522517 A | 8/2011 |
| JP | 2011524742 A | 9/2011 |
| JP | 2012504402 A | 2/2012 |
| JP | 2012507295 A | 3/2012 |
| WO | 9638557 A1 | 12/1996 |
| WO | 2008100805 | 8/2008 |
| WO | 2008127710 A2 | 10/2008 |
| WO | 2009018386 | 2/2009 |
| WO | 2009083804 A2 | 7/2009 |
| WO | 2009085462 A1 | 7/2009 |
| WO | 2009102421 A2 | 8/2009 |
| WO | 2009111691 A2 | 9/2009 |
| WO | 2009126834 A2 | 10/2009 |
| WO | 2009133208 A1 | 11/2009 |
| WO | 2009142773 A2 | 11/2009 |
| WO | 2009146463 | 12/2009 |
| WO | 2010039248 A1 | 4/2010 |
| WO | 2010051274 | 5/2010 |
| WO | 2010115551 A1 | 10/2010 |
| WO | 2011110642 A2 | 9/2011 |
| WO | 2011130324 A1 | 10/2011 |
| WO | 2011131746 A2 | 10/2011 |
| WO | 2011151412 A1 | 12/2011 |
| WO | 2012158818 | 11/2012 |
| WO | 2012162426 | 11/2012 |
| WO | 2014081954 A1 | 5/2014 |
| WO | 2014165093 A2 | 10/2014 |

OTHER PUBLICATIONS

Goldberg et al., "Engineering a targeted delivery platform using Centyrins", Protein Engineering, Design & Selection, vol. 29, No. 12, pp. 563-572, 2016.

Adjei et al., "Early Clinical Development of ARQ197, a Selective, Non-ADP-Competitive Inhibitor Targeting MET Tyrosine Kinase for the Treatment of Advanced Cancers," The Oncologist, vol. 16, pp. 788-799 (2011).

Alfthlan et al., "Properties of a single-chain antibody containing different linker peptides," Protein Engineering, vol. 8, No. 7, pp. 725-731 (1995).

Baselga et al., "Critical Update and Emerging Trends in Epidermal Growth Factor Receptor Targeting in Cancer," Journal of Clinical Oncology, vol. 23, No. 11, pp. 2445-2459 (2005).

Batley et al., "Inhibition of FGF-1 Receptor Tyrosine Kinase Activity by PD 161570, a New Protein-Tyrosine Kinase Inhibitor," Life Sciences, vol. 62, No. 20, pp. 143-150 (1998).

Bean et al., "MET amplification occurs with or without T790M mutations in EGFR mutant lung tumors with acquired resistance to gefitinib or erlotinib," Proceedings of the National Academy of Science, vol. 104, No. 52, pp. 20932-20937 (2007).

Berzofsky et al., "Antigen-antibody Interaction," Chapter 23, Fundamental Immunology, edited by W.E. Paul, Raven Press, New York, 595-644 (1984).

Birtalan et al., "The Intrinsic Contributions of Tyrosine, Serine, Glycine and Arginine to the Affinity and Specificity of Antibodies," Journal of Molecular Biology, vol. 377, pp. 1518-1528 (2008).

Bork et al., "Proposed acquisition of an animal protein domain by bacteria," Proceedings of the National Academy of Science, UsSA, vo. 89, pp. 8990-8994 (1992).

Cappuzzo et al., "Epidermal Growth Factor Receptor Gene and Protein and Gefitinib Sensitivity in Non-small-Cell Lung Cancer," Journal of the National Cancer Institute, vol. 97, pp. 643-655 (2005).

Christensen et al., "c-Met as a target for human cancer and characterization of inhibitors for therapeutic intervention," Cancer Letters, vol. 225, pp. 1-26 (2005).

Cooper et al., "Molecular cloning of a new transforming gene from a chemically transformed human cell line," Nature, vol. 311, pp. 29-33 (1984).

DeRoock et al., "Effects of KRAS, BRAF, NRAS, and PIK3CA mutations on the efficacy of cetuximab plus chemotherapy in chemotherapy-refractory metastatic colorectal cancer: a retrospective consortium analysis," Lancet Oncology, vol. 11, pp. 753-762 (2010).

Downward et al., "Autophosphorylation sites on the epidermal growth factor receptor," Nature, vol. 311, pp. 483-485 (1984).

Engelman et al., "MET Amplification Leads to Gefitinib Resistance in Lung Cancer by Activating ERBB3 Signaling," Science, vol. 316, pp. 1039-1043 (2007).

Ferguson, Kathryn M., "Structure-Based View of Epidermal Growth Factor Receptor Regulation," Annual Review of Biophysics, vol. 37, pp. 535-373 (2008).

GenBank Accession No. NP 001120972.

Gill et al., "Monoclonal Anti-epidermal Growth Factor Receptor Antibodies Which Are Inhibitors of Epidermal Growth =actor Binding and Antagonists of Epidermal Growth Factor-stimulated tyrosine Protein Kinase Activity," The Journal of Biological Chemistry, vol. 259, No. 12, pp. 7755-7760 (1984).

Goldstein et al., "Biological efficacy of a chimeric antibody to the epidermal growth factor receptor in a human tumor xenograft model," Clinical Cancer Research, vol. 1, pp. 1311-1318 (1995).

Grünwald et al., "Developing Inhibitors of the Epidermal Growth Factor Receptor for Cancer Treatment," Journal of the National Cancer Institute, vol. 95, No. 12, pp. 851-867 (2003).

Hallewell et al., "Genetically Engineered Polymers of Human CuZN Superoxide Dismutase," The Journal of Thological Chemistry, vol. 264, No. 9, pp. 5260-5268 (1989).

Hanes et al., "In vitro selection and evolution of functional proteins by using ribosome display," Proceedings of the National Academy of Sciences USA, vol. 94, pp. 4937-4942 (1997).

Hirsch et al, "Combination of EGFR gene copy number and protein expression predicts outcome for advanced non-small-cell lung cancer patients treated with gefitnib," Annals of Oncology, vol. 18, pp. 752-760 (2007).

Hynes et al., "ERBB Receptors and Cancer: the Complexity of Targeted Inhibitors," Nature Reviews, vol. 5, pp. 341-356 (2005).

Ichimura et al., "Expression of c-met/HGF Receptor in Human Non-small Cell Lung Carcinomas in vitro and in vivo and Its Prognostic Significance," Japan Journal of Cancer Research, vol. 87. pp. 1063-1069 (1996).

Jacobs et al., "Design of novel FN3 domains with high stability by a consensus sequence approach," Protein Engineering, Design & Selection, vol. 25, No. 3, pp. 107-117 (2012).

Jacobs et al., "FN3 Domain Engineering", Protein Engineering, pp. 145-162, 2012.

Jänne et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, vol. 12, No. 14 Suppl, pp. 4416s-4420s (2006).

Lehmann et al., "Engineering proteins for thermostability: the use of sequence alignments versus rational design and directed evolution," Current Opinion in Biotechnology, vol. 12, pp. 371-375 (2001).

Li et al., "Skin toxicities associated with epidermal growth factor receptor inhibitors," Target Oncology, vol. 4, pp. 107-119 (2009).

Linardou et al., "Somatic EGFR mutations and efficacy of tyrosine kinase inhibitors in NSCLC," National Review of Clinical Oncology, vol. 6, pp. 352-366 (2009).

(56) References Cited

OTHER PUBLICATIONS

Ma et al., "c-Met: Structure, functions and potential for therapeutic inhibition," Cancer and Metastasis Reviews, vol. 22, pp. 309-325 (2003).
Meinke et al., "Cellulose-Binding Polypeptides from Cellulomonas fimi: Endoglucanase D (CenD), a Family A b-1,4-Glucanase," Journal of Bacteriology, vol. 175, No. 7, pp. 1910-1918 (1993).
Mendelsohn et al., "Epidermal Growth Factor Receptor Targeting in Cancer," Seminars in Oncology, vol. 33, pp. 369-385 (2006).
Mendelsohn et al., "The EGF receptor family as targets for cancer therapy," Oncogene, vol. 19, pp. 6550-6565 (2000).
Määttä et al., "Proteolytic Cleavage and Phosphorylation of a Tumor-associated ErbB4 Isoform Promote Ligand-Independent Survival and Cancer Cell Growth," Molecular Biology, vol. 17, pp. 67-79 (2006).
NCBI Reference Sequence NP_005219.2, "Epidermal Growth Factor Receptor Isoform a Precursor [*Homo sapiens*]," pp. 1-14 (May 18, 2014).
Odegrip et al., "CIS display: In vitro selection of peptides from libraries of protein-DNA complexes," Proceedings of the National Academy of Science USA, vol. 101, No. 9, pp. 2806-2810 (2004).
Olson et al., "Design, expression, and stability of a diverse protein library based on the human fibronectin type III domain," Protein Science, vol. 16, pp. 476-484 (2007).
Panek et al.,"In Vitro Pharmacological Characterization of PD 166285, a New Nanomolar Potent and Broadly Active Protein Tyrosine Kinase Inhibitor," The Journal of Pharmacology and Experimental Therapeutics, vol. 283, No. 3, pp. 1433-1444 (1997).
Peters et al., "MET: a promising anticancer therapeutic target," Nature Reviews Clinical Oncology, vol. 9, pp. 314-326 (2012).
Prewett et al., "Mouse-Human chimeric Anti-Epidermal Growth Factor Receptor Antibody C225 Inhibits the Growth of Human Renal Cell Carcinoma Xenografts in Nude Mice," Clinical Cancer Research, vol. 4, pp. 2957-2966 (1998).
Riely et al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, vol. 12, No. 3, pp. 839-844 (2006).
Roberts et al., "RNA-peptide fusions for the in vitro selection of peptides and proteins," Proceedings of the National Academy of Science USA, vol. 94, pp. 12297-12302 (1997).
Robinson et al., "Covalent Attachment of Arc Repressor Subunits by a Peptide Linker Enhances Affinity for Operator DNA," Biochemistry, vol. 35, pp. 109-116 (1996).
Sakakura et al., "Gains, Losses, and Amplifications of Genomic Materials in Primary Gastric Cancers Analyzed by comparative Genomic Hybridization," Genes, Chromosomes & Cancer, vol. 24, pp. 299-305 (1999).
Schmidt et al., "Novel mutations of the MET proto-oncogene in papillary rental carcinomas," Oncogene, vol. 18, pp. 2343-2350 (1999).
Siegfried et al., "The Clinical Significance of Hepatocyte Growth Factor for Non-Small Cell Lung Cancer," Annals of Thoracic Surgery, vol. 66, pp. 1915-1918 (1998).
Sierra et al., "c-Met as a potential therapeutic target and biomarker in cancer," Therapeutic Advances in Medical Oncology, vol. 3, No. 51, pp. 521-535 (2011).
Spigel et al., "Final efficacy results from OAM4558g, a randomized phase Ii study evaluating MetMAb or placebo in combination with erlotinib in advanced NSCLC", Journal of Clinical Oncology 29, No. 15, pp. 7505-7505, May 2011 (Abstract Only).
Stamos et al., "Crystal structure of the HGF b-chain in complex with the Sema domain of the Met receptor," The EMBO Journal, vol. 23, pp. 2325-2335 (2004).
Jacobs et al., "Fusion to a highly stable consensus albumin binding domain allows for tunable pharmacokinetics", Protein Engineering, Design & Selection, vol. 28, No. 10, pp. 385-393, 2015.
Strohl, William R., "Optimization of Fc-mediated effector functions of monoclonal antibodies," Current Opinion in Biotechnology, vol. 20, pp. 685-691 (2009).
SwissProt Accession No. P00533.2, "Epidermal Growth Factor Receptor," pp. 1-49 (Jun. 11, 2014).
Turke et al., "Preexistence and Clonal Selection of MET Amplification in EGFR Mutant NSCLC," Cancer Cell, vol. 17, pp. 77-88 (2010).
Ullrich et al., "Human epidermal growth factor receptor cDNA sequence and aberrant expression of the amplified gene in A431 epidermoid carcinoma cells," Nature, vol. 309, pp. 418-425 (1984).
Watanabe et al., "Gene Cloning of Chitinase A1 from Bacillus circulans WL-12 Revealed Its Evolutionary Relationship to Serratia Chitinase and to the Type III Homology Units of Fibronectin," Journal of Biological Chemistry, vol. 265, pp. 15659-15665 (1990).
Zhang et al., "Complete disulfide bond assignment of a recombinant immunoglobulin G4 monoclonal antibody," Analytical Biochemistry, vol. 311, pp. 1-9 (2002).

Figure 1A

| SEQ ID NO: | | |
|---|---|---|
| 18 | LPAPKNLVVSEVTEDSLRLSWADP-HGFYDSFLIQYQESEKVGEAINLTVPGSERSYDLTG | (60) |
| 19 | LPAPKNLVVSEVTEDSLRLSWFYD-RDGYDSFLIQYQESEKVGEAINLTVPGSERSYDLTG | |
| 20 | LPAPKNLVVSEVTEDSLRLSWGYN-GDHFDSFLIQYQESEKVGEAINLTVPGSERSYDLTG | |
| 21 | LPAPKNLVVSEVTEDSLRLSWDDP-RGFYESFLIQYQESEKVGEAINLTVPGSERSYDLTG | |
| 22 | LPAPKNLVVSEVTEDSLRLSWTWP-YADLDSFLIQYQESEKVGEAINLTVPGSERSYDLTG | |
| 23 | LPAPKNLVVSEVTEDSLRLSWGYN-GDHFDSFLIQYQESEKVGEAINLTVPGSERSYDLTG | |
| 24 | LPAPKNLVVSEVTEDSLRLSWDYDLGDHFDSFLIQYQESEKVGEAINLTVPGSERSYDLTG | |
| 25 | LPAPKNLVVSEVTEDSLRLSWDDP-WAFYESFLIQYQESEKVGEAINLTVPGSERSYDLTG | |
| 27 | LPAPKNLVVSEVTEDSARLSWDDP-WAFYESFLIQYQESEKVGEAIVLTVPGSERSYDLTG | |
| 29 | LPAPKNLVVSEVTEDSARLSWTWP-YADLDSFLIQYQESEKVGEAIVLTVPGSERSYDLTG | |
| 107 | LPAPKNLVVSEVTEDSARLSWADP-HGFYDSFLIQYQESEKVGEAIVLTVPGSERSYDLTG | |
| 108 | LPAPKNLVVSEVTEDSARLSWDDP-WAFYESFLIQYQESEKVGEAIVLTVPGSERSYDLTG | |
| 109 | LPAPKNLVVSEVTEDSARLSWDDP-HAFYESFLIQYQESEKVGEAIVLTVPGSERSYDLTG | |
| 110 | LPAPKNLVVSEVTEDSARLSWADP-HGFYDSFLIQYQESEKVGEAIVLTVPGSERSYDLTG | |
| | **************** : *:*******************:********** | |

| 18 | LKPGTEYTVSIYGVHNVYKDTNMRGLPLSAEFTT | (94) |
|---|---|---|
| 19 | LKPGTEYTVSIYGVHNVYKDTNMRGLPLSAEFTT | |
| 20 | LKPGTEYTVSIYGVHNVYKDTNMRGLPLSAEFTT | |
| 21 | LKPGTEYTVSIYGVHNVYKDTNMRGLPLSAEFTT | |
| 22 | LKPGTEYTVSIYGVHNVYKDTNMRGLPLSAEFTT | |
| 23 | LKPGTEYTVSIYGVHNVYKDTNMRGLPLSAEFTT | |
| 24 | LKPGTEYTVSIYGVHNVYKDTNMRGLPLSAEFTT | |
| 25 | LKPGTEYTVSIYGVHNVYKDTNMRGLPLSAEFTT | |
| 27 | LKPGTEYTVSIYGVHNVYKDTNMRGLPLSAEFTT | |
| 29 | LKPGTEYTVSIYGVHNVYKDTNMRGLPLSAEFTT | |
| 107 | LKPGTEYTVSIYGVHNVYKDTNMRGLIPLSAIFTT | |
| 108 | LKPGTEYTVSIYGVHNVYKDTNIRGLIPLSAIFTT | |
| 109 | LKPGTEYTVSIYGVHNVYKDTNIRGLIPLSAIFTT | |
| 110 | LKPGTEYTVSIYGVHNVYKDTNIRGLIPLSAIFTT | |
| | ************************* *:******: | |

Figure 1B

```
SEQ ID
NO:
26   LPAPKNLVVSEVTEDSLRLSNTAP-DAAFDSFLIQYQESEKVGEAINLTVPGSERSYDLTG   (60)
28   LPAPKNLVVSEVTEDSARLSWTAP-DAAFDSFLIQYQESEKVGEAIVLTVPGSERSYDLTG
     ******************:***** ***********************:***********

26   LKPGTEYTVSIYGVLGSYVFEHDVMLPLSAEFTT   (94)
28   LKPGTEYTVSIYGVLGSYVFEHDVMLPLSAIFTT
     ***************************** ***
```

Figure 4.

```
              A         AB      B         BC
TENCON27 (1)  LPAPKNLVVSRV TEDS ARLSW TAPDAAFDS  (30)
TCL14    (1)  LPAPKNLVVSRVTEDSARLSWTAPDAAFDS     (30)

C         CD       D       DE      E
TENCON27 (31) FLIQYQE SEKVGE AIVLTVP GSERSYDLT G  (60)
TCL14    (31) FXIXYXE XXXXGE AIVLTVPGSERSYDLTG    (60)

EF        F       FG        G
TENCON27 (61) LKPGTEYTVSIYGV KGGHRSN PLSAIFTT     (89)
TCL14    (61) LKPGTEYXVXIXGVKGGXXSXPLSAIFTT       (89)
```

Figure 5A.

| SEQ ID NO: | Sequence |
|---|---|
| 32 | LPAPKNLVVSRVTEDSARLSWTAPDAAFDSFWIRYDEVVGGEAIVLTVPGSERSYDLTG (60) |
| 33 | LPAPKNLVVSRVTEDSARLSWTAPDAAFDSFFIRYDEFLRSGEAIVLTVPGSERSYDLTG |
| 34 | LPAPKNLVVSRVTEDSARLSWTAPDAAFDSFWIRYFEFLGSGEAIVLTVPGSERSYDLTG |
| 35 | LPAPKNLVVSRVTEDSARLSWTAPDAAFDSFWIRYFEFLGSGEAIVLTVPGSERSYDLTG |
| 36 | LPAPKNLVVSRVTEDSARLSWTAPDAAFDSFVIRYFEFLGSGEAIVLTVPGSERSYDLTG |
| 37 | LPAPKNLVVSRVTEDSARLSWTAPDAAFDSFWIRYLEFLGGGEAIVLTVPGSERSYDLTG |
| 38 | LPAPKNLVVSRVTEDSARLSWTAPDAAFDSFWIRYFEFLGSGEAIVLTVPGSERSYDLTG |
| 39 | LPAPKNLVVSRVTEDSARLSWTAPDAAFDSFWIRYFEFLGSGEAIVLTVPGSERSYDLTD |
| 40 | LPAPKNLVVSRVTEDSARLSWTAPDAAFDSFWIRYFEFLGSGEAIVLTVPGSERSYDLTG |
| 41 | LPAPKNLVVSRVTEDSARLSWTAPDAAFDSFWIRYFEFLGSGEAIVLTVPGSERSYDLTG |
| 42 | LPAPKNLVVSRVTEDSARLSWTAPDAAFDSFWIRYFEFLGSGEAIVLTVPGSERSYDLTG |
| 43 | LPAPKNLVVSRVTEDSARLSWTAPDAAFDSFWIRYFEFLGSGEAIVLTVPGSERSYDLTG |
| 44 | LPAPKNLVVSRVTEDSARLSWTAPDAAFDSFWIRYFEFLGSGEAIVLTVPGSERSYDLTG |
| 45 | LPAPKNLVVSRVTEDSARLSWTAPDAAFDSFWIRYFEFLGSGEAIVLTVPGSERSYDLTG |
| 46 | LPAPKNLVVSRVTEDSARLSWTAPDAAFDSFWIRYFEFTAGEAIVLTVPGSERSYDLTG |
| 47 | LPAPKNLVVSRVTEDSARLSWTAPDAAFDSFWIRYFEFTTAGEAIVLSTGEAIVLTVPGSERSYDLTG |
| 48 | LPAPKNLVVSRVTEDSARLSWTAPDAAFDSFWIRYFELLSTGEAIVLTVPGSERSYDLTG |
| 49 | LPAPKNLVVSRVTEDSARLSWTAPDAAFDSFWIRYEEFVSKGEAIVLTVPGSERSYDLTG |
| 111 | LPAPKNLVVSRVTEDSARLSWTAPDAAFDSFWIRYFEFLGSGEAIVLTVPGSERSYDLTG |
| 112 | LPAPKNLVVSRVTEDSARLSWTAPDAAFDSFWIRYFEFVGSGEAIVLTVPGSERSYDLTG |
| 113 | LPAPKNLVVSRVTEDSARLSWTAPDAAFDSFWIRYFEFVSKGDAIVLTVPGSERSYDLTG |
| 114 | LPAPKNLVVSRVTEDSARLSWTAPDAAFDSFWIRYFEFLGSGEAIVLTVPGSERSYDLTG |

Figure 5B.

| SEQ ID NO: | | |
|---|---|---|
| 32 | LKPGTEYYVNILGVKGGSISVPLSAIFTT | |
| 33 | LKPGTEYWTILGVKGGLVSTPLSAIFTT | |
| 34 | LKPGTEYIVNIMGVRGGSISHPLSAIFTT | |
| 35 | LKPGTEYVVNILGVKGGGLSVPLSAIFTT | |
| 36 | LKPGTEYVVQILGVRGGYISIPLSAIFTT | |
| 37 | LKPGTEYVVQIMGVKGGTVSPPLSAIFTT | |
| 38 | LKPGTEYVVGINGVKGGYISYPLSAIFTT | |
| 39 | LKPGTEYGVTINGVKGGRVSTPLSAIFTT | |
| 40 | LKPGTEYVVQIIGVKGGHISLPLSAIFTT | |
| 41 | LKPGTEYVVNIMGVKGGKISPPLSAIFTT | (89) |
| 42 | LKPGTEYAVNIMGVKGGRVSVPLSAIFTT | |
| 43 | LKPGTEYVVQILGVKGGSISVPLSAIFTT | |
| 44 | LKPGTEYVVNIMGVKGGSISYPLSAIFTT | |
| 45 | LKPGTEYVVQILGVRGGYISIPLSAIFTT | |
| 46 | LKPGTEYVVQIMGVKGGTVSPPLSAIFTT | |
| 47 | LKPGTEYVVNIMGVKGGSISPPLSAIFTT | |
| 48 | LKPGTEYVVNIMGVKGGSISPPLSAIFTT | |
| 49 | LKPGTEYVVNILGVKGGSISPPLSAIFTT | |
| 111 | LKPGTEYVVNILGVKGGGKISPPLSAIFTT | |
| 112 | LKPGTEYVVNILGVKGGSISPPLSAIFTT | |
| 113 | LKPGTEYVVNILSVKGGSISPPLSAIFTT | |
| 114 | ***** ***** : *** : *** ******* | |

CYSTEINE ENGINEERED FIBRONECTIN TYPE III DOMAIN BINDING MOLECULES

CROSS-REFERENCE TO RELATED APPLICATIONS

This application is a continuation of U.S. patent application Ser. No. 14/512,801, filed on Oct. 13, 2014, which claims the benefit of U.S. Provisional Application Ser. No. 61/890,539, filed 14 Oct. 2013. The entire contents of the aforementioned applications are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "689303-4U2 Sequence Listing" and a creation date of Dec. 14, 2018, and having a size of 345 kb. The sequence listing submitted via EFS-Web is part of the specification and is herein incorporated by reference in its entirety.

FIELD OF THE INVENTION

The present invention relates to binding molecules engineered with cysteine residues and methods of making and using the same. More particularly, the invention is directed to fibronectin type III (FN3) domain molecules that may bind to EGFR and/or c-Met that are cysteine engineered.

BACKGROUND OF THE INVENTION

Epidermal growth factor receptor (EGFR or ErbB1 or HER1) is a transmembrane glycoprotein of 170 kDa that is encoded by the c-erbB1 proto-oncogene. EGFR is a member of the human epidermal growth factor receptor (HER) family of receptor tyrosine kinases (RTK) which includes HER2 (ErbB2), HER3 (ErbB3) and HER4 (ErbB4). These RTKs share a homologous structure that consists of a ligand-binding extracellular domain (ECD), a single span transmembrane domain and an intracellular domain that contain catalytic kinase domain and a C-terminal tail. EGFR signaling is initiated by ligand binding followed by induction of conformational change, dimerization and trans-autophosphorylation of the receptor (Ferguson et al., Annu Rev Biophys, 37: 353-73, 2008) which initiates a signal transduction cascade that ultimately affects a wide variety of cellular functions, including cell proliferation and survival. Increases in expression or kinase activity of EGFR have been linked with a range of human cancers, making EGFR an attractive target for therapeutic intervention (Mendelsohn et al., Oncogene 19: 6550-6565, 2000; Grunwald et al., J Natl Cancer Inst 95: 851-67, 2003; Mendelsohn et al., Semin Oncol 33: 369-85, 2006). Furthermore, increases in both the EGFR gene copy number and protein expression have been associated with favorable responses to the EGFR tyrosine kinase inhibitor, IRESSA™ (gefitinib), in non-small cell lung cancer (Hirsch et al., Ann Oncol 18:752-60, 2007).

EGFR therapies include both small molecules and anti-EGFR antibodies, approved for treatment of colorectal cancer, pancreatic cancer, head and neck cancer, and non-small cell lung cancer (NSCLC) (Baselga and Arteaga, J Clin Oncol 23:2445-2459 (20005; Gill et al., J Biol Chem, 259:7755-7760, 1984; Goldstein et al., Clin Cancer Res, 1:131 1-1318; 1995; Prewett et al., Clin Cancer Res, 4:2957-2966, 1998).

Efficacy of anti-EGFR therapies may depend on tumor type and EFGR mutation/amplification status in the tumor, and may result in skin toxicity (De Roock et al., Lancet Oncol 11 :753-762, 2010; Linardou et al., Nat Rev Clin Oncol, 6: 352-366, 2009; Li and Perez-Soler, Targ Oncol 4: 107-119, 2009). EGFR tyrosine kinase inhibitors (TKI) are commonly used as $2^{nd}$ line therapies for non small cell lung cancer (NSCLC), but often stop working within twelve months due to resistance pathways (Riely et al., Clin Cancer Res 12: 839-44, 2006).

c-Met encodes a tyrosine kinase receptor. It was first identified as a proto-oncogene in 1984 after it was found that treatment with a carcinogen resulted in a constitutively active fusion protein TPR-MET (Cooper et al., Nature 311:29-33, 1984). Activation of c-Met through its ligand HGF stimulates a plethora of cell processes including growth, motility, invasion, metastasis, epithelial-mesenchymal transition, angiogenesis/wound healing, and tissue regeneration (Christensen et al., Cancer Lett 225:1-26, 2005; Peters and Adjei, Nat Rev Clin Oncol 9:314-26, 2012). c-Met is synthesized as a single chain protein that is proteolytically cleaved into a 50 kDa alpha- and 140 kDa beta-subunit linked by a disulphide bond (Ma et al., Cancer and Metastasis Reviews, 22: 309-325, 2003). c-Met is structurally similar to other membrane receptors such as Ron and Sea and is comprised of an extracellular ligand-binding domain, a transmembrane domain, and a cytoplasmic domain (containing the tyrosine kinase domain and a C-terminal tail region). The exact stoichiometry of HGF:c-Met binding is unclear, but it is generally believed that two HGF molecules bind to two c-Met molecules leading to receptor dimerization and autophosphorylation at tyrosines 1230, 1234, and 1235 (Stamos et al., The EMBO Journal 23: 2325-2335, 2004). Ligand-independent c-Met autophosphorylation can also occur due to gene amplification, mutation or receptor over-expression.

c-Met is frequently amplified, mutated or over-expressed in many types of cancer including gastric, lung, colon, breast, bladder, head and neck, ovarian, prostate, thyroid, pancreatic, and CNS. Missense mutations typically localized to the kinase domain are commonly found in hereditary papillary renal carcinomas (PRCC) and in 13% of sporadic PRCCs (Schmidt et al., Oncogene 18: 2343-2350, 1999). In contrast, c-Met mutations localized to the semaphorin or juxtamembrane domains of c-Met are frequently found in gastric, head and neck, liver, ovarian, NSCLC and thyroid cancers (Ma et al., Cancer and Metastasis Reviews, 22: 309-325, 2003; Sakakura et al., Chromosomes and Cancer, 1999. 24:299-305). c-Met amplification has been detected in brain, colorectal, gastric, and lung cancers, often correlating with disease progression (Ma et al., Cancer and Metastasis Reviews, 22: 309-325, 2003). Up to 4% and 20% of non-small cell lung cancer (NSCLC) and gastric cancers, respectively, exhibit c-Met amplification (Sakakura et al., Chromosomes and Cancer, 1999. 24:299-305: Sierra and Tsao, Therapeutic Advances in Medical Oncology, 3:S21-35, 2011). Even in the absence of gene amplification, c-Met overexpression is frequently observed in lung cancer (Ichimura et al., Jpn J Cancer Res, 87:1063-9, 1996). Moreover, in clinical samples, nearly half of lung adenocarcinomas exhibited high levels of c-Met and HGF, both of which correlated with enhanced tumor growth rate, metastasis and poor prognosis (Sierra and Tsao, Therapeutic Advances in Medical Oncology, 3:S21-35, 2011; Siegfried et al., Ann Thorac Surg 66: 1915-8, 1998).

Nearly 60% of all tumors that become resistant to EGFR tyrosine kinase inhibitors increase c-Met expression, amplify c-Met, or increase its only known ligand, HGF (Turke et al., Cancer Cell, 17:77-88, 2010), suggesting the existence of a compensatory pathway for EGFR through c-Met. c-Met amplification was first identified in cultured cells that became resistant to gefinitib, an EGFR kinase inhibitor, and exhibited enhanced survival through the Her3 pathway (Engelman et al., Science, 316:1039-43, 2007). This was further validated in clinical samples where nine of 43 patients with acquired resistance to either erlotinib or gefitinib exhibited c-Met amplification, compared to only two of 62 untreated patients. Interestingly, four of the nine treated patients also acquired the EGFR activating mutation, T790M, demonstrating simultaneous resistance pathways (Beat et al., Proc Natl Acad Sci USA, 104:20932-7, 2007).

The individual roles of both EGFR and c-Met in cancer is now well established, making these targets attractive for combination therapy. Both receptors signal through the same survival and anti-apoptotic pathways (ERK and AKT); thus, inhibiting the pair in combination may limit the potential for compensatory pathway activation thereby improving overall efficacy. Combination therapies targeting EGFR and c-Met are tested in clinical trials with Tarceva (erlotinib) in combination with anti-c-Met monovalent antibody for NSCL (Spigel et al., 2011 ASCO Annual Meeting Proceedings 2011, Journal of Clinical Oncology: Chicago, Ill. p. 7505) and Tarceva (erlotinib) in combination with ARQ-197, a small molecule inhibitor of c-Met (Adjei et al., Oncologist, 16:788-99, 2011). Combination therapies or bispecific anti-EGFR/c-Met molecules have been disclosed for example in: Int. Pat. Publ. No. WO2008/127710, U.S. Pat. Publ. No. US2009/0042906, Int. Pat. Publ. No. WO2009/111691, Int. Pat. Publ. No. WO2009/126834, Int. Pat. Publ. No. WO2010/039248, Int. Pat. Publ. No. WO2010/115551.

Current small molecule and large molecule (i.e. antibody) approaches to antagonize EGFR and/or c-Met signaling pathways for therapy may be sub-optimal due to possible lack of specificity with small molecules and therefore potential off-target activity and dose-limiting toxicity encountered with small molecule inhibitors. Typical bivalent antibodies may result in clustering of membrane bound receptors and unwanted activation of the downstream signaling pathways, and monovalent antibodies (half arms) pose significant complexity and cost to the manufacturing process.

Accordingly, the need exists for additional monospecific and bispecific EGFR and/or c-Met inhibitors that also have the additional capability of conjugating cytotoxic drugs thus targeting these potent compounds to the EGFR/c-met-expressing tumor cells, enhancing the anti-tumor activity of these EGFR/c-Met inhibitors. While antibody drug conjugates exist in the art, conventional means of attaching a drug moiety generally leads to a heterogeneous mixture of molecules where the drug moieties are attached at a number of sites on the antibody. For example, cytotoxic drugs have typically been conjugated to antibodies through the often-numerous lysine residues of an antibody, generating a heterogeneous antibody-drug conjugate mixture. Depending on reaction conditions, the heterogeneous mixture typically contains a distribution of antibodies with from 0 to about 8, or more, attached drug moieties. In addition, within each subgroup of conjugates with a particular integer ratio of drug moieties to antibodies, is a potentially heterogeneous mixture where the drug moiety is attached at various sites on the antibody. Analytical and preparative methods are inadequate to separate and characterize the antibody-drug conjugate species molecules within the heterogeneous mixture resulting from a conjugation reaction. Antibodies are large, complex and structurally diverse biomolecules, often with many reactive functional groups. Their reactivities with linker reagents and drug-linker intermediates are dependent on factors, such as pH, concentration, salt concentration, and co-solvents. Furthermore, the multistep conjugation process may be non-reproducible due to difficulties in controlling the reaction conditions and characterizing reactants and intermediates.

Chemical conjugation via cysteines present in antibodies has also been demonstrated. However, engineering in cysteine thiol groups by the mutation of various amino acid residues of a protein to cysteine amino acids is potentially problematic, particularly in the case of unpaired (free Cys) residues or those that are relatively accessible for reaction or oxidation. Unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys groups are unavailable for active site participation and interactions. In addition, the protein may be rendered inactive or nonspecific, by misfolding or loss of tertiary structure (Zhang et al (2002) Anal. Biochem. 311: 1-9).

Thus, a need exists for a molecule that can undergo homogeneous chemical conjugation and avoid the issues faced by antibody conjugates.

SUMMARY OF THE INVENTION

The present invention provides an isolated cysteine engineered fibronectin type III (FN3) domain comprising at least one cysteine substitution at a position selected from the group consisting of residues 6, 8, 10, 11, 14, 15, 16, 20, 30, 34, 38, 40, 41, 45, 47, 48, 53, 54, 59, 60, 62, 64, 70, 88, 89, 90, 91, and 93 of the FN3 domain based on SEQ ID NO: 27, and the equivalent positions in related FN3 domains. A cysteine substitution at a position in the domain or protein comprises a replacement of the existing amino acid residue with a cysteine residue.

The present invention also provides an isolated cysteine engineered fibronectin type III (FN3) domain comprising the amino acid sequence of SEQ ID NO: 27 with at least one cysteine substitution from the amino acid sequence of SEQ ID NO: 27 and specifically binds epidermal growth factor receptor (EGFR) and blocks binding of epidermal growth factor (EGF) to EGFR.

The present invention further provides an isolated cysteine engineered fibronectin type III (FN3) domain comprising the amino acid sequence of SEQ ID NO: 114 with at least one cysteine substitution from the amino acid sequence of SEQ ID NO: 114, and specifically binds hepatocyte growth factor receptor (c-Met) and blocks binding of hepatocyte growth factor (HGF) to c-Met.

The present invention provides novel positions at which cysteine substitutions may be made to generate the cysteine engineered FN3 domains. Said positions include one or more of residues 6, 8, 10, 11, 14, 15, 16, 20, 30, 34, 38, 40, 41, 45, 47, 48, 53, 54, 59, 60, 62, 64, 70, 88, 89, 90, 91, or 93 of SEQ ID NOS: 11-114 and/or 122-137.

An aspect of the invention is a process to prepare the isolated cysteine engineered FN3 domains by mutagenizing a nucleic acid sequence of a parent FN3 domain by replacing one or more amino acid residues with a cysteine residue to encode the cysteine engineered FN3 domain; expressing the cysteine engineered FN3 domain; and isolating the cysteine engineered FN3 domain.

Another aspect of the invention is a chemically-conjugated, isolated cysteine engineered FN3 domain wherein the FN3 domain is covalently attached to a chemical reagent comprising a maleimide moiety.

Another embodiment of the invention is a chemically-conjugated, isolated cysteine engineered FN3 domain that can inhibit the growth of EGFR-overexpressing and/or c-Met-expressing tumor cell lines.

The present application also provides an isolated cysteine engineered bispecific FN3 molecule comprising a first fibronectin type III (FN3) domain and a second FN3 domain, wherein the first and second FN3 domains comprise cysteine substitutions at a position selected from the group consisting of residues 6, 8, 10, 11, 14, 15, 16, 20, 30, 34, 38, 40, 41, 45, 47, 48, 53, 54, 59, 60, 62, 64, 70, 88, 89, 90, 91, and 93, specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met.

Another aspect of the invention is a chemically-conjugated, isolated cysteine engineered bispecific molecule wherein the bispecific molecule is covalently attached to a chemical reagent comprising a maleimide moiety.

A further aspect of the invention is a process to prepare the isolated cysteine engineered bispecific FN3 by mutagenizing a nucleic acid sequence of a parent FN3 bispecific molecule by replacing one or more amino acid residues with cysteine residues to encode the cysteine engineered bispecific molecule; expressing the cysteine engineered molecule; and isolating the cysteine engineered bispecific molecule.

BRIEF DESCRIPTION OF THE DRAWINGS

FIGS. 1A and 1B. Amino acid alignment of the EGFR-binding FN3 domains. The BC and FG loops are boxed at residues 22-28 and 75-86 of SEQ ID NO: 18. Some variants include thermal stability improving L17A, N46K and E86I substitutions (residue numbering according to Tencon SEQ ID NO: 1).

FIG. 4. Sequence alignment of the Tencon27 scaffold (SEQ ID NO: 99) and a TCL14 library (SEQ ID NO: 100) having randomized C-CD-F-FG alternative surface. The loop residues are boxed. Loops and strands are indicated above the sequences.

FIGS. 5A and 5B. Sequence alignment of the c-Met-binding FN3 domains. The C loop and the CD strand and the F loop and the FG strand are boxed and span residues 29-43 and 65-81.

Figure 2:
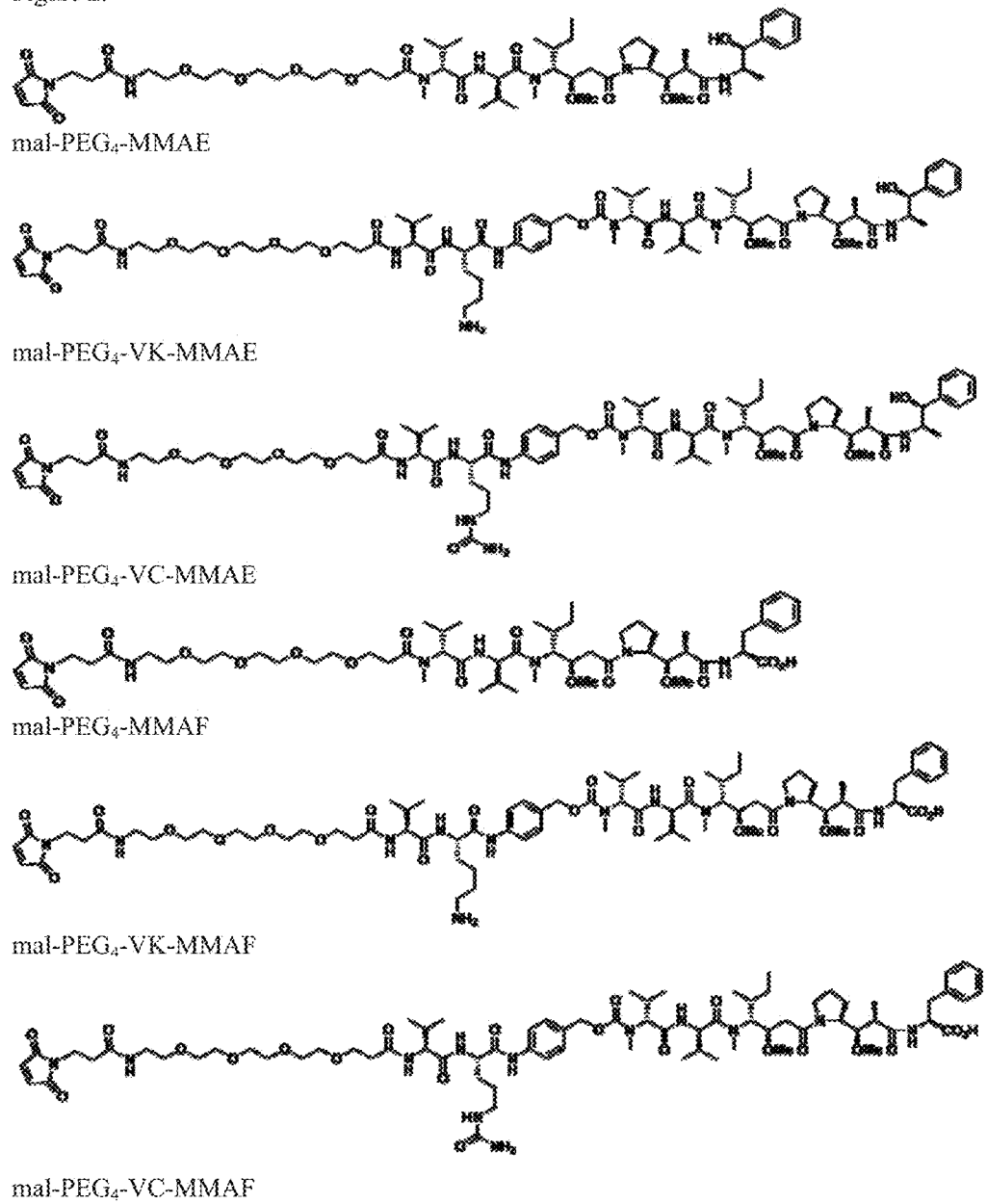
FIG. 2. Cytotoxin/linker structures.

(bispecific EGFR/c-Met molecule refers to p54AR4-83v2-p114AR7P94-A3-ABD (ECB38); the other therapies are crizotinib, erlotinib, cetuximab, and the combination of crizotinib and erlotinib).

DETAILED DESCRIPTION OF THE INVENTION

The term "fibronectin type III (FN3) domain" (FN3 domain) as used herein refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. Publ. No. 2010/0216708. Individual FN3 domains are referred to by domain number and protein name, e.g., the $3^{rd}$ FN3 domain of tenascin (TN3), or the $10^{th}$ FN3 domain of fibronectin (FN10).

The term "substituting" or "substituted" or "mutating" or "mutated" as used herein refers to altering, deleting of inserting one or more amino acids or nucleotides in a polypeptide or polynucleotide sequence to generate a variant of that sequence.

The term "randomizing" or "randomized" or "diversified" or "diversifying" as used herein refers to making at least one substitution, insertion or deletion in a polynucleotide or polypeptide sequence.

"Variant" as used herein refers to a polypeptide or a polynucleotide that differs from a reference polypeptide or a reference polynucleotide by one or more modifications for example, substitutions, insertions or deletions.

The term "specifically binds" or "specific binding" as used herein refers to the ability of the FN3 domain of the invention to bind to a predetermined antigen with a dissociation constant ($K_D$) of $1\times10^{-6}$ M or less, for example $1\times10^{-7}$ M or less, $1\times10^{-8}$ M or less, $1\times10^{-9}$ M or less, $1\times10^{-10}$ M or less, $1\times10^{-11}$ M or less, $1\times10^{-12}$ M or less, or $1\times10^{-13}$ M or less. Typically the FN3 domain of the invention binds to a predetermined antigen (i.e. EGFR or c-Met) with a $K_D$ that is at least ten fold less than its $K_D$ for a nonspecific antigen (for example BSA or casein) as measured by surface plasmon resonance using for example a Proteon Instrument (BioRad). Thus, a bispecific EGFR/c-Met FN3 domain containing molecule of the invention specifically binds to each EGFR and c-Met with a binding affinity ($K_D$) of at least $1\times10^{-6}$ M or less for both EGFR and c-Met. The isolated FN3 domain of the invention that specifically binds to a predetermined antigen may, however, have cross-reactivity to other related antigens, for example to the same predetermined antigen from other species (homologs).

The term "library" refers to a collection of variants. The library may be composed of polypeptide or polynucleotide variants.

The term "stability" as used herein refers to the ability of a molecule to maintain a folded state under physiological conditions such that it retains at least one of its normal functional activities, for example, binding to a predetermined antigen such as EGFR or c-Met.

"Epidermal growth factor receptor" or "EGFR" as used here refers to the human EGFR (also known as HER-1 or Erb-B 1 (Ullrich et al., Nature 309:418-425, 1984) having the sequence shown in SEQ ID NO: 73 and in GenBank accession number NP_005219, as well as naturally-occurring variants thereof. Such variants include the well known EGFRvIII and other alternatively spliced variants (e.g., as identified by SwissProt Accession numbers P00533-1, P00533-2, P00533-3, P00533-4), variants GLN-98, ARG-266, Lys-521, ILE-674, GLY-962, and PRO-988 (Livingston et al., NIEHS-SNPs, environmental genome project, NIEHS ES15478).

"EGFR ligand" as used herein encompasses all (e.g., physiological) ligands for EGFR, including EGF, TGF-α, heparin binding EGF (HB-EGF), amphiregulin (AR), and epiregulin (EPI).

"Epidermal growth factor" (EGF) as used herein refers to the well known 53 amino acid human EGF having an amino acid sequence shown in SEQ ID NO: 74.

"Hepatocyte growth factor receptor" or "c-Met" as used herein refers to the human c-Met having the amino acid sequence shown in SEQ ID NO: 101 or in GenBank Accession No: NP_001120972 and natural variants thereof.

"Hepatocyte growth factor" (HGF) as used herein refers to the well known human HGF having the amino acid sequence shown in SEQ ID NO: 102 which is cleaved to form a dimer of an alpha and beta chain linked by a disulfide bond.

"Blocks binding" or "inhibits binding", as used herein interchangeably refers to the ability of the FN3 domains of the invention of the bispecific EGFR/c-Met FN3 domain containing molecule to block or inhibit binding of the EGFR ligand such as EGF to EGFR and/or HGF to c-Met, and encompass both partial and complete blocking/inhibition. The blocking/inhibition of EGFR ligand such as EGF to EGFR and/or HGF to c-Met by the FN3 domain or the bispecific EGFR/c-Met FN3 domain containing molecule of the invention reduces partially or completely the normal level of EGFR signaling and/or c-Met signaling when compared to the EGFR ligand binding to EGFR and/or HGF binding to c-Met without blocking or inhibition. The FN3 domain or the bispecific EGFR/c-Met FN3 domain containing molecule of the invention "blocks binding" of the EGFR ligand such as EGF to EGFR and/or HGF to c-Met when the inhibition is at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%. Inhibition of binding can be measured using well known methods, for example by measuring inhibition of binding of biotinylated EGF on EGFR expressing A431 cells exposed to the FN3 domain or the bispecific EGFR/c-Met FN3 domain containing molecule of the invention using FACS, and using methods described herein, or measuring inhibition of binding of biotinylated HGF on c-Met extracellular domain using well known methods and methods described herein.

The term "EGFR signaling" refers to signal transduction induced by EGFR ligand binding to EGFR resulting in autophosphorylation of at least one tyrosine residue in the EGFR. An exemplary EGFR ligand is EGF.

"Neutralizes EGFR signaling" as used herein refers to the ability of the FN3 domain of the invention to inhibit EGFR signaling induced by EGFR ligand such as EGF by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%.

The term "c-Met signaling" refers to signal transduction induced by HGF binding to c-Met resulting in autophosphorylation of at least one tyrosine residue in the c-Met. Typically at least one tyrosine residue at positions 1230, 1234 or 1235 is autophosphorylated upon HGF binding.

"Neutralizes c-Met signaling" as used herein refers to the ability of the FN3 domain of the invention to inhibit c-Met signaling induced by HGF by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%

"Overexpress", "overexpressed" and "overexpressing" as used herein interchangeably refer to a cancer or malignant cell that has measurably higher levels of EGFR and/or c-Met on the surface compared to a normal cell of the same tissue type. Such overexpression may be caused by gene amplification or by increased transcription or translation. EGFR and/or c-Met expression and overexpression can be measured using well know assays using for example ELISA, immunofluorescence, flow cytometry or radioimmunoassay on live or lysed cells. Alternatively, or additionally, levels of EGFR and/or c-Met-encoding nucleic acid molecules may be measured in the cell for example using fluorescent in situ hybridization, Southern blotting, or PCR techniques. EGFR and/or c-Met is overexpressed when the level of EGFR and/or c-Met on the surface of the cell is at least 1.5-fold higher when compared to the normal cell.

"Tencon" as used herein refers to the synthetic fibronectin type III (FN3) domain having the sequence shown in SEQ ID NO: 1 and described in U.S. Pat. Publ. No. US2010/0216708.

A "cancer cell" or a "tumor cell" as used herein refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

The term "vector" means a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than about 50 amino acids may be referred to as "peptides".

The term "bispecific EGFR/c-Met molecule" or "bispecific EGFR/c-Met FN3 domain containing molecule" as used herein refers to a molecule comprising an EGFR binding FN3 domain and a distinct c-Met binding FN3 domain that are covalently linked together either directly or via a linker. An exemplary bispecific EGFR/c-Met binding molecule comprises a first FN3 domain specifically binding EGFR and a second FN3 domain specifically binding c-Met.

"Valent" as used herein refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Mixture" as used herein refers to a sample or preparation of two or more FN3 domains not covalently linked together. A mixture may consist of two or more identical FN3 domains or distinct FN3 domains.

Compositions of Matter

The present invention provides cysteine engineered monospecific and bispecific EGFR and/or c-Met binding FN3 domain containing molecules and methods of making and using them.

Monospecific EGFR Binding Molecules

The present invention provides fibronectin type III (FN3) domains that bind specifically to epidermal growth factor receptor (EGFR) and block binding of epidermal growth factor (EGF) to EGFR, and thus can be widely used in therapeutic and diagnostic applications. The present invention provides polynucleotides encoding the FN3 domains of the invention or complementary nucleic acids thereof, vectors, host cells, and methods of making and using them.

The FN3 domains of the invention bind EGFR with high affinity and inhibit EGFR signaling, and may provide a benefit in terms of specificity and reduced off-target toxicity when compared to small molecule EGFR inhibitors, and improved tissue penetration when compared to conventional antibody therapeutics.

One embodiment of the invention an isolated fibronectin type III (FN3) domain that specifically binds epidermal growth factor receptor (EGFR) and blocks binding of epidermal growth factor (EGF) to EGFR.

The FN3 domains of the invention may block EGF binding to the EGFR with an $IC_{50}$ value of less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M in a competition assay employing A431 cells and detecting amount of fluorescence from bound biotinylated EGF using streptavidin-phycoerythrin conjugate at 600 nM on A431 cells incubated with or without the FN3 domains of the invention. Exemplary FN3 domains may block EGF binding to the EGFR with an $IC_{50}$ value between about $1\times10^{-9}$ M to about $1\times10^{-7}$ M, such as EGFR binding FN3 domains having the amino acid sequence of SEQ ID NOs: 18-29, 107-110, or 122-137. The FN3 domains of the invention may block EGF binding to the EGFR by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of EGF to the EGFR in the absence of the FN3 domains of the invention using the same assay conditions.

The FN3 domain of the invention may inhibit EGFR signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of FN3 domains of the invention using the same assay conditions.

Binding of a ligand such as EGF to EGFR stimulates receptor dimerization, autophosphorylation, activation of the receptor's internal, cytoplasmic tyrosine kinase domain, and initiation of multiple signal transduction and transactivation pathways involved in regulation of DNA synthesis (gene activation) and cell cycle progression or division. Inhibition of EGFR signaling may result in inhibition in one or more EGFR downstream signaling pathways and therefore neutralizing EGFR may have various effects, including inhibition of cell proliferation and differentiation, angiogenesis, cell motility and metastasis.

EGFR signaling may be measured using various well know methods, for example measuring the autophosphorylation of the receptor at any of the tyrosines Y1068, Y1148, and Y1173 (Downward et al., Nature 311:483-5, 1984) and/or phosphorylation of natural or synthetic substrates. Phosphorylation can be detected using well known methods such as an ELISA assay or a western blot using a phosphotyrosine specific antibody. Exemplary assays can be found in Panek et al., J Pharmacol Exp Thera 283:1433-44, 1997 and Batley et al., Life Sci 62:143-50, 1998.

In one embodiment, the FN3 domain of the invention inhibits EGF-induced EGFR phosphorylation at EGFR residue position Tyrosine 1173 with an $IC_{50}$ value of less than about $2.5\times10^{-6}$ M, for example less than about $1\times10^{-6}$ M, less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M when measured in A431 cells using 50 ng/mL human EGF.

In one embodiment, the FN3 domain of the invention inhibits EGF-induced EGFR phosphorylation at EGFR residue position Tyrosine 1173 with an $IC_{50}$ value between about $1.8\times10^{-8}$ M to about $2.5\times10^{-6}$ M when measured in A431 cells using 50 ng/mL human EGF. Such exemplary FN3 domains are those having the amino acid sequence of SEQ ID NOs: 18-29, 107-110, or 122-137.

In one embodiment, the FN3 domain of the invention binds human EGFR with a dissociation constant ($K_D$) of less than about $1\times10^{-8}$ M, for example less than about $1\times10^{-9}$ M, less than about $1\times10^{-10}$ M, less than about $1\times10^{-11}$ M, less than about $1\times10^{-12}$ M, or less than about $1\times10^{-13}$ M as determined by surface plasmon resonance or the Kinexa method, as practiced by those of skill in the art. In some embodiments, the FN3 domain of the invention binds human EGFR with a $K_D$ of between about $2\times10^{-10}$ to about $1\times10^{-8}$ M. The affinity of a FN3 domain for EGFR can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are preferably made with standardized solutions of protein scaffold and antigen, and a standardized buffer, such as the buffer described herein.

Exemplary FN3 domains of the invention that bind EGFR include FN3 domains of SEQ ID NOs: 18-29, 107-110, or 122-137.

In one embodiment, the FN3 domain that specifically binds EGFR comprises an amino acid sequence at least 87% identical to the amino acid sequence of SEQ ID NO: 27.

In one embodiment, the FN3 domain that specifically binds EGFR comprises
an FG loop comprising the sequence HNVYK DTNX$_9$ RGL (SEQ ID NO: 179) or the sequence LGSYVFEHDV-ML (SEQ ID NO: 180), wherein X$_9$ is M or I; and
a BC loop comprising the sequence X$_1$X$_2$X$_3$X$_4$X$_5$X$_6$X$_7$X$_8$ (SEQ ID NO: 181), wherein
X$_1$ is A, T, G or D;
X$_2$ is A, D, Y or W;
X$_3$ is P, D or N;
X$_4$ is L or absent;
X$_5$ is D, H, R, G, Y or W;
X$_6$ is G, D or A;
X$_7$ is A, F, G, H or D; and
X$_8$ is Y, F or L.

The FN3 domains of the invention that specifically bind EGFR and inhibit autophosphorylation of EGFR may comprise as a structural feature an FG loop comprising the sequence HNVYKDTNX$_9$RGL (SEQ ID NO: 179) or the sequence LGSYVFEHDVML (SEQ ID NO: 180), wherein X$_9$ is M or I. Such FN3 domains may further comprise a BC loop of 8 or 9 amino acids in length and defined by the sequence X$_1$X$_2$X$_3$X$_4$X$_5$X$_6$X$_7$X$_8$ (SEQ ID NO: 181), and inhibit EGFR autophosphorylation with an $IC_{50}$ value of less than about $2.5\times10^{-6}$ M, and with an $IC_{50}$ value of between about between about $1.8\times10^{-8}$ M to about $2.5\times10^{-6}$ M when measured in A431 cells using 50 ng/mL human EGF.

The FN3 domains of the invention that specifically bind EGFR and inhibit autophosphorylation of EGFR further comprise the sequence of
LPAPKNLVVSEVTEDSLRLSWX$_1$X$_2$X$_3$X$_4$X$_5$X$_6$X$_7$X$_8$D-SFLIQYQESEKVGEAINLTVP GSERSYDLTGLKPGTE-YTVSIYGVHNVYKDTNX$_9$RGLPLSAEFTT (SEQ ID NO: 182), or the sequence LPAPKNLVVSEVTEDSLRL-SWX$_1$X$_2$X$_3$X$_4$X$_5$X$_6$X$_7$X$_8$DSFLIQYQESEKVGEAINLTVP GSERSYDLTGLKPGTEYTVSIYGVLGSYVFEHDVM-LPLSAEFTT (SEQ ID NO: 183), wherein
X$_1$ is A, T, G or D;
X$_2$ is A, D, Y or W;
X$_3$ is P, D or N;
X$_4$ is L or absent;
X$_5$ is D, H, R, G, Y or W;
X$_6$ is G, D or A;
X$_7$ is A, F, G, H or D;
X$_8$ is Y, F or L; and
X$_9$ is M or I The EGFR binding FN3 domains can be generated and tested for their ability to inhibit EGFR autophosphorylation using well known methods and methods described herein.

Another embodiment of the invention is an isolated FN3 domain that specifically binds EGFR, wherein the FN3 domain comprises the sequence shown in SEQ ID NOs: 18-29, 107-110, or 122-137.

In some embodiments, the EGFR binding FN3 domains comprise an initiator methionine (Met) linked to the N-terminus or a cysteine (Cys) linked to a C-terminus of a particular FN3 domain, for example to facilitate expression and/or conjugation of half-life extending molecules.

Another embodiment of the invention is an isolated fibronectin type III (FN3) domain that specifically binds EGFR and blocks binding of EGF to the EGFR, wherein the FN3 domain is isolated from a library designed based on Tencon sequence of SEQ ID NO: 1.

Monospecific c-Met Binding Molecules

The present invention provides fibronectin type III (FN3) domains that bind specifically to hepatocyte growth factor receptor (c-Met) and block binding of hepatocyte growth factor (HGF) to c-Met, and thus can be widely used in therapeutic and diagnostic applications. The present invention provides polynucleotides encoding the FN3 domains of the invention or complementary nucleic acids thereof, vectors, host cells, and methods of making and using them.

The FN3 domains of the invention bind c-Met with high affinity and inhibit c-Met signaling, and may provide a benefit in terms of specificity and reduced off-target toxicity when compared to small molecule c-Met inhibitors, and improved tissue penetration when compared to conventional antibody therapeutics. The FN3 domains of the invention are monovalent, therefore preventing unwanted receptor clustering and activation that may occur with other bivalent molecules.

One embodiment of the invention an isolated fibronectin type III (FN3) domain that specifically binds hepatocyte growth factor receptor (c-Met) and blocks binding of hepatocyte growth factor (HGF) to c-Met.

The FN3 domains of the invention may block HGF binding to c-Met with an $IC_{50}$ value of about less than about $1 \times 10^{-7}$ M, less than about $1 \times 10^{-8}$ M, less than about $1 \times 10^{-9}$ M, less than about $1 \times 10^{-10}$ M, less than about $1 \times 10^{-11}$ M, or less than about $1 \times 10^{-12}$ M in an assay detecting inhibition of binding of biotinylated HGF to c-Met-Fc fusion protein in the presence of the FN3 domains of the invention. Exemplary FN3 domains my block HGF binding to the c-Met with an $IC_{50}$ value between about $2 \times 10^{-10}$ M to about $6 \times 10^{-8}$. The FN3 domains of the invention may block HGF binding to c-Met by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of HGF to c-Met in the absence of the FN3 domains of the invention using the same assay conditions.

The FN3 domain of the invention may inhibit c-Met signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of FN3 domains of the invention using the same assay conditions.

Binding of HGF to c-Met stimulates receptor dimerization, autophosphorylation, activation of the receptor's internal, cytoplasmic tyrosine kinase domain, and initiation of multiple signal transduction and transactivation pathways involved in regulation of DNA synthesis (gene activation) and cell cycle progression or division. Inhibition of c-Met signaling may result in inhibition in one or more c-Met downstream signaling pathways and therefore neutralizing c-Met may have various effects, including inhibition of cell proliferation and differentiation, angiogenesis, cell motility and metastasis.

c-Met signaling may be measured using various well know methods, for example measuring the autophosphorylation of the receptor on at least one tyrosine residues Y1230, Y1234 or 11235, and/or phosphorylation of natural or synthetic substrates. Phosphorylation can be detected, for example, using an antibody specific for phosphotyrosine in an ELISA assay or on a western blot. Some assays for tyrosine kinase activity (Panek et al., J Pharmacol Exp Thera 283:1433-44, 1997; Batley et al., Life Sci 62:143-50, 1998).

In one embodiment, the FN3 domain of the invention inhibits HGF-induced c-Met phosphorylation at c-Met residue position 1349 with an $IC_{50}$ value of less than about $1 \times 10^{-6}$ M, less than about $1 \times 10^{-7}$ M, less than about $1 \times 10^{-8}$ M, less than about $1 \times 10^{-9}$ M, less than about $1 \times 10^{-10}$ M, less than about $1 \times 10^{-11}$ M, or less than about $1 \times 10^{-12}$ M when measured in NCI-H441 cells using 100 ng/mL recombinant human HGF.

In one embodiment, the FN3 domain of the invention inhibits HGF-induced c-Met phosphorylation at c-Met tyrosine Y1349 with an $IC_{50}$ value between about $4 \times 10^{-9}$ M to about $1 \times 10^{-6}$ M when measured in NCI-H441 cells using 100 ng/mL recombinant human HGF.

In one embodiment, the FN3 domain of the invention binds human c-Met with an dissociation constant ($K_D$) of equal to or less than about $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, $1 \times 10^{-13}$ M, $1 \times 10^{-14}$ M, or $1 \times 10^{-15}$ M as determined by surface plasmon resonance or the Kinexa method, as practiced by those of skill in the art. I some embodiments, the FN3 domain of the invention binds human c-Met with a $K_D$ of between about $3 \times 10^{-10}$ to about $5 \times 10^{-8}$ M. The affinity of a FN3 domain for c-Met can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are preferably made with standardized solutions of protein scaffold and antigen, and a standardized buffer, such as the buffer described herein.

Exemplary FN3 domains of the invention that bind c-Met include FN3 domains having the amino acid sequence of SEQ ID NOs: 32-49 or 111-114.

In one embodiment, the FN3 domain that specifically binds c-Met comprises an amino acid sequence at least 83% identical to the amino acid sequence of SEQ ID NO: 41.

In one embodiment, the FN3 domain that specifically binds c-Met comprises
a C strand and a CD loop comprising the sequence DSFX$_{10}$IRYX$_{11}$E X$_{12}$X$_{13}$X$_{14}$X$_{15}$GX$_{16}$ (SEQ ID NO: 184), wherein
X$_{10}$ is W, F or V;
X$_{11}$ is D, F or L;
X$_{12}$ is V, F or L;
X$_{13}$ is V, L or T;
X$_{14}$ is V, R, G, L, T or S;
X$_{15}$ is G, S, A, T or K; and
X$_{16}$ is E or D; and
a F strand and a FG loop comprising the sequence TEYX$_{17}$VX$_{18}$IX$_{19}$X$_{20}$V KGGX$_{21}$X$_{22}$SX$_{23}$ (SEQ ID NO: 185), wherein
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L; and
X$_{23}$ is V, T, H, I, P, Y, T or L.

The FN3 domains of the invention that specifically bind c-Met and inhibit autophosphorylation of c-Met further comprises the sequence:
LPAPKNLVVSRVTEDSARLSWTAPDAAF DSFX$_{10}$IRYX$_{11}$E X$_{12}$X$_{13}$X$_{14}$X$_{15}$GX$_{16}$ AIVLTVPGSERSYDLTGL-KPGTEYX$_{17}$VX$_{18}$IX$_{19}$X$_{20}$VKGGX$_{21}$X$_{22}$SX$_{23}$PLSAEFTT (SEQ ID NO: 186),
wherein
X$_{10}$ is W, F or V; and
X$_{11}$ is D, F or L;
X$_{12}$ is V, F or L;
X$_{13}$ is V, L or T;
X$_{14}$ is V, R, G, L, T or S;

X$_{15}$ is G, S, A, T or K;
X$_{16}$ is E or D;
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L; and
X$_{23}$ is V, T, H, I, P, Y, T or L.

Another embodiment of the invention is an isolated FN3 domain that specifically binds c-Met, wherein the FN3 domain comprises the sequence shown in SEQ ID NOs: 32-49 or 111-114.

Another embodiment of the invention is an isolated fibronectin type III (FN3) domain that specifically binds c-Met and blocks binding of HGF to the c-Met, wherein the FN3 domain is isolated from a library designed based on Tencon sequence of SEQ ID NO: 1.

Isolation of EGFR or c-Met FN3 Domains from a Library Based on Tencon Sequence

Tencon (SEQ ID NO: 1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, can be randomized in order to construct libraries of fibronectin type III (FN3) domains that can be used to select novel molecules that bind EGFR. Table 1 shows positions and sequences of each loop and beta-strand in Tencon (SEQ ID NO: 1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface and is shown in FIG. 4 and detailed generation of such libraries is described in U.S. patent application Ser. No. 13/852,930.

Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improve thermal stability. Exemplary Tencon variants are described in US Pat. Publ. No. 2011/0274623, and include Tencon27 (SEQ ID NO: 99) having substitutions E11R, L17A, N46V, E86I when compared to Tencon of SEQ ID NO: 1.

TABLE 1

| FN3 domain | Tencon (SEQ ID NO: 1) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries can be randomized at chosen residue positions using a random or defined set of amino acids. For example, variants in the library having random substitutions can be generated using NNK codons, which encode all 20 naturally occurring amino acids. In other diversification schemes, DVK codons can be used to encode amino acids Ala, Trp, Tyr, Lys, Thr, Asn, Lys, Ser, Arg, Asp, Glu, Gly, and Cys. Alternatively, NNS codons can be used to give rise to all 20 amino acid residues and simultaneously reducing the frequency of stop codons. Libraries of FN3 domains with biased amino acid distribution at positions to be diversified can be synthesized for example using Slonomics® technology (http:_// www_sloning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well known IUB code.

The FN3 domains specifically binding EGFR or c-Met of the invention can be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., *Proc Natl Acad Sci USA* 101, 2806-2810, 2004), and assaying the library for specific binding to EGFR and/or c-Met by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains specifically binding EGFR or c-Met are further characterized for their ability to block EGFR ligand such as EGF binding to EGFR, or HGF binding to c-Met, and for their ability to inhibit EGFR and/or c-Met signaling using methods described herein.

The FN3 domains specifically binding to EGFR or c-Met of the invention can be generated using any FN3 domain as a template to generate a library and screening the library for molecules specifically binding EGFR or c-Met using methods provided within. Exemplar FN3 domains that can be used are the 3rd FN3 domain of tenascin C (TN3) (SEQ ID NO: 75), Fibcon (SEQ ID NO: 76), and the 10$^{th}$ FN3 domain of fibronectin (FN10) (SEQ ID NO: 77). Standard cloning and expression techniques are used to clone the libraries into a vector or synthesize double stranded cDNA cassettes of the library, to express, or to translate the libraries in vitro. For example ribosome display (Hanes and Pluckthun, *Proc Natl Acad Sci USA*, 94, 4937-4942, 1997), mRNA display (Roberts and Szostak, *Proc Natl Acad Sci USA*, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/085462; U.S. Pat. Nos. 6,969,108; 6,172,197; 5,223,409; 6,582,915; 6,472,147).

The FN3 domains specifically binding EGFR or c-Met of the invention can be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, *Curr Opin Biotechnol*, 12, 371-375, 2001). High thermal stability may increase the yield of the expressed protein, improve solubility or activity, decrease immunogenicity, and minimize the need of a cold chain in manufacturing. Residues that can be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues can be incorporated to the FN3 domains or the bispecific FN3 domain containing molecules of the invention.

Another embodiment of the invention is an isolated FN3 domain that specifically binds EGFR and blocks binding of EGF to EGFR, comprising the sequence shown in SEQ ID NOs: 18-29, 107-110, 122-137, further comprising substitutions at one or more residue positions corresponding to positions 11, 14, 17, 37, 46, 73, and 86 in Tencon (SEQ ID NO: 1).

Another embodiment of the invention is an isolated FN3 domain that specifically binds c-Met and blocks binding of HGF to c-Met, comprising the sequence shown in SEQ ID NOs: 32-49 or 111-114, further comprising substitutions at one or more residue positions corresponding to positions 11, 14, 17, 37, 46, 73, and 86 in Tencon (SEQ ID NO: 1).

Exemplary substitutions are substitutions E11N, E14P, L17A, E37P, N46V, G73Y and E86I (numbering according to SEQ ID NO: 1).

In some embodiments, the FN3 domains of the invention comprise substitutions corresponding to substitutions L17A, N46V, and E86I in Tencon (SEQ ID NO: 1).

The FN3 domains specifically binding EGFR (FIG. 1) have an extended FG loop when compared to Tencon (SEQ ID NO: 1). Therefore, the residues corresponding to residues 11, 14, 17, 37, 46, 73, and 86 in Tencon (SEQ ID NO: 1) are residues 11, 14, 17, 37, 46, 73 and 91 in EGFR FN3 domains shown in FIGS. 1A and 1B except for the FN3 domain of SEQ ID NO: 24, wherein the corresponding residues are residues 11, 14, 17, 38, 74, and 92 due to an insertion of one amino acid in the BC loop.

Another embodiment of the invention is an isolated FN3 domain that specifically binds EGFR and blocks binding of EGF to EGFR comprising the amino acid sequence shown in SEQ ID NOs: 18-29, 107-110, or 122-137, optionally having substitutions corresponding to substitutions L17A, N46V, and E86I in Tencon (SEQ ID NO: 1).

Another embodiment of the invention is an isolated FN3 domain that specifically binds c-Met and blocks binding of HGF to c-Met comprising the amino acid sequence shown in SEQ ID NOs: 32-49 or 111-114, optionally having substitutions corresponding to substitutions L17A, N46V, and E86I in Tencon (SEQ ID NO: 1).

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("TM") temperature, the temperature in ° Celsius (° C.) at which half of the molecules become unfolded, using standard methods. Typically, the higher the TM, the more stable the molecule. In addition to heat, the chemical environment also changes the ability of the protein to maintain a particular three dimensional structure.

In one embodiment, the FN3 domains binding EGFR or c-Met of the invention exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the TM.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid (CH$_3$COOH), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

In one embodiment, the FN3 domains of the invention binding EGFR or c-Met exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same scaffold prior to engineering measured by using guanidinium hydrochloride as a chemical denaturant. Increased stability can be measured as a function of decreased tryptophan fluorescence upon treatment with increasing concentrations of guanidine hydrochloride using well known methods.

The FN3 domains of the invention may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include $(GS)_2$, (SEQ ID NO: 78), $(GGGGS)_5$ (SEQ ID NO: 79), $(AP)_2$ (SEQ ID NO: 80), $(AP)_5$ (SEQ ID NO: 81), $(AP)_{10}$ (SEQ ID NO: 82), $(AP)_{20}$ (SEQ ID NO: 83), $A(EAAAK)_5AAA$ (SEQ ID NO: 84), linkers. The dimers and multimers may be linked to each other in a N to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Bispecific EGFR/c/Met Binding Molecules

The bispecific EGFR/c-Met FN3 domain containing molecules of the invention may provide a benefit in terms of specificity and reduced off-target toxicity when compared to small molecule EGFR inhibitors, and improved tissue penetration when compared to conventional antibody therapeutics. The present invention is based at least in part on the surprising finding that the bispecific EGFR/c-Met FN3 domain containing molecules of the invention provide a significantly improved synergistic inhibitory effect when compared to a mixture of EGFR-binding and c-Met-binding FN3 domains. The molecules may be tailored to specific affinity towards both EGFR and c-Met to maximize tumor penetration and retention.

One embodiment of the invention is an isolated bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met.

The bispecific EGFR/c-Met FN3 domain containing molecules of the invention can be generated by covalently linking any EGFR-binding FN3 domain and any c-Met-binding FN3 domain of the invention directly or via a linker. Therefore, the first FN3 domain of the bispecific molecule may have characteristics as described above for the EGFR-binding FN3 domains, and the second FN3 domain of the bispecific molecule may have characteristics as described above for the c-Met-binding FN3 domains.

In one embodiment, the first FN3 domain of the bispecific EGFR/c-Met FN3 domain containing molecule inhibits EGF-induced EGFR phosphorylation at EGFR residue Tyrosine 1173 with an $IC_{50}$ value of less than about $2.5\times10^{-6}$ M when measured in A431 cells using 50 ng/mL human EGF, and the second FN3 domain of the bispecific EGFR/c-Met FN3 domain containing molecule inhibits HGF-induced c-Met phosphorylation at c-Met residue Tyrosine 1349 with an $IC_{50}$ value of less than about $1.5\times10^{-6}$ M when measured in NCI-H441 cells using 100 ng/mL human HGF.

In another embodiment, the first FN3 domain of the bispecific EGFR/c-Met FN3 domain containing molecule inhibits EGF-induced EGFR phosphorylation at EGFR residue Tyrosine 1173 with an $IC_{50}$ value of between about $1.8\times10^{-8}$ M to about $2.5\times10^{-6}$ M when measured in A431 cells using 50 ng/mL human EGF, and the second FN3 domain of the bispecific EGFR/c-Met FN3 domain containing molecule inhibits HGF-induced c-Met phosphorylation at c-Met residue Tyrosine 1349 with an $IC_{50}$ value between about $4\times10^{-9}$ M to about $1.5\times10^{-6}$ M when measured in NCI-H441 cells using 100 ng/mL human HGF.

In another embodiment, the first FN3 domain of the bispecific EGFR/c-Met FN3 domain containing molecule binds human EGFR with a dissociation constant ($K_D$) of less than about $1\times10^{-8}$ M, and the second FN3 domain of the bispecific EGFR/c-Met FN3 domain containing molecule binds human c-Met with a $K_D$ of less than about $5\times10^{-8}$ M.

In the bispecific molecule binding both EGFR and c-Met, the first FN3 domain binds human EGFR with a $K_D$ of between about $2\times10^{-10}$ to about $1\times10^{-8}$ M, and the second FN3 domain binds human c-Met with a $K_D$ of between about $3\times10^{-10}$ to about $5\times10^{-8}$ M.

The affinity of the bispecific EGFR/c-Met molecule for EGFR and c-Met can be determined as described above for the monospecific molecules.

The first FN3 domain in the bispecific EGFR/c-Met molecule of the invention may block EGF binding to EGFR with an $IC_{50}$ value of between about $1\times10^{-9}$ M to about $1.5\times10^{-7}$ M in an assay employing A431 cells and detecting amount of fluorescence from bound biotinylated EGF using streptavidin-phycoerythrin conjugate at 600 nM on A431 cells incubated with or without the first FN3 domain. The first FN3 domain in the bispecific EGFR/c-Met molecule of the invention may block EGF binding to the EGFR by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of EGF to EGFR in the absence of the first FN3 domains using the same assay conditions.

The second FN3 domain in the bispecific EGFR/c-Met molecule of the invention may block HGF binding to c-Met with an $IC_{50}$ value of between about $2\times10^{-10}$ M to about $6\times10^{-8}$ M in an assay detecting inhibition of binding of biotinylated HGF to c-Met-Fc fusion protein in the presence of the second FN3 domain. The second FN3 domain in the bispecific EGFR/c-Met molecule may block HGF binding to c-Met by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of HGF to c-Met in the absence of the second FN3 domain using the same assay conditions.

The bispecific EGFR/c-Met molecule of the invention may inhibit EGFR and/or c-Met signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of the bispecific EGFR/c-Met molecule of the invention using the same assay conditions.

EGFR and c-Met signaling may be measured using various well know methods as described above for the monospecific molecules.

The bispecific EGFR/c-Met molecules of the invention comprising the first FN3 domain specifically binding EGFR and the second FN3 domain specifically binding c-Met provide a significantly increased synergistic inhibition of EGFR and c/Met signaling and tumor cell proliferation when compared to the synergistic inhibition observed by a mixture of the first and the second FN3 domain. Synergistic inhibition can be assessed for example by measuring inhibition of ERK phosphorylation by the bispecific EGFR/c-Met FN3 domain containing molecules and by a mixture of two monospecific molecules, one binding EGFR and the other c-Met. The bispecific EGFR/c-Met molecules of the invention may inhibit ERK phosphorylation with an $IC_{50}$ value at least about 100 fold smaller, for example at least 500, 1000, 5000 or 10,000 fold smaller when compared to the $IC_{50}$ value for a mixture of two monospecific FN3 domains, indicating at least 100 fold increased potency for the bispecific EGFR/c-Met FN3 domain containing molecules when compared to the mixture of two monospecific FN3 domains. Exemplary bispecific EGFR-c-Met FN3 domain containing molecules may inhibit ERK phosphorylation with and $IC_{50}$ value of about $5 \times 10^{-9}$ M or less. ERK phosphorylation can be measured using standard methods and methods described herein.

The bispecific EGFR/c-Met FN3 domain containing molecule of the invention may inhibit H292 cell proliferation with an $IC_{50}$ value that is at least 30-fold less when compared to the $IC_{50}$ value of inhibition of H292 cell growth with a mixture of the first FN3 domain and the second FN3, wherein the cell proliferation is induced with medium containing 10% FBS supplemented with 7.5 ng/mL HGF. The bispecific molecule of the invention may inhibit tumor cell proliferation with an $IC_{50}$ value that is about 30, 40, 50, 60, 70, 80, 90, 100, 150, 200, 300, 400, 500, 600, 700, 800, or about 1000 fold less when compared to the $IC_{50}$ value of inhibition of tumor cell proliferation with a mixture of the first FN3 domain and the second FN3 domain. Inhibition of tumor cell proliferation can be measured using standard methods and methods described herein.

Another embodiment of the invention is a bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met, wherein
  the first FN3 domain comprises
    an FG loop comprising the sequence HNVYKDTNX$_9$RGL (SEQ ID NO: 179) or the sequence LGSYVFEHDVML (SEQ ID NO: 180), wherein X$_9$ is M or I; and
    a BC loop comprising the sequence X$_1$X$_2$X$_3$X$_4$X$_5$X$_6$X$_7$X$_8$ (SEQ ID NO: 181), wherein
      X$_1$ is A, T, G or D;
      X$_2$ is A, D, Y or W;
      X$_3$ is P, D or N;
      X$_4$ is L or absent;
      X$_5$ is D, H, R, G, Y or W;
      X$_6$ is G, D or A;
      X$_7$ is A, F, G, H or D; and
      X$_8$ is Y, F or L; and
  the second FN3 domain comprises
    a C strand and a CD loop comprising the sequence DSFX$_{10}$IRYX$_{11}$E X$_{12}$X$_{13}$X$_{14}$X$_{15}$GX$_{16}$ (SEQ ID NO: 184), wherein
      X$_{10}$ is W, F or V;
      X$_{11}$ is D, F or L;
      X$_{12}$ is V, F or L;
      X$_{13}$ is V, L or T;
      X$_{14}$ is V, R, G, L, T or 5;
      X$_{15}$ is G, S, A, T or K; and
      X$_{16}$ is E or D; and
    a F strand and a FG loop comprising the sequence TEYX$_{17}$VX$_{18}$IX$_{19}$X$_{20}$V KGGX$_{21}$X$_{22}$SX$_{23}$ (SEQ ID NO: 185), wherein
      X$_{17}$ is Y, W, I, V, G or A;
      X$_{18}$ is N, T, Q or G;
      X$_{19}$ is L, M, N or I;
      X$_{20}$ is G or S;
      X$_{21}$ is S, L, G, Y, T, R, H or K;
      X$_{22}$ is I, V or L; and
      X$_{23}$ is V, T, H, I, P, Y, T or L.

In another embodiment, the bispecific molecule comprises the first FN3 domain that binds EGFR comprising the sequence:
LPAPKNLVVSEVTEDSLRLSWX$_1$X$_2$X$_3$X$_4$X$_5$X$_6$X$_7$X$_8$D-SFLIQYQESEKVGEAINLTVPGSERSYDLTGLKPGT-EYTVSIYGVHNVYKDTNX$_9$RGL PLSAEFTT (SEQ ID NO: 182), or the sequence LPAPKNLVVSEVTEDSL-RLSWX$_1$X$_2$X$_3$X$_4$X$_5$X$_6$X$_7$X$_8$ DSFLIQYQESEKVGEAIN-LTVP GSERSYDLTGLKPGTEYTVSIYGV LGSYVFE-HDVMLPLSAEFTT (SEQ ID NO: 183), wherein in the SEQ ID NOs: X and X;
  X$_1$ is A, T, G or D;
  X$_2$ is A, D, Y or W;
  X$_3$ is P, D or N;
  X$_4$ is L or absent;
  X$_5$ is D, H, R, G, Y or W;
  X$_6$ is G, D or A;
  X$_7$ is A, F, G, H or D;
  X$_8$ is Y, F or L; and
  X$_9$ is M or I.

In another embodiment, the bispecific molecule comprises the second FN3 domain that binds c-Met comprising the sequence LPAPKNLVVSRVTEDSARLSWTAPDAAF DSFX$_{10}$IRYX$_{11}$E X$_{12}$X$_{13}$X$_{14}$X$_{15}$GX$_{16}$ AIVLTVPGSERSYDLTGLKPG TEYX$_{17}$VX$_{18}$IX$_{19}$X$_{20}$VKGGX$_{21}$X$_{22}$SX$_{23}$PLSAEFTT (SEQ ID NO: 186),
wherein
  X$_{10}$ is W, F or V; and
  X$_{11}$ is D, F or L;
  X$_{12}$ is V, F or L;
  X$_{13}$ is V, L or T;
  X$_{14}$ is V, R, G, L, T or 5;
  X$_{15}$ is G, S, A, T or K;
  X$_{16}$ is E or D;
  X$_{17}$ is Y, W, I, V, G or A;
  X$_{18}$ is N, T, Q or G;
  X$_{19}$ is L, M, N or I;
  X$_{20}$ is G or S;
  X$_{21}$ is S, L, G, Y, T, R, H or K;
  X$_{22}$ is I, V or L; and
  X$_{23}$ is V, T, H, I, P, Y, T or L.

Exemplary bispecific EGFR/c-Met FN3 domain containing molecules comprise the amino acid sequence shown in SEQ ID NOs: 50-72, 106, 118-121, or 138-165.

The bispecific EGFR/c-Met molecules of the invention comprise certain structural characteristics associated with their functional characteristics, such as inhibition of EGFR autophosphorylation, such as the FG loop of the first FN3 domain that binds EGFR comprising the sequence HNVYKDTNX$_9$RGL (SEQ ID NO: 179) or the sequence LGSYVFEHDVML (SEQ ID NO: 180), wherein X$_9$ is M or I.

In one embodiment, the bispecific EGFR/c-Met FN3 domain containing molecules of the invention
  inhibit EGF-induced EGFR phosphorylation at EGFR residues Tyrosine 1173 with and $IC_{50}$ value of less than about $8 \times 10^{-7}$ M when measured in A431 cells using 50 ng/mL human EGF;

inhibit HGF-induced c-Met phosphorylation at c-Met residues Tyrosine 1349 with and $IC_{50}$ value of less than about $8.4 \times 10^{-7}$ M when measured in NCI-H441 cells using 100 ng/mL human HGF;

inhibit HGF-induced NCI-H292 cell proliferation with an $IC_{50}$ value of less than about $9.5 \times 10^{-6}$ M wherein the cell proliferation is induced with 10% FBS containing 7.5 ng HGF;

bind EGFR with a $K_D$ of less than about $2.0 \times 10^{-8}$ M;

bind c-Met with a $K_D$ of less than about $2.0 \times 10^{-8}$ M.

In another embodiment, the bispecific EGFR/c-Met FN3 domain containing molecules of the invention inhibit EGF-induced EGFR phosphorylation at EGFR residues Tyrosine 1173 with and $IC_{50}$ of between about $4.2 \times 10^{-9}$ M and $8 \times 10^{-7}$ M when measured in A431 cells using 50 ng/mL human EGF;

inhibit HGF-induced c-Met phosphorylation at c-Met residues Tyrosine 1349 with and $IC_{50}$ value of between about $2.4 \times 10^{-8}$ M to about $8.4 \times 10^{-7}$ M when measured in NCI-H441 cells using 100 ng/mL human HGF;

inhibit HGF-induced NCI-H292 cell proliferation with an $IC_{50}$ value between about $2.3 \times 10^{-8}$ M to about $9.5 \times 10^{-6}$ M wherein the cell proliferation is induced with 10% FBS containing 7.5 ng HGF;

bind EGFR with a $K_D$ of between about $2 \times 10^{-10}$ M to about $2.0 \times 10^{-8}$ M;

bind c-Met with a $K_D$ of between about $1 \times 10^{-9}$ M to about $2.0 \times 10^{-8}$ M.

In one embodiment, bispecific EGFR/c-Met molecules comprise the EGFR-binding FN3 domain comprising the sequence LPAPKNLVVSEVTEDSLRLSWX$_1$X$_2$X$_3$X$_4$X$_5$X$_6$X$_7$X$_8$DSFLIQYQESEKVGEAINLTVP GSERSYDL TG LKPGTEYTVSIYGV HNVYKDTNX$_9$RGL PLSAEFTT (SEQ ID NO: 182), wherein $X_1$ is D;
$X_2$ is D;
$X_3$ is P;
$X_4$ is absent;
$X_5$ is H or W;
$X_6$ is A;
$X_7$ is F;
$X_8$ is Y; and
$X_9$ is M or I; and the c-Met-binding FN3 domain comprising the sequence PAPKNLVVSRVTEDSARLSWTAPDAAF DSFX$_{10}$IRYX$_{11}$E X$_{12}$X$_{13}$X$_{14}$X$_{15}$GX$_{16}$ AIVLTVPGSERSY DLTGLKPG TEYX$_{17}$VX$_{18}$IX$_{19}$X$_{20}$VKGGX$_{21}$X$_{22}$SX$_{23}$ PL SAEFTT (SEQ ID NO: 186), wherein $X_{10}$ is W;
$X_{11}$ is F;
$X_{12}$ is F;
$X_{13}$ is V or L;
$X_{14}$ is G or S;
$X_{15}$ is S or K;
$X_{16}$ is E or D;
$X_{17}$ is V;
$X_{18}$ is N;
$X_{19}$ is L or M;
$X_{20}$ is G or S;
$X_{21}$ is S or K;
$X_{22}$ is I; and
$X_{23}$ is P.

Exemplary bispecific EGFR/c-Met molecules are those having the sequence shown in SEQ ID NOs: 57, 61, 62, 63, 64, 65, 66, 67 and 68.

The bispecific molecules of the invention may further comprise substitutions at one or more residue positions in the first FN3 domain and/or the second FN3 domain corresponding to positions 11, 14, 17, 37, 46, 73, and 86 in Tencon (SEQ ID NO: 1) as described above, and a substitution at position 29. Exemplary substitutions are substitutions E11N, E14P, L17A, E37P, N46V, G73Y, E86I and D29E (numbering according to SEQ ID NO: 1). Skilled in the art will appreciate that other amino acids can be used for substitutions, such as amino acids within a family of amino acids that are related in their side chains as described infra. The generated variants can be tested for their stability and binding to EGFR and/or c-Met using methods herein.

In one embodiment, the bispecific EGFR/c-Met FN3 domain containing molecule comprises the first FN3 domain that binds specifically EGFR and the second FN3 domain that binds specifically c-Met, wherein the first FN3 domain comprises the sequence: LPAPKNLVVSX$_{24}$VTX$_{25}$ DSX$_{26}$ RLSWDDPX$_{27}$AFYX$_{28}$SFLIQYQX$_{29}$SEKVGEAIX$_{30}$ LTVPGSERS YDLTGLKPGTEYTVSIYX$_{31}$ VHNVYKD-TNX$_{32}$RGLPLSAX$_{33}$FTT (SEQ ID NO: 187), wherein $X_{24}$ is E, N or R;
$X_{25}$ is E or P;
$X_{26}$ is L or A;
$X_{27}$ is H or W;
$X_{28}$ is E or D;
$X_{29}$ is E or P;
$X_{30}$ is N or V;
$X_{31}$ is G or Y;
$X_{32}$ is M or I; and
$X_{33}$ is E or I;

and the second FN3 domain comprises the sequence: LPAPKNLVVSX$_{34}$VTX$_{35}$DSX$_{36}$RLSWTAPDAAFDSF-WIRYFX$_{37}$FX$_{38}$X$_{39}$X$_{40}$GX$_{41}$AIX$_{42}$LTVPGSE RSYDLTG LKPGTEYVVNIX$_{43}$X$_{44}$VKGGX$_{45}$ISPPLSAX$_{46}$FTT (SEQ ID NO: 188); wherein $X_{34}$ is E, N or R;
$X_{35}$ is E or P;
$X_{36}$ is L or A;
$X_{37}$ is E or P;
$X_{38}$ is V or L;
$X_{39}$ is G or S;
$X_{40}$ is S or K;
$X_{41}$ is E or D;
$X_{42}$ is N or V;
$X_{43}$ is L or M;
$X_{44}$ is G or S;
$X_{45}$ is S or K; and
$X_{46}$ is E or I.

In other embodiments, the bispecific EGFR/c-Met FN3 domain containing molecule comprises the first FN3 domain comprising an amino acid sequence at least 87% identical to the amino acid sequence of SEQ ID NO: 27, and the second FN3 domain comprising an amino acid sequence at least 83% identical to the amino acid sequence of SEQ ID NO: 41.

The bispecific EGFR/c-Met FN3 domain containing molecules of the invention may be tailored to a specific affinity towards EGFR and c-Met to maximize tumor accumulation.

Another embodiment of the invention is an isolated bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met, wherein the first FN3 domain and the second FN3 domain is isolated from a library designed based on Tencon sequence of SEQ ID NO: 1.

The bispecific EGFR/c-Met FN3 domain containing molecule of the invention can be generated by covalently coupling the EGFR-binding FN3 domain and the c-Met binding FN3 domain of the invention using well known methods. The FN3 domains may be linked via a linker, for example a linker containing poly-glycine, glycine and serine, or alanine and proline. Exemplary linker include $(GS)_2$, (SEQ ID NO: 78), $(GGGGS)_5$ (SEQ ID NO: 79), $(AP)_2$ (SEQ ID NO: 80), $(AP)_5$ (SEQ ID NO: 81), $(AP)_{10}$ (SEQ ID NO: 82), $(AP)_{20}$ (SEQ ID NO: 83), $A(EAAAK)_5AAA$ (SEQ ID NO: 84), linkers. The use of naturally occurring as well as artificial peptide linkers to connect polypeptides into novel linked fusion polypeptides is well known in the literature (Hallewell et al., J Biol Chem 264, 5260-5268, 1989; Alfthan et al., *Protein Eng.* 8, 725-731, 1995; Robinson & Sauer, *Biochemistry* 35, 109-116, 1996; U.S. Pat. No. 5,856,456). The bispecific EGFR/c-Met molecules of the invention may be linked together from a C-terminus of the first FN3 domain to the N-terminus of the second FN3 domain, or from the C-terminus of the second FN3 domain to the N-terminus of the first FN3 domain. Any EGFR-binding FN3 domain may be covalently linked to a c-Met-binding FN3 domain. Exemplary EGFR-binding FN3 domains are domains having the amino acid sequence shown in SEQ ID NOs: 18-29, 107-110, and 122-137, and exemplary c-Met binding FN3 domains are domains having the amino acid sequence shown in SEQ ID NOs: 32-49 and 111-114. The EGFR-binding FN3 domains to be coupled to a bispecific molecule may additionally comprise an initiator methionine (Met) at their N-terminus.

Variants of the bispecific EGFR/c-Met FN3 domain containing molecules are within the scope of the invention. For example, substitutions can be made in the bispecific EGFR/c-Met FN3 domain containing molecule as long as the resulting variant retains similar selectivity and potency towards EGFR and c-Met when compared to the parent molecule. Exemplary modifications are for example conservative substitutions that will result in variants with similar characteristics to those of the parent molecules. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Non-conservative substitutions can be made to the bispecific EGFR/c-Met FN3 domain containing molecule that involves substitutions of amino acid residues between different classes of amino acids to improve properties of the bispecific molecules. Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The bispecific EGFR/c-Met FN3 domain containing molecules of the invention may be generated as dimers or multimers, for example, as a means to increase the valency and thus the avidity of target molecule binding. The multimers may be generated by linking one or more EGFR-binding FN3 domains and one or more c-Met-binding FN3 domain to form molecules comprising at least three individual FN3 domains that are at least bispecific for either EGFR or c-Met, for example by the inclusion of an amino acid linker using well known methods.

Another embodiment of the invention is a bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met comprising the amino acid sequence shown in SEQ ID NOs: 50-72 or 106.

Half-Life Extending Moieties

The bispecific EGFR/c-Met FN3 domain containing molecules or the monospecific EGFR or c-Met binding FN3 domains of the present invention may incorporate other subunits for example via covalent interaction. In one aspect of the invention, the bispecific EGFR/c-Met FN3 domain containing molecules of the invention further comprise a half-life extending moiety. Exemplary half-life extending moieties are albumin, albumin-binding proteins and/or domains, transferrin and fragments and analogues thereof, and Fc regions. An exemplary albumin-binding domain is shown in SEQ ID NO: 117.

All or a portion of an antibody constant region may be attached to the molecules of the invention to impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and can be further modified by modifying residues in the Fc responsible for these activities (for review; see Strohl, *Curr Opin Biotechnol.* 20, 685-691, 2009).

Additional moieties may be incorporated into the bispecific molecules of the invention such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules of the invention.

A pegyl moiety may for example be added to the bispecific or monospecific molecules of the invention by incorporating a cysteine residue to the C-terminus of the molecule and attaching a pegyl group to the cysteine using well known methods. Exemplary bispecific molecules with the C-terminal cysteine are those having the amino acid sequence shown in SEQ IN NO: 170-178.

Monospecific and bispecific molecules of the invention incorporating additional moieties may be compared for functionality by several well known assays. For example, altered properties of monospecific and/or bispecific molecules due to incorporation of Fc domains and/or Fc domain variants may be assayed in Fc receptor binding assays using soluble forms of the receptors, such as the FcγRT, FcγRII, FcγRIII or FcRn receptors, or using well known cell-based assays measuring for example ADCC or CDC, or evaluating pharmacokinetic properties of the molecules of the invention in in vivo models.

Polynucleotides, Vectors, Host Cells

The invention provides for nucleic acids encoding the EGFR-binding or c-Met binding FN3 domains or the bispecific EGFR/c-Met FN3 domain containing molecules of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the protein scaffolds and libraries of the protein scaffolds of the invention are also within the scope of the invention.

One embodiment of the invention is an isolated polynucleotide encoding the FN3 domain specifically binding EGFR having the amino acid sequence of SEQ ID NOs: 18-29, 107-110, or 122-137.

One embodiment of the invention is an isolated polynucleotide comprising the polynucleotide sequence of SEQ ID NOs: 97-98 or 168-169.

One embodiment of the invention is an isolated polynucleotide encoding the FN3 domain specifically binding c-Met having the amino acid sequence of the sequence shown in SEQ ID NOs: 32-49 or 111-114.

One embodiment of the invention is an isolated polynucleotide encoding the bispecific EGFR/-c-Met FN3 domain containing molecule having the amino acid sequence of SEQ ID NOs: 50-72, 106, 118-121 or 138-165.

One embodiment of the invention is an isolated polynucleotide comprising the polynucleotide sequence of SEQ ID NOs: 115-116 or 166-167.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

Another embodiment of the invention is a host cell comprising the vector of the invention. A monospecific EGFR-binding or c-Met binding FN3 domain or bispecific EGFR/c-Met FN3 domain containing molecule of the invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{11d}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

Another embodiment of the invention is a method of producing the isolated FN3 domain specifically binding EGFR or c-Met of the invention or the isolated bispecific EGFR/c-Met FN3 domain containing molecule of the invention, comprising culturing the isolated host cell of the invention under conditions such that the isolated FN3 domain specifically binding EGFR or c-Met or the isolated bispecific EGFR-c-Met FN3 domain containing molecule is expressed, and purifying the domain or molecule.

The FN3 domain specifically binding EGFR or c-Met or the isolated bispecific EGFR/c-Met FN3 domain containing molecule of the invention can be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Uses of Bispecific EGFR/c-Met FN3 Domain Containing Molecules and EGFR-Binding or c-Met Binding FN3 Domains of the Invention The bispecific EGFR/c-Met FN3 domain containing molecules, the EGFR binding FN3 domains or the c-Met binding FN3 domains of the invention may be used to diagnose, monitor, modulate, treat, alleviate, help prevent the incidence of, or reduce the symptoms of human disease or specific pathologies in cells, tissues, organs, fluid, or, generally, a host. The methods of the invention may be used to treat an animal patient belonging to any classification. Examples of such animals include mammals such as humans, rodents, dogs, cats and farm animals.

One aspect of the invention is a method for inhibiting growth or proliferation of cells that express EGFR and/or c-Met, comprising contacting the cells with the isolated bispecific EGFR/c-Met FN3 domain containing molecule, the EGFR binding FN3 domain or the c-Met binding FN3 domain of the invention.

Another aspect of the invention is a method for inhibiting growth or metastasis of EGFR and/or c-Met-expressing tumor or cancer cells in a subject comprising administering to the subject an effective amount of the isolated bispecific EGFR/c-Met FN3 domain containing molecule, the EGFR binding FN3 domain or the c-Met binding FN3 domain of the invention so that the growth or metastasis of EGFR- and/or c-Met-expressing tumor or cancer cell is inhibited.

The bispecific EGFR/c-Met FN3 domain containing molecule, the EGFR binding FN3 domain or the c-Met binding FN3 domain of the invention may be used for treatment of any disease or disorder characterized by abnormal activation or production of EGFR, c-Met, EGF or other EGFR ligand or HGF, or disorder related to EGFR or c-Met expression, which may or may not involve malignancy or cancer, where abnormal activation and/or production of EGFR, c-Met, EGF or other EGFR ligand, or HGF is occurring in cells or tissues of a subject having, or predisposed to, the disease or disorder.

The bispecific EGFR/c-Met FN3 domain containing molecule of the invention may be used for treatment of tumors, including cancers and benign tumors. Cancers that are amenable to treatment by the bispecific molecules of the invention include those that overexpress EGFR and/or c-Met. Exemplary cancers that are amenable to treatment by the bispecific molecules of the invention include epithelial cell cancers, breast cancer, ovarian cancer, lung cancer, non-small cell lung cancer (NSCLC), lung adenocarcinoma, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, gastric cancer, cancer of the thymus, colon cancer, thyroid cancer, liver cancer, or sporadic or hereditary papillary renal carcinoma (PRCC).

The FN3 domains that specifically bind c-Met and block binding of HGF to c-Met of the invention may be for treatment of tumors, including cancers and benign tumors. Cancers that are amenable to treatment by the c-Met binding FN3 domains of the invention include those that overexpress c-Met. Exemplary cancers that are amenable to treatment by the FN3 domains of the invention include epithelial cell cancers, breast cancer, ovarian cancer, lung cancer, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, and cancer of the thymus.

The FN3 domains that specifically bind EGFR and blocks binding of EGF to the EGFR of the invention may be used for treatment of tumors, including cancers and benign tumors. Cancers that are amenable to treatment by the FN3 domains of the invention include those that overexpress EGFR or variants. Exemplary cancers that are amenable to treatment by the FN3 domains of the invention include epithelial cell cancers, breast cancer, ovarian cancer, lung cancer, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, and cancer of the thymus.

Administration/Pharmaceutical Compositions

For therapeutic use, the bispecific EGFR/c-Met FN3 domain containing molecules, the EGFR-binding FN3 domains or the c-Met-binding FN3 domains of the invention may be prepared as pharmaceutical compositions containing an effective amount of the domain or molecule as an active ingredient in a pharmaceutically acceptable carrier. The term "carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the bispecific EGFR/c-Met FN3 domain containing molecules, the EGFR binding FN3 domains or the c-Met binding FN3 domains of the invention may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of the FN3 domain of the invention. Similarly, a pharmaceutical composition of the invention for intravenous infusion could be made up to contain about 250 ml of sterile Ringer's solution, and about 1 mg to about 30 mg, e.g. about 5 mg to about 25 mg of the bispecific EGFR/c-Met FN3 domain containing molecule, the EGFR binding FN3 domain or the c-Met binding FN3 domain of the invention. Actual methods for preparing parenterally administrable compositions are well known and are described in more detail in, for example, "Remington's Pharmaceutical Science", 15th ed., Mack Publishing Company, Easton, Pa.

The bispecific EGFR/c-Met FN3 domain containing molecules, the EGFR-binding FN3 domains or the c-Met-binding FN3 domains of the invention can be lyophilized for storage and reconstituted in a suitable carrier prior to use. This technique has been shown to be effective with conventional protein preparations and art-known lyophilization and reconstitution techniques can be employed.

The bispecific EGFR/c-Met FN3 domain containing molecules, the EGFR-binding FN3 domains or the c-Met-binding FN3 domains may be administered to a subject in a single dose or the administration may be repeated, e.g. after one day, two days, three days, five days, six days, one week, two weeks, three weeks, one month, five weeks, six weeks, seven weeks, two months or three months. The repeated administration can be at the same dose or at a different dose. The administration can be repeated once, twice, three times, four times, five times, six times, seven times, eight times, nine times, ten times, or more.

The bispecific EGFR/c-Met FN3 domain containing molecules, the EGFR-binding FN3 domains or the c-Met-binding FN3 domains may be administered in combination with a second therapeutic agent simultaneously, sequentially or separately. The second therapeutic agent may be a chemotherapeutic agent, an anti-angiogenic agent, or a cytotoxic drug. When used for treating cancer, the bispecific EGFR/c-Met FN3 domain containing molecules, the EGFR-binding FN3 domains or the c-Met-binding FN3 domains may be used in combination with conventional cancer therapies, such as surgery, radiotherapy, chemotherapy or combinations thereof. Exemplary agents that can be used in combination with the FN3 domains of the invention are antagonists of HER2, HER3, HER4, VEGF, and protein tyrosine kinase inhibitors such as Iressa® (gefitinib) and Tarceva (erlotinib).

While having described the invention in general terms, the embodiments of the invention will be further disclosed in the following examples that should not be construed as limiting the scope of the claims.

EXAMPLE 1. CONSTRUCTION OF TENCON LIBRARIES

Tencon (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

Tencon:
(SEQ ID NO 1)
LPAPKNLVVSEVTEDSLRLSWTAPDAAFDSFLIQYQESEKVGEAINLT
VPGSERSYDLTGLKPGTEYTVSIYGVKGGHRSNPLSAEFTT:

Construction of TCL1 Library

A library designed to randomize only the FG loop of Tencon (SEQ ID NO: 1), TCL1, was constructed for use with the cis-display system (Jacobs et al., Protein Engineering, Design, and Selection, 25:107-117, 2012). In this system, a single-strand DNA incorporating sequences for a Tac promoter, Tencon library coding sequence, RepA coding sequence, cis-element, and ori element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and ori elements. These two halves are combined by restriction digest in order to produce the entire construct. The TCL1 library was designed to incorporate random amino acids only in the FG loop of Tencon, KGGHRSN (SEQ ID NO: 86). NNS codons were used in the construction of this library, resulting in the possible incorporation of all 20 amino acids and one STOP codon into the FG loop. The TCL1 library contains six separate sub-libraries, each having a different randomized FG loop length, from 7 to 12 residues, in order to further increase diversity. Design of tencon-based libraries are shown in Table 2.

TABLE 2

| Library | BC Loop Design | FG Loop Design |
|---|---|---|
| WT Tencon | TAPDAAFD* | KGGHRSN** |
| TCL1 | TAPDAAFD* | XXXXXXX |
|  |  | XXXXXXXX |
|  |  | XXXXXXXXX |
|  |  | XXXXXXXXXX |
|  |  | XXXXXXXXXXX |
|  |  | XXXXXXXXXXXX |
| TCL2 | ######## | #####S## |

*TAPDAAFD: residues 22-28 of SEQ ID NO: 1;
**KGGHRSN: SEQ ID NO: 86
X refers to degenerate amino acids encoded by NNS codons.
# refers to the "designed distribution of amino acids" described in the text.

To construct the TCL1 library, successive rounds of PCR were performed to append the Tac promoter, build degeneracy into the F:G loop, and add necessary restriction sites for final assembly. First, a DNA sequence containing the promoter sequence and Tencon sequence 5' of the FG loop was generated by PCR in two steps. DNA corresponding to the full Tencon gene sequence was used as a PCR template with primers POP2220 (SEQID NO: 2) and TC5'toFG (SEQID NO: 3). The resulting PCR product from this reaction was used as a template for the next round of PCR amplification with primers 130mer (SEQID NO: 4) and Tc5'toFG to complete the appending of the 5' and promoter sequences to Tencon. Next, diversity was introduced into the F:G loop by amplifying the DNA product produced in the first step with forward primer POP2222 (SEQID NO: 5), and reverse primers TCF7 (SEQID NO: 6), TCF8 (SEQID NO: 7), TCF9 (SEQID NO: 8), TCF10 (SEQID NO: 9), TCF11 (SEQID N NO: 10), or TCF12 (SEQID NO: 11), which contain degenerate nucleotides. At least eight 100 µL PCR reactions were performed for each sub-library to minimize PCR cycles and maximize the diversity of the library. At least 5 µg of this PCR product were gel-purified and used in a subsequent PCR step, with primers POP2222 (SEQ ID NO: 5) and POP2234 (SEQID NO: 12), resulting in the attachment of a 6×His tag and NotI restriction site to the 3' end of the Tencon sequence. This PCR reaction was carried out using only fifteen PCR cycles and at least 500 ng of template DNA. The resulting PCR product was gel-purified, digested with NotI restriction enzyme, and purified by Qiagen column.

The 3' fragment of the library is a constant DNA sequence containing elements for display, including a PspOMI restriction site, the coding region of the repA gene, and the cis- and ori elements. PCR reactions were performed using a plasmid (pCR4Blunt) (Invitrogen) containing this DNA fragment with M13 Forward and M13 Reverse primers. The resulting PCR products were digested by PspOMI overnight and gel-purified. To ligate the 5' portion of library DNA to the 3' DNA containing the repA gene, 2 pmol of 5' DNA were ligated to an equal molar amount of 3' repA DNA in the presence of NotI and PspOMI enzymes and T4 ligase. After overnight ligation at 37° C., a small portion of the ligated DNA was run on a gel to check ligation efficiency. The ligated library product was split into twelve PCR amplifications and a 12-cycle PCR reaction was run with primer pair POP2250 (SEQID NO: 13) and DidLigRev (SEQID NO: 14). The DNA yield for each sub-library of TCL1 library ranged from 32-34 µg.

To assess the quality of the library, a small portion of the working library was amplified with primers Tcon5new2 (SEQID NO: 15) and Tcon6 (SEQID NO: 16), and was cloned into a modified pET vector via ligase-independent cloning. The plasmid DNA was transformed into BL21-GOLD (DE3) competent cells (Stratagene) and 96 randomly picked colonies were sequenced using a T7 promoter primer. No duplicate sequences were found. Overall, approximately 70-85% of clones had a complete promoter and Tencon coding sequence without frame-shift mutation. The functional sequence rate, which excludes clones with STOP codons, was between 59% and 80%.

Construction of TCL2 Library

TCL2 library was constructed in which both the BC and FG loops of Tencon were randomized and the distribution of amino acids at each position was strictly controlled. Table 3 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" of Table 3 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TABLE 3

| Residue Position* | WT residues | Distribution in the TCL2 library |
|---|---|---|
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

The 5' fragment of the TCL2 library contained the promoter and the coding region of Tencon (SEQ ID NO: 1), which was chemically synthesized as a library pool (Sloning Biotechnology). This pool of DNA contained at least $1 \times 10^{11}$ different members. At the end of the fragment, a BsaI restriction site was included in the design for ligation to RepA.

The 3' fragment of the library was a constant DNA sequence containing elements for display including a 6×His tag, the coding region of the repA gene, and the cis-element. The DNA was prepared by PCR reaction using an existing DNA template (above), and primers LS1008 (SEQID NO: 17) and DidLigRev (SEQID NO: 14). To assemble the complete TCL2 library, a total of 1 µg of BsaI-digested 5' Tencon library DNA was ligated to 3.5 µg of the 3' fragment that was prepared by restriction digestion with the same enzyme. After overnight ligation, the DNA was purified by Qiagen column and the DNA was quantified by measuring absorbance at 260 nm. The ligated library product was amplified by a 12-cycle PCR reaction with primer pair POP2250 (SEQID NO: 13) and DidLigRev (SEQID NO: 14). A total of 72 reactions were performed, each containing 50 ng of ligated DNA products as a template. The total yield of TCL2 working library DNA was about 100 µg. A small portion of the working library was sub-cloned and sequenced, as described above for library TCL1. No duplicate sequences were found. About 80% of the sequences contained complete promoter and Tencon coding sequences with no frame-shift mutations.

Construction of TCL14 Library

The top (BC, DE, and FG) and the bottom (AB, CD, and EF) loops, e.g., the reported binding surfaces in the FN3 domains are separated by the beta-strands that form the center of the FN3 structure. Alternative surfaces residing on the two "sides" of the FN3 domains having different shapes than the surfaces formed by loops only are formed at one side of the FN3 domain by two anti-parallel beta-strands, the C and the F beta-strands, and the CD and FG loops, and is herein called the C-CD-F-FG surface.

A library randomizing an alternative surface of Tencon was generated by randomizing select surface exposed residues of the C and F strands, as well as portions of the CD and FG loops as shown in FIG. 4. A Tencon variant, Tencon27 (SEQ ID NO: 99) having following substitutions when compared to Tencon (SEQ ID NO: 1) was used to generate the library; E11R L17A, N46V, E86I. A full description of the methods used to construct this library is described in U.S. patent application Ser. No. 13/852,930.

EXAMPLE 2: SELECTION OF FIBRONECTIN TYPE III (FN3) DOMAINS THAT BIND EGFR AND INHIBIT EGF Binding Library Screening Cis-display was used to select EGFR binding domains from the TCL1 and TCL2 libraries. A recombinant human extracellular domain of EGFR fused to an IgG1 Fc (R&D Systems) was biotinylated using standard methods and used for panning (residues 25-645 of full length EGFR of SEQ ID NO: 73). For in vitro transcription and translation (ITT), 2-6 µg of library DNA were incubated with 0.1 mM complete amino acids, 1× S30 premix components, and 30 µL of S30 extract (Promega) in a total volume of 100 µL and incubated at 30° C. After 1 hour, 450 µL of blocking solution (PBS pH 7.4, supplemented with 2% bovine serum albumin, 100 µg/mL herring sperm DNA, and 1 mg/mL heparin) were added and the reaction was incubated on ice for 15 minutes. EGFR-Fc:EGF complexes were assembled at molar ratios of 1:1 and 10:1 EGFR to EGF by mixing recombinant human EGF (R&D Systems) with biotinylated recombinant EGFR-Fc in blocking solution for 1 hour at room temperature. For binding, 500 µL of blocked ITT reactions were mixed with 100 µL of EGFR-Fc:EGF complexes and incubated for 1 hour at room temperature, after which bound complexes were pulled down with magnetic neutravidin or streptavidin beads (Seradyne). Unbound library members were removed by successive washes with PBST and PBS. After washing, DNA was eluted from the bound complexes by heating to 65° C. for 10 minutes, amplified by PCR, and attached to a DNA fragment encoding RepA by restriction digestion and ligation for further rounds of panning High affinity binders were isolated by successively lowering the concentration of target EGFR-Fc during each round from 200 nM to 50 nM and increasing the washing stringency. In rounds 4 and 5, unbound and weakly bound FN3 domains were removed by washing in the presence of a 10-fold molar excess of non-biotinylated EGFR-Fc overnight in PBS.

Following panning, selected FN3 domains were amplified by PCR using oligos Tcon5new2 (SEQID NO: 15) and Tcon6 (SEQID NO: 16), subcloned into a pET vector modified to include a ligase independent cloning site, and transformed into BL21-GOLD (DE3) (Stratagene) cells for soluble expression in *E. coli* using standard molecular biology techniques. A gene sequence encoding a C-terminal poly-histidine tag was added to each FN3 domain to enable purification and detection. Cultures were grown to an optical density of 0.6-0.8 in 2YT medium supplemented with 100 µg/mL carbenicillin in 1-mL 96-well blocks at 37° C. before the addition of IPTG to 1 mM, at which point the temperature was reduced to 30° C. Cells were harvested approximately 16 hours later by centrifugation and frozen at −20° C. Cell lysis was achieved by incubating each pellet in 0.6 mL of BugBuster® HT lysis buffer (Novagen EMD Biosciences) with shaking at room temperature for 45 minutes.

Selection of FN3 Domains that Bind EGFR on Cells

To assess the ability of different FN3 domains to bind EGFR in a more physiological context, their ability to bind A431 cells was measured. A431 cells (American Type Culture Collection, cat. #CRL-1555) over-express EGFR with ~2×10$^6$ receptors per cell. Cells were plated at 5,000/well in opaque black 96-well plates and allowed to attach overnight at 37° C., in a humidified 5% $CO_2$ atmosphere. FN3 domain-expressing bacterial lysates were diluted 1,000-fold into FACS stain buffer (Becton Dickinson) and incubated for 1 hour at room temperature in triplicate plates. Lysates were removed and cells were washed 3 times with 150 µL/well of FACS stain buffer. Cells were incubated with 50 µL/well of anti-penta His-Alexa488 antibody conjugate (Qiagen) diluted 1:100 in FACS stain buffer for 20 minutes at room temperature. Cells were washed 3 times with 150 µL/well of FACS stain buffer, after which wells were filled with 100 µL of FACS stain buffer and read for fluorescence at 488 nm using an Acumen eX3 reader. Bacterial lysates containing FN3 domains were screened for their ability to bind A431 cells (1320 crude bacterial lysates for TCL1 and TCL2 libraries) and 516 positive clones were identified, where binding was ≥10-fold over the background signal. 300 lysates from the TCL14 library were screened for binding, resulting in 58 unique FN3 domain sequences that bind to EGFR.

Selection of FN3 Domains that Inhibit EGF Binding to EGFR on Cells

To better characterize the mechanism of EGFR binding, the ability of various identified FN3 domain clones to bind EGFR in an EGF-competitive manner was measured using A431 cells and run in parallel with the A431 binding assay screen. A431 cells were plated at 5,000/well in opaque black 96-well plates and allowed to attach overnight at 37° C., in a humidified 5% $CO_2$ atmosphere. Cells were incubated with 50 µL/well of 1:1,000 diluted bacterial lysate for 1 hour at room temperature in triplicate plates. Biotinylated EGF (Invitrogen, cat. #E-3477) was added to each well to give a final concentration of 30 ng/mL and incubated for 10 minutes at room temperature. Cells were washed 3 times with 150 µL/well of FACS stain buffer. Cells were incubated with 50 µL/well of streptavidin-phycoerythrin conjugate (Invitrogen) diluted 1:100 in FACS stain buffer for 20 minutes at room temperature. Cells were washed 3 times with 150 µL/well of FACS stain buffer, after which wells were filled with 100 µL of FACS stain buffer and read for fluorescence at 600 nm using an Acumen eX3 reader.

Bacterial lysates containing the FN3 domains were screened in the EGF competition assay described above. 1320 crude bacterial lysates from TCL1 and TCL2 libraries were screened resulting in 451 positive clones that inhibited EGF binding by >50%.

Expression and Purification of Identified FN3 Domains Binding EGFR

His-tagged FN3 domains were purified from clarified *E. coli* lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

Size Exclusion Chromatography Analysis

Size exclusion chromatography was used to determine the aggregation state of the FN3 domains binding EGFR. Aliquots (10 µL) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. Centyrins that exhibited high levels of aggregation by SEC were excluded from further analysis.

Off-Rate of Selected EGFR-Binding FN3 Domains from EGFR-Fc

Select EGFR-binding FN3 domains were screened to identify those with slow off-rates ($k_{off}$) in binding to EGFR-Fc on a ProteOn XPR-36 instrument (Bio-Rad) to facilitate selection of high affinity binders. Goat anti-human Fc IgG (R&D systems), at a concentration of 5 µg/mL, was directly immobilized via amine coupling (at pH 5.0) on all 6 ligand channels in horizontal orientation on the chip with a flow rate of 30 µL/min in PBS containing 0.005% Tween-20. The immobilization densities averaged about 1500 Response Units (RU) with less than 5% variation among different channels. EGFR-Fc was captured on the anti-human Fc IgG surface to a density around 600 RU in vertical ligand orientation. All tested FN3 domains were normalized to a concentration of 1 µM and tested for their binding in horizontal orientation. All 6 analyte channels were used for the FN3 domains to maximize screening throughput. The dissociation phase was monitored for 10 minutes at a flow rate of 100 µL/min. The inter-spot binding signals were used as references to monitor non-specific binding between analytes and the immobilized IgG surface, and were subtracted from all binding responses. The processed binding data were locally fit to a 1:1 simple Langmuir binding model to extract the $k_{off}$ for each FN3 domain binding to captured EGFR-Fc.

Inhibition of EGF-Stimulated EGFR Phosphorylation

Purified EGFR-binding FN3 domains were tested for their ability to inhibit EGF-stimulated phosphorylation of EGFR in A431 cells at a single concentration. EGFR phosphorylation was monitored using the EGFR phospho(Tyr1173) kit (Meso Scale Discovery). Cells were plated at 20,000/well in clear 96-well tissue culture-treated plates (Nunc) in 100 µL/well of RPMI medium (Gibco) containing GlutaMAX™ with 10% fetal bovine serum (FBS) (Gibco) and allowed to attach overnight at 37° C. in a humidified 5% $CO_2$ atmosphere. Culture medium was removed completely and cells were starved overnight in 100 µL/well of medium containing no FBS at 37° C. in a humidified 5% $CO_2$ atmosphere. Cells were then treated with 100 µL/well of pre-warmed (37° C.) starvation medium containing EGFR-binding FN3 domains at a concentration of 2 µM for 1 hour at 37° C. in a humidified 5% $CO_2$ atmosphere. Controls were treated with starvation medium only. Cells were stimulated by the addition and gentle mixing of 100 µL/well of pre-warmed (37° C.) starvation medium containing 100 ng/mL recombinant human EGF (R&D Systems, cat. #236-EG), for final concentrations of 50 ng/mL EGF and 1 µM EGFR-binding FN3 domain, and incubation at 37° C., 5% $CO_2$ for 15 minutes. One set of control wells was left un-stimulated as negative controls. Medium was completely removed and cells were lysed with 100 µL/well of Complete Lysis Buffer (Meso Scale Discovery) for 10 minutes at room temperature with shaking, as per the manufacturer's instructions. Assay plates configured for measuring EGFR phosphorylated on tyrosine 1173 (Meso Scale Discovery) were blocked with the provided blocking solution as per the manufacturer's instructions at room temperature for 1.5-2 hours. Plates were then washed 4 times with 200 µL/well of 1× Tris Wash Buffer (Meso Scale Discovery). Aliquots of cell lysate (30 µL/well) were transferred to assay plates, which were covered with plate sealing film (VWR) and incubated at room temperature with shaking for 1 hour. Assay plates were washed 4 times with 200 µL/well of Tris Wash Buffer, after which 25 µL of ice-cold Detection Antibody Solution (Meso Scale Discovery) were added to each well, being careful not to introduce bubbles. Plates were incubated at room temperature with shaking for 1 hour, followed by 4 washes with 200 µL/well of Tris Wash Buffer. Signals were detected by addition of 150 µL/well of Read Buffer (Meso Scale Discovery) and reading on a SECTOR® Imager 6000 instrument (Meso Scale Discovery) using manufacturer-installed assay-specific default settings. Percent inhibition of the EGF-stimulated positive control signal was calculated for each EGFR-binding FN3 domain.

Inhibition of EGF-stimulated EGFR phosphorylation was measured for 232 identified clones from the TCL1 and TCL2 libraries. 22 of these clones inhibited EGFR phosphorylation by ≥50% at 1 µM concentration. After removal of clones that either expressed poorly or were judged to be multimeric by size exclusion chromatography, nine clones were carried forward for further biological characterization. The BC and FG loop sequences of these clones are shown in Table 4. Eight of the nine selected clones had a common FG loop sequence (HNVYKDTNMRGL; SEQ ID NO: 95) and areas of significant similarity were seen between several clones in their BC loop sequences.

TABLE 4

| FN3 Domain | BC Loop | | FG Loop | |
|---|---|---|---|---|
| Clone ID | SEQ ID NO: | Sequence | SEQ ID NO: | Sequence | SEQ ID NO: |
| P53A1R5-17 | 18 | ADPHGFYD | 87 | HNVYKDTNMRGL | 95 |
| P54AR4-17 | 19 | TYDRDGYD | 88 | HNVYKDTNMRGL | 95 |
| P54AR4-47 | 20 | WDPFSFYD | 89 | HNVYKDTNMRGL | 95 |
| P54AR4-48 | 21 | DDPRGFYE | 90 | HNVYKDTNMRGL | 95 |
| P54AR4-73 | 22 | TWPYADLD | 91 | HNVYKDTNMRGL | 95 |
| P54AR4-74 | 23 | GYNGDHFD | 92 | HNVYKDTNMRGL | 95 |
| P54AR4-81 | 24 | DYDLGVYD | 93 | HNVYKDTNMRGL | 95 |
| P54AR4-83 | 25 | DDPWDFYE | 94 | HNVYKDTNMRGL | 95 |
| P54CR4-31 | 26 | TAPDAAFD | 85 | LGSYVFEHDVM | 96 |

EXAMPLE 3: CHARACTERIZATION OF EGFR-BINDING FN3 DOMAINS THAT INHIBIT EGF BINDING LARGE-SCALE EXPRESSION, PURIFICATION, AND ENDOTOXIN REMOVAL

The 9 FN3 domains shown in Table 4 were scaled up to provide more material for detailed characterization. An overnight culture containing each EGFR-binding FN3 domain variant was used to inoculate 0.8 L of Terrific broth medium supplemented with 100 µg/mL ampicillin at a 1/80 dilution of overnight culture into fresh medium, and incubated with shaking at 37° C. The culture was induced when the optical density at 600 nm reached ~1.2-1.5 by addition of IPTG to a final concentration of 1 mM and the temperature was reduced to 30° C. After 4 hours, cells were collected by centrifugation and the cell pellet was stored at –80° C. until needed.

For cell lysis, the thawed pellet was resuspended in 1× BugBuster® supplemented with 25 U/mL Benzonase® (Sigma-Aldrich) and 1 kU/mL rLysozyme™ (Novagen EMD Biosciences) at a ratio of 5 mL of BugBuster® per gram of pellet. Lysis proceeded for 1 hour at room temperature with gentle agitation, followed by centrifugation at 56,000×g for 50 minutes at 4° C. The supernatant was collected and filtered through a 0.2 um filter, then loaded on to a 5-mL HisTrap FF column pre-equilibrated with Buffer A (50 mM Tris-HCl pH 7.5, 500 mM NaCl, 10 mM imidazole) using a GE Healthcare ÅKTAexplorer 100 s chromatography system. The column was washed with 20 column volumes of Buffer A and further washed with 16% Buffer B (50 mM Tris-HCl pH7.5, 500 mM NaCl, 250 mM imidazole) for 6 column volumes. The FN3 domains were eluted with 50% B for 10 column volumes, followed by a gradient from 50-100% B over 6 column volumes. Fractions containing the FN3 domain protein were pooled, concentrated using a Millipore 10K MWCO concentrator, and filtered before loading onto a HiLoad™ 16/60 Superdex™ 75 column (GE Healthcare) pre-equilibrated with PBS. The protein monomer peak eluting from the size exclusion column was retained.

Endotoxins were removed using a batch approach with ActiClean Etox resin (Sterogene Bioseparations). Prior to endotoxin removal, the resin was pre-treated with 1 N NaOH for 2 hours at 37° C. (or overnight at 4° C.) and washed extensively with PBS until the pH had stabilized to ~7 as measured with pH indicator paper. The purified protein was filtered through a 0.2 μm filter before adding to 1 mL of Etox resin at a ratio of 10 mL of protein to 1 mL of resin. The binding of endotoxin to resin was allowed to proceed at room temperature for at least 2 hours with gentle rotation. The resin was removed by centrifugation at 500×g for 2 minutes and the protein supernatant was retained. Endotoxin levels were measured using EndoSafe®-PTS™ cartridges and analyzed on an EndoSafe®-MCS reader (Charles River). If endotoxin levels were above 5 EU/mg after the first Etox treatment, the above procedure was repeated until endotoxin levels were decreased to ≤5 EU/mg. In cases where the endotoxin level was above 5 EU/mg and stabilized after two consecutive treatments with Etox, anion exchange or hydrophobic interaction chromatography conditions were established for the protein to remove the remaining endotoxins.

Affinity Determination of Selected EGFR-Binding FN3 Domains to EGFR-Fc (EGFR-Fc Affinity)

Binding affinity of selected EGFR-binding FN3 domains to recombinant EGFR extracellular domain was further characterized by surface Plasmon resonance methods using a Proteon Instrument (BioRad). The assay set-up (chip preparation, EGFR-Fc capture) was similar to that described above for off-rate analysis. Selected EGFR binding FN3 domains were tested at 1 μM concentration in 3-fold dilution series in the horizontal orientation. A buffer sample was also injected to monitor the baseline stability. The dissociation phase for all concentrations of each EGFR-binding FN3 domain was monitored at a flow rate of 100 μL/min for 30 minutes (for those with $k_{off}$~$10^{-2}$ $s^{-1}$ from off-rate screening), or 1 hour (for those with $k_{off}$~$10^{-3}$ $s^{-1}$ or slower). Two sets of reference data were subtracted from the response data: 1) the inter-spot signals to correct for the non-specific interactions between the EGFR-binding FN3 domain and the immobilized IgG surface; 2) the buffer channel signals to correct for baseline drifting due to the dissociation of captured EGFR-Fc surface over time. The processed binding data at all concentrations for each FN3 domain were globally fit to a 1:1 simple Langmuir binding model to extract estimates of the kinetic ($k_{on}$, $k_{off}$) and affinity ($K_D$) constants. Table 5 shows the kinetic constants for each of the constructs, with the affinity varying from 200 pM to 9.6 nM.

Binding of Selected EGFR-Binding FN3 Domains to EGFR on Cells (A431 Cell Binding Assay)

A431 cells were plated at 5,000/well in opaque black 96-well plates and allowed to attach overnight at 37° C., in a humidified 5% $CO_2$ atmosphere. Purified EGFR-binding FN3 domains (1.5 nM to 30 μM) were added to the cells (in 50 uL) for 1 hour at room temperature in triplicate plates. Supernatant was removed and cells were washed 3 times with 150 μL/well of FACS stain buffer. Cells were incubated with 50 μL/well of anti-penta His-Alexa488 antibody conjugate (Qiagen) diluted 1:100 in FACS stain buffer for 20 minutes at room temperature. Cells were washed 3 times with 150 μL/well of FACS stain buffer, after which wells were filled with 100 μL of FACS stain buffer and read for fluorescence at 488 nm using an Acumen eX3 reader. Data were plotted as raw fluorescence signal against the logarithm of the FN3 domain molar concentration and fitted to a sigmoidal dose-response curve with variable slope using GraphPad Prism 4 (GraphPad Software) to calculate $EC_{50}$ values. Table 5 reports the $EC_{50}$ for each of the constructs ranging from 2.2 to >20 μM.

Inhibition of EGF Binding to EGFR on Cells Using Selected EGFR-Binding FN3 Domains (A431 Cell EGF Competition Assay)

A431 cells were plated at 5,000/well in opaque black 96-well plates and allowed to attach overnight at 37° C., in a humidified 5% $CO_2$ atmosphere. Purified EGFR-binding FN3 domains (1.5 nM to 30 μM) were added to the cells (50 μL/well) for 1 hour at room temperature in triplicate plates. Biotinylated EGF (Invitrogen, Cat #: E-3477) was added to each well to give a final concentration of 30 ng/mL and incubated for 10 minutes at room temperature. Cells were washed 3 times with 150 μL/well of FACS stain buffer. Cells were incubated with 50 μL/well of streptavidin-phycoerythrin conjugate (Invitrogen) diluted 1:100 in FACS stain buffer for 20 minutes at room temperature. Cells were washed 3 times with 150 μL/well of FACS stain buffer, after which wells were filled with 100 μL of FACS stain buffer and read for fluorescence at 600 nm using an Acumen eX3 reader. Data were plotted as the raw fluorescence signal against the logarithm of FN3 domain molar concentration and fitted to a sigmoidal dose-response curve with variable slope using GraphPad Prism 4 (GraphPad Software) to calculate $IC_{50}$ values. Table 5 reports the $IC_{50}$ values ranging from 1.8 to 121 nM.

Inhibition of EGF-Stimulated EGFR Phosphorylation (Phoshpo-EGRF Assay)

Select FN3 domains that significantly inhibited EGF-stimulated EGFR phosphorylation were assessed more completely by measuring $IC_{50}$ values for inhibition. Inhibition of EGF-stimulated EGFR phosphorylation was assessed at varying FN3 domain concentrations (0.5 nM to 10 μL) as described above in "inhibition of EGF stimulated EGFR phosphorylation". Data were plotted as electrochemiluminescence signal against the logarithm of the FN3 domain molar concentration and $IC_{50}$ values were determined by fitting data to a sigmoidal dose response with variable slope using GraphPad Prism 4 (GraphPad Software). Table 5 reports the $IC_{50}$ values ranging from 18 nM to >2.5 μM.

Inhibition of Human Tumor Cell Growth (NCI-H292 Growth and NCI-H322 Growth Assay)

Inhibition of EGFR-dependent cell growth was assessed by measuring viability of the EGFR over-expressing human tumor cell lines, NCI-H292 and NCI-H322 (American Type Culture Collection, cat. #CRL-1848 & #CRL-5806, respectively), following exposure to EGFR-binding FN3 domains. Cells were plated at 500 cells/well (NCI-H292) or 1,000 cells/well (NCI-H322) in opaque white 96-well tissue culture-treated plates (Nunc) in 100 μL/well of RPMI medium (Gibco) containing GlutaMAX™ and 10 mM HEPES, supplemented with 10% heat inactivated fetal bovine serum (Gibco) and 1% penicillin/streptomycin (Gibco), and allowed to attach overnight at 37° C. in a humidified 5% $CO_2$ atmosphere. Cells were treated by addition of 5 μL/well of phosphate-buffered saline (PBS) containing a concentration range of EGFR-binding FN3 domains. Controls were treated with 54/well of PBS only or 25 mM ethylenediaminetetraacetic acid in PBS. Cells were incubated at 37° C., 5% $CO_2$ for 120 hours. Viable cells were detected by addition of 754/well of CellTiter-Glo® reagent (Promega), followed by mixing on a plate shaker for 2 minutes, and incubation in the dark at room temperature for a further 10 minutes. Plates were read on a SpectraMax M5 plate reader (Molecular Devices) set to luminescence mode, with a read time of 0.5 seconds/well against a blank of medium only. Data were plotted as a percentage of PBS-treated cell growth against the logarithm of FN3 domain molar concentration. $IC_{50}$ values were determined by fitting data to the equation for a sigmoidal dose response with variable slope using GraphPad Prism 4 (GraphPad Software). Table 5 shows $IC_{50}$ values ranging from 5.9 nM to 1.15 μM and 9.2 nM to >3.1 μM, using the NCI-H292 and NCI-H322 cells respectively. Table 5 Shows the Summary of Biological Properties of EGFR-Binding FN3 Domains for Each Assay.

TABLE 5

| FN3 Domain Clone ID | SEQ ID NO: | EGFR-Fc Affinity (nM) | A431 Cell Binding $EC_{50}$ (nM) | A431 Cell EGF Competition $IC_{50}$ (nM) | Phospho-EGFR $IC_{50}$ (nM) | NCI-H292 Growth $IC_{50}$ (nM) | NCI-H322 Growth $IC_{50}$ (nM) |
|---|---|---|---|---|---|---|---|
| P53A1R5-17 | 18 | 1.89 | 4.0 | 9.8 | >2500 | 86 | 65 |
| P54AR4-17 | 19 | 9.62 | 16 | 21 | 184 | ND | ND |
| P54AR4-47 | 20 | 2.51 | 8.6 | 7.1 | 295 | 44 | 39 |
| P54AR4-48 | 21 | 7.78 | 12 | 9.8 | 170 | ND | ND |
| P54AR4-73 | 22 | 0.197 | 9.4 | 4.6 | 141 | 83 | 73 |
| P54AR4-74 | 23 | ND | 77 | ND | ND | ND | ND |
| P54AR4-81 | 24 | ND | 84 | 121 | ND | ND | ND |
| P54AR4-83 | 25 | 0.255 | 2.2 | 1.8 | 18 | 5.9 | 9.2 |
| P54CR4-31 | 26 | 0.383 | >20000 | 55 | 179 | 1150 | >3073 |

EXAMPLE 4: ENGINEERING OF EGFR-BINDING FN3 DOMAINS

A subset of the EGFR binding FN3 domains was engineered to increase the conformational stability of each molecule. The mutations L17A, N46V, and E86I (described in US Pat. Publ. No. 2011/0274623) were incorporated into clones P54AR4-83, P54CR4-31, and P54AR4-37 by DNA synthesis. The new mutants, P54AR4-83v2, P54CR431-v2, and P54AR4-37v2 were expressed and purified as described above. Differential scanning calorimetry in PBS was used to assess the stability of each mutant in order to compare it to that of the corresponding parent molecule. Table 6 shows that each clone was stabilized significantly, with an average increase in the $T_m$ of 18.5° C.

TABLE 6

| FN3 domain Clone | SEQ ID NO: | $T_m$ (° C.) |
|---|---|---|
| P54AR4-83 | 25 | 50.6 |
| P54AR4-83v2 | 27 | 69.8 |
| P54CR4-31 | 26 | 60.9 |

TABLE 6-continued

| FN3 domain Clone | SEQ ID NO: | $T_m$ (° C.) |
|---|---|---|
| P54CR4-31v2 | 28 | 78.9 |
| P54AR4-37 | 22 | 45.9 |
| P54AR4-37v2 | 29 | 64.2 |

EXAMPLE 5: CYSTEINE ENGINEERING AND CHEMICAL CONJUGATION OF EGFR-BINDING FN3 DOMAINS

Cysteine mutants of FN3 domains are made from the base Tencon molecule and variants thereof that do not have cysteine residues. These mutations may be made using standard molecular biology techniques known in the art to incorporate a unique cysteine residue into the base Tencon sequence (SEQ ID NO: 1) or other FN3 domains in order to serve as a site for chemical conjugation of small molecule drugs, fluorescent tags, polyethylene glycol, or any number of other chemical entities. The site of mutation to be selected should meet certain criteria. For example, the Tencon molecule mutated to contain the free cysteine should: (i) be highly expressed in *E. coli*, (ii) maintain a high level of solubility and thermal stability, and (iii) maintain binding to the target antigen upon conjugation. Since the Tencon scaffold is only ~90-95 amino acids, single-cysteine variants can easily be constructed at every position of the scaffold to rigorously determine the ideal position(s) for chemical conjugation.

Each individual amino acid residue, from positions 1-95 (or 2-96 when the N-terminal methionine is present) of the P54AR4-83v2 mutant (SEQ ID NO: 27), which binds EGFR, was mutated to cysteine to assess the best chemical conjugation sites.

Construction, Expression and Purification

The amino acid sequence of each individual cysteine variant of P54AR4-83v2 was reverse translated into nucleic acid sequences encoding the proteins using preferred codons for *E. coli* expression and a synthetic gene was produced (DNA 2.0). These genes were cloned into a pJexpress401 vector (DNA 2.0) for expression driven by a T5 promoter sequence and transformed into *E. coli* strain BL21 (Agilent). The P54AR4-83v2 "cys scan" library was provided as glycerol stocks arrayed into a 96-well plate and the expression and purification of each followed the same procedure described in Example 2.

Chemical Conjugation

For the P54AR4-83v2 "cys scan" library, conjugation was integrated into the purification process. Cysteine variants in clarified lysate were bound to Ni-NTA resin in 96-well format using His-trap HP plates (catalog #28-4008-29, GE Healthcare) by adding lysate to the wells and centrifugation at 100×g for 5 min. The resin was washed 3 times with buffer A, and then N-ethyl maleimide (NEM) was added as 500 µL of a 1.5 mM solution. Following a one-hour room temperature incubation on a rotisserie shaker, excess NEM was removed by centrifugation and three washes with buffer A. Conjugated cysteine variants was eluted with 2×150 µL of buffer B and exchanged into PBS with MultiScreen Filter Plates with Ultracel-10 membrane (catalog #MAUF1010, Millipore) or with 96-well PD MultiTrap plates (catalog #28-9180-06, GE Healthcare). Conjugates were characterized by mass spectrometry (Table 7). Cysteine variants that expressed poorly (less than 0.1 mg of protein obtained from a 5 mL culture or no protein detected by mass spectrometry) or conjugated poorly to NEM (less than 80% conjugated, as determined by mass spectrometry) were excluded from further analysis. This eliminated L1C, W21C, Q36C, E37C, A44C, D57C, L61C, Y67C, and F92C due to poor expression and A17C, L19C, I33C, Y35C, Y56C, L58C, T65C, V69C, I71C, and T94C due to low conjugation efficiency.

TABLE 7

| Cysteine Variant of P54AR4-83v2 | Protein Yield (mg) | Conjugation |
|---|---|---|
| L1C | 0.58 | no protein detected |
| P2C | 0.28 | yes |
| A3C | 1.05 | yes |
| P4C | 0.77 | yes |
| K5C | 0.19 | yes |
| N6C | 0.56 | yes |
| L7C | 0.96 | yes |
| V8C | 1.40 | yes |
| V9C | 0.92 | yes |
| S10C | 0.91 | yes |
| E11C | 0.82 | yes |
| V12C | 0.76 | yes |
| T13C | 0.53 | yes |
| E14C | 1.05 | yes |
| D15C | 1.12 | yes |
| S16C | 0.65 | yes |
| A17C | 0.70 | no |
| R18C | 1.14 | yes |
| L19C | 0.47 | no |
| S20C | 1.02 | yes |
| W21C | 0.09 | no protein |
| D22C | 0.80 | yes |
| D23C | 0.90 | yes |
| P24C | 0.63 | yes |
| W25C | 1.24 | yes |
| A26C | 1.34 | yes |
| F27C | 0.92 | yes |
| Y28C | 1.15 | yes |
| E29C | 1.10 | yes |
| S30C | 0.80 | yes |
| F31C | 0.75 | yes |
| L32C | 0.64 | yes |
| I33C | 0.09 | no |
| Q34C | 1.14 | yes |
| Y35C | 0.85 | no |
| Q36C | 0.04 | no protein |
| E37C | 0.84 | no protein |
| S38C | 0.80 | yes |
| E39C | 0.72 | yes |
| K40C | 1.20 | yes |
| V41C | 0.99 | yes |
| G42C | 1.27 | yes |
| E43C | 0.22 | yes |
| A44C | 0.07 | yes |
| I45C | 1.14 | yes |
| V46C | 0.14 | yes |
| L47C | 1.12 | yes |
| T48C | 1.22 | yes |

TABLE 7-continued

| Cysteine Variant of P54AR4-83v2 | Protein Yield (mg) | Conjugation |
|---|---|---|
| V49C | 1.10 | yes |
| P50C | 0.69 | yes |
| G51C | 1.15 | yes |
| S52C | 0.24 | yes |
| E53C | 1.13 | yes |
| R54C | 1.55 | yes |
| S55C | 0.88 | yes |
| Y56C | 1.71 | no |
| D57C | 0.09 | no protein |
| L58C | 0.59 | no |
| T59C | 0.80 | yes |
| G60C | 1.24 | yes |
| L61C | 0.05 | no protein |
| K62C | 1.12 | yes |
| P63C | 1.44 | yes |
| G64C | 1.30 | yes |
| T65C | 0.90 | no |
| E66C | 0.20 | yes |
| Y67C | 0.06 | no protein |
| T68C | 0.76 | yes |
| V69C | 0.62 | no |
| S70C | 0.59 | yes |
| I71C | 0.77 | no |
| Y72C | 1.22 | |
| G73C | 0.83 | yes |
| V74C | 0.52 | yes |
| H75C | 0.55 | yes |
| N76C | 1.10 | yes |
| V77C | 1.12 | yes |
| Y78C | 1.29 | yes |
| K79C | 0.29 | yes |
| D80C | 1.23 | yes |
| T81C | 0.59 | yes |
| N82C | 0.14 | yes |
| M83C | 1.03 | yes |
| R84C | 1.40 | yes |
| G85C | 1.17 | yes |
| L86C | 0.52 | yes |
| P87C | 1.53 | yes |
| L88C | 1.68 | yes |
| S89C | 1.20 | yes |
| A90C | 0.71 | yes |
| I91C | 0.64 | yes |
| F92C | 0.05 | no protein |
| T93C | 0.64 | yes |
| T94C | 0.26 | ~50% conjugated |
| G95C | 0.88 | yes |
| 83v2His$_6$-cys (SEQ ID NOs: 217 and 255) | 1.28 | yes |

Analytical Size-Exclusion Chromatography

Size exclusion chromatography for each NEM-conjugated cysteine variants of P54AR4-83v2 was performed as described in Example 2. Table 8 summarizes the results. The percent monomer for each protein was determined by integrating the Abs280 signal and comparing the peak in the monomer region (5.5-6 minutes) to the peaks in the oligomer region (4-5.3 minutes).

TABLE 8

| Cysteine Variant of P54AR4-83v2 | Percent monomer |
|---|---|
| L1C | 100 |
| P2C | 86 |
| A3C | 100 |
| P4C | 100 |
| K5C | 100 |
| N6C | 94 |
| L7C | 93 |
| V8C | 91 |
| V9C | double peak |

TABLE 8-continued

| Cysteine Variant of P54AR4-83v2 | Percent monomer |
|---|---|
| S10C | 80 |
| E11C | 100 |
| V12C | 66 |
| T13C | 82 |
| E14C | 96 |
| D15C | 97 |
| S16C | 75 |
| A17C | 93 |
| R18C | 93 |
| L19C | 83 |
| S20C | 94 |
| W21C | no protein |
| D22C | 85 |
| D23C | 100 |
| P24C | 88 |
| W25C | 76 |
| A26C | 95 |
| F27C | 97 |
| Y28C | 92 |
| E29C | 85 |
| S30C | 94 |
| F31C | 57 |
| L32C | 100 |
| I33C | 100 |
| Q34C | 97 |
| Y35C | 100 |
| Q36C | 100 |
| E37C | 87 |
| S38C | 93 |
| E39C | 100 |
| K40C | 97 |
| V41C | 98 |
| G42C | 87 |
| E43C | 100 |
| A44C | 100 |
| I45C | 97 |
| V46C | 100 |
| L47C | 100 |
| T48C | 90 |
| V49C | 88 |
| P50C | 100 |
| G51C | 96 |
| S52C | 100 |
| E53C | 97 |
| R54C | 96 |
| S55C | 100 |
| Y56C | 97 |
| D57C | 100 |
| L58C | 67 |
| T59C | 100 |
| G60C | 100 |
| L61C | no protein |
| K62C | 95 |
| P63C | 92 |
| G64C | 100 |
| T65C | 83 |
| E66C | 100 |
| Y67C | no protein |
| T68C | 100 |
| V69C | 90 |
| S70C | 100 |
| I71C | double peak |
| Y72C | 100 |
| G73C | 66 |
| V74C | 100 |
| H75C | 100 |
| N76C | 94 |
| V77C | 92 |
| Y78C | 90 |
| K79C | 100 |
| D80C | 79 |
| T81C | 86 |
| N82C | 100 |
| M83C | 91 |
| R84C | 100 |
| G85C | 95 |
| L86C | 83 |
| P87C | 98 |
| L88C | 98 |
| S89C | 96 |
| A90C | 100 |
| I91C | 100 |
| F92C | no protein |
| T93C | 100 |
| T94C | 100 |
| G95C | 100 |
| 83v2His$_6$-cys (SEQ ID NOs: 217 and 255) | 97 |

EGFR Binding Assay

Relative binding affinity of the NEM-conjugated cysteine variants of P54AR4-83v2 to EGFR was assessed as described in Example 2. Table 9 summarizes the data showing the ratios of each cysteine variant EGFR binding affinity relative to the P54AR4-83v2 parent protein. Cysteine conjugates that had reduced binding to EGFR (<65% of the signal observed with P54AR4-83v2 parent when treated with 10 nM protein) as determined by the ELISA assay were excluded from further analysis: P2C, A3C, P4C, K5C, L7C, D23C, W25C, F27C, Y28C, F31C, S55C, G73C, H75C, V77C, Y78C, T81C, N82C, M83C, and G85C.

TABLE 9

| Cysteine Variant of P54AR4-83v2 | Amount of Variant in Assay: 500 nM | 100 nM | 10 nM |
|---|---|---|---|
| P2C | 0.01 | 0.00 | 0.00 |
| A3C | 0.82 | 0.88 | 0.34 |
| P4C | 0.12 | 0.02 | 0.02 |
| K5C | 0.92 | 1.06 | 0.61 |
| N6C | 0.89 | 1.01 | 0.76 |
| L7C | 0.90 | 1.00 | 0.35 |
| V8C | 0.90 | 1.03 | 0.96 |
| V9C | 0.93 | 1.03 | 0.94 |
| S10C | 0.96 | 1.07 | 0.83 |
| E11C | 0.95 | 1.08 | 0.90 |
| V12C | 0.93 | 1.06 | 0.87 |
| T13C | 0.90 | 1.04 | 0.87 |
| E14C | 1.15 | 1.27 | 1.11 |
| D15C | 0.97 | 1.09 | 0.98 |
| S16C | 0.63 | 1.05 | 0.88 |
| R18C | 0.94 | 1.05 | 0.86 |
| S20C | 0.91 | 1.05 | 0.81 |
| D22C | 0.90 | 1.02 | 0.84 |
| D23C | 0.40 | 0.20 | 0.02 |
| P24C | 0.83 | 0.85 | 0.45 |
| W25C | 0.70 | 0.64 | 0.38 |
| A26C | 0.95 | 1.06 | 0.95 |
| F27C | 0.23 | 0.07 | 0.00 |
| Y28C | 0.09 | 0.01 | 0.00 |
| E29C | 0.93 | 1.07 | 0.89 |
| S30C | 0.90 | 1.02 | 0.90 |
| F31C | 0.62 | 0.34 | 0.04 |
| L32C | 0.91 | 1.01 | 0.87 |
| Q34C | 0.94 | 1.03 | 0.89 |
| S38C | 0.82 | 0.93 | 0.80 |
| E39C | 0.90 | 1.00 | 0.90 |
| K40C | 0.86 | 0.95 | 0.88 |
| V41C | 0.95 | 0.99 | 0.92 |
| G42C | 0.90 | 0.99 | 0.84 |
| E43C | 0.92 | 1.04 | 0.68 |
| I45C | 0.93 | 1.04 | 0.91 |
| V46C | 0.90 | 1.01 | 0.61 |
| L47C | 0.91 | 1.02 | 0.92 |
| T48C | 0.93 | 1.00 | 0.88 |
| V49C | 0.98 | 1.01 | 0.96 |
| P50C | 0.97 | 1.05 | 0.91 |
| G51C | 0.92 | 1.03 | 0.88 |

TABLE 9-continued

| Cysteine Variant of P54AR4-83v2 | Amount of Variant in Assay: 500 nM | 100 nM | 10 nM |
|---|---|---|---|
| S52C | 0.93 | 1.03 | 0.78 |
| E53C | 0.91 | 1.02 | 0.91 |
| R54C | 0.93 | 1.01 | 0.89 |
| S55C | 0.11 | 0.00 | 0.00 |
| T59C | 0.93 | 1.04 | 0.83 |
| G60C | 0.93 | 1.02 | 0.86 |
| K62C | 0.61 | 0.73 | 0.64 |
| P63C | 0.92 | 1.02 | 0.95 |
| G64C | 1.36 | 1.42 | 1.28 |
| E66C | ND | ND | ND |
| T68C | 0.95 | 1.04 | 0.83 |
| S70C | 0.93 | 1.01 | 0.86 |
| Y72C | 0.93 | 1.00 | 0.93 |
| G73C | 0.21 | 0.02 | 0.00 |
| V74C | 0.95 | 1.01 | 0.76 |
| H75C | 0.25 | 0.19 | 0.07 |
| N76C | 0.91 | 0.97 | 0.75 |
| V77C | 0.03 | 0.00 | 0.03 |
| Y78C | 0.68 | 0.63 | 0.31 |
| K79C | 0.93 | 0.99 | 0.90 |
| D80C | 0.91 | 0.97 | 0.70 |
| T81C | 1.02 | 0.90 | 0.50 |
| N82C | 0.96 | 0.97 | 0.56 |
| M83C | 0.24 | 0.04 | 0.07 |
| R84C | 0.98 | 1.04 | 0.91 |
| G85C | 0.29 | 0.02 | 0.19 |
| L86C | 0.92 | 0.96 | 0.77 |
| P87C | 0.91 | 0.93 | 0.73 |
| L88C | 0.97 | 1.03 | 0.95 |
| S89C | 1.04 | 1.02 | 0.97 |
| A90C | 1.01 | 1.05 | 0.94 |
| I91C | 1.00 | 1.01 | 0.90 |
| T93C | 1.04 | 1.05 | 0.96 |
| G95C | 1.00 | 1.03 | 1.01 |
| 83v2His$_6$-cys (SEQ ID NOs: 217 and 255) | 1.00 | 1.00 | 1.00 |

Thermal Stability

The thermal stability of cysteine-NEM conjugates was assessed by differential scanning calorimetry (DSC). The only the conjugates tested were those determined to express at high levels, conjugate efficiently, and retain EGFR binding. Additionally, cysteine variants within the BC and FG loops were excluded. Stability data was generated by heating a 400 μL aliquot of the variant from 25° C. to 100° C. at a scan rate of 1° C. per minute in a VP-DSC instrument (MicroCal). A second identical scan was completed on the sample in order to assess the reversibility of thermal folding/unfolding. Data was fitted to a 2-state unfolding model in order to calculate the melting temperature (Table 10). Cys variants with reduced melting temperatures (<63° C., or >8° C. below the P54AR4-83v2 parent) or that demonstrated irreversible unfolding were excluded from further analysis: V9C, V12C, T13C, R18C, E29C, E39C, G42C, V49C, P50C, G51C, P63C.

TABLE 10

| Cysteine Variant of P54AR4-83v2 | First Scan Tm (° C.) | Second Scan Tm (° C.) | Reversible? |
|---|---|---|---|
| N6C | 71 | 70 | Y |
| V8C | 69 | 69 | Y |
| V9C | 46 | 46 | N |
| S10C | 68 | 68 | Y |
| E11C | 71 | 72 | Y |
| V12C | 58 | 58 | Y |
| T13C | 63 | 63 | Y |
| E14C | 70 | 71 | Y |
| D15C | 73 | 73 | Y |
| S16C | 68 | 68 | Y |
| R18C | 62 | 62 | Y |
| S20C | 70 | 70 | Y |
| E29C | 63 | 66 | Y |
| S30C | 71 | 71 | Y |
| L32C | 71 | 70 | Y |
| Q34C | 75 | 74 | Y |
| S38C | 65 | 65 | Y |
| E39C | 67 | 69 | N |
| K40C | 70 | 70 | Y |
| V41C | 71 | 71 | Y |
| G42C | 65 | 67 | N |
| I45C | 69 | 68 | Y |
| L47C | 67 | 67 | Y |
| T48C | 72 | 72 | Y |
| V49C | 54 | 55 | N |
| P50C | 63 | 65 | N |
| G51C | 61 | 61 | Y |
| E53C | 76 | 75 | Y |
| R54C | 65 | 65 | Y |
| T59C | 67 | 67 | Y |
| G60C | 66 | 66 | Y |
| K62C | 65 | 65 | Y |
| P63C | 60 | 62 | N |
| G64C | 70 | 70 | Y |
| T68C | 72 | 72 | Y |
| S70C | 73 | 72 | Y |
| Y72C | 70 | 69 | Y |
| V74C | 68 | 67 | Y |
| L88C | 70 | 70 | Y |
| S89C | 72 | 71 | Y |
| A90C | 67 | 67 | Y |
| I91C | 70 | 69 | Y |
| T93C | 69 | 69 | Y |
| 83v2His$_6$-cys (SEQ ID NOs: 217 and 255) | 71 | 71 | Y |
| P54AR4-83v2 (SEQ ID NO: 27) | 71 | 71 | Y |

Cytotoxicity Assay

P54AR4-83v2 cysteine variants were conjugated to the cytotoxic tubulin inhibitor momomethyl auristatin F (MMAF) via an enzyme-cleavable Val-Cit linker or a non-cleavable PEG$_4$ linker (VC-MMAF; see FIG. 2) using the methodology described for the NEM conjugation. The 32 variants that remained after exclusions at the previous steps were conjugated along with the P54AR4-83v2 parent (SEQ ID NOS: 217 and 255 and Tencon (SEQ ID NO: 265) as a negative control.

Cell killing was assessed by measuring viability of the EGFR-overexpressing human tumor cell line H1573 following exposure to the cysteine variant-cytotoxin conjugates. Cells were plated in black-well, clear bottomed, tissue culture-treated plates (Falcon 353219) at 7000/well in 100 μL/well of phenol red free RPMI media (Gibco 11835-030) with 5% fetal bovine serum (Gibco). Cells were allowed to attach overnight at 37° C. in a humidified 5% CO$_2$ atmosphere. Medium was aspirated from 96-well plate and cells were treated with 50 uL of fresh media and 50 uL of 2× inhibitor made up in fresh media. Cell viability was determined by an endpoint assay with Cell TiterGlo (Promega) at 70 hours. IC$_{50}$ values were determined by fitting data to the equation for a sigmoidal dose response with variable slope using GraphPad Prism 5 (GraphPad Software). Table 11 reports IC$_{50}$ values obtained from analysis of the CellTiter Glo data. The average IC$_{50}$ of two replicates of the 83v2-cys/vcMMAF conjugate was 0.7 nM. Four of the 32 conjugates tested had IC$_{50}$ values more than two times that of the parent (above 1.4 nM) and were discarded: L32C, T68C, Y72C, and V74C. Additionally, three conjugates gave $IC_{50}$ values over two times more potent than the parent and may be especially suitable for formatting into drug conjugates: N6C, E53C, and T93C.

TABLE 11

| Variant | IC50 (nM) |
|---|---|
| N6C | 0.16 |
| V8C | 0.35 |
| S10C | 0.43 |
| E11C | 0.94 |
| E14C | 0.34 |
| D15C | 0.33 |
| S16C | 0.75 |
| S20C | 0.36 |
| S30C | 0.78 |
| L32C | 2.92 |
| Q34C | 0.74 |
| S38C | 0.76 |
| K40C | 0.73 |
| V41C | 1.13 |
| I45C | 0.63 |
| L47C | 1.03 |
| T48C | 0.59 |
| E53C | 0.09 |
| R54C | 0.37 |
| T59C | 0.44 |
| G60C | 1.00 |
| K62C | 1.25 |
| G64C | 0.36 |
| T68C | 3.70 |
| S70C | 1.14 |
| Y72C | 1.85 |
| V74C | 3.13 |
| L88C | 0.81 |
| S89C | 0.94 |
| A90C | 1.00 |
| I91C | 0.54 |
| T93C | 0.20 |
| 83v2His$_6$-cys (SEQ ID NOs: 217 and 255) | 0.61 |
| 83v2His$_6$-cys (SEQ ID NOs: 217 and 255) | 0.79 |
| WT | 146.00 |
| WT | 166.30 |

Final Cysteine Variants

Figure 3:
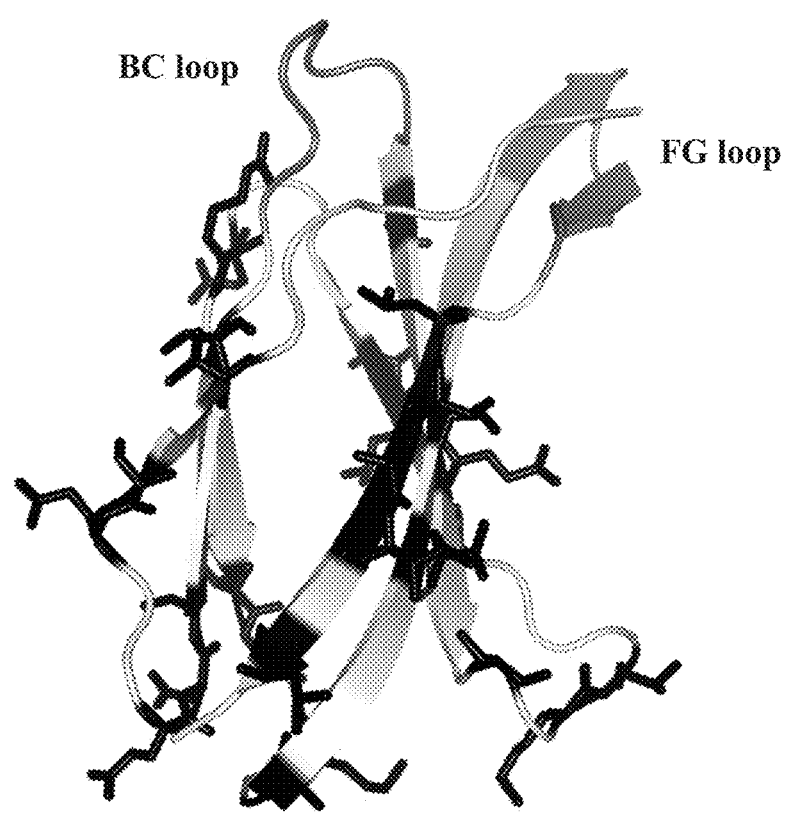
FIG. 3. Ribbon representation of the crystal structure of P54AR4-83v2 protein (SEQ ID NO: 27). Final positions identified as tolerant of cysteine substitutions are shown as sticks and colored solid black. Binding loops BC/FG are colored shaded gray.

Of the 96 positions tested, 28 of the cysteine variants were found to meet the criteria of retention of high expression level in *E. coli*, efficient conjugation via thiol-maleimide chemistry, retention of binding to target antigen EGFR, retention of thermostability and reversible unfolding properties, and retention of killing of cells with high EGFR expression when the cysteine variant is conjugated to a cytotoxic drug. These positions are: N6C (SEQ ID NOS: 210 and 248), V8C (SEQ ID NOS: 189 and 227), S10C (SEQ ID NOS: 190 and 228), E11C (SEQ ID NOS: 191 and 229), E14C (SEQ ID NOS: 192 and 230), D15C (SEQ ID NOS: 193 and 231), S16C (SEQ ID NOS: 194 and 232), 520C (SEQ ID NOS: 195 and 233), 530C (SEQ ID NOS: 196 and 234), Q34C (SEQ ID NOS: 197 and 235), S38C (SEQ ID NOS: 198 and 236), K40C (SEQ ID NOS: 199 and 237), V41C (SEQ ID NOS: 200 and 238), I45C (SEQ ID NOS: 201 and 239), L47C (SEQ ID NOS: 202 and 240), T48C (SEQ ID NOS: 203 and 241), E53C (SEQ ID NOS: 204 and 242), R54C (SEQ ID NOS: 205 and 243), T59C (SEQ ID NOS: 206 and 244), G60C (SEQ ID NOS: 207 and 245), K62C (SEQ ID S 208 and 246), G64C (SEQ ID NOS: 209 and 247), T68C (SEQ ID NOS: 210 and 248), 570C (SEQ ID NOS: 211 and 249), L88C (SEQ ID NOS: 212 and 250), S89C (SEQ ID NOS: 213 and 251), A90C (SEQ ID NOS: 214 and 252), I91C (SEQ ID NOS: 215 and 253), and T93C (SEQ ID NOS: 216 and 254). The locations of these 28 positions within the structure of the 83v2 protein are shown in FIG. 3.

EXAMPLE 6: SELECTION OF FIBRONECTIN TYPE III (FN3) DOMAINS THAT BIND C-MET AND INHIBIT HGF BINDING

Panning on Human c-Met

The TCL14 library was screened against biotinylated-human c-Met extracellular domain (bt-c-Met) to identify FN3 domains capable of specifically binding c-Met. For selections, 3 µg of TCL14 library was in vitro transcribed and translated (IVTT) in *E. Coli* S30 Linear Extract (Promega, Madison, Wis.) and the expressed library blocked with Cis Block (2% BSA (Sigma-Aldrich, St. Louis, Mo.), 100 µg/ml Herring Sperm DNA (Promega), 1 mg/mL heparin (Sigma-Aldrich)). For selections, bt-c-Met was added at concentrations of 400 nM (Round 1), 200 nM (Rounds 2 and 3) and 100 nM (Rounds 4 and 5). Bound library members were recovered using neutravidin magnetic beads (Thermo Fisher, Rockford, Ill.) (Rounds 1, 3, and 5) or streptavidin magnetic beads (Promega) (Rounds 2 and 4) and unbound library members were removed by washing the beads 5-14 times with 500 uL PBS-T followed by 2 washes with 500 µL PBS.

Additional selection rounds were performed to identify FN3 domains molecules with improved affinities. Briefly, outputs from round 5 were prepared as described above and subjected to additional iterative rounds of selection with the following changes: incubation with bt-c-Met was decreased from 1 hour to 15 minutes and bead capture was decreased from 20 minutes to 15 minutes, bt-c-Met decreased to 25 nM (Rounds 6 and 7) or 2.5 nM (Rounds 8 and 9), and an additional 1 hour wash was performed in the presence of an excess of non-biotinylated c-Met. The goal of these changes was to simultaneously select for binders with a potentially faster on-rate and a slower off-rate yielding a substantially lower $K_D$.

Rounds 5, 7 and 9 outputs were PCR cloned into a modified pET15 vector (EMD Biosciences, Gibbstown, N.J.) containing a ligase independent cloning site (pET15-LIC) using TCON6 (SEQ ID No. 30) and TCON5 E86I short (SEQ ID No. 31) primers, and the proteins were expressed as C-terminal His6-tagged proteins after transformations and IPTG induction (1 mM final, 30° C. for 16 hours) using standard protocols. The cells were harvested by centrifugation and subsequently lysed with Bugbuster HT (EMD Biosciences) supplemented with 0.2 mg/mL Chicken Egg White Lysozyme (Sigma-Aldrich). The bacterial lysates were clarified by centrifugation and the supernatants were transferred to new 96 deep-well plates.

Screening for FN3 Domains that Inhibit HGF Binding to c-Met

FN3 domains present in *E. coli* lysates were screened for their ability to inhibit HGF binding to purified c-Met extracellular domain in a biochemical format. Recombinant human c-Met Fc chimera (0.5 µg/mL in PBS, 100 µL/well) was coated on 96-well White Maxisorp Plates (Nunc) and incubated overnight at 4° C. The plates were washed two times with 300 µl/well of Tris-buffered saline with 0.05% Tween 20 (TBS-T, Sigma-Aldrich) on a Biotek plate washer. Assay plates were blocked with StartingBlock T20 (200 µL/well, Thermo Fisher Scientific, Rockland, Ill.) for 1 hour at room temperature (RT) with shaking and again washed twice with 300 µl of TBS-T. FN3 domain lysates were diluted in StartingBlock T20 (from 1:10 to 1:100,000) using the Hamilton STARplus robotics system. Lysates (50 µL/well) were incubated on assay plates for 1 hour at RT with shaking. Without washing the plates, bt-HGF (1 µg/mL in StartingBlock T20, 50 µL/well, biotinylated) was added to the plate for 30 min at RT while shaking. Control wells containing Tencon27 lysates received either Starting Block T20 or diluted bt-HGF. Plates were then washed four times with 300 µl/well of TBS-T and incubated with 100 µl/well of Streptavidin-HRP (1:2000 in TBS-T, Jackson Immunoresearch, West Grove, Pa.) for 30-40 minutes at RT with shaking. Again the plates were washed four times with TBS-T. To develop signal, POD Chemiluminescence Substrate (50 µL/well, Roche Diagnostics, Indianapolis, Ind.), prepared according to manufacturer's instructions, was added to the plate and within approximately 3 minutes luminescence was read on the Molecular Devices M5 using SoftMax Pro. Percent inhibition was determined using the following calculation: 100~((RLU$_{sample}$-Mean RLU$_{No\ bt\text{-}HGF\ control}$)/(Mean RLU$_{bt\text{-}HGF\ control}$-Mean RLU$_{no\ bt\text{-}HGF\ control}$)*100). Percent inhibition values of 50% or greater were considered hits.

High-Throughput Expression and Purification of FN3 Domains

His-tagged FN3 domains were purified from clarified *E. coli* lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

IC$_{50}$ Determination of Inhibition of HGF Binding to c-Met

Select FN3 domains were further characterized in the HGF competition assay. Dose response curves for purified FN3 domains were generated utilizing the assay described above (starting concentrations of 5 µM). Percent inhibition values were calculated. The data were plotted as % inhibition against the logarithm of FN3 domain molar concentrations and IC$_{50}$ values were determined by fitting data to a sigmoidal dose response with variable slope using GraphPad Prism 4.

35 unique sequences were identified from Round 5 to exhibit activity at dilutions of 1:10, with IC$_{50}$ values ranging from 0.5 to 1500 nM. Round 7 yielded 39 unique sequences with activity at dilutions of 1:100 and IC$_{50}$ values ranging from 0.16 to 2.9 nM. 66 unique sequences were identified from Round 9, where hits were defined as being active at dilutions of 1:1000. IC$_{50}$ values as low as 0.2 nM were observed in Round 9 (Table 13).

EXAMPLE 7: CHARACTERIZATION OF FN3 DOMAINS THAT BIND C-MET AND INHIBIT HGF BINDING

FN3 domains were expressed and purified as described above in Example 2. Size exclusion chromatography and kinetic analysis was done as described above in Examples 1 and 2, respectively. Table 12 shows the sequences of the C-strand, CD loop, F-strand, and FG loop, and a SEQ ID NO: for the entire amino acid sequence for each domain.

TABLE 12

| Clone Name | SEQ ID NO: | C loop | CD strand | F loop | FG strand |
|---|---|---|---|---|---|
| P114AR5P74-A5 | 32 | FDSFW IRYDE | VVVGGE | TEYYV NILGV | KGGSISV |
| P114AR5P75-E9 | 33 | FDSFF IRYDE | FLRSGE | TEYWV TILGV | KGGLVST |
| P114AR7P92-F3 | 34 | FDSFW IRYFE | FLGSGE | TEYIV NIMGV | KGGSISH |
| P114AR7P92-F6 | 35 | FDSFW IRYFE | FLGSGE | TEYVV NILGV | KGGGLSV |
| P114AR7P92-G8 | 36 | FDSFV IRYFE | FLGSGE | TEYVV QILGV | KGGYISI |
| P114AR7P92-H5 | 37 | FDSFW IRYLE | FLLGGE | TEYVV QIMGV | KGGTVSP |
| P114AR7P93-D11 | 38 | FDSFW IRYFE | FLGSGE | TEYVV GINGV | KGGYISY |
| P114AR7P93-G8 | 39 | FDSFW IRYFE | FLGSGE | TEYGV TINGV | KGGRVST |
| P114AR7P93-H9 | 40 | FDSFW IRYFE | FLGSGE | TEYVV QIIGV | KGGHISL |
| P114AR7P94-A3 | 41 | FDSFW IRYFE | FLGSGE | TEYVV NIMGV | KGGKISP |
| P114AR7P94-E5 | 42 | FDSFW IRYFE | FLGSGE | TEYAV NIMGV | KGGRVSV |
| P114AR7P95-B9 | 43 | FDSFW IRYFE | FLGSGE | TEYVV QILGV | KGGSISV |
| P114AR7P95-D3 | 44 | FDSFW IRYFE | FLGSGE | TEYVV NIMGV | KGGSISY |
| P114AR7P95-D4 | 45 | FDSFW IRYFE | FLGSGE | TEYVV QILGV | KGGYISI |
| P114AR7P95-E3 | 46 | FDSFW IRYFE | FLGSGE | TEYVV QIMGV | KGGTVSP |
| P114AR7P95-F10 | 47 | FDSFW IRYFE | FTTAGE | TEYVV NIMGV | KGGSISP |
| P114AR7P95-G7 | 48 | FDSFW IRYFE | LLSTGE | TEYVV NIMGV | KGGSISP |
| P114AR7P95-H8 | 49 | FDSFW IRYFE | FVSKGE | TEYVV NIMGV | KGGSISP |

C loop residues correspond to residues 28-37 of indicated SEQ ID NO:
CD strand residues correspond to residues 38-43 of indicated SEQ ID NO:
F loop residues correspond to residues 65-74 of indicated SEQ ID NO:
FG strand residues correspond to residues 75-81 of indicated SEQ ID NO:

Binding of Selected c-Met-Binding FN3 Domains to c-Met on Cells

NCI-H441 cells (Cat #HTB-174, American Type Culture Collection, Manassas, Va.) were plated at 20,000 cells per well in Poly-D-lysine coated black clear bottom 96-well plates (BD Biosciences, San Jose, Calif.) and allowed to attach overnight at 37° C., 5% CO$_2$. Purified FN3 domains (50 µL/well; 0 to 1000 nM) were added to the cells for 1 hour at 4° C. in duplicate plates. Supernatant was removed and cells were washed three times with FACS stain buffer (150 µL/well, BD Biosciences, cat #554657). Cells were incubated with biotinylated-anti HIS antibody (diluted 1:160 in FACS stain buffer, 50 µL/well, R&D Systems, cat #BAM050) for 30 minutes at 4° C. Cells were washed three times with FACS stain buffer (150 µL/well), after which wells were incubated with anti mouse IgG1-Alexa 488 conjugated antibody (diluted 1:80 in FACS stain buffer, 50 µL/well, Life Technologies, cat #A21121) for 30 minutes at 4° C. Cells were washed three times with FACS stain buffer (150 µL/well) and left in FACS stain buffer (50 µL/well). Total fluorescence was determined using an Acumen eX3 reader. Data were plotted as raw fluorescence signal against the logarithm of the FN3 domain molar concentration and fitted to a sigmoidal dose-response curve with variable slope using GraphPad Prism 4 (GraphPad Software) to calculate $EC_{50}$ values. FN3 domains were found to exhibit a range of binding activities, with $EC_{50}$ values between 1.4 and 22.0, as shown in Table 13.

Inhibition of HGF-Stimulated c-Met Phosphorylation

Purified FN3 domains were tested for their ability to inhibit HGF-stimulated phosphorylation of c-Met in NCI-H441, using the c-Met phospho(Tyr1349) kit from Meso Scale Discovery (Gaithersburg, Md.). Cells were plated at 20,000/well in clear 96-well tissue culture-treated plates in 100 µL/well of RPMI medium (containing Glutamax and HEPES, Life Technologies) with 10% fetal bovine serum (FBS; Life Technologies) and allowed to attach overnight at 37° C., 5% $CO_2$. Culture medium was removed completely and cells were starved overnight in serum-free RPMI medium (100 µL/well) at 37° C., 5% $CO_2$. Cells were then replenished with fresh serum-free RPMI medium (100 µL/well) containing FN3 domains at a concentration of 20 µM and below for 1 hour at 37° C., 5% $CO_2$. Controls were treated with medium only. Cells were stimulated with 100 ng/mL recombinant human HGF (100 µL/well, R&D Systems cat #294-HGN) and incubated at 37° C., 5% $CO_2$ for 15 minutes. One set of control wells was left un-stimulated as negative controls. Medium was then completely removed and cells were lysed with Complete Lysis Buffer (50 Meso Scale Discovery) for 10 minutes at RT with shaking, as per manufacturer's instructions. Assay plates configured for measuring phosphorylated c-Met were blocked with the provided blocking solution as per the manufacturer's instructions at room temperature for 1 hour. Plates were then washed three times with Tris Wash Buffer (200 µL/well, Meso Scale Discovery). Cell lysates (30 µL/well) were transferred to assay plates, and incubated at RT with shaking for 1 hour. Assay plates were then washed four times with Tris Wash Buffer, after which ice-cold Detection Antibody Solution (25 Meso Scale Discovery) was added to each well for 1 hr at RT with shaking. Plates were again rinsed four times with Tris Wash Buffer. Signals were detected by addition of 150 Read Buffer (150 Meso Scale Discovery) and reading on a SECTOR® Imager 6000 instrument (Meso Scale Discovery) using manufacturer-installed assay-specific default settings. Data were plotted as electrochemiluminescence signal against the logarithm of FN3 domain molar concentration and $IC_{50}$ values were determined by fitting data to a sigmoidal dose response with variable slope using GraphPad Prism 4. FN3 domains were found to inhibit phosphorylated c-Met with IC50 values ranging from 4.6 to 1415 nM as shown in Table 13.

Inhibition of Human Tumor Cell Growth

Inhibition of c-Met-dependent cell growth was assessed by measuring viability of U87-MG cells (American Type Culture Collection, cat #HTB-14), following exposure to c-Met-binding FN3 domains. Cells were plated at 8000 cells per well in opaque white 96-well tissue culture-treated plates (Nunc) in 100 µL/well of RPMI medium, supplemented with 10% FBS and allowed to attach overnight at 37° C., 5% $CO_2$. Twenty-four hours after plating, medium was aspirated and cells were replenished with serum-free RPMI medium. Twenty-four hours after serum starvation, cells were treated by addition of serum-free medium containing c-Met-binding FN3 domains (30 µL/well). Cells were incubated at 37° C., 5% $CO_2$ for 72 hours. Viable cells were detected by addition of 100 µL/well of CellTiter-Glo® reagent (Promega), followed by mixing on a plate shaker for 10 minutes. Plates were read on a SpectraMax M5 plate reader (Molecular Devices) set to luminescence mode, with a read time of 0.5 seconds/well. Data were plotted as raw luminescence units (RLU) against the logarithm of FN3 domain molar concentration. $IC_{50}$ values were determined by fitting data to an equation for a sigmoidal dose response with variable slope using GraphPad Prism 4. Table 13 reports $IC_{50}$ values ranging from 1 nM to >1000 nM.

TABLE 13

Summary of biological properties of c-Met-binding FN3 domains.

| Clone | | Affinity | HGF competition | H441 Cell binding | pMet inhibition in H441 cells | Inhbibition of Proliferation of U87-MG cells |
| --- | --- | --- | --- | --- | --- | --- |
| Name | SEQ ID NO: | (Kd, nM) | IC50 (nM) | (EC50, nM) | (IC50, nM) | (IC50, nM) |
| P114AR5P74-A5 | 32 | 10.1 | 5.2 | 18.7 | 1078 | 464.4 |
| P114AR5P75-E9 | 33 | 45.8 | 51.9 | ND | 1415 | 1193.9 |
| P114AR7P92-F3 | 34 | 0.4 | 0.2 | 1.5 | 8.3 | 2.7 |
| P114AR7P92-F6 | 35 | 3.1 | 2.2 | 4.9 | 165.3 | 350.5 |
| P114AR7P92-G8 | 36 | 1.0 | 1.6 | 5.9 | 155.3 | 123.9 |
| P114AR7P92-H5 | 37 | 11.6 | ND | 22.0 | 766.4 | 672.3 |
| P114AR7P93-D11 | 38 | ND | ND | 2.3 | 16 | 14.4 |
| P114AR7P93-G8 | 39 | 6.9 | 1 | 3.8 | 459.5 | 103.5 |
| P114AR7P93-H9 | 40 | 3.3 | 2.9 | 12.9 | 288.2 | 269.9 |
| P114AR7P94-A3 | 41 | 0.4 | 0.2 | 1.4 | 5 | 9.3 |
| P114AR7P94-E5 | 42 | 4.2 | 0.7 | 3.4 | 124.3 | 195.6 |
| P114AR7P95-B9 | 43 | 0.5 | 0.3 | ND | 9.8 | 17.4 |
| P114AR7P95-D3 | 44 | 0.3 | 0.2 | 1.5 | 4.6 | 1.7 |
| P114AR7P95-D4 | 45 | 0.4 | ND | 1.4 | 19.5 | 19.4 |
| P114AR7P95-E3 | 46 | 1.5 | ND | 3.2 | 204.6 | 209.2 |
| P114AR7P95-F10 | 47 | 4.2 | 1.4 | 4.4 | 187.6 | 129.7 |
| P114AR7P95-G7 | 48 | 20.0 | ND | 11.3 | 659.3 | 692 |
| P114AR7P95-H8 | 49 | 3.7 | ND | 4.1 | 209.8 | 280.7 |

Thermal Stability of c-Met-Binding FN3 Domains
Differential Scanning Calorimetry in PBS was Used to Assess the Stability of Each FN3 Domain.
Results of the Experiment are Shown in Table 14.

TABLE 14

| Clone | | Thermal Stability |
|---|---|---|
| Name | SEQ ID NO: | (Tm, C) |
| P114AR5P74-A5 | 32 | 74.1 |
| P114AR5P75-E9 | 33 | ND |
| P114AR7P92-F3 | 34 | 81.5 |
| P114AR7P92-F6 | 35 | 76.8 |
| P114AR7P92-G8 | 36 | 90.9 |
| P114AR7P92-H5 | 37 | 87 |
| P114AR7P93-D11 | 38 | ND |
| P114AR7P93-G8 | 39 | 76.8 |
| P114AR7P93-H9 | 40 | 88.2 |
| P114AR7P94-A3 | 41 | 86.2 |
| P114AR7P94-E5 | 42 | 80 |
| P114AR7P95-B9 | 43 | 86.3 |
| P114AR7P95-D3 | 44 | 82 |
| P114AR7P95-D4 | 45 | 85.3 |
| P114AR7P95-E3 | 46 | 94.2 |
| P114AR7P95-F10 | 47 | 85.2 |
| P114AR7P95-G7 | 48 | 87.2 |
| P114AR7P95-H8 | 49 | 83 |

EXAMPLE 8. GENERATION AND CHARACTERIZATION OF BISPECIFIC ANTI-EGFR/C-MET MOLECULES

Generation of Bispecific EGFR/c-Met Molecules

Numerous combinations of the EGFR and c-Met-binding FN3 domains described in Examples 1-6 were joined into bispecific molecules capable of binding to both EGFR and c-Met. Additionally, EGFR-binding FN3 domains having amino acid sequences shown in SEQ ID NOs: 107-110 and c-Met binding FN3 domains having amino acid sequences shown in SEQ ID NOs: 111-114 were made and joined into bispecific molecules. Synthetic genes were created to encode for the amino acid sequences described in SEQ ID No. 50-72 and 106 (Table 15) such that the following format was maintained: EGFR-binding FN3 domain followed by a peptide linker followed by a c-Met-binding FN3 domain. A poly-histidine tag was incorporated at the C-terminus to aid purification. In addition to those molecules described in Table 15, the linker between the two FN3 domains was varied according to length, sequence composition and structure according to those listed in Table 16. It is envisioned that a number of other linkers could be used to link such FN3 domains Bispecific EGFR/c-Met molecules were expressed and purified from *E. coli* as described for monospecific EGFR or c-Met FN3 domains using IMAC and gel filtration chromatography steps.

TABLE 15

| Bispecifcic EGFR/c-Met molecule | | EGFR-binding FN3 comain | | cMET-binding FN3 domain | | Linker | |
|---|---|---|---|---|---|---|---|
| Clone ID | SEQ ID | Clone ID | SEQ ID | Clone ID | SEQ ID | Sequence | SEQ ID |
| ECB1 | 50 | P54AR4-83v2 | 27 | P114AR5P74-A5 | 32 | (GGGGS)$_4$ | 79 |
| ECB2 | 51 | P54AR4-83v2 | 27 | P114AR7P94-A3 | 41 | (GGGGS)$_4$ | 79 |
| ECB3 | 52 | P54AR4-83v2 | 27 | P114AR7P93-H9 | 40 | (GGGGS)$_4$ | 79 |
| ECB4 | 53 | P54AR4-83v2 | 27 | P114AR5P75-E9 | 33 | (GGGGS)$_4$ | 79 |
| ECB5 | 54 | P53A1R5-17v2 | 107 | P114AR7P94-A3 | 41 | (GGGGS)$_4$ | 79 |
| ECB6 | 55 | P53A1R5-17v2 | 107 | P114AR7P93-H9 | 40 | (GGGGS)$_4$ | 79 |
| ECB7 | 56 | P53A1R5-17v2 | 107 | P114AR5P75-E9 | 33 | (GGGGS)$_4$ | 79 |
| ECB15 | 57 | P54AR4-83v2 | 27 | P114AR7P94-A3 | 41 | (AP)$_5$ | 81 |
| ECB27 | 58 | P54AR4-83v2 | 27 | P114AR5P74-A5 | 32 | (AP)$_5$ | 81 |
| ECB60 | 59 | P53A1R5-17v2 | 107 | P114AR7P94-A3 | 41 | (AP)$_5$ | 81 |
| ECB37 | 60 | P53A1R5-17v2 | 107 | P114AR5P74-A5 | 32 | (AP)$_5$ | 81 |
| ECB94 | 61 | P54AR4-83v22 | 108 | P114AR7P94-A3v22 | 111 | (AP)$_5$ | 81 |
| ECB95 | 62 | P54AR4-83v22 | 108 | P114AR9P121-A6v2 | 112 | (AP)$_5$ | 81 |
| ECB96 | 63 | P54AR4-83v22 | 108 | P114AR9P122-A7v2 | 113 | (AP)$_5$ | 81 |
| ECB97 | 64 | P54AR4-83v22 | 108 | P114AR7P95-C5v2 | 114 | (AP)$_5$ | 81 |
| ECB106 | 65 | P54AR4-83v23 | 109 | P114AR7P94-A3v22 | 111 | (AP)$_5$ | 81 |
| ECB107 | 66 | P54AR4-83v23 | 109 | P114AR9P121-A6v2 | 112 | (AP)$_5$ | 81 |
| ECB108 | 67 | P54AR4-83v23 | 109 | P114AR9P122-A7v2 | 113 | (AP)$_5$ | 81 |
| ECB109 | 68 | P54AR4-83v23 | 109 | P114AR7P95-C5v2 | 114 | (AP)$_5$ | 81 |
| ECB118 | 69 | P53A1R5-17v22 | 110 | P114AR7P94-A3v22 | 111 | (AP)$_5$ | 81 |

TABLE 15-continued

| Bispecifcic EGFR/c-Met molecule | | EGFR-binding FN3 comain | | cMET-binding FN3 domain | | Linker | |
|---|---|---|---|---|---|---|---|
| Clone ID | SEQ ID | Clone ID | SEQ ID | Clone ID | SEQ ID | Sequence | SEQ ID |
| ECB119 | 70 | P53A1R5-17v22 | 110 | P114AR9P121-A6v2 | 112 | (AP)$_5$ | 81 |
| ECB120 | 71 | P53A1R5-17v22 | 110 | P114AR9P122-A7v2 | 113 | (AP)$_5$ | 81 |
| ECB121 | 72 | P53A1R5-17v22 | 110 | P114AR7P95-C5v2 | 114 | (AP)$_5$ | 81 |
| ECB91 | 106 | P54AR4-83v22 | 108 | P114AR7P95-C5v2 | 114 | (AP)$_5$ | 81 |
| ECB18 | 118 | P54AR4-83v2 | 27 | P114AR5P74-A5 | 32 | (AP)$_5$ | 81 |
| ECB28 | 119 | P53A1R5-17v2 | 107 | P114AR5P74-A5 | 32 | (AP)$_5$ | 81 |
| ECB38 | 120 | P54AR4-83v2 | 27 | P114AR7P94-A3 | 41 | (AP)$_5$ | 81 |
| ECB39 | 121 | P53A1R5-17v2 | 107 | P114AR7P94-A3 | 41 | (AP)$_5$ | 81 |

TABLE 16

| Linker | SEQ ID NO: | Linker ength in amino acids | Structure |
|---|---|---|---|
| GS | 78 | 2 | Disordered |
| GGGGS | 105 | 5 | Disordered |
| (GGGGS)$_4$ | 79 | 20 | Disordered |
| (AP)$_2$ | 80 | 4 | Rigid |
| (AP)$_5$ | 81 | 5 | Rigid |
| (AP)$_{10}$ | 82 | 20 | Rigid |
| (AP)$_{20}$ | 83 | 40 | Rigid |
| A(EAAAK)$_5$AAA | 84 | 29 | α-helical |

Bispecific EGFR/c-Met Molecules Enhance Potency Compared to Monospecific Molecules Alone, Suggesting Avidity NCI-H292 cells were plated in 96 well plates in RPMI medium containing 10% FBS. 24 hours later, medium was replaced with serum free RPMI. 24 hours after serum starvation, cells were treated with varying concentrations of FN3 domains: either a high affinity monospecific EGFR FN3 domain (P54AR4-83v2), a weak affinity monospecific c-Met FN3 domain (P114AR5P74-A5), the mixture of the two monospecific EGFR and c-Met FN3 domains, or a bispecific EGFR/c-Met molecules comprised of the low affinity c-Met FN3 domain linked to the high affinity EGFR FN3 domain (ECB1). Cells were treated for 1 h with the monosopecific or bispecific molecules and then stimulated with EGF, HGF, or a combination of EGF and HGF for 15 minutes at 37° C., 5% CO$_2$. Cells were lysed with MSD Lysis Buffer and cell signaling was assessed using appropriate MSD Assay plates, according to manufacturer's instructions, as described above.

Figure 6:
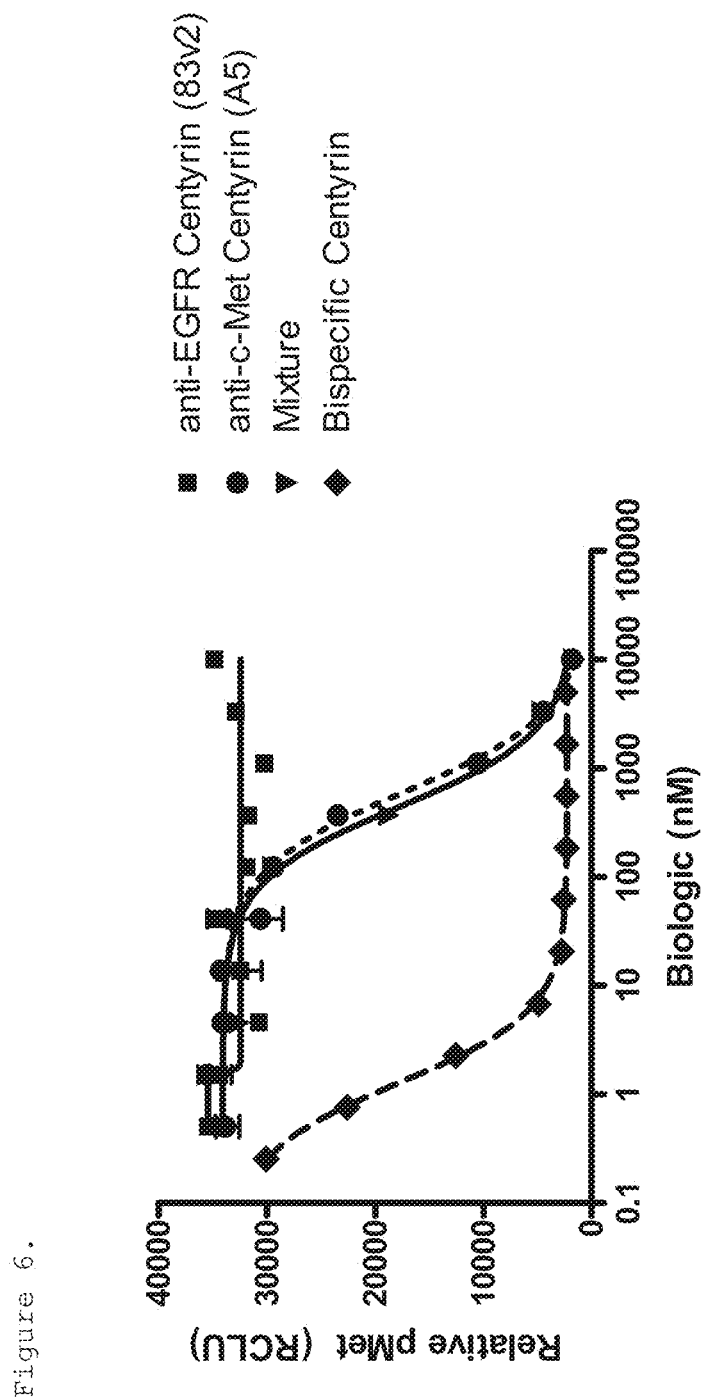
FIG. 6. Inhibition of c-Met phosphorylation in H292 cells pre-treated with monospecific or bispecific FN3 domain containing molecules and stimulated with HGF is shown. Substantial increase in the potency of the bispecific EGFR/c-Met molecule (ECB1) was observed when compared to a monospecific c-Met-binding FN3 domain (P114AR5P74-A5, shown as A5 in the Figure) on its own or in combination with an EGFR-binding FN3 domain (P54AR4-83v2, shown as 83v2 in the Figure).

The low affinity c-Met FN3 domain inhibited phosphorylation of c-Met with an IC$_{50}$ of 610 nM (FIG. 6). As expected the EGFR FN3 domain was not able to inhibit c-Met phosphorylation and the mixture of the mono-specific molecules looked identical to the c-Met FN3 domain alone. However, the bi-specific EGFR/c-Met molecule inhibited phosphorylation of c-Met with an IC$_{50}$ of 1 nM (FIG. 6), providing more than a 2-log shift in improving potency relative to the c-Met monospecific alone.

Figure 7:
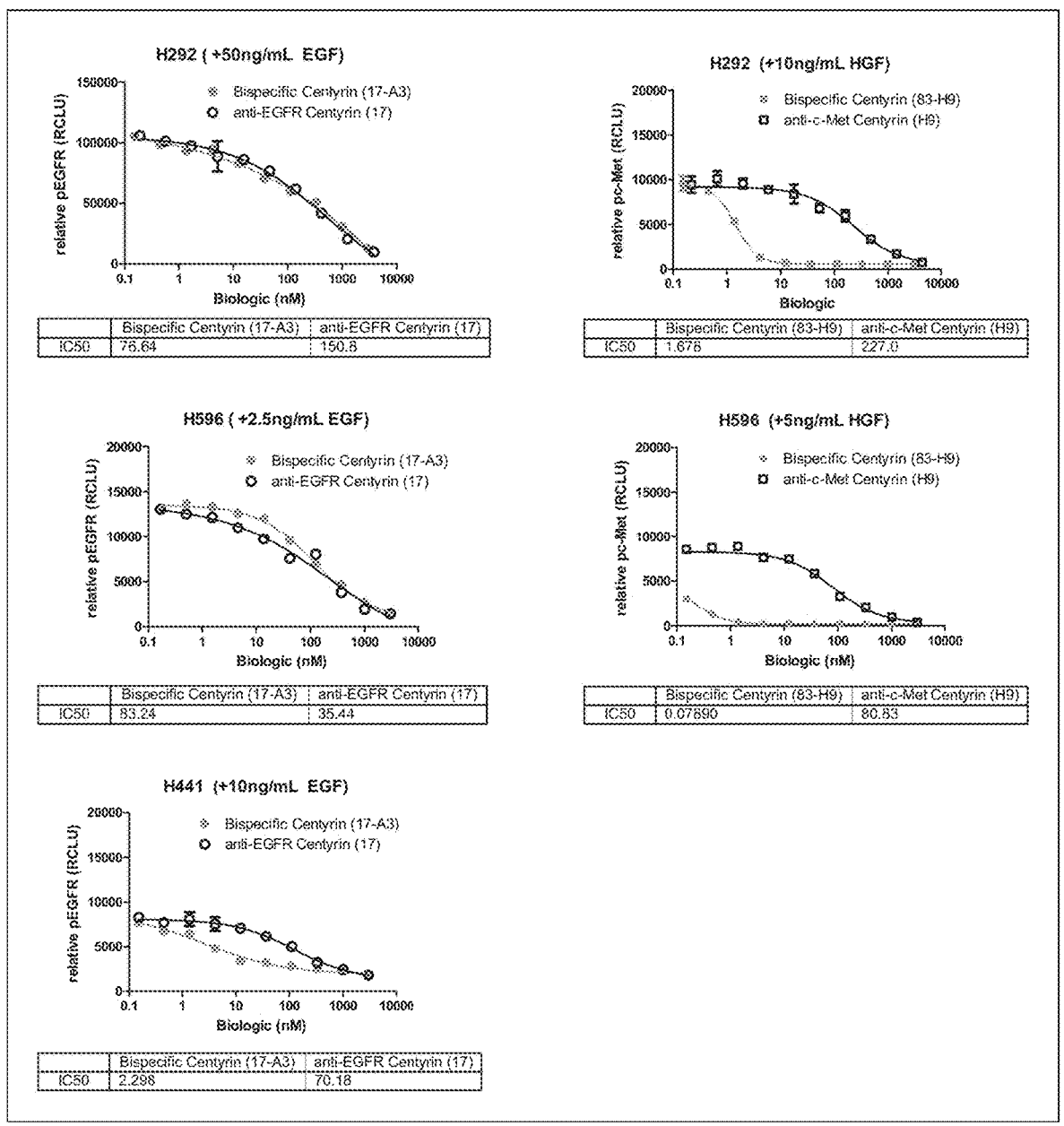
FIG. 7. Inhibition of EGFR and c-Met phosphorylation in cells pre-treated with monospecific or bispecific FN3 domain containing molecules. In cell lines expressing high levels of EGFR, H292 (A) and H596 (B), anti-EGFR monospecific and bispecific FN3 domain containing molecules are equally potent at decreasing EGFR phosphorylation. In cell lines expressing low levels of EGFR relative to c-Met, H441 (C), bispecific EGFR/c-Met molecules improve the potency for inhibition of EGFR phosphorylation compared to the monospecific EGFR-binding FN3 domain alone. In cell lines with low levels of c-Met, relative to EGFR, H292 (D) and H596 (E), inhibition of c-Met phosphorylation is significantly potentiated with bispecific EGFR/c-Met molecule, compared to monospecific c-Met-binding FN3 domain only. Molecules used in the study were: bispecific ECB5 (shown as 17-A3 in the Figure), monospecific EGFR-binding FN3 domain P53A1R5-17 (shown as "17" in the Figure), bispecific EGFR/c-Met molecule ECB3 (shown as 83-H9 in the Figure), and monospecific c-Met binding FN3 domain P114AR7P93-H9 (shown as H9 in the Figure).
Figure 8:
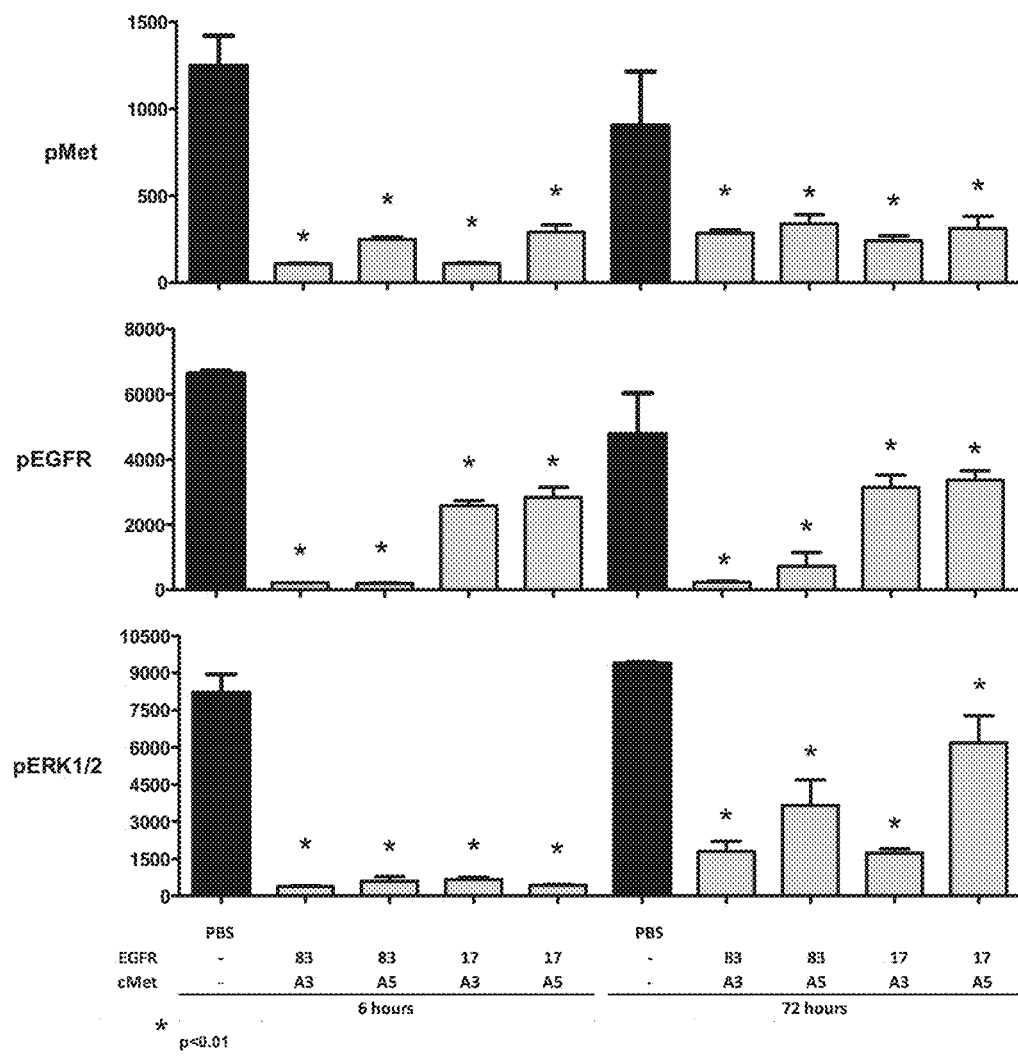
FIG. 8. Pharmacodynamic signaling in tumors isolated from mice dosed with bispecific EGFR/c-Met molecules for 6 h or 72 h is shown. All molecules significantly reduced c-Met, EGFR and ERK phosphorylation at both 6 h and 72 h, the degree if inhibition was dependent on the affinity of the FN3 domains to EGFR and/or c-Met. Bispecific molecules were generated by joining EGFR-binding FN3 domain with a high (83 is p54AR4-83v2) or medium ("17v2" in the Figure is P53A1R5-17v2) affinity to a c-Met-binding FN3 domain with high ("A3" in the Figure is P114AR7P94-A3) or medium ("A5" in the Figure is P114AR5P74-A5) affinity.

The potential for the bispecific EGFR/c-Met molecule to enhance the inhibition of c-Met and/or EGFR phosphorylation through an avidity effect was evaluated in multiple cell types with variable c-Met and EGFR densities and ratios (FIG. 7). NCI-H292, NCI-H441, or NCI-H596 cells were plated in 96 well plates in RPMI medium containing 10% FBS. 24 hours later, medium was replaced with serum free RPMI. 24 hours after serum starvation, cells were treated with varying concentrations of either monospecific EGFR-binding FN3 domain, monospecific c-Met FN3 domain, or a bispecific EGFR/c-Met molecule (ECB5, comprised of P53A1R5-17v2 and P114AR7P94-A3). Cells were treated for 1 h with the monospecific or bispecific molecules and then stimulated with EGF, HGF, or a combination of EGF and HGF for 15 minutes at 37° C., 5% CO$_2$. Cells were lysed with MSD Lysis Buffer and cell signaling was assessed using appropriate MSD Assay plates, according to manufacturer's instructions, as described above.

FIG. 7 (A-C) shows the inhibition of EGFR using a monospecific EGFR-binding FN3 domain compared to a bispecific EGFR/cMet molecule in three different cell lines. To assess avidity in an EGFR phosphorylation assay, a medium affinity EGFR-binding FN3 domain (1.9 nM) (P53A1R5-17v2) was compared to a bispecific EGFR/c-Met molecule containing the same EGFR-binding FN3 domain linked to a high-affinity c-Met-binding FN3 domain (0.4 nM) (P114AR7P94-A3). In H292 and H596 cells, inhibition of phosphorylation of EGFR was comparable for the monospecific and bispecific molecules (FIGS. 7A and 7B), likely because these cell lines have a high ratio of EGFR to c-Met receptors. To test this theory, inhibition of EGFR phosphorylation was evaluated in NCI-H441 cells which exhibit more c-Met receptors than EGFR. Treatment of NCI-H441 cells with the bispecific EGFR/c-Met molecule decreased the IC$_{50}$ for inhibition of EGFR phosphorylation compared to the monospecific EGFR-binding FN3 domain by 30-fold (FIG. 7C).

The potential for enhanced potency with a bi-specific EGFR/c-Met molecule was evaluated in a c-Met phosphorylation assay using a molecule with a high affinity to EGFR (0.26 nM) and medium affinity to c-Met (10.1 nM). In both NCI-H292 and NCI-H596 cells, the inhibition of phosphorylation of c-Met was enhanced with the bispecific molecule compared to the monospecific c-Met-binding FN3 domain, by 134 and 1012 fold, respectively (FIGS. 7D and 7E).

It was verified that the enhanced potency for inhibition of EGFR and c-Met phosphorylation with the bispecific EGFR/c-Met molecules translated into an enhanced inhibition of signaling and proliferation. For these experiments, the mixture of FN3 EGFR-binding and c-Met-binding FN3 domains was compared to a bispecific EGFR/c-Met molecule. As described in Tables 17 and 18, the $IC_{50}$ values for ERK phosphorylation (Table 17) and proliferation of H292 cells (Table 18) were decreased when cells were treated with the bispecific EGFR/c-Met molecule compared to the mixture of the monospecific binders. The $IC_{50}$ for inhibition of ERK phosphorylation for the bi-specific EGFR/c-Met molecule was 143-fold lower relative to the mixture of the two monospecific EGFR and c-Met FN3 domains, showing the effect of avidity to the potency of the molecules in this assay. In Table 17, the monospecific EGFR- and c-Met binding FN3 domains do not fully inhibit activity and therefore the $IC_{50}$ values shown should be considered lower limits. The proliferation assay was completed using different combinations EGFR and c-Met binding FN3 domains either as a mixture or linked in a bispecific format. The $IC_{50}$ for inhibition of proliferation for the bispecific EGFR/c-Met molecule was 34-236-fold lower relative to the mixture of the monospecific parent EGFR or c-Met binding FN3 domains. This confirmed that the avidity effect observed at the level of the receptors (FIG. 6 and FIG. 7) translates into an improvement in inhibiting cell signaling (Table 17) and cell proliferation (Table 18).

TABLE 17

| Specificity of the FN3-domain molecule | Clone # | Type | IC50 (nM) (ERK phosphorylation) |
|---|---|---|---|
| EGFR | P54AR4-83v2 | monospecific | >10,000 |
| c-Met | P114AR5P74-A5 | monospecific | 2366 |
| EGFR or c-Met | P54AR4-83v2 + P114AR5P74-A5 | mixture of monospecific molecules | 798.4 |
| EGFR and c-Met | ECB1 | bispecific | 5.6 |

TABLE 18

| EGFR-binding FN3 domain (affinity) | c-Met binding FN3 domain (affinity) | IC50 for mixture of monospecifics (nM) | IC50 for bispecific (nM) | Fold increase in IC50 for bispecific/ mixture of monospecifics |
|---|---|---|---|---|
| P54AR4-83v2 (0.26 nM) | P114ARP94-A3 (0.4 nM) | 36.5 | 1.04 | 35 |
| P54AR4-83v2 (0.26 nM) | P114AR7P93-H9 (3.3 nM) | 274.5 | 8.05 | 34 |
| P54AR4-83v2 (0.26 nM) | P114AR5P74-A5 (10.1 nM) | 1719 | 7.29 | 236 |

In Vivo Tumor Xenografts: PK/PD

In order to determine efficacy of the monospecific and bispecific FN3 domain molecules in vivo, tumor cells were engineered to secrete human HGF (murine HGF does not bind to human HGF). Human HGF was stably expressed in NCI-H292 cells using lentiviral infection (Lentiviral DNA vector expressing human HGF (Accession #X16322) and lentiviral packaging kit from Genecopoeia). After infection, HGF-expressing cells were selected with 4 μg/mL puromycin (Invitrogen). Human HGF protein was detected in the conditioned medium of pooled cells using assay plates from MesoScale Discovery.

SCID Beige mice were subcutaneously inoculated with NCI-H292 cells expressing human HGF ($2.0 \times 10^6$ cells in Cultrex (Trevigen) in a volume of 200 μL) on the dorsal flank of each animal. Tumor measurements were taken twice weekly until tumor volumes ranged between 150-250 $mm^3$. Mice were then given a single IP dose of bispecific EGFR/c-Met molecules (linked to an albumin binding domain to increase half-life) or PBS vehicle. At 6 h or 72 h after dosing, tumors were extracted and immediately frozen in liquid nitrogen. Blood samples were collected via cardiac puncture into 3.8% citrate containing protease inhibitors. Immediately after collection, the blood samples were centrifuged and the resulting plasma was transferred to sample tubes and stored at —80° C. Tumors were weighed, cut into small pieces, and lysed in Lysing Matrix A tubes (LMA) containing RIPA buffer with HALT protease/phosphatase inhibitors (Pierce), 50 mM sodium fluoride (Sigma), 2 mM activated sodium orthovanadate (Sigma), and 1 mM PMSF (MesoScale Discovery). Lysates were removed from LMA matrix and centrifuged to remove insoluble protein. The soluble tumor protein was quantified with a BCA protein assay and diluted to equivalent protein levels in tumor lysis buffer. Phosphorylated c-Met, EGFR and ERK were measured using assay plates from MesoScale Discovery (according to Manufacturer's protocol and as described above).

FIG. 6 shows the results of the experiments. Each bispecific EGFR/c-Met molecule significantly reduced the levels of phosphorylated c-Met, EGFR, and ERK at both 6 h and 72 h. The data presented in FIG. 6 show the importance of inhibiting both c-Met and EGFR simultaneously and how the affinity of the bispecific EGFR/c-Met molecule for each receptor plays a role in inhibition of downstream ERK. The molecules containing the high affinity EGFR-binding FN3 domains (P54AR4-83v2; shown as "8" in the Figure, $K_D$=0.26 nM) inhibited phosphorylation of EGFR to a larger extent compared to those containing the medium affinity EGFR-binding FN3 domains (P53A1R5-17v2; shown as "17" in the figure $K_D$=1.9 nM) at both 6 h and 72 h. All four bispecific molecules tested completely inhibited phosphorylation of ERK at the 6 hour time point, regardless of affinity. At the 72 hour time point, the molecules containing the tight affinity c-Met-binding domain (P114AR7P94-A3; shown as "A3" in the figure $K_D$=0.4 nM) significantly inhibited phosphorylation of ERK compared to the medium affinity c-Met-binding FN3 domain (P114AR5P74-A5; shown as "A5" in the Figure; $K_D$=10.1 nM; FIG. 6).

Figure 9:
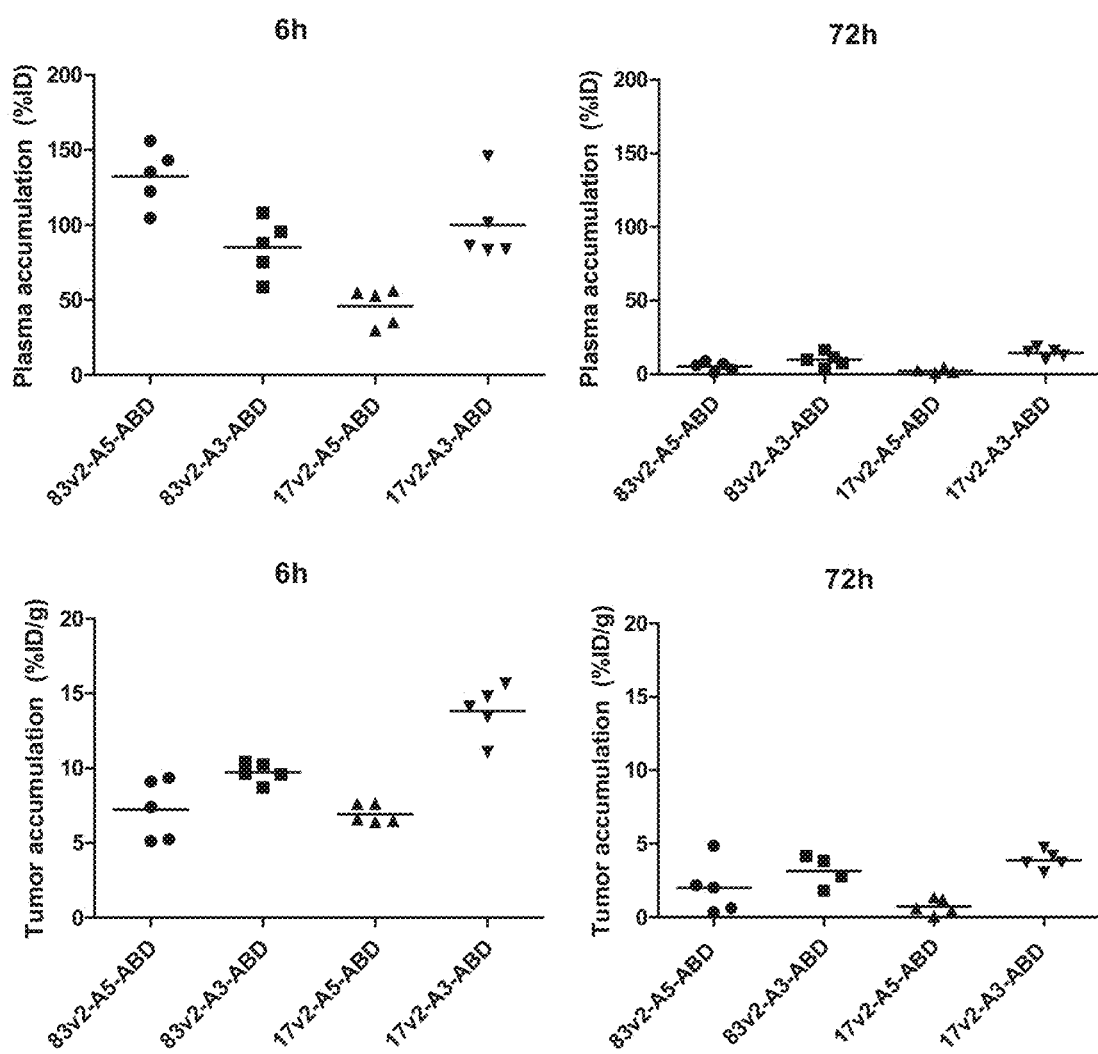
FIG. 9: Plasma (top) and tumor (bottom) accumulation of bispecific EGFR/cMet molecules of variable affinities linked to an albumin binding domain (ABD) are shown 6 h (left) and 72 h (right) after IP dosing. Six hours after dosing, tumor accumulation is maximal in mice dosed with a bispecific molecule harboring a medium affinity EGFR-binding FN3 domain (17v2) and high affinity c-Met binding domain (83v2). The bispecific molecules incorporated high or medium affinity EGFR or c-Met binding FN3 domains as follows: 83v2-A5-ABD (ECB18; high/medium for EGFR/cMet) 83v2-A3-ABD (ECB38; high/high) 17v2-A5 (ECB28; medium/medium) 17v2-A3-ABD (ECB39; medium/high). 83v2 refers to p54AR4-83v2; 17v2 refers to p53A1R5-17v2; A3 refers to p114AR7P94-A3; A5 refers to p114AR5P74-A5.

The concentration of each bispecific EGFR/c-Met molecule was measured at 6 and 72 hours after dosing in the blood and in the tumor (FIG. 9). Interestingly, the bispecific molecule with the medium affinity EGFR-binding domain (P53A1R5-17v2; $K_D$=1.9 nM) but high affinity c-Met-binding FN3 domain (P114AR7P94-A3; $K_D$=0.4 nM) had significantly more tumor accumulation at 6 hours relative to the other molecules, while the difference is diminished by 72 hours. It can be hypothesized that cells outside the tumor have lower levels of both EGFR and c-Met surface expression and therefore the medium affinity EGFR molecule doesn't bind to normal tissue as tightly compared to the higher affinity EGFR-binding FN3 domain. Therefore there is more free medium affinity EGFR-binding FN3 domain available to bind in the tumor. Therefore, identifying the appropriate affinities to each receptor may allow for identification of a therapeutic with decreased systemic toxicities and increased tumor accumulation.

Tumor Efficacy Studies with Bispecific EGFR/c-Met Molecules

Figure 10:
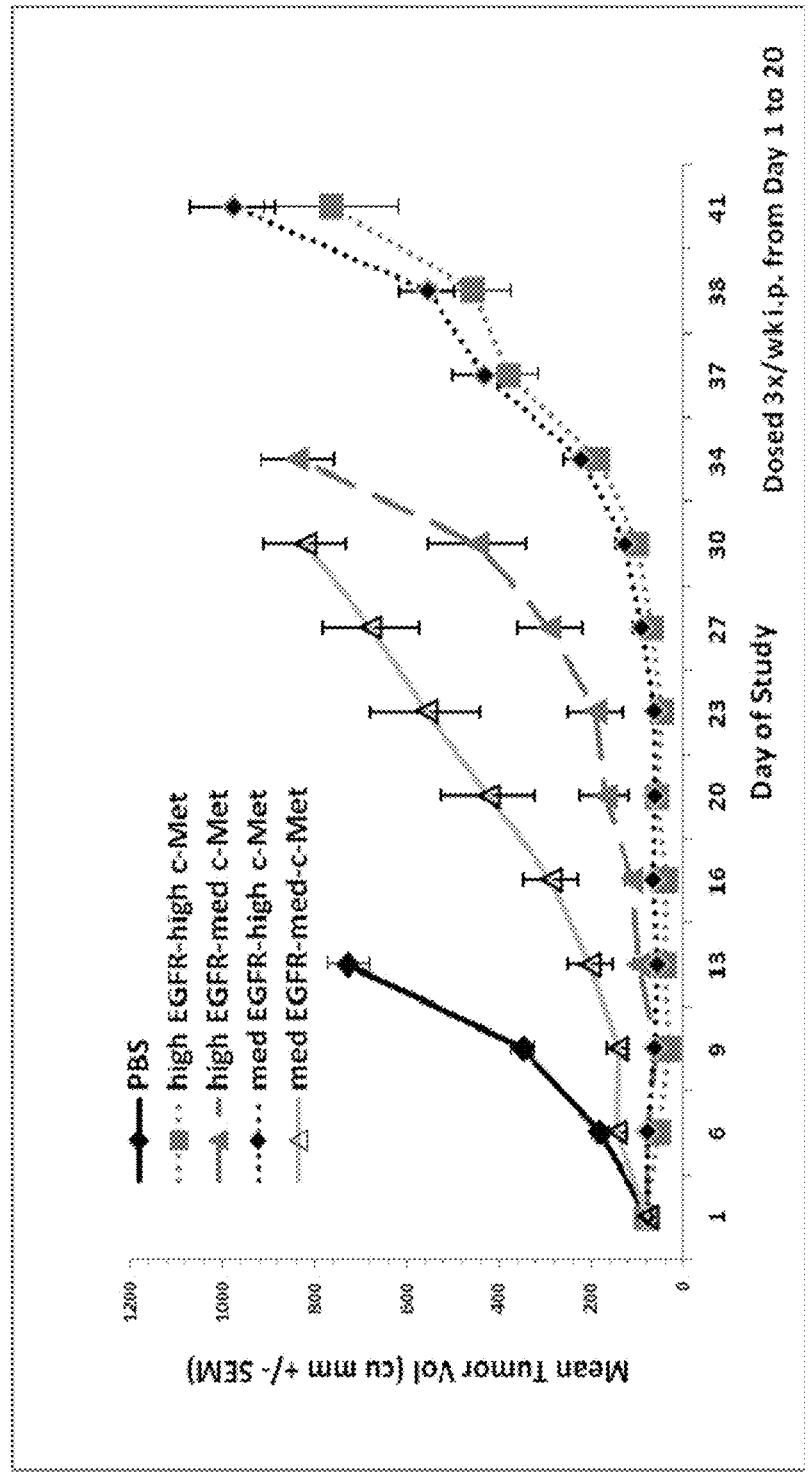
FIG. 10. H292-HGF tumor xenografts were implanted into SCID beige mice. When tumors reached an average volume of approximately 80 mm³, mice were dosed three times per week with bispecific EGFR/c-Met molecules (25 mg/kg) or PBS vehicle. All bispecific molecules reduced tumor growth, the tumor growth inhibition (TGI) being dependent on the affinities of the molecules for c-Met and EGFR. (high EGFR-high cMet refers to p54AR4-83v2-p114AR7P94-A3 (ECB38); high EGFR-med cMet refers to p54AR4-83v2-p114AR5P74-A5 (ECB18); med EGFR-high cMet refers to p53A1R5-17v2-p114AR7P94-A3 (ECB39); med EGFR-med-cMet refers to p53A1R5-17-p114AR5P74-A 5 (ECB28)).

SCID Beige mice were subcutaneously inoculated with NCI-H292 cells expressing human HGF ($2.0 \times 10^6$ cells in Cultrex (Trevigen) in 200 µL) in the dorsal flank of each animal. One week after implantation, mice were stratified into groups with equivalent tumor volumes (mean tumor volume=77.9+/−1.7 mm$^3$). Mice were dosed three times per week with the bispecific molecules and tumor volumes were recorded twice weekly. Tumor growth inhibition (TGI) was observed with four different bispecific molecules, with variable affinities for c-Met and EGFR. FIG. 10 shows the benefit of inhibiting both c-Met and EGFR as a delay in tumor growth was observed in the mice treated with molecules containing the high affinity EGFR-binding FN3 domain compared to the medium affinity EGFR-binding FN3 domain when the c-Met-binding FN3 domain was medium affinity (open vs. closed triangles, P54AR4-83v2-P114AR5P74-A5 compared to P53A1R5-17-P114AR5P74-A5). In addition, the data shows the importance of having a high affinity c-Met-binding FN3 domain as bispecific molecules containing either the high or medium affinity EGFR-binding FN3 domain but high affinity c-Met-binding FN3 domain showed the most efficacy (dotted gray and black lines, P54AR4-83v2-P114AR7P94-A3 and P53A1R5-17v2-P114AR7P94-A3).

Efficacy of Bispecfic Molecule and Other Inhibitors of EGFR and c-Met

Figure 11:
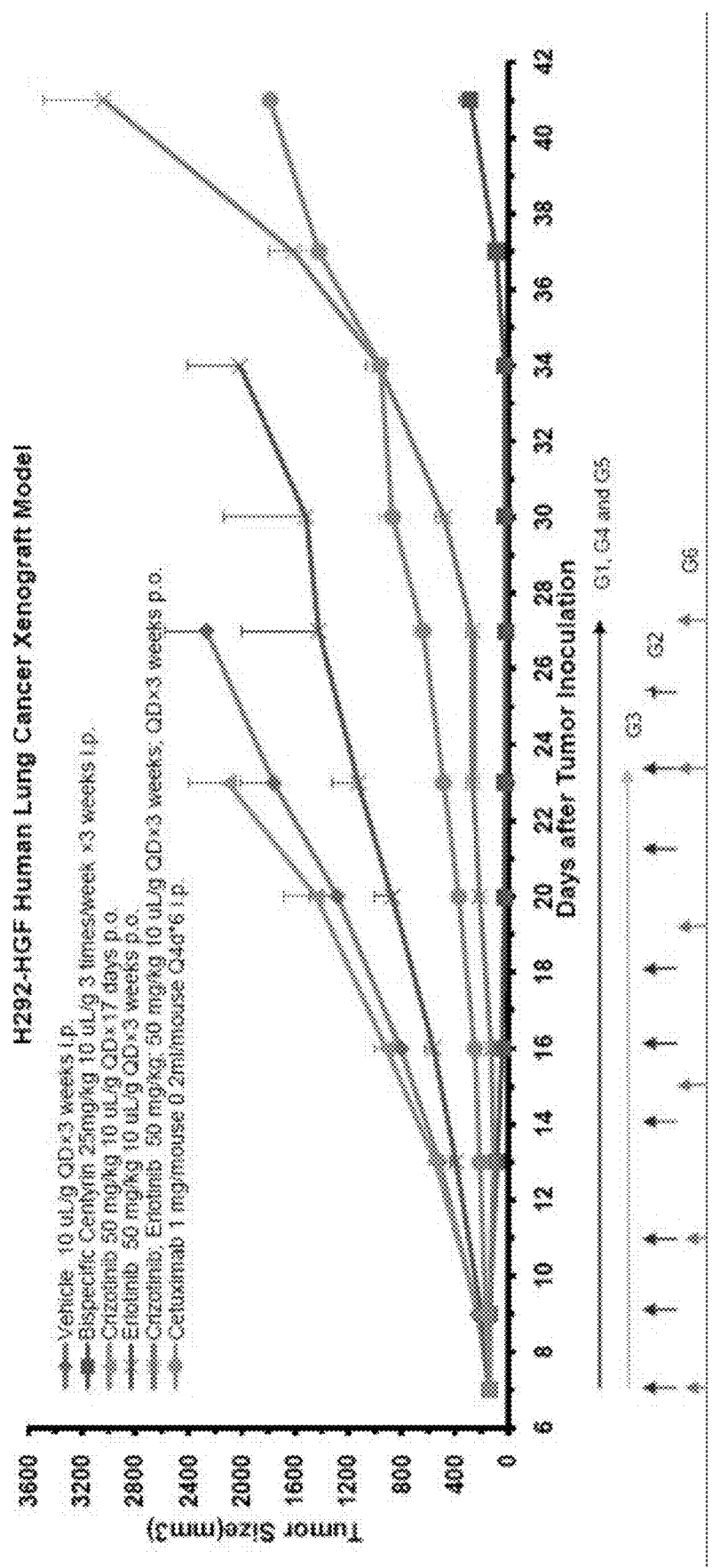
FIG. 11. H292-HGF tumor xenografts were implanted into SCID beige mice and they were treated with different therapies. The anti-tumor activity of the therapies is shown.

The in vivo therapeutic efficacies of a bispecific EGFR/c-Met molecule (ECB38) and the small molecule inhibitors crizotinib (c-Met inhibitor) and erlotinib (EGFR inhibitor), cetuximab (anti-EGFR antibody), each as a single agent, and the combination of crizotnib and erlontinib, were evaluated in the treatment of subcutaneous H292-HGF human lung cancer xenograft model in SCID/Beige mice (FIG. 11).

The H292-HGF cells were maintained in vitro in RPMI1640 medium supplemented with fetal bovine serum (10% v/v), and L-glutamine (2 mM) at 37° C. in an atmosphere of 5% CO2 in air. The cells were routinely subcultured twice weekly by trypsin-EDTA treatment. The cells growing in an exponential growth phase were harvested and counted for tumor inoculation.

Each mouse was inoculated subcutaneously at the right flank region with H292-HGF tumor cells ($2 \times 10^6$) in 0.1 ml of PBS with cultrex (1:1) for tumor development. The treatments were started when the mean tumor size reached 139 mm$^3$. The test article administration and the animal numbers in each study group were shown in the following experimental design table (Table 26). The date of tumor cell inoculation was denoted as day 0.

TABLE 26

| Group | N | Treatment | Dose (mg/kg) | Dosing Route | Planned Schedule | Actual Schedule |
|---|---|---|---|---|---|---|
| 1 | 10 | Vehicle Control | 0 | i.p. | QD × 3 weeks | QD × 3 weeks |
| 2 | 10 | bispecific EGFR/c-Met molecule | 25 | i.p. | 3 times/week × 3 weeks | 3 times/week × 3 weeks |
| 3 | 10 | Crizotinib | 50 | p.o. | QD × 3 weeks | QD × 17 days |
| 4 | 10 | Erlotinib | 50 | p.o. | QD × 2 weeks | QD × 3 weeks |
| 5 | 10 | Crizotinib | 50 | p.o. | QD × 3 weeks | QD × 3 weeks |
|   |    | Erlotinib | 50 | p.o. | QD × 2 weeks | QD × 3 weeks |
| 6 | 10 | Cetuximab | 1 mg/mouse | i.p. | Q4d*6 | Q4d*6 |

N: animal number; p.o.: oral administration; i.p.: intraperitoneal injection 3 times/week: doses were given on days 1, 3 and 5 of the week.
QD: once daily Q4d: once every four days; the interval of the combination of crizotinib and erlotinib was 0.5 hrs; dosing volume was adjusted based on body weight (10 l/g); a: dosing was not given on day 14 post grouping.

Before commencement of treatment, all animals were weighed and the tumor volumes were measured. Since the tumor volume can affect the effectiveness of any given treatment, mice were assigned into groups using randomized block design based upon their tumor volumes. This ensures that all the groups are comparable at the baseline. The randomized block design was used to assign experimental animals to groups. First, the experimental animals were divided into homogeneous blocks according to their initial tumor volume. Secondly, within each block, randomization of experimental animals to treatments was conducted. Using randomized block design to assign experimental animals ensured that each animal had the same probability of being assigned to a given treatment and therefore systematic error was reduced.

At the time of routine monitoring, the animals were checked for any effects of tumor growth and treatments on normal behavior, such as mobility, visual estimation of food and water consumption, body weight gain/loss (body weights were measured twice weekly), eye/hair matting and any other abnormal effect.

The major endpoint was whether tumor growth can be delayed or tumor bearing mice can be cured. Tumor size was measured twice weekly in two dimensions using a caliper, and the volume was expressed in mm$^3$ using the formula:

$V=0.5$ a×b$^2$ where a and b are the long and short diameters of the tumor, respectively. The tumor size was then used for calculations of both T-C and T/C values. T-C was calculated with T as the time (in days) required for the mean tumor size of the treatment group to reach 1000 mm$^3$, and C was the time (in days) for the mean tumor size of the control group to reach the same size. The T/C value (in percent) was an indication of antitumor efficacy; T and C were the mean volume of the treated and control groups, respectively, on a given day. Complete tumor regression (CR) is defined as tumors that are reduced to below the limit of palpation (62.5 mm$^3$). Partial tumor regression (PR) is defined as tumors that are reduced from initial tumor volume. A minimum duration of CR or PR in 3 or more successive tumor measurements is required for a CP or PR to be considered durable.

Animals for which the body weight loss exceeded 20%, or for which the mean tumor size of the group exceeds 2000 mm$^3$ were euthanized. The study was terminated after two weeks of observation after the final dose.

Summary statistics, including mean and the standard error of the mean (SEM), are provided for the tumor volume of each group at each time point (shown in Table 19 below). Statistical analyses of difference in tumor volume among the groups were evaluated using a one-way ANOVA followed by individual comparisons using Games-Howell (equal variance not assumed). All data were analyzed using SPSS 18.0. p<0.05 was considered to be statistically significant.

TABLE 19

Tumor Sizes in Treatment Groups

| | | Tumor volume (mm$^3$)a | | | | |
|---|---|---|---|---|---|---|
| Days | Vehicle | bispecific EGFR/c-Met molecule at 25 mg/kg | Crizotinib at 50 mg/kg | Erlotinib at 50 mg/kg | Crizotinib; Erlotinib at 50 mg/kg; 50 mg/kg | Cetuximab at 1 mg/mouse |
| 7  | 139 ± 7    | 137 ± 7 | 140 ± 9    | 141 ± 8    | 139 ± 8  | 139 ± 10 |
| 9  | 230 ± 20   | 142 ± 7 | 217 ± 20   | 201 ± 19   | 134 ± 9  | 168 ± 13 |
| 13 | 516 ± 45   | 83 ± 6  | 547 ± 43   | 392 ± 46   | 109 ± 10 | 212 ± 20 |
| 16 | 808 ± 104  | 44 ± 7  | 914 ± 92   | 560 ± 70   | 127 ± 15 | 252 ± 28 |
| 20 | 1280 ± 209 | 30 ± 6  | 1438 ± 239 | 872 ± 136  | 214 ± 30 | 371 ± 48 |
| 23 | 1758 ± 259 | 23 ± 7  | 2102 ± 298 | 1122 ± 202 | 265 ± 40 | 485 ± 61 |
| 27 | 2264 ± 318 | 21 ± 5  | —          | 1419 ± 577 | 266 ± 42 | 640 ± 82 |
| 30 | —          | 23 ± 6  | —          | 1516 ± 623 | 482 ± 61 | 869 ± 100 |

The mean tumor size of the vehicle treated group (Group 1) reached 1,758 mm$^3$ at day 23 after tumor inoculation. Treatment with the bispecific EGFR/c-Met molecule at 25 mg/kg dose level (Group 2) led to complete tumor regression (CR) in all mice which were durable in >3 successive tumor measurements (average TV=23 mm$^3$, T/C value=1%, p=0.004 compared with the vehicle group at day 23).

Treatment with Crizotinib as a single agent at 50 mg/kg dose level (Group 3) showed no antitumor activity; the mean tumor size was 2,102 mm$^3$ at day 23 (T/C value=120%, p=0.944 compared with the vehicle group).

Treatment with Erlotinib as a single agent at 50 mg/kg dosing level (Group 4) showed minor antitumor activity, but no significant difference was found compared with the vehicle group; the mean tumor size was 1,122 mm$^3$ at day 23 (T/C value=64%, p=0.429 compared with the vehicle group), with 4 days of tumor growth delay at tumor size of 1,000 mm$^3$ compared with the vehicle group.

The combination of Crizotinib (50 mg/kg, Group 5) and Erlotinib (50 mg/kg, Group 5) showed significant antitumor activity; the mean tumor size was 265 mm$^3$ at day 23 (T/C=15%; p=0.008), with 17 days of tumor growth delay at tumor size of 1,000 mm$^3$ compared with the vehicle group.

Cetuximab at 1 mg/mouse dosing level as a single agent (Group 6) showed significant antitumor activities; the mean tumor size was 485 mm$^3$ at day 23 (T/C=28%; p=0.018), with 17 days of tumor growth delay at tumor size of 1,000 mm$^3$ compared with the vehicle group. FIG. 11 shows the anti-tumor activities of the various therapies.

TABLE 20

Anti-Tumor Activity

| Treatment | Tumor Size (mm$^3$)a at day 23 | T/C (%) | T-C (days) at 1000 mm$^3$ | P value |
|---|---|---|---|---|
| Vehicle | 1758 ± 259 | — | — | — |
| bispecific EGFR/c-Met molecule (25 mg/kg) | 23 ± 7 | 1 | — | 0.004 |
| Crizotinib (50 mg/kg) | 2102 ± 298 | 120 | −1 | 0.944 |
| Erlotinib (50 mg/kg) | 1122 ± 202 | 64 | 4 | 0.429 |
| Crizotinib + Erlotinib (50 mg/kg + 50 mg/kg) | 265 ± 40 | 15 | 17 | 0.008 |
| Cetuximab (1 mg/mouse) | 485 ± 61 | 28 | 17 | 0.018 |

Medium to severe body weight loss was observed in the vehicle group which might be due to the increasing tumor burden; 3 mice died and 1 mouse were euthanized when BWL>20% by day 23. Slight toxicity of the bispecific EGFR/c-Met molecule was observed in Group 2; 3 mice were euthanized when BWL>20% during the treatment period; the body weight was gradually recovered when the treatment was withdrawn during the 2 weeks of observation period. More severe body weight loss was observed in the Crizotinib or Erlotinib monotherapy group compared to the vehicle group, suggesting the treatment related toxicity. The combination of Crizotinib and Erlotinib was generally tolerated during the dosing phase, but severe body weight loss was observed at the end of the study, which might be due to the resumption of the fast tumor growth during the non-treatment period. The monotherapy of Cetuximab was well tolerated in the study; body weight loss was only observed at the end of the study due to the resume of the tumor growth.

In summary, the bispecific EGFR/c-Met molecule at 25 mg/kg (3 times/week×3 weeks) produced a complete response in H292-HGF human lung cancer xenograft model in SCID/Beige mice. The treatment was tolerated in 7 out of 10 mice, and resulted in severe body weight loss in 3 out of 10 mice. FIG. 11 and Table 20 shows the impact of the various therapies on tumor size during the time points after treatment.

EXAMPLE 9: HALF-LIFE EXTENSION OF THE BISPECIFIC EGFR/C-MET MOLECULES

Numerous methods have been described to reduce kidney filtration and thus extend the serum half-life of proteins including modification with polyethylene glycol (PEG) or other polymers, binding to albumin, fusion to protein domains which bind to albumin or other serum proteins, genetic fusion to albumin, fusion to IgG Fc domains, and fusion to long, unstructured amino acid sequences.

Bispecific EGFR/c-Met molecules were modified with PEG in order to increase the hydrodynamic radius by incorporating a free cysteine at the C-terminus of the molecule. Most commonly, the free thiol group of the cysteine residue is used to attach PEG molecules that are functionalized with maleimide or iodoacetemide groups using standard methods. Various forms of PEG can be used to modify the protein including linear PEG of 1000, 2000, 5000, 10,000, 20,000, or 40,000 kDa. Branched PEG molecules of these molecular weights can also be used for modification. PEG groups may also be attached through primary amines in the bispecific EGFR/c-Met molecules in some instances.

In addition to PEGylation, the half-life of bispecific EGFR/c-Met molecules was extended by producing these proteins as fusion molecules with a naturally occurring 3-helix bundle serum albumin binding domain (ABD) or a consensus albumin binding domain (ABDCon). These protein domains were linked to the C-terminus of the c-Met-binding FN3 domain via any of the linkers described in Table 16. The ABD or ABDCon domain may also be placed between the EGFR-binding FN3 domain and the c-Met binding FN3 domain in the primary sequence.

EXAMPLE 10: CHARACTERIZATION OF SELECT BISPECIFIC EGFR/C-MET MOLECULES

Select EGFR/c-Met molecules were characterized for their affinity to both EGFR and c-Met, their ability to inhibit EGFR and c-Met autophosphorylation, and their effect on proliferation of HGF cells. Binding affinity of the bispecific EGFR/c-Met molecules to recombinant EGFR and/or c-Met extracellular domain was further by surface Plasmon resonance methods using a Proteon Instrument (BioRad) according to protocol described in Example 3. Results of the characterization are shown in Table 21.

TABLE 21

| | $K_D$ (EGFR, nM) | $K_D$ (c-Met, nM) | pMet inhibition in H441 cells (IC50, nM) | H292 pEGFR inhibition in H292 cells (IC50, nM) | H292-HGF Proliferation inhibition in HGF-induced H292 cells (IC50, nM) |
|---|---|---|---|---|---|
| ECB15 | 0.2 | 2.6 | n/a | 4.2 | 23 |
| ECB94 | 1 | 4.3 | 53.8 | 5.1 | 29.6 |
| ECB95 | 1.1 | 6.2 | 178.8 | 13.6 | 383.4 |
| ECB96 | 1.6 | 22.1 | 835.4 | 24.7 | 9480 |
| ECB97 | 1.3 | 1.7 | 24.2 | 16.6 | 31.0 |
| ECB106 | 16.7 | 5.1 | 53.3 | 367.4 | 484.5 |
| ECB107 | 16.9 | 9 | 29.9 | 812.3 | 2637 |
| ECB108 | 15.3 | 25.5 | 126.2 | 814.4 | 11372 |
| ECB109 | 17.3 | 2.1 | 26 | 432 | 573.6 |

EXAMPLE 11: GENERATION AND CHARACTERIZATION OF CYSTEINE ENGINEERED BISPECIFIC ANTI-EGFR/C-MET MOLECULES

Generation of Bispecific EGFR/c-Met Molecules

Based on the data generated from the cysteine scanning of the P54AR4-83v2 mutant (Example 5), cysteine mutants were also designed in a bispecific anti-EGFR/c-Met molecule denoted ECB147 (SEQ ID NOS: 218 and 256), which consists of the P54AR4-83v2 (SEQ ID NO: 27), the cMet binder P114AR7P95-05v2 (SEQ ID NO: 114), and an albumin binding domain for half-life extension. These three domains are connected by (Ala-Pro)$_5$ linkers (SEQ ID NO: 81). Variants with one, two, or four cysteines were designed with substitutions at the C-terminus, in the linker regions, or at the Lys-62 position of one of the FN3 domains (SEQ ID NOS: 219-225 and 257-263). Another bispecific variant, ECB82cys (SEQ ID NOS: 226 and 264) consists of P54AR4-83v2 (SEQ ID NO: 27), P114AR7P94-A3v22 (SEQ ID NO: 111), and a variant of the albumin-binding domain, all three domains connected by AP linkers, and a single C-terminal cysteine. An additional cysteine variant of the non-targeted Tencon scaffold (SEQ ID NO: 265) was also used for the construction of control conjugates. All the variants were constructed, expressed, and purified as described in previous examples. Purity was assessed by SDS-PAGE analysis. Analytical size exclusion chromatography using a Superdex 75 5/150 column (GE Healthcare) shows that the FN3 domain preparations are free of aggregates and elute at a time consistent with a monomeric protein. Mass spectrometry determined the masses to be in agreement with the theoretical masses (Table 22).

TABLE 22

| Variant Name | Expected MW (Da) | Experimental MW (Da) |
| --- | --- | --- |
| ECB147v1 | 27895 | 27894 |
| ECB147v2 | 27838 | 27837 |
| ECB147v3 | 27877 | 27876 |
| ECB147v4 | 27895 | 27894 |
| ECB147v5 | 27813 | 27812 |
| ECB147v6 | 27838 | 27837 |
| ECB147v7 | 27927 | 27926 |
| P54AR4-83v2-cys | 11789 | 11790 |
| Tencon-cys | 10820 | |

Chemical Conjugation

To chemically conjugate the purified bispecific cysteine variants to maleimide-containing molecules, the proteins were first reduced with TCEP to generate free thiols. 1-2 mg of each bispecific cysteine variant was mixed with an excess of TCEP at neutral pH (Sigma catalog #646547) and incubated at RT for 30-60 minutes. TCEP was removed by adding 3 volumes of saturated ammonium sulfate solution (4.02 M) to precipitate the cysteine variants. After centrifugation at 16000-20000×g at 4° C. for 20 min and removal of the supernatant, the protein pellet was dissolved in PBS or sodium phosphate buffer and mixed immediately with a 5- to 10-fold excess of the maleimide-containing molecule. The reaction was incubated for 30-60 minutes at room temperature and then quenched with an excess of a free thiol, such as cysteine or β-mercaptoethanol, to scavenge excess maleimide. The unbound maleimide was removed with Zeba desalting columns (Thermo catalog #89890), by preparative SEC with a Tosoh G3000SWx1 column (#P4619-14N; 7.8 mm×30 cm; 5 µm), or by binding the cysteine variant to Ni-NTA resin, washing, and eluting essentially as described above. Conjugates were characterized by SDS-PAGE and mass spectrometry. This general method was used to conjugate bispecific cysteine variants to fluorescein maleimide (Thermo catalog #62245), PEG24-maleimide (Quanta Biodesign catalog #10319), and maleimide-cytotoxin molecules with a variety of linkers (see structures in FIG. 2).

Inhibition of EGF-Stimulated EGFR Phosphorylation

Purified bispecific PEG24-maleimide conjugates were tested for their ability to inhibit EGF-stimulated phosphorylation of EGFR in the human tumor cell line NCI-H292 (American Type Culture Collection, cat. #CRL-1848) using the EGFR phospho(Tyr1173) kit from Meso Scale Discovery (Gaithersburg, Md.) and as described in Example 3. The conjugates were compared to unmodified ECB38 (SEQID No. 109), which differs from ECB147 by two amino acids. The conjugates and ECB38 inhibited EGFR with similar $IC_{50}$ values, as shown in Table 23, demonstrating that modification at the designed sites does not significantly affect target binding.

TABLE 23

| Protein Name | $IC_{50}$ (nM) |
| --- | --- |
| ECB38 | 2.3 |
| ECB147v3-PEG24 | 1.6 |
| ECB147v5-PEG24 | 0.9 |
| ECB147v6-PEG24 | 1.4 |
| ECB147v7-PEG24 | 1.4 |

Inhibition of HGF-Stimulated c-Met Phosphorylation

Purified bispecific PEG24-maleimide conjugates were also tested for their ability to inhibit HGF-stimulated phosphorylation of c-Met in NCI-H292 cells, using the c-Met phosphor (Tyr1349) kit from Meso Scale Discovery (Gaithersburg, Md.), and as described in Example 7. The conjugates and ECB38 inhibited cMet with similar $IC_{50}$ values as shown in Table 24, demonstrating that modification at these sites does not significantly alter target binding.

TABLE 24

| Protein Name | $IC_{50}$ (nM) |
| --- | --- |
| ECB38 | 1.3 |
| ECB147v3-PEG24 | 0.5 |
| ECB147v5-PEG24 | 0.4 |
| ECB147v6-PEG24 | 0.4 |
| ECB147v7-PEG24 | 0.5 |

Cytotoxicity Assay

Conjugates consisting of ECB147 cysteine variants, 83v2-cys, or Tencon-cys linked to a cytotoxic tubulin inhibitor from the auristatin family (FIG. 2) were tested for target-dependent cytotoxicity in cancer cells. The inhibitor was linked to the cysteine-containing protein via a non-cleavable $PEG_4$ linker or an enzyme-cleavable valine-citrulline or valine-lysine linker. Cell killing was assessed by measuring viability of the EGFR-overexpressing human tumor cell lines H1573 and A431 as well as the EGFR-negative tumor cell line MDA-MB-435 following exposure to the protein-cytotoxin conjugates using the procedure described in Example 4. Table 25 reports $IC_{50}$ values obtained from analysis of either the CellTiter Glo or IncuCyte object count data at the 66, 72, or 90 hour time point. The protein-drug conjugates showed potent cell-killing of cells that express the target antigen EGFR. The multi-drug conjugates also demonstrated increased cytotoxicity in many of the cell lines tested.

TABLE 25

| Conjugate | IC50 H1537 (nM) | IC50 A431 (nM) | IC50 MDA-MB-435 (nM) |
| --- | --- | --- | --- |
| MMAE conjugates | | | |
| TenconCys-mal-$PEG_4$-MMAE | ND | >500 | |
| TenconCys-mal-$PEG_4$-VC-MMAE | ND | 841 | poor fit |
| TenconCys-mal-$PEG_4$-VK-MMAE | ND | 4.5 | poor fit |
| 83v2cys-mal-$PEG_4$-MMAE | ND | >500 | |
| 83v2cys-mal-$PEG_4$-VC-MMAE | ND | 315 | 512 |
| 83v2cys-mal-$PEG_4$-VK-MMAE | ND | 19.6 | 62 |

TABLE 25-continued

| Conjugate | IC50 H1537 (nM) | IC50 A431 (nM) | IC50 MDA-MB-435 (nM) |
|---|---|---|---|
| MMAF conjugates | | | |
| TenconCys-mal-PEG$_4$-MMAF | ND | >1000 | |
| TenconCys-mal-PEG$_4$-VC-MMAF | 996 1541 | >500 | >500 |
| TenconCys-mal-PEG$_4$-VK-MMAF | ND | >500 | >500 |
| 83v2cys-mal-PEG$_4$-MMAF | ND | >1000 | |
| 83v2cys-mal-PEG$_4$-VC-MMAF | 1.19 1.05 | 1.6 | >500 |
| 83v2cys-mal-PEG$_4$-VK-MMAF | ND | 3.9 | >500 |
| ECB147v3-(mal-PEG$_4$-VC-MMAF)$_4$ | 0.15 0.075 | 0.0078 0.0197 | ND |
| ECB147v5-(mal-PEG$_4$-VC-MMAF)$_2$ | 0.056 0.050 | 0.087 0.071 | ND |
| ECB82cys-mal-PEG$_4$-VC-MMAF | 0.576 0.249 | 1.1 0.64 | ND |

SEQUENCE LISTING

| SEQ ID NO: | Type | Species | Description | Sequence |
|---|---|---|---|---|
| 1 | PRT | Artificial | Tencon | LPAPKNLVVSEVTEDSLRLSWTAPDAAFDSFLIQYQESEKVGEAINLT VPGSERSYDLTGLKPGTEYTVSIYGVKGGHRSNPLSAEFTT |
| 2 | DNA | Artificial | POP2220 | GGAAACAGGATCTACCATGCTGCCGGCGCCGAAAAACCTGGTTGT TTCTGAAGTTACC |
| 3 | DNA | Artificial | TC5'toFG | AACACCGTAGATAGAAACGGT |
| 4 | DNA | Artificial | 130 mer | CGGCGGTTAGAACGCGGCTACAATTAATACATAACCCCATCCCCC TGTTGACAATTAATCATCGGCTCGTATAATGTGTGGAATTGTGAGC GGATAACAATTTCACACAGGAAACAGGATCTACCATGCTG |
| 5 | DNA | Artificial | POP2222 | CGGCGGTTAGAACGCGGCTAC |
| 6 | DNA | Artificial | TCF7 | GGTGGTGAATTCCGCAGACAGCGGSNNSNNSNNSNNSNNSNNSNN AACACCGTAGATAGAAACGGT |
| 7 | DNA | Artificial | TCF8 | GGTGGTGAATTCCGCAGACAGCGGSNNSNNSNNSNNSNNSNNSNN SNNAACACCGTAGATAGAAACGGT |
| 8 | DNA | Artificial | TCF9 | GGTGGTGAATTCCGCAGACAGCGGSNNSNNSNNSNNSNNSNNSNN SNNSNNAACACCGTAGATAGAAACGGT |
| 9 | DNA | Artificial | TCF10 | GGTGGTGAATTCCGCAGACAGCGGSNNSNNSNNSNNSNNSNNSNN SNNSNNSNNAACACCGTAGATAGAAACGGT |
| 10 | DNA | Artificial | TCF11 | GGTGGTGAATTCCGCAGACAGCGGSNNSNNSNNSNNSNNSNNSNN SNNSNNSNNSNNAACACCGTAGATAGAAACGGT |
| 11 | DNA | Artificial | TCF12 | GGTGGTGAATTCCGCAGACAGCGGSNNSNNSNNSNNSNNSNNSNN SNNSNNSNNSNNSNNAACACCGTAGATAGAAACGGT |
| 12 | DNA | Artificial | POP2234 | AAGATCAGTTGCGGCCGCTAGACTAGAACCGCTGCCATGGTGATG GTGATGGTGACCGCCGGTGGTGAATTCCGCAGACAG |
| 13 | DNA | Artificial | POP2250 | CGGCGGTTAGAACGCGGCTACAATTAATAC |
| 14 | DNA | Artificial | DidLigRev | CATGATTACGCCAAGCTCAGAA |
| 15 | DNA | Artificial | Tcon5new2 | GAGCCGCCGCCACCGGTTTAATGGTGATGGTGATGGT GACCACCGGTGGTGAATTCCGCAGACAG |
| 16 | DNA | Artificial | Tcon6 | AAGAAGGAGAACCGGTATGCTGCCGGCGCCGAAAAAC |
| 17 | DNA | Artificial | LS1008 | TTTGGGAAGCTTCTAGGTCTCGGCGGTCACCATCACC ATCACCATGGCAGCGGTTCTAGTCTAGCGGCCCCAAC TGATCTTCACCAAAC |
| 18 | PRT | Artificial | P53A1R5-17 without met | LPAPKNLVVSEVTEDSLRLSWADPHGFYDSFLIQYQES EKVGEAINLTVPGSERSYDLTGLKPGTEYTVSIYGVHN VYKDTNMRGLPLSAEFTT |
| 19 | PRT | Artificial | P54AR4-17 without met | LPAPKNLVVSEVTEDSLRLSWTYDRDGYDSFLIQYQES EKVGEAINLTVPGSERSYDLTGLKPGTEYTVSIYGVHN VYKDTNMRGLPLSAEFTT |

SEQUENCE LISTING

| SEQ ID NO: | Type | Species | Description | Sequence |
|---|---|---|---|---|
| 20 | PRT | Artificial | P54AR4-47 without met | LPAPKNLVVSEVTEDSLRLSWGYNGDHFDSFLIQYQES EKVGEAINLTVPGSERSYDLTGLKPGTEYTVSIYGVHN VYKDTNMRGLPLSAEFTT |
| 21 | PRT | Artificial | P54AR4-48 without met | LPAPKNLVVSEVTEDSLRLSWDDPRGFYESFLIQYQES EKVGEAINLTVPGSERSYDLTGLKPGTEYTVSIYGVHN VYKDTNMRGLPLSAEFTT |
| 22 | PRT | Artificial | P54AR4-37 without met | LPAPKNLVVSEVTEDSLRLSWTWPYADLDSFLIQYQES EKVGEAINLTVPGSERSYDLTGLKPGTEYTVSIYGVHN VYKDTNMRGLPLSAEFTT |
| 23 | PRT | Artificial | 54AR4-74 without met | LPAPKNLVVSEVTEDSLRLSWGYNGDHFDSFLIQYQES EKVGEAINLTVPGSERSYDLTGLKPGTEYTVSIYGVHN VYKDTNMRGLPLSAEFTT |
| 24 | PRT | Artificial | P54AR4-81 without met | LPAPKNLVVSEVTEDSLRLSWDYDLGVYFDSFLIQYQE SEKVGEAINLTVPGSERSYDLTGLKPGTEYTVSIYGVH NVYKDTNMRGLPLSAEFTT |
| 25 | PRT | Artificial | P54AR4-83 without met | LPAPKNLVVSEVTEDSLRLSWDDPWAFYESFLIQYQES EKVGEAINLTVPGSERSYDLTGLKPGTEYTVSIYGVHN VYKDTNMRGLPLSAEFTT |
| 26 | PRT | Artificial | P54CR4-31 without Met | LPAPKNLVVSEVTEDSLRLSWTAPDAAFDSFLIQYQES EKVGEAINLTVPGSERSYDLTGLKPGTEYTVSIYGVLG SYVFEHDVMLPLSAEFTT |
| 27 | PRT | Artificial | P54AR4-83v2 without Met | LPAPKNLVVSEVTEDSARLSWDDPWAFYESFLIQYQES EKVGEAIVLTVPGSERSYDLTGLKPGTEYTVSIYGVHN VYKDTNMRGLPLSAIFTT |
| 28 | PRT | Artificial | P54CR4-31v2 without Met | LPAPKNLVVSEVTEDSARLSWTAPDAAFDSFLIQYQES EKVGEAIVLTVPGSERSYDLTGLKPGTEYTVSIYGVLG SYVFEHDVMLPLSAIFTT |
| 29 | PRT | Artificial | P54AR4-73v2 wihtout Met | LPAPKNLVVSEVTEDSLRLSWTWPYADLDSFLIQYQES EKVGEAINLTVPGSERSYDLTGLKPGTEYTVSIYGVHN VYKDTNMRGLPLSAEFTT |
| 30 | DNA | Artificial | TCON6 | AAG AAG GAG AAC CGG TAT GCT GCC GGC GCC GAA AAA C |
| 31 | DNA | Artificial | TCON5 E86Ishort | GAG CCG CCG CCA CCG GTT TAA TGG TGA TGG TG TGG TGA CCA CCG GTG GTG AAG ATC GCA GAC AG |
| 32 | PRT | Artificial | P114AR5P74-A5 | LPAPKNLVVSRVTEDSARLSWTAPDAAFDSFWIRYDEV VVGGEAIVLTVPGSERSYDLTGLKPGTEYYVNILGVKG GSISVPLSAIFTT |
| 33 | PRT | Artificial | P114AR5P75-E9 | LPAPKNLVVSRVTEDSARLSWTAPDAAFDSFFIRYDEF LRSGEAIVLTVPGSERSYDLTGLKPGTEYVVVTILGVKG GLVSTPLSAIFTT |
| 34 | PRT | Artificial | P114AR7P92-F3 | LPAPKNLVVSRVTEDSARLSWTAPDAAFDSFWIRYFEF GSGEAIVLTVPGSERSYDLTGLKPGTEYIVNIMGVKGG SISHPLSAIFTT |
| 35 | PRT | Artificial | P114AR7P92-F6 | LPAPKNLVVSRVTEDSARLSWTAPDAAFDSFWIRYFEF LGSGEAIVLTVPGSERSYDLTGLKPGTEYVVNILGVKGG GLSVPLSAIFTT |
| 36 | PRT | Artificial | P114AR7P92-G8 | LPAPKNLVVSRVTEDSARLSWTAPDAAFDSFVIRYFEF LGSGEAIVLTVPGSERSYDLTGLKPGTEYVVQILGVKGG YISIPLSAIFTT |
| 37 | PRT | Artificial | P114AR7P92-H5 | LPAPKNLVVSRVTEDSARLSWTAPDAAFDSFWIRYLEF LLGGEAIVLTVPGSERSYDLTGLKPGTEYVVQIMGVKGG TVSPPLSAIFTT |

SEQUENCE LISTING

| SEQ ID NO: | Type | Species | Description | Sequence |
|---|---|---|---|---|
| 38 | PRT | Artificial | P114AR7P93-D11 | LPAPKNLVVSRVTEDSARLSWTAPDAAFDSFWIRYFEF LGSGEAIVLTVPGSERSYDLTGLKPGTEYVVGINGVKGG YISYPLSAIFTT |
| 39 | PRT | Artificial | P114AR7P93-G8 | LPAPKNLVVSRVTEDSARLSWTAPDAAFDSFWIRYFEF LGSGEAIVLTVPGSERSYDLTDLKPGTEYGVTINGVKG GRVSTPLSAIFTT |
| 40 | PRT | Artificial | P114AR7P93-H9 | LPAPKNLVVSRVTEDSARLSWTAPDAAFDSFWIRYFEF LGSGEAIVLTVPGSERSYDLTGLKPGTEYVVQIIGVKGG HISLPLSAIFTT |
| 41 | PRT | Artificial | P114AR7P94-A3 | LPAPKNLVVSRVTEDSARLSWTAPDAAFDSFWIRYFEF LGSGEAIVLTVPGSERSYDLTGLKPGTEYVVNIMGVKGG KISPPLSAIFTT |
| 42 | PRT | Artificial | P114AR7P94-E5 | LPAPKNLVVSRVTEDSARLSWTAPDAAFDSFWIRYFEF LGSGEAIVLTVPGSERSYDLTGLKPGTEYAVNIMGVKG GRVSVPLSAIFTT |
| 43 | PRT | Artificial | P114AR7P95-B9 | LPAPKNLVVSRVTEDSARLSWTAPDAAFDSFWIRYFEF LGSGEAIVLTVPGSERSYDLTGLKPGTEYVVQILGVKGG SISVPLSAIFTT |
| 44 | PRT | Artificial | P114AR7P95-D3 | LPAPKNLVVSRVTEDSARLSWTAPDAAFDSFWIRYFEF LGSGEAIVLTVPGSERSYDLTGLKPGTEYVVNIMGVKGG SISYPLSAIFTT |
| 45 | PRT | Artificial | P114AR7P95-D4 | LPAPKNLVVSRVTEDSARLSWTAPDAAFDSFWIRYFEF LGSGEAIVLTVPGSERSYDLTGLKPGTEYVVQILGVKGG YISIPLSAIFTT |
| 46 | PRT | Artificial | P114AR7P95-E3 | LPAPKNLVVSRVTEDSARLSWTAPDAAFDSFWIRYFEF LGSGEAIVLTVPGSERSYDLTGLKPGTEYVVQIMGVKGG TVSPPLSAIFTT |
| 47 | PRT | Artificial | P114AR7P95-F10 | LPAPKNLVVSRVTEDSARLSWTAPDAAFDSFWIRYFEF TTAGEAIVLTVPGSERSYDLTGLKPGTEYVVNIMGVKGG SISPPLSAIFTT |
| 48 | PRT | Artificial | P114AR7P95-G7 | LPAPKNLVVSRVTEDSARLSWTAPDAAFDSFWIRYFEL LSTGEAIVLTVPGSERSYDLTGLKPGTEYVVNIMGVKGG SISPPLSAIFTT |
| 49 | PRT | Artificial | P114AR7P95-H8 | LPAPKNLVVSRVTEDSARLSWTAPDAAFDSFWIRYFEF VSKGEAIVLTVPGSERSYDLTGLKPGTEYVVNIMGVKGG SISPPLSAIFTT |
| 50 | PRT | Artificial | ECB1 | MLPAPKNLVVSEVTEDSARLSWDDPWAFYESFLIQYQE SEKVGEAIVLTVPGSERSYDLTGLKPGTEYTVSIYGVH NVYKDTNMRGLPLSAIFTTGGGGSGGGGSGGGGSGGGG SMLPAPKNLVVSRVTEDSARLSWTAPDAAFDSFWIRYD EVVVGGEAIVLTVPGSERSYDLTGLKPGTEYYVNILGV KGGSISVPLSAIFTT |
| 51 | PRT | Artificial | ECB2 | MLPAPKNLVVSEVTEDSARLSWDDPWAFYESFLIQYQE SEKVGEAIVLTVPGSERSYDLTGLKPGTEYTVSIYGVH NVYKDTNMRGLPLSAIFTTGGGGSGGGGSGGGGSGGGG SLPAPKNLVVSRVTEDSARLSWTAPDAAFDSFWIRYFE FLGSGEAIVLTVPGSERSYDLTGLKPGTEYVVNIMGVK GGKISPPLSAIFTT |
| 52 | PRT | Artificial | ECB3 | MLPAPKNLVVSEVTEDSARLSWDDPWAFYESFLIQYQE SEKVGEAIVLTVPGSERSYDLTGLKPGTEYTVSIYGVH NVYKDTNMRGLPLSAIFTTGGGGSGGGGSGGGGSGGGG SMLPAPKNLVVSRVTEDSARLSWTAPDAAFDSFWIRYF EFLGSGEAIVLTVPGSERSYDLTGLKPGTEYVVQIIGV KGGHISLPLSAIFTT |
| 53 | PRT | Artificial | ECB4 | MLPAPKNLVVSEVTEDSARLSWDDPWAFYESFLIQYQE SEKVGEAIVLTVPGSERSYDLTGLKPGTEYTVSIYGVH NVYKDTNMRGLPLSAIFTTGGGGSGGGGSGGGGSGGGG SMLPAPKNLVVSRVTEDSARLSWTAPDAAFDSFFIRYD |

SEQUENCE LISTING

| SEQ ID NO: | Type | Species | Description | Sequence |
|---|---|---|---|---|
| | | | | EFLRSGEAIVLTVPGSERSYDLTGLKPGTEYWVTILGV KGGLVSTPLSAIFTT |
| 54 | PRT | Artificial | ECB5 | MLPAPKNLVVSEVTEDSARLSWADPHGFYDSFLIQYQE SEKVGEAIVLTVPGSERSYDLTGLKPGTEYTVSIYGVH NVYKDTNMRGLPLSAIFTTGGGGSGGGGSGGGGSGGGG SMLPAPKNLVVSRVTEDSARLSWTAPDAAFDSFWIRYF EFLGSGEAIVLTVPGSERSYDLTGLKPGTEYVVNIMGV KGGKISPPLSAIFTT |
| 55 | PRT | Artificial | ECB6 | MLPAPKNLVVSEVTEDSARLSWADPHGFYDSFLIQYQE SEKVGEAIVLTVPGSERSYDLTGLKPGTEYTVSIYGVH NVYKDTNMRGLPLSAIFTTGGGGSGGGGSGGGGSGGGG SMLPAPKNLVVSRVTEDSARLSWTAPDAAFDSFWIRYF EFLGSGEAIVLTVPGSERSYDLTGLKPGTEYVVQIIGV KGGHISLPLSAIFTT |
| 56 | PRT | Artificial | ECB7 | MLPAPKNLVVSEVTEDSARLSWADPHGFYDSFLIQYQE SEKVGEAIVLTVPGSERSYDLTGLKPGTEYTVSIYGVH NVYKDTNMRGLPLSAIFTTGGGGSGGGGSGGGGSGGGG SMLPAPKNLVVSRVTEDSARLSWTAPDAAFDSFWIRYF EFLGSGEAIVLTVPGSERSYDLTGLKPGTEYVVQIIGV KGGHISLPLSAIFTT |
| 57 | PRT | Artificial | ECB15 | MLPAPKNLVVSEVTEDSARLSWDDPWAFYESFLIQYQE SEKVGEAIVLTVPGSERSYDLTGLKPGTEYTVSIYGVH NVYKDTNMRGLPLSAIFTTAPAPAPAPAPLPAPKNLVV SRVTEDSARLSWTAPDAAFDSFWIRYFEFLGSGEAIVL TVPGSERSYDLTGLKPGTEYVVNIMGVKGGKISPPLSA IFTT |
| 58 | PRT | Artificial | ECB27 | MLPAPKNLVVSEVTEDSARLSWDDPWAFYESFLIQYQE SEKVGEAIVLTVPGSERSYDLTGLKPGTEYTVSIYGVH NVYKDTNMRGLPLSAIFTTAPAPAPAPAPLPAPKNLVV SRVTEDSARLSWTAPDAAFDSFWIRYDEVVGGEAIVL TVPGSERSYDLTGLKPGTEYYVNILGVKGGSISVPLSA IFTT |
| 59 | PRT | Artificial | ECB60 | MLPAPKNLVVSEVTEDSARLSWADPHGFYDSFLIQYQE SEKVGEAIVLTVPGSERSYDLTGLKPGTEYTVSIYGVH NVYKDTNMRGLPLSAIFTTAPAPAPAPAPMLPAPKNLV SRVTEDSARLSWTAPDAAFDSFWIRYFEFLGSGEAIVL TVPGSERSYDLTGLKPGTEYVVNIMGVKGGKISPPLSA IFTT |
| 60 | PRT | Artificial | ECB37 | MLPAPKNLVVSEVTEDSARLSWADPHGFYDSFLIQYQE SEKVGEAIVLTVPGSERSYDLTGLKPGTEYTVSIYGVH NVYKDTNMRGLPLSAIFTTAPAPAPAPAPLPAPKNLVV SRVTEDSARLSWTAPDAAFDSFWIRYDEVVGGEAIVL TVPGSERSYDLTGLKPGTEYYVNILGVKGGSISVPLSA IFTT |
| 61 | PRT | Artificial | ECB94 | MLPAPKNLVVSEVTEDSARLSWDDPWAFYESFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFLGSGEAIVL TVPGSERSYDLTGLKPGTEYVVNILGVKGGKISPPLSA IFTT |
| 62 | PRT | Artificial | ECB95 | MLPAPKNLVVSEVTEDSARLSWDDPWAFYESFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFVGSGEAIVL TVPGSERSYDLTGLKPGTEYVVNILGVKGGSISPPLSA IFTT |
| 63 | PRT | Artificial | ECB96 | MLPAPKNLVVSEVTEDSARLSWDDPWAFYESFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFVSKGDAIVL TVPGSERSYDLTGLKPGTEYVVNILGVKGGSISPPLSA IFTT |

SEQUENCE LISTING

| SEQ ID NO: | Type | Species | Description | Sequence |
|---|---|---|---|---|
| 64 | PRT | Artificial | ECB97 | MLPAPKNLVVSEVTEDSARLSWDDPWAFYESFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFLGSGEAIVL TVPGSERSYDLTGLKPGTEYVVNILSVKGGSISPPLSA IFTT |
| 65 | PRT | Artificial | ECB106 | MLPAPKNLVVSEVTEDSARLSWDDPHAFYESFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFLGSGEAIVL TVPGSERSYDLTGLKPGTEYVVNILGVKGGKISPPLSA IFTT |
| 66 | PRT | Artificial | ECB107 | MLPAPKNLVVSEVTEDSARLSWDDPHAFYESFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFVGSGEAIVL TVPGSERSYDLTGLKPGTEYVVNILGVKGGSISPPLSA IFTT |
| 67 | PRT | Artificial | ECB108 | MLPAPKNLVVSEVTEDSARLSWDDPHAFYESFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFVSKGDAIVL TVPGSERSYDLTGLKPGTEYVVNILGVKGGSISPPLSA IFTT |
| 68 | PRT | Artificial | ECB109 | MLPAPKNLVVSEVTEDSARLSWDDPHAFYESFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFLGSGEAIVL TVPGSERSYDLTGLKPGTEYVVNILSVKGGSISPPLSA IFTT |
| 69 | PRT | Artificial | ECB118 | MLPAPKNLVVSEVTEDSARLSWADPHGFYDSFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFLGSGEAIVL TVPGSERSYDLTGLKPGTEYVVNILGVKGGKISPPLSA IFTT |
| 70 | PRT | Artificial | ECB119 | MLPAPKNLVVSEVTEDSARLSWADPHGFYDSFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFVGSGEAIVL TVPGSERSYDLTGLKPGTEYVVNILGVKGGSISPPLSA IFTT |
| 71 | PRT | Artificial | ECB120 | MLPAPKNLVVSEVTEDSARLSWADPHGFYDSFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFVSKGDAIVL TVPGSERSYDLTGLKPGTEYVVNILGVKGGSISPPLSA IFTT |
| 72 | PRT | Artificial | ECB121 | MLPAPKNLVVSEVTEDSARLSWADPHGFYDSFLIQYQE SEKVGEAIVLTVPGSERSYDLTGLKPGTEYTVSIYGVH NVYKDTNIRGLPLSAIFTTAPAPAPAPAPLPAPKNLVV SRVTEDSARLSWTAPDAAFDSFWIRYFEFLGSGEAIVL TVPGSERSYDLTGLKPGTEYVVNILSVKGGSISPPLSA IFTT |

SEQ ID NO: 73, PRT, *Homo Sapiens*, EGFR
```
  1 mrpsgtagaa llallaalcp asraleekkv cqgtsnkltq lgtfedhfls lqrmfnncev
 61 vlgnleityv qrnydlsflk tigevagyvl ialntverip lenlqiirgn myyensyala
121 vlsnydankt glkelpmrnl qeilhgavrf snnpalcnve sigwrdivss dflsnmsmdf
181 qnhlgscqkc dpscpngscw gageencqkl tkiicaqqcs grcrgkspsd cchnqcaagc
241 tgpresdclv crkfrdeatc kdtcpplmly npttyqmdvn pegkysfgat cvkkcprnyv
```

| SEQ ID NO: | Type | Species | Description | Sequence |
|---|---|---|---|---|

```
 301 vtdhgscvra cgadsyemee dgvrkckkce gperkvcngi gigefkdsls inatnikhfk 361 nctsisgdlh ilpvafrgds fthtppldpq eldilktvke itgflliqaw penrtdlhaf 421 enleiirgrt kqhgqfslav vslnitslgl rslkeisdgd viisgnknlc yantinwkkl 481 fgtsgqktki isnrgensck atgqvchalc spegcwgpep rdcvscrnvs rgrecvdkcn 541 llegeprefv enseciqchp eclpqamnit ctgrgpdnci qcahyidgph cvktcpagvm 601 genntivwky adaghvchlc hpnctygctg pglegcptng pkipsiatgm vgalllllvv 661 algiglfmrr rhivrkrtlr rllgerelve pltpsgeapn qallrilket efkkikvlgs 721 gafgtvykgl wipegekvki pvaikelrea tspkankeil deayvmasvd nphvcrllgi 781 cltstvglit qlmpfgcllld yvrehkdnig sqyllnwcvq iakgmnyled rrlvhrdlaa 841 rnvlvktpqh vkitdfglak llgaeekeyh aeggkvpikw malesilhri ythqsdvwsy 901 gvtvwelmtf gskpydgipa seissilekg erlpqppict idvymimvkc wmidadsrpk 961 freliiefsk mardpqrylv iqgdermhlp sptdsnfyra lmdeedmddv vdadeylipq 1021 qgffsspsts rtpllsslsa tsnnstvaci drnglqscpi kedsflqrys sdptgalted 1081 siddtflpvp eyinqsvpkr pagsvqnpvy hnqpinpaps rdphyqdphs tavgnpeyln 1141 tvqptcvnst fdspahwaqk gshqisldnp dyqqdffpke akpngifkgs taenaeylrv 1201 apqssefiga
```

| | | | | |
|---|---|---|---|---|
| 74 | PRT | Homo sapiens | EGF | NSDSECPLSHDGYCLHDGVCMYIEALDKYACNCVVGYIG ERCQYRDLKWWELR |

SEQ ID NO: 75, PRT, Homo Sapiens, Tenascin-C

```
   1 mgamtqllag vflaflalat eggvlkkvir hkrqsgvnat lpeenqpvvf nhvyniklpv 61 gsqcsvdles asgekdlapp sepsesfqeh tvdgenqivf thriniprra cgcaaapdvk 121 ellsrleele nlvsslreqc tagagccclqp atgrldtrpf csgrgnfste gcgcvcepgw 181 kgpncsepec pgnchlrgrc idgqcicddg ftgedcsqla cpsdcndqgk cvngvcicfe 241 gyagadcsre icpvpcseeh gtcvdglcvc hdgfagddcn kplclnncyn rgrcvenecv 301 cdegftgedc selicpndcf drgrcingtc yceegftged cgkptcphac htqgrceegq 361 cvcdegfagv dcsekrcpad chnrgrcvdg rcecddgftg adcgelkcpn gcsghgrcvn 421 gqcvcdegyt gedcsqlrcp ndchsrgrcv egkcvceqgf kgydcsdmsc pndchqhgrc 481 vngmcvcddg ytgedcrdrq cprdcsnrgl cvdgqcvced gftgpdcael scpndchgqg 541 rcvngqcvch egfmgkdcke qrcpsdchgq grcvdgqcic hegftgldcg qhscpsdcnn 601 lgqcvsgrci cnegysgedc sevsppkdlv vtevteetvn lawdnemrvt eylvvytpth 661 egglemqfry pgdqtstiiq elepgveyfi rvfailenkk sipvsarvat ylpapeglkf 721 ksiketsvev ewdpldiafe tweiifrnmn kedegeitks lrrpetsyrq tglapgqeye 781 islhivknnt rgpglkrvtt trldapsqie vkdvtdttal itwfkplaei dgieltygik 841 dvpgdrttid ltedenqysi gnlkpdteye vslisrrgdm ssnpaketft tgldaprnlr 901 rvsqtdnsit lewrngkaai dsyrikyapi sggdhaevdv pksqqattkt tltglrpgte 961 ygigvsavke dkesnpatin aateldtpkd lqvsetaets ltllwktpla kfdryrinys 1021 lptgqwvgvq lprnttsyvl rglepgqeyn vlltaekgrh kskparvkas tegapelenl
```

SEQUENCE LISTING

| SEQ ID NO: | Type | Species | Description | Sequence |
|---|---|---|---|---|
| | | | | 1081 tvtevgwdgl rinwtaadqa yehfiiqvqe ankveaarnl tvpgslravd ipglkaatpy |
| | | | | 1141 tvsiygviqg yrtpvlsaea stgetpnlge vvvaevgwda lklnwtapeg ayeyffiqvq |
| | | | | 1201 eadtveaaqn ltvpgglrst dlpglkaath ytitirgvtq dfsttplsve vlteevpdmg |
| | | | | 1261 nitvtevswd alrinwttpd gtydgftiqv geadqveeah nitvpgslrs meipglragt |
| | | | | 1321 pytvtlhgev rghstrplav evvtedlpql gdlaysevgw dglrinwtaa dnayehfviq |
| | | | | 1381 vqevnkveaa qnitlpgslr avdipgleaa tpyrvsiygv irgyrtpvls aeastakepe |
| | | | | 1441 ignlnvsdit pesfnlswma tdgifetfti eiidsnrlle tveynisgae rtahisglpp |
| | | | | 1501 stdfivylsg lapsirtkti satattealp llenitisdi npygftvswm asenafdsfl |
| | | | | 1561 vtvvdsgkll dpqeftlsgt qrklelrgli tgigyevmvs gftqghqtkp lraeivteae |
| | | | | 1621 pevdnllvsd atpdgvfdnf vlkirdtkkg sepleitlla pertrditgl |
| | | | | 1681 reateyeiel ygiskgrrsq tvsaiattam gspkevifsd itensatvsw raptaqvesf |
| | | | | 1741 rityvpitgg tpsmvtvdgt ktqtrlvkli pgveylvsii amkgfeesep vsgsfttald |
| | | | | 1801 gpsglvtani tdsealarwq paiatvdsyv isytgekvpe itrtvsgntv eyaltdlepa |
| | | | | 1861 teytlrifae kgpqksstit akfttdldsp rdltatevqs etalltwrpp rasvtgyllv |
| | | | | 1921 yesvdgtvke vivgpdttsy sladlspsth ytakiqalng plrsnmigti fttigllypf |
| | | | | 1981 pkdcsqamln gdttsglyti ylngdkaeal evfcdmtsdg ggwivflrrk ngrenfyqnw |
| | | | | 2041 kayaagfgdr reefwlgldn lnkitaggqy elrvdlrdhg etafavydkf svgdaktryk |
| | | | | 2101 lkvegysgta gdsmayhngr sfstfdkdtd saitncalsy kgafwyrnch rvnlmgrygd |
| | | | | 2161 nnhsqgvnwf hwkghehsiq faemklrpsn frnlegrrkr a |
| 76 | PRT | Artificial | Fibcon | Ldaptdlqvtnvtdtsitvswtppsatitgyritytpsngpgepkelt vppsstsvtitgltpgveyvvslyalkdnqespplvgtqtt |
| 77 | PRT | Artificial | 10th FN3 domain of fibronectin (FN10) | VSDVPRDLEVVAATPTSLLISWDAPAVTVRYYRITYGETGGNSPV QEFTVPGSKSTATISGLKPGVDYTITVYAVTGRGDSPASSKPISINY RT |
| 78 | PRT | Artificial | Linker | GSGS |
| 79 | PRT | Artificial | Linker | GGGGSGGGGSGGGGSGGGGSGGGGS |
| 80 | PRT | Artificial | Linker | APAP |
| 81 | PRT | Artificial | Linker | APAPAPAP |
| 82 | PRT | Artificial | Linker | APAPAPAPAPAPAPAP |
| 83 | PRT | Artificial | Linker | APAPAPAPAPAPAPAPAPAPAPAPAPAPAPAPAPAP |
| 84 | PRT | Artificial | Linker | AEAAAKEAAAKEAAAKEAAAKEAAAKAAA |
| 85 | PRT | Artificial | Tencon BC loop | TAPDAAFD |
| 86 | PRT | Artificial | Tencon GF loop | KGGHRSN |
| 87 | PRT | Artificial | P53A1R5-17 BC loop | ADPHGFYD |
| 88 | PRT | Artificial | P54AR4-17 BC loop | TYDRDGYD |
| 89 | PRT | Artificial | P54AR4-47 BC loop | WDPFSFYD |
| 90 | PRT | Artificial | P54AR4-48 BC loop | DDPRGFYE |
| 91 | PRT | Artificial | P54AR4-73 BC loop | TWPYADLD |

SEQUENCE LISTING

| SEQ ID NO: | Type | Species | Description | Sequence |
|---|---|---|---|---|
| 92 | PRT | Artificial | P54AR4-74 BC loop | GYNGDHFD |
| 93 | PRT | Artificial | P54AR4-81 BC loop | DYDLGVYD |
| 94 | PRT | Artificial | P54AR4-83 BC loop | DDPWDFYE |
| 95 | PRT | Artificial | FG loops of EGFR | HNVYKDTNMRGL |
| 96 | PRT | Artificial | FG loops of EGFR | LGSYVFEHDVM |
| 97 | DNA | Artificial | >EGFR part ECB97; P54AR4-83v22 | Atgttgccagcgccgaagaacctggtagttagcgaggttactgaggac agcgcgcgtctgagctgggacgatccgtgggcgttctacgagagctttct gatccagtatcaagagagcgagaaagtcggtgaagcgattgtgctgac cgtcccgggctccgagcgttcctacgacctgaccggtttgaagccgggt accgagtatacggtgagcatctacggtgttcacaatgtctataaggaca ctaatatccgcggtctgcctctgagcgccattttcaccacc |
| 98 | DNA | Artificial | >EGFR part ECB15; P54AR4-83v2 | Atgctgccagcccctaagaatctggtcgtgagcgaagtaaccgagga cagcgcccgcctgagctgggacgacccgtgggcgttctatgagtcttttcc tgattcagtatcaagaaagcgaaaaagttggcgaagcgatcgtcctga ccgtcccgggtagcgagcgctcctacgatctgaccggcctgaaaccgg gtacggagtacacggtgtccatttacggtgttcacaatgtgtataaagac accaacatgcgtggcctgccgctgtcggcgattttcaccacc |
| 99 | PRT | Artificial | tencon 27 | LPAPKNLVVSRVTEDSARLSWTAPDAAFDSFLIQYQ ESEKVGEAIVLTVPGSERSYDLTGLKPGTEYTVSIYG VKGGHRSNPLSAIFTT |
| 100 | PRT | Artificial | TCL14 library | LPAPKNLVVSRVTEDSARLSWTAPDAAFDSFXIXYX EXXXXGEAIVLTVPGSERSYDLTGLKPGTEYXVXIXG VKGGXXSXPLSAIFTT |

>SEQ ID NO: 101
PRT
*Homo sapiens*
cMet

```
   1 mkapavlapg ilvllftivq rsngeckeal aksemnvnmk yqlpnftaet piqnvilheh
  61 hiflgatnyi yvineedlqk vaeyktgpvl ehpdcfpcqd csskanlsgg vwkdninmal
 121 vvdtyyddql iscgsvnrgt cqrhvfphnh tadiqsevhc ifspqieeps qcpdcvvsal
 181 gakvlssvkd rfinffvgnt inssyfpdhp lhsisvrrlk etkdgfmflt dqsyidvlpe
 241 frdsypikyv hafesnnfiy fltvgretld aqtfhtriir fcsinsglhs ymemplecil
 301 tekrkkrstk kevfnilqaa yvskpgaqla rqigaslndd ilfgvfaqsk pdsaepmdrs
 361 amcafpikyv ndffnkivnk nnvrclqhfy gpnhehcfnr tllrnssgce arrdeyrtef
 421 ttalqrvdlf mgqfsevllt sistfikgdl tianlgtseg rfmqvvvsrs gpstphvnfl
 481 ldshpvspev ivehtlnqng ytivitgkki tkipinglgc rhfqscsqcl sappfvqcgw
 541 chdkcvrsee clsgtwtqqi clpaiykvfp nsapleggtr lticgwdfgf rrnnkfdlkk
 601 trvllgnesc tltlsestmn tlkctvgpam nkhfnmsiii snghgttqys tfsyvdpvit
 661 sispkygpma ggtlltltgn ylnsgnsrhi siggktctlk sysnsilecy tpaqtistef
 721 avklkidlan retsifsyre dpivyeihpt ksfistwwke pinivsflfc fasggstitg
 781 vgknlnsysv prmvinvhea grnftvacqh rsnseiicct tpslqqlnlq lplktkaffm
 841 ldgilskyfd liyvhnpvfk pfekpvmism gnenvleikg ndidpeavkg evlkvgnksc
 901 enihlhseav lctvpndllk lnselniewk qaisstvlgk vivqpdqnft gliagvvsis
 961 talllllgff lwlkkrkgik dlgselvryd arvhtphldr lvsarsyspt temvsnesvd
1021 yratfpedqf pnssqngscr qvqypltdms piltsgdsdi sspllqntvh idlsalnpel
```

-continued

SEQUENCE LISTING

```
1081 vgavqhvvig psslivhfne vigrghfgcv yhgtlldndg kkihcavksl nritdigevs 1141 qfltegilmk dfshpnvlsl lgiclrsegs plvvlpymkh gdlinfirne thnptvkdli 1201 gfglqvakgm kylaskkfvh rdlaarncml dekftvkvad fglardmydk eyysvhnktg 1261 aklpvkwmal eslqtqkftt ksdvwsfgvl lwelmtrgap pypdvntfdi tvyllqgrrl 1321 lqpeycpdpl yevmlkcwhp kaemrpsfse lvsrisaifs tfigehyvhv natyvnvkcv 1381 apypsllsse dnaddevdtr pasfwets
```

| SEQ ID NO: | Type | Species | Description | Sequence |
|---|---|---|---|---|
| 102 | PRT | Homo sapiens | HGF | QRKRRNTIHEFKKSAKTTLIKIDPALKIK TKKVNTADQCANRCTRNKGLPFTCKAFVFDKARKQCLWFPFNSMSSGV KKEFGHEFDLYENKDYIRNCIIGKGRSYKGTVSITKSGIKCQPWSSMI PHEHSFLPSSYRGKDLQENYCRNPRGEEGGPWCFTSNPEVRYEVCDIP QCSEVECMTCNGESYRGLMDHTESGKICQRWDHQTPHRHKFLPERYPD KGFDDNYCRNPDGQPRPWCYTLDPHTRWEYCAIKTCADNTMNDTDVPL ETTECIQGQGEGYRGTVNTIWNGIPCQRWDSQYPHEHDMTPENFKCKD LRENYCRNPDGSESPWCFTTDPNIRVGYCSQIPNCDMSHGQDCYRGNG KNYMGNLSQTRSGLTCSMWDKNMEDLHRHIFWEPDASKLNENYCRNPD DDAHGPWCYTGNPLIPWDYCPISRCEGDTTPTIVNLDHPVISCAKTKQ LRVVNGIPTRTNIGWMVSLRYRNKHICGGSLIKESWVLTARQCFPSRD LKDYEAWLGIHDVHGRGDEKCKQVLNVSQLVYGPEGSDLVLMKLARPA VLDDFVSTIDLPNYGCTIPEKTSCSVYGWGYTGLINYDGLLRVAHLYN IGNEKCSQHHRGKVTLNESEICAGAEKIGSGPCEGDYGGPLVCEQHKM RMVLGVIVPGRGCAIPNRPGIFVRVAYYAKWIHKIILTYKVPQS |
| 103 | DNA | Artificial | >cMET part ECB97 P114AR7P95-C5v2 | Ctgccggctccgaagaacttggtggtgagccgtgttaccgaagatagc gcacgcctgagctggacggcaccggatgcggcgttcgatagcttctgg attcgctattttgagtttctgggtagcggtgaggcaattgttctgacg gtgccgggctctgaacgctcctacgatttgaccggtctgaaaccgggc accgagtatgtggtgaacattctgagcgttaagggcggtagcatcagc ccaccgctgagcgcgatcttcacgactggtggttgc |
| 104 | DNA | Artificial | >cMET part ECB15 P114AR7P94-A3 | Ctgccggcaccgaagaacctggttgtcagccgtgtgaccgaggatag cgcacgtttgagctggaccgctccggatgcagccttttgacagcttctg gattcgttactttgaatttctgggtagcggtgaggcgatcgttctgac ggtgccgggctctgaacgcagctatgatttgacgggcctgaagccggg tactgagtacgtggttaacatcatgggcgttaagggtggtaaaatcag cccgccattgtccgcgatctttaccacg |
| 105 | PRT | Artificial | linker | GGGGS |
| 106 | PRT | Artificial | ECB91 | mlpapknlvvsevtedsarlswddpwafyesfliqyqesekvgeaivl tvpgsersydltglkpgteytvsiygvhnvykdtnirglplsaiftta papapapapLPAPKNLVVSRVTEDSARLSWTAPDAAFDSFWIRYFEFL GSGEAIVLTVPGSERSYDLTGLKPGTEYVVNILSVKGGSISPPLSAIF TT |
| 107 | PRT | Artificial | P53A1R5-17v2 | lpapknlvvsevtedsarlswadphgfydsfliqyqesekvgeaivlt vpgsersydltglkpgteytvsiygvhnvykdtnmrglplsaiftt |
| 108 | PRT | Artificial | P54AR4-83v22 | lpapknlvvsevtedsarlswddpwafyesfliqyqesekvgeaivlt ypgsersydltglkpgteytvsiygvhnvykdtnirglplsaiftt |
| 109 | PRT | Artificial | P54AR4-83v23 | lpapknlvvsevtedsarlswddphafyesfliqyqesekvgeaivlt ypgsersydltglkpgteytvsiygvhnvykdtnirglplsaiftt |
| 110 | PRT | Artificial | P53A1R5-17v22 | lpapknlvvsevtedsarlswadphgfydsfliqyqesekvgeaivlt ypgsersydltglkpgteytvsiygvhnvykdtnirglplsaiftt |
| 111 | PRT | Artificial | P114AR7P94-A3v22 | lpapknlvvsrvtedsarlswtapdaafdsfwiryfeflgsgeaivlt ypgsersydltglkpgteyvvnilgykggkispplsaiftt |
| 112 | PRT | Artificial | P114AR9P121-A6v2 | LPAPKNLVVSRVTEDSARLSWTAPDAAFDSFWIRYFEFVGSGEAI VLTVPGSERSYDLTGLKPGTEYVVNILGVKGGSISPPLSAIFTT |
| 113 | PRT | Artificial | P114AR9P122-A7v2 | LPAPKNLVVSRVTEDSARLSWTAPDAAFDSFWIRYFEFVSKGDAI VLTVPGSERSYDLTGLKPGTEYVVNILGVKGGSISPPLSAIFTT |
| 114 | PRT | Artificial | P114AR7P95-C5v2 | LPAPKNLVVSRVTEDSARLSWTAPDAAFDSFWIRYFEFLGSGEAI VLTVPGSERSYDLTGLKPGTEYVVNILSVKGGSISPPLSAIFTT |

| SEQ ID NO: | Type | Species | Description | Sequence |
|---|---|---|---|---|
| 115 | DNA | Artificial | ECB97 | atgttgccagcgccgaagaacctggtagttagcgaggttactgaggac agcgcgcgtctgagctgggacgatccgtgggcgttctacgagagctttct gatccagtatcaagagagcgagaaagtcggtgaagcgattgtgctgac cgtcccgggctccgagcgttcctacgacctgaccggtttgaagccggt accgagtatacggtgagcatctacggtgttcacaatgtctataaggaca ctaaatatccgcggtctgcctctgagcgccattttcaccaccgcaccggc accggctccggctcctgccccgctgccggctccgaagaacttggtggtg agccgtgttaccgaagatagcgcacgcctgagctggacggcaccgga tgcggcgttcgatagcttctggattcgctattttgagtttctgggtagc ggtgaggcaattgttctgacggtgccgggctctgaacgctcctacgatt tgaccggtctgaaaccggggcaccgagtatgtggtgaacattctgagcgt taagggcggtagcatcagcccaccgctgagcgcgatcttcacgactggt ggttgc |
| 116 | DNA | Artificial | ECB15 | atgctgccagccctaagaatctggtcgtgagcgaagtaaccgaggac agcgcccgcctgagctgggacgacccgtgggcgttctatgagtctttcct gattcagtatcaagaaagcgaaaaagttggcgaagcgatcgtcctgac cgtcccgggtagcgagcgctcctacgatctgaccggcctgaaaccggg tacggagtacacggtgtccatttacggtgttcacaatgtgtataaagaca ccaacatgcgtgggcctgccgctgtcggcgattttcaccaccgcgcctgc gccagcgcctgcaccggctccgctgccggcaccgaagaacctggttgt cagccgtgtgaccgaggatagcgcacgtttgagctggaccgctccgga tgcagccttgacagcttctggattcgttacttgaatttctgggtagc ggtgaggcgatcgttctgacggtgccgggctctgaacgcagctatgatt tgacgggcctgaagccgggtactgagtacgtggttaacatcatgggcgt taagggtggtaaaatcagcccgccattgtccgcgatctttaccacg |
| 117 | PRT | Artificial | albumin binding domain | tidewllkeakekaieelkkagitsdyyfdlinkaktvegvnalkd eilka |
| 118 | PRT | Artificial | ECB18 | mlpapknlvvsevtedsarlswddpwafyesfligygesekvgeaivltv pgsersydltglkpgteytvsiygvhnvykdtnmrglplsaifttapapa papaplpapknlvvsrvtedsarlswtapdaafdsfwiryevvvggeai vltvpgsersydltglkpgteyyvnilgvkggsisvplsaifttapapap apaplaeakvlanreldkygvsdyyknlinnaktvegvkalldeilaalp |
| 119 | PRT | Artificial | ECB28 | mlpapknlvvsevtedsarlswadphgfydsfligygesekvgeaivltv pgsersydltglkpgteytvsiygvhnvykdtnmrglplsaifttapapa papaplpapknlvvsrvtedsarlswtapdaafdsfwiryevvvggeai vltvpgsersydltglkpgteyyvnilgvkggsisvplsaifttapapap apaplaeakvlanreldkygvsdyyknlinnaktvegvkalldeilaalp |
| 120 | PRT | Artificial | ECB38 | mlpapknlvvsevtedsarlswddpwafyesfligygesekvgeaivltv pgsersydltglkpgteytvsiygvhnvykdtnmrglplsaifttapapa papaplpapknlvvsrvtedsarlswtapdaafdsfwiryfeflgsgeai vltvpgsersydltglkpgteyyvnimgvkggkispplsaifttapapap apaplaeakvlanreldkygvsdyyknlinnaktvegvkalldeilaalp |
| 121 | PRT | Artificial | ECB39 | mlpapknlvvsevtedsarlswadphgfydsfligygesekvgeaivltv pgsersydltglkpgteytvsiygvhnvykdtnmrglplsaifttapapa papaplpapknlvvsrvtedsarlswtapdaafdsfwiryfeflgsgeai vltvpgsersydltglkpgteyyvnimgvkggkispplsaifttapapap apaplaeakvlanreldkygvsdyyknlinnaktvegvkalldeilaalp |
| 122 | PRT | Artificial | P53A1R5-17 wth Met | MLPAPKNLVVSEVTEDSLRLSWADPHGFYDSFLIQY QESEKVGEAINLTVPGSERSYDLTGLKPGTEYIVSIY GVHNVYKDTNMRGLPLSAEFTT |
| 123 | PRT | Artificial | P54AR4-17 with Met | MLPAPKNLVVSEVTEDSLRLSWTYDRDGYDSFLIQY QESEKVGEAINLTVPGSERSYDLTGLKPGTEYIVSIY GVHNVYKDTNMRGLPLSAEFTT |
| 124 | PRT | Artificial | P54AR4-47 with Met | MLPAPKNLVVSEVTEDSLRLSWGYNGDHFDSFLIQY QESEKVGEAINLTVPGSERSYDLTGLKPGTEYIVSIY GVHNVYKDTNMRGLPLSAEFTT |
| 125 | PRT | Artificial | P54AR4-48 with Met | MLPAPKNLVVSEVTEDSLRLSWDDPRGFYESFLIQY QESEKVGEAINLTVPGSERSYDLTGLKPGTEYIVSIY GVHNVYKDTNMRGLPLSAEFTT |

SEQUENCE LISTING

| SEQ ID NO: | Type | Species | Description | Sequence |
|---|---|---|---|---|
| 126 | PRT | Artificial | P54AR4-73 with Met | MLPAPKNLVVSEVTEDSLRLSWTWPYADLDSFLIQY QESEKVGEAINLTVPGSERSYDLTGLKPGTEYIVSIY GVHNVYKDTNMRGLPLSAEFTT |
| 127 | PRT | Artificial | 54AR4-74 with Met | MLPAPKNLVVSEVTEDSLRLSWGYNGDHFDSFLIQY QESEKVGEAINLTVPGSERSYDLTGLKPGTEYIVSIY GVHNVYKDTNMRGLPLSAEFTT |
| 128 | PRT | Artificial | P54AR4-81 with Met | MLPAPKNLVVSEVTEDSLRLSWDYDLGVYFDSFLIQ YQESEKVGEAINLIVPGSERSYDLTGLKPGTEYIVSI YGVHNVYKDTNMRGLPLSAEFTT |
| 129 | PRT | Artificial | P54AR4-83 with Met | MLPAPKNLVVSEVTEDSLRLSWDDPWAFYESFLIQY QESEKVGEAINLIVPGSERSYDLTGLKPGTEYIVSIY GVHNVYKDTNMRGLPLSAEFTT |
| 130 | PRT | Artificial | P54CR4-31 with Met | MLPAPKNLVVSEVTEDSLRLSWTAPDAAFDSFLIQY QESEKVGEAINLTVPGSERSYDLTGLKPGTEYTVSIY GVLGSYVFEHDVMLPLSAEFTT |
| 131 | PRT | Artificial | P54AR4-83v2 with Met | MLPAPKNLVVSEVTEDSARLSWDDPWAFYESFLIQY QESEKVGEAIVLTVPGSERSYDLTGLKPGTEYTVSIY GVHNVYKDTNMRGLPLSAIFTT |
| 132 | PRT | Artificial | P54CR4-31v2 with Met | MLPAPKNLVVSEVTEDSARLSWTAPDAAFDSFLIQY QESEKVGEAIVLTVPGSERSYDLTGLKPGTEYTVSIY GVLGSYVFEHDVMLPLSAIFTT |
| 133 | PRT | Artificial | P54AR4-73v2 with Met | MLPAPKNLVVSEVTEDSLRLSWTWPYADLDSFLIQY QESEKVGEAINLTVPGSERSYDLTGLKPGTEYTVSIY GVHNVYKDTNMRGLPLSAEFTT |
| 134 | PRT | Artificial | P53A1R5-17v2 with Met | mlpapknlvvsevtedsarlswadphgfydsfliqy qesekvgeaivltvpgsersydltglkpgteytvsiy gvhnvykdtnmrglplsaifttt |
| 135 | PRT | Artificial | P54AR4-83v22 with Met | mlpapknlvvsevtedsarlswddpwalyesfliqy qesekvgeaivltypgsersydltglkpgteytvsiy gvhnvykdtnirglplsaifttt |
| 136 | PRT | Artificial | P54AR4-83v23 with Met | mlpapknlvvsevtedsarlswddphafyesfliqy qesekvgeaivltypgsersydltglkpgteytvsiy gvhnvykdtnirglplsaifttt |
| 137 | PRT | Artificial | P53A1R5-17v22 with Met | mlpapknlvvsevtedsarlswadphgfydsfliqy qesekvgeaivltypgsersydltglkpgteytvsiy gvhnvykdtnirglplsaifttt |
| 138 | PRT | Artificial | ECB1 without Met | LPAPKNLVVSEVTEDSARLSWDDPWAFYESFLIQYQ ESEKVGEAIVLTVPGSERSYDLTGLKPGTEYTVSIY GVHNVYKDTNMRGLPLSAIFTTGGGGSGGGGSGGGG SGGGGSMLPAPKNLVVSRVTEDSARLSWTAPDAAFD SFWIRYDEVVGGEAIVLTVPGSERSYDLTGLKPGT EYYVNILGVKGGSISVPLSAIFTT |
| 139 | PRT | Artificial | ECB2 without Met | LPAPKNLVVSEVTEDSARLSWDDPWAFYESFLIQYQ ESEKVGEAIVLTVPGSERSYDLTGLKPGTEYTVSIY GVHNVYKDTNMRGLPLSAIFTTGGGGSGGGGSGGGG SGGGGSLPAPKNLVVSRVTEDSARLSWTAPDAAFDS FWIRYFEFLGSGEAIVLTVPGSERSYDLTGLKPGTE YVVNIMGVKGGKISPPLSAIFTT |
| 140 | PRT | Artificial | ECB3 without Met | LPAPKNLVVSEVTEDSARLSWDDPWAFYESFLIQYQ ESEKVGEAIVLTVPGSERSYDLTGLKPGTEYTVSIY GVHNVYKDTNMRGLPLSAIFTTGGGGSGGGGSGGGG SGGGGSMLPAPKNLVVSRVTEDSARLSWTAPDAAFD SFWIRYFEFLGSEAIVLTVPGSERSYDLTGLKPGT EYVVQIIGVKGGHISLPLSAIFTT |
| 141 | PRT | Artificial | ECB4 without Met | LPAPKNLVVSEVTEDSARLSWDDPWAFYESFLIQYQ ESEKVGEAIVLTVPGSERSYDLTGLKPGTEYIVSIY GVHNVYKDTNMRGLPLSAIFTTGGGGSGGGGSGGGG SGGGGSMLPAPKNLVVSRVTEDSARLSWTAPDAAFD |

| SEQ ID NO: | Type | Species | Description | Sequence |
|---|---|---|---|---|
| | | | | SFFIRYDEFLRSGEAIVLTVPGSERSYDLTGLKPGT EYWVTILGVKGGLVSTPLSAIFTT |
| 142 | PRT | Artificial | ECB5 without Met | LPAPKNLVVSEVTEDSARLSWADPHGFYDSFLIQYQ ESEKVGEAIVLTVPGSERSYDLTGLKPGTEYIVSIY GVHNVYKDTNMRGLPLSAIFTTGGGGSGGGGSGGGG SGGGGSMLPAPKNLVVSRVTEDSARLSWTAPDAAFD SFWIRYFEFLGSGEAIVLTVPGSERSYDLTGLKPGT EYVVNIMGVKGGKISPPLSAIFTT |
| 143 | PRT | Artificial | ECB6 without Met | LPAPKNLVVSEVTEDSARLSWADPHGFYDSFLIQYQ ESEKVGEAIVLTVPGSERSYDLTGLKPGTEYIVSIY GVHNVYKDTNMRGLPLSAIFTTGGGGSGGGGSGGGG SGGGGSMLPAPKNLVVSRVTEDSARLSWTAPDAAFD SFWIRYFEFLGSGEAIVLTVPGSERSYDLTGLKPGT EYVVQIIGVKGGHISLPLSAIFTT |
| 144 | PRT | Artificial | ECB7 without Met | LPAPKNLVVSEVTEDSARLSWADPHGFYDSFLIQYQ ESEKVGEAIVLTVPGSERSYDLTGLKPGTEYIVSIY GVHNVYKDTNMRGLPLSAIFTTGGGGSGGGGSGGGG SGGGGSMLPAPKNLVVSRVTEDSARLSWTAPDAAFD SFWIRYFEFLGSGEAIVLTVPGSERSYDLTGLKPGT EYVVQIIGVKGGHISLPLSAIFTT |
| 145 | PRT | Artificial | ECB15 without Met | LPAPKNLVVSEVTEDSARLSWDDPWAFYESFLIQYQ ESEKVGEAIVLTVPGSERSYDLTGLKPGTEYIVSIY GVHNVYKDTNMRGLPLSAIFTTAPAPAPAPAPLPAP KNLWSRVTEDSARLSWTAPDAAFDSFWIRYFEFLGS GEAIVLTVPGSERSYDLTGLKPGTEYVVNIMGVKGG KISPPLSAIFTT |
| 146 | PRT | Artificial | ECB27 without Met | LPAPKNLVVSEVTEDSARLSWDDPWAFYESFLIQYQ ESEKVGEAIVLTVPGSERSYDLTGLKPGTEYIVSIY GVHNVYKDTNMRGLPLSAIFTTAPAPAPAPAPLPAP KNLWSRVTEDSARLSWTAPDAAFDSFWIRYDEVVVG GEAIVLTVPGSERSYDLTGLKPGTEYVVNILGVKGG SISVPLSAIFTT |
| 147 | PRT | Artificial | ECB60 without Met | LPAPKNLVVSEVTEDSARLSWADPHGFYDSFLIQYQ ESEKVGEAIVLTVPGSERSYDLTGLKPGTEYIVSIY GVHNVYKDTNMRGLPLSAIFTTAPAPAPAPAPMLPA PKNLVVSRVTEDSARLSWTAPDAAFDSFWIRYFEFL GSGEAIVLTVPGSERSYDLTGLKPGTEYVVNIMGVK GGKISPPLSAIFTT |
| 148 | PRT | Artificial | ECB37 without Met | LPAPKNLVVSEVTEDSARLSWADPHGFYDSFLIQYQ ESEKVGEAIVLTVPGSERSYDLTGLKPGTEYIVSIY GVHNVYKDTNMRGLPLSAIFTTAPAPAPAPAPLPAP KNLWSRVTEDSARLSWTAPDAAFDSFWIRYDEVVVG GEAIVLTVPGSERSYDLTGLKPGTEYVVNILGVKGG SISVPLSAIFTT |
| 149 | PRT | Artificial | ECB94 without Met | LPAPKNLVVSEVTEDSARLSWDDPWAFYESFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFLG SGEAIVLTVPGSERSYDLTGLKPGTEYVVNILGVKG GKISPPLSAIFTT |
| 150 | PRT | Artificial | ECB95 without Met | LPAPKNLVVSEVTEDSARLSWDDPWAFYESFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFVG SGEAIVLTVPGSERSYDLTGLKPGTEYVVNILGVKG GSISPPLSAIFTT |
| 151 | PRT | Artificial | ECB96 without Met | LPAPKNLVVSEVTEDSARLSWDDPWAFYESFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFVS KGDAIVLTVPGSERSYDLTGLKPGTEYVVNILGVKG GSISPPLSAIFTT |

SEQUENCE LISTING

| SEQ ID NO: | Type | Species | Description | Sequence |
|---|---|---|---|---|
| 152 | PRT | Artificial | ECB97 without Met | LPAPKNLVVSEVTEDSARLSWDDPWAFYESFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFLG SGEAIVLTVPGSERSYDLTGLKPGTEYVVNILSVKG GSISPPLSAIFTT |
| 153 | PRT | Artificial | ECB106 without Met | LPAPKNLVVSEVTEDSARLSWDDPHAFYESFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFLG SGEAIVLTVPGSERSYDLTGLKPGTEYVVNILGVKG GKISPPLSAIFTT |
| 154 | PRT | Artificial | ECB107 without Met | LPAPKNLVVSEVTEDSARLSWDDPHAFYESFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFVG SGEAIVLTVPGSERSYDLTGLKPGTEYVVNILGVKG GSISPPLSAIFTT |
| 155 | PRT | Artificial | ECB108 without Met | LPAPKNLVVSEVTEDSARLSWDDPHAFYESFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFVS KGDAIVLTVPGSERSYDLTGLKPGTEYVVNILGVKG GSISPPLSAIFTT |
| 156 | PRT | Artificial | ECB109 without Met | LPAPKNLVVSEVTEDSARLSWDDPHAFYESFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFLG SGEAIVLTVPGSERSYDLTGLKPGTEYVVNILSVKG GSISPPLSAIFTT |
| 157 | PRT | Artificial | ECB118 without Met | LPAPKNLVVSEVTEDSARLSWADPHGFYDSFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFLG SGEAIVLTVPGSERSYDLTGLKPGTEYVVNILGVKG GKISPPLSAIFTT |
| 158 | PRT | Artificial | ECB119 without Met | LPAPKNLVVSEVTEDSARLSWADPHGFYDSFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFVG SGEAIVLTVPGSERSYDLTGLKPGTEYVVNILGVKG GSISPPLSAIFTT |
| 159 | PRT | Artificial | ECB120 without Met | LPAPKNLVVSEVTEDSARLSWADPHGFYDSFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFVS KGDAIVLTVPGSERSYDLTGLKPGTEYVVNILGVKG GSISPPLSAIFTT |
| 160 | PRT | Artificial | ECB121 without Met | LPAPKNLVVSEVTEDSARLSWADPHGFYDSFLIQYQ ESEKVGEAIVLTVPGSERSYDLTGLKPGTEYIVSIY GVHNVYKDTNIRGLPLSAIFTTAPAPAPAPAPLPAP KNLVVSRVTEDSARLSWTAPDAAFDSFWIRYFEFLG SGEAIVLTVPGSERSYDLTGLKPGTEYVVNILSVKG GSISPPLSAIFTT |
| 161 | PRT | Artificial | ECB91 without Met | lpapknlvvsevtedsarlswddpwafyesfliqyq esekvgeaivltvpgsersydltglkpgteytvsiy gvhnvykdtnirglplsaifttapapapapaplpap KNLVVSRVTEDSARLSWTAPDAAFDSFWIRYFEFLG SGEAIVLTVPGSERSYDLTGLKPGTEYVVNILSVKG GSISPPLSAIFTT |
| 162 | PRT | Artificial | ECB18 without Met | lpapknlvvsevtedsarlswddpwafyesfliqyq esekvgeaivltvpgsersydltglkpgteytvsiy gvhnvykdtnmrglplsaifttapapapapaplpap |

SEQUENCE LISTING

| SEQ ID NO: | Type | Species | Description | Sequence |
|---|---|---|---|---|
| | | | | knlvvsrvtedsarlswtapdaafdsfwirydevvv ggeaivltvpgsersydltglkpgteyyvnilgvkg gsisvplsaifttapapapapaplaeakvlanreld kygvsdyyknlinnaktvegvkallldeilaalp |
| 163 | PRT | Artificial | ECB28 without Met | lpapknlvvsevtedsarlswadphgfydsfliqyq esekvgeaivltvpgsersydltglkpgteytvsiy gvhnvykdtnmrglplsaifttapapapapaplpap knlvvsrvtedsarlswtapdaafdsfwirydevvv ggeaivltvpgsersydltglkpgteyyvnilgvkg gsisvplsaifttapapapapaplaeakvlanreld kygvsdyyknlinnaktvegvkallldeilaalp |
| 164 | PRT | Artificial | ECB38 without Met | lpapknlvvsevtedsarlswddpwafyesfliqyq esekvgeaivltvpgsersydltglkpgteytvsiy gvhnvykdtnmrglplsaifttapapapapaplpap knlvvsrvtedsarlswtapdaafdsfwiryfeflg sgeaivltvpgsersydltglkpgteyyvnimgvkg gkispplsaifttapapapapaplaeakvlanreld kygvsdyyknlinnaktvegvkallldeilaalp |
| 165 | PRT | Artificial | ECB39 without Met | lpapknlvvsevtedsarlswadphgfydsfliqyq esekvgeaivltvpgsersydltglkpgteytvsiy gvhnvykdtnmrglplsaifttapapapapaplpap knlvvsrvtedsarlswtapdaafdsfwiryfeflg sgeaivltvpgsersydltglkpgteyyvnimgvkg gkispplsaifttapapapapaplaeakvlanreld kygvsdyyknlinnaktvegvkallldeilaalp |
| 166 | DNA | Artificial | ECB97 without Met | ttgccagcgccgaagaacctggtagttagcgaggttactgaggacagc gcgcgtctgagctgggacgatccgtgggcgttctacgagagctttctgat ccagtatcaagagagcgagaaagtcggtgaagcgattgtgctgaccgt cccgggctccgagcgttcctacgacctgaccggtttgaagccgggtacc gagtatacggtgagcatctacggtgttcacaatgtctataaggacactaa tatccgcggtctgcctctgagcgccattttcaccaccgcaccggcaccg gctccggctcctgcccgctgccggctccgaagaacttggtggtgagcc gtgttaccgaagatagcgcacgcctgagctggacggcaccggatgcg gcgttcgatagcttctggattcgctattttgagtttctgggtagcggtg aggcaattgttctgacggtgccgggctctgaacgctcctacgatttgac cggtctgaaaccgggcaccgagtatgtggtgaacattctgagcgttaag ggcggtagcatcagcccaccgctgagcgcgatcttcacgactggtggtt gc |
| 167 | DNA | Artificial | ECB15 without Met | ctgccagcccctaagaatctggtcgtgagcgaagtaaccgaggacag cgcccgcctgagctgggacgacccgtgggcgttctatgagtctttcctga ttcagtatcaagaaagcgaaaaagttggcgaagcgatcgtcctgaccg tcccgggtagcgagcgctcctacgatctgaccggcctgaaaccgggta cggagtacacggtgtccatttacggtgttcacaatgtgtataaagacacc aacatgcgtggcctgccgctgtcggcgattttcaccaccgcgcctgcgc cagcgcctgcaccggctccgctgccggcaccgaagaacctggttgtca gccgtgtgaccgaggatagcgcacgtttgagctggaccgctccggatg cagcctttgacagcttctggattcgttactttgaatttctgggtagcgg tgaggcgatcgttctgacggtgccgggctctgaacgcagctatgatttg acgggcctgaagccgggtactgagtacgtggttaacatcatgggcgtta agggtggtaaaatcagcccgccattgtccgcgatcttttaccacg |
| 168 | DNA | Artificial | >EGFR part ECB97; P54AR4-83v22 without met | ttgccagcgccgaagaacctggtagttagcgaggttactgaggacagc gcgcgtctgagctgggacgatccgtgggcgttctacgagagctttctgat ccagtatcaagagagcgagaaagtcggtgaagcgattgtgctgaccgt cccgggctccgagcgttcctacgacctgaccggtttgaagccgggtacc gagtatacggtgagcatctacggtgttcacaatgtctataaggacactaa tatccgcggtctgcctctgagcgccattttcaccacc |
| 169 | DNA | Artificial | >EGFR part ECB15; P54AR4-83v2 without Met | ctgccagcccctaagaatctggtcgtgagcgaagtaaccgaggacag cgcccgcctgagctgggacgacccgtgggcgttctatgagtctttcctga ttcagtatcaagaaagcgaaaaagttggcgaagcgatcgtcctgaccg tcccgggtagcgagcgctcctacgatctgaccggcctgaaaccgggta cggagtacacggtgtccatttacggtgttcacaatgtgtataaagacacc aacatgcgtggcctgccgctgtcggcgattttcaccacc |
| 170 | PRT | Artificial | ECB94 with C-ter cysteine | MLPAPKNLVVSEVTEDSARLSWDDPWAFYESFLIQY QESEKVGEAIVLTVPGSERSYDLTGLKPGTEYTVSI YGVHNVYKDTNIRGLPLSAIFTTAPAPAPAPAPLPA |

SEQUENCE LISTING

| SEQ ID NO: | Type | Species | Description | Sequence |
|---|---|---|---|---|
| | | | | PKNLVVSRVTEDSARLSWTAPDAAFDSFWIRYFEFL GSGEAIVLTVPGSERSYDLTGLKPGTEYVVNILGVK GGKISPPLSAIFTTC |
| 171 | PRT | Artificial | ECB95 with C-ter cysteine | MLPAPKNLVVSEVTEDSARLSWDDPWAFYESFLIQY QESEKVGEAIVLIVPGSERSYDLTGLKPGTEYTVSI YGVHNVYKDTNIRGLPLSAIFTTAPAPAPAPAPLPA PKNLVVSRVTEDSARLSWTAPDAAFDSFWIRYFEFV GSGEAIVLTVPGSERSYDLTGLKPGTEYVVNILGVK GGSISPPLSAIFTTC |
| 172 | PRT | Artificial | ECB96 with C-ter cysteine | MLPAPKNLVVSEVTEDSARLSWDDPWAFYESFLIQY QESEKVGEAIVLTVPGSERSYDLTGLKPGTEYTVSI YGVHNVYKDTNIRGLPLSAIFTTAPAPAPAPAPLPA PKNLVVSRVTEDSARLSWTAPDAAFDSFWIRYFEFV SKGDAIVLTVPGSERSYDLTGLKPGTEYVVNILGVK GGSISPPLSAIFTTC |
| 173 | PRT | Artificial | ECB97 with C-ter cysteine | MLPAPKNLVVSEVTEDSARLSWDDPWAFYESFLIQY QESEKVGEAIVLTVPGSERSYDLTGLKPGTEYTVSI YGVHNVYKDTNIRGLPLSAIFTTAPAPAPAPAPLPA PKNLVVSRVTEDSARLSWTAPDAAFDSFWIRYFEFL GSGEAIVLTVPGSERSYDLTGLKPGTEYVVNILSVK GGSISPPLSAIFTTC |
| 174 | PRT | Artificial | ECB106 with C-ter cysteine | MLPAPKNLVVSEVTEDSARLSWDDPHAFYESFLIQY QESEKVGEAIVLTVPGSERSYDLTGLKPGTEYTVSI YGVHNVYKDTNIRGLPLSAIFTTAPAPAPAPAPLPA PKNLVVSRVTEDSARLSWTAPDAAFDSFWIRYFEFL GSGEAIVLTVPGSERSYDLTGLKPGTEYVVNILGVK GGKISPPLSAIFTTC |
| 175 | PRT | Artificial | ECB107 with C-ter cysteine | MLPAPKNLVVSEVTEDSARLSWDDPHAFYESFLIQY QESEKVGEAIVLTVPGSERSYDLTGLKPGTEYTVSI YGVHNVYKDTNIRGLPLSAIFTTAPAPAPAPAPLPA PKNLVVSRVTEDSARLSWTAPDAAFDSFWIRYFEFV GSGEAIVLTVPGSERSYDLTGLKPGTEYVVNILGVK GGSISPPLSAIFTTC |
| 176 | PRT | Artificial | ECB108 with C-ter cysteine | MLPAPKNLVVSEVTEDSARLSWDDPHAFYESFLIQY QESEKVGEAIVLTVPGSERSYDLTGLKPGTEYTVSI YGVHNVYKDTNIRGLPLSAIFTTAPAPAPAPAPLPA PKNLVVSRVTEDSARLSWTAPDAAFDSFWIRYFEFV SKGDAIVLTVPGSERSYDLTGLKPGTEYVVNILGVK GGSISPPLSAIFTTC |
| 177 | PRT | Artificial | ECB109 with C-ter cysteine | MLPAPKNLVVSEVTEDSARLSWDDPHAFYESFLIQY QESEKVGEAIVLTVPGSERSYDLTGLKPGTEYTVSI YGVHNVYKDTNIRGLPLSAIFTTAPAPAPAPAPLPA PKNLVVSRVTEDSARLSWTAPDAAFDSFWIRYFEFL GSGEAIVLTVPGSERSYDLTGLKPGTEYVVNILSVK GGSISPPLSAIFTTC |
| 178 | PRT | Artificial | ECB91 with C-ter cysteine | mlpapknlvvsevtedsarlswddpwafyesfliqy qesekvgeaivltvpgsersydltglkpgteytvsi ygvhnvykdtnirglplsaifttapapapapapLPA PKNLVVSRVTEDSARLSWTAPDAAFDSFWIRYFEFL GSGEAIVLTVPGSERSYDLTGLKPGTEYVVNILSVK GGSISPPLSAIFTTC |

>SEQ ID NO: 179
PRT
Artificial
An FG loop of EGFR binding FN3 domain
HNVYKDTNX$_9$RGL;
wherein
X$_9$ is M or I >SEQ ID NO: 180
PRT
Artificial
A FG loop of EGFR binding FN3 domain (SEQ ID NO: 180)

| SEQ ID NO: | Type | Species | Description | Sequence |
|---|---|---|---|---|

LGSYVFEHDVML,

>SEQ ID NO: 181
PRT
Artificial
a BC loop of EGFR binding FN3 domain
(SEQ ID NO: 181)

$X_1X_2X_3X_4X_5X_6X_7X_8$,
wherein
$X_1$ is A, T, G or D;
$X_2$ is A, D, Y or W;
$X_3$ is P, D or N;
$X_4$ is L or absent;
$X_5$ is D, H, R, G, Y or W;
$X_6$ is G, D or A;
$X_7$ is A, F, G, H or D;
and
$X_8$ is Y, F or L.

>SEQ ID NO: 182
PRT
Artificial
EGFR binding FN3 domain
(SEQ ID NO: 182)

LPAPKNLVVSEVTEDSLRLSWX$_1$X$_2$X$_3$X$_4$X$_5$X$_6$X$_7$X$_8$DSFLIQYQESEKVGEAINLTVP
GSERSYDLTGLKPGTEYTVSIYGVHNVYKDTNX$_9$RGLPLSAEFTT,
$X_1$ is A, T, G or D;
$X_2$ is A, D, Y or W;
$X_3$ is P, D or N;
$X_4$ is L or absent;
$X_5$ is D, H, R, G, Y or W;
$X_6$ is G, D or A;
$X_7$ is A, F, G, H or D;
$X_8$ is Y, F or L;
and
$X_9$ is M or I >SEQ ID NO: 183
PRT
Artificial
EGFR binding FN3 domain
(SEQ ID NO: 183)

LPAPKNLVVSEVTEDSLRLSWX$_1$X$_2$X$_3$X$_4$X$_5$X$_6$X$_7$X$_8$DSFLIQYQESEKVGEAINLTVP
GSERSYDLTGLKPGTEYTVSIYGVLGSYVFEHDVMLPLSAEFTT,
wherein
$X_1$ is A, T, G or D;
$X_2$ is A, D, Y or W;
$X_3$ is P, D or N;
$X_4$ is L or absent;
$X_5$ is D, H, R, G, Y or W;
$X_6$ is G, D or A;
$X_7$ is A, F, G, H or D;
and
$X_8$ is Y, F or L.

>SEQ ID NO: 184
PRT
Artificial
A C-met binding FN3 domain C strand and a CD loop sequence
(SEQ ID NO: 184)

DSFX$_{10}$IRYX$_{11}$EX$_{12}$X$_{13}$X$_{14}$X$_{15}$GX$_{16}$,
wherein
$X_{10}$ is W, F or V;
$X_{11}$ is D, F or L;
$X_{12}$ is V, F or L;
$X_{13}$ is V, L or T;
$X_{14}$ is V, R, G, L, T or S;
$X_{15}$ is G, S, A, T or K;
and
$X_{16}$ is E or D;
and

>SEQ ID NO: 185

SEQUENCE LISTING

| SEQ ID NO: | Type | Species | Description | Sequence |
|---|---|---|---|---|

PRT
Artificial
A c-Met binding FN3 domain F strand and a FG loop
(SEQ ID NO: 185)

TEYX$_{17}$VX$_{18}$IX$_{19}$X$_{20}$VKGGX$_{21}$X$_{22}$SX$_{23}$,
wherein
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L;
and
X$_{23}$ is V, T, H, I, P, Y, T or L.

>SEQ ID NO: 186
PRT
Artificial
a c-Met binding FN3 domain
(SEQ ID NO: 186)

LPAPKNLVVSRVTEDSARLSWTAPDAAF DSFX$_{10}$IRYX$_{11}$EX$_{12}$X$_{13}$X$_{14}$X$_{15}$GX$_{16}$
AIVLTVPGSERSYDLTGLKPGTEYX$_{17}$VX$_{18}$IX$_{19}$X$_{20}$VKGGX$_{21}$X$_{22}$SX$_{23}$PLSAEFTT,
wherein
X$_{10}$ is W, F or V;
and
X$_{11}$ is D, F or L;
X$_{12}$ is V, F or L;
X$_{13}$ is V, L or T;
X$_{14}$ is V, R, G, L, T or S;
X$_{15}$ is G, S, A, T or K;
X$_{16}$ is E or D;
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L;
and
X$_{23}$ is V, T, H, I, P, Y, T or L.

>SEQ ID NO: 187
PRT
Artificial
EGFR FN3 domain of a bispecific EGFR/c-Met FN3 domain containing molecule
(SEQ ID NO: 187)

LPAPKNLVVSX$_{24}$VTX$_{25}$DSX$_{26}$RLSWDDPX$_{27}$AFYX$_{28}$SFLIQYQX$_{29}$SEKVGEAIX$_{30}$LTVPGSERS
YDLTGLKPGTEYTVSIYX$_{31}$VHNVYKDTNX$_{32}$RGLPLSAX$_{33}$FTT,
wherein
X$_{24}$ is E, N or R;
X$_{25}$ is E or P;
X$_{26}$ is L or A;
X$_{27}$ is H or W;
X$_{28}$ is E or D;
X$_{29}$ is E or P;
X$_{30}$ is N or V;
X$_{31}$ is G or Y;
X$_{32}$ is M or I;
and
X$_{33}$ is E or I;

>SEQ ID NO: 188
c-Met FN3 domain of a bispecific EGFR/c-Met FN3 domain containing molecule
(SEQ ID NO: 188)

LPAPKNLVVSX$_{34}$VTX$_{35}$DSX$_{36}$RLSWTAPDAAFDSFWIRYFX$_{37}$FX$_{38}$X$_{39}$X$_{40}$GX$_{41}$AIX$_{42}$LTVPGSE
RSYDLTGLKPGTEYVVNIX$_{43}$X$_{44}$VKGGX$_{45}$ISPPLSAX$_{46}$FTT;
wherein
X$_{34}$ is E, N or R;
X$_{35}$ is E or P;
X$_{36}$ is L or A;
X$_{37}$ is E or P;
X$_{38}$ is V or L;
X$_{39}$ is G or S;
X$_{40}$ is S or K;

-continued

SEQUENCE LISTING

| SEQ ID NO: | Type | Species | Description | Sequence |
|---|---|---|---|---|
| | | | $X_{41}$ is E or D; $X_{42}$ is N or V; $X_{43}$ is L or M; $X_{44}$ is G or S; $X_{45}$ is S or K; and $X_{46}$ is E or I. | |
| 189 | PRT | Artificial | P54AR4-83v2-V9C with methionine | MLPAPKNLCVSEVTEDSARLSWDDPWAF YESFLIQYQESEKVGEAIVLTVPGSERSYDL TGLKPGTEYTVSIYGVHNVYKDTNMRGLP LSAIFTT |
| 190 | PRT | Artificial | P54AR4-83v2-S11C with methionine | MLPAPKNLVVCEVTEDSARLSWDDPWAF YESFLIQYQESEKVGEAIVLTVPGSERSYDL TGLKPGTEYTVSIYGVHNVYKDTNMRGLP LSAIFTT |
| 191 | PRT | Artificial | P54AR4-83v2-E12C with methionine | MLPAPKNLVVSCVTEDSARLSWDDPWAF YESFLIQYQESEKVGEAIVLTVPGSERSYDL TGLKPGTEYTVSIYGVHNVYKDTNMRGLP LSAIFTT |
| 192 | PRT | Artificial | P54AR4-83v2-E15C with methionine | MLPAPKNLVVSEVTCDSARLSWDDPWAF YESFLIQYQESEKVGEAIVLTVPGSERSYDL TGLKPGTEYTVSIYGVHNVYKDTNMRGLP LSAIFTT |
| 193 | PRT | Artificial | P54AR4-83v2-D16C with methionine | MLPAPKNLVVSEVTECSARLSWDDPWAF YESFLIQYQESEKVGEAIVLTVPGSERSYDL TGLKPGTEYTVSIYGVHNVYKDTNMRGLP LSAIFTT |
| 194 | PRT | Artificial | P54AR4-83v2-S17C with methionine | MLPAPKNLVVSEVTEDCARLSWDDPWAF YESFLIQYQESEKVGEAIVLTVPGSERSYDL TGLKPGTEYTVSIYGVHNVYKDTNMRGLP LSAIFTT |
| 195 | PRT | Artificial | P54AR4-83v2-S21C with methionine | MLPAPKNLVVSEVTEDSARLCWDDPWAF YESFLIQYQESEKVGEAIVLTVPGSERSYDL TGLKPGTEYTVSIYGVHNVYKDTNMRGLP LSAIFTT |
| 196 | PRT | Artificial | P54AR4-83v2-S31C with methionine | MLPAPKNLVVSEVTEDSARLSWDDPWAF YECFLIQYQESEKVGEAIVLTVPGSERSYD LTGLKPGTEYTVSIYGVHNVYKDTNMRGL PLSAIFTT |
| 197 | PRT | Artificial | P54AR4-83v2-Q35C with methionine | MLPAPKNLVVSEVTEDSARLSWDDPWAF YESFLICYQESEKVGEAIVLTVPGSERSYDL TGLKPGTEYTVSIYGVHNVYKDTNMRGLP LSAIFTT |
| 198 | PRT | Artificial | P54AR4-83v2-S39C with methionine | MLPAPKNLVVSEVTEDSARLSWDDPWAF YESFLIQYQECEKVGEAIVLTVPGSERSYDL TGLKPGTEYTVSIYGVHNVYKDTNMRGLP LSAIFTT |
| 199 | PRT | Artificial | P54AR4-83v2-K41C with methionine | MLPAPKNLVVSEVTEDSARLSWDDPWAF YESFLIQYQESECVGEAIVLTVPGSERSYDL TGLKPGTEYTVSIYGVHNVYKDTNMRGLP LSAIFTT |
| 200 | PRT | Artificial | P54AR4-83v2-V42C with methionine | MLPAPKNLVVSEVTEDSARLSWDDPWAF YESFLIQYQESEKCGEAIVLTVPGSERSYDL TGLKPGTEYTVSIYGVHNVYKDTNMRGLP LSAIFTT |
| 201 | PRT | Artificial | P54AR4-83v2-I46C with methionine | MLPAPKNLVVSEVTEDSARLSWDDPWAF YESFLIQYQESEKVGEACVLTVPGSERSYDL TGLKPGTEYTVSIYGVHNVYKDTNMRGLP LSAIFTT |

SEQUENCE LISTING

| SEQ ID NO: | Type | Species | Description | Sequence |
|---|---|---|---|---|
| 202 | PRT | Artificial | P54AR4-83v2-L48C with methionine | MLPAPKNLVVSEVTEDSARLSWDDPWAF YESFLIQYQESEKVGEAIVCTVPGSERSYDL TGLKPGTEYTVSIYGVHNVYKDTNMRGLP LSAIFTT |
| 203 | PRT | Artificial | P54AR4-83v2-T49C with methionine | MLPAPKNLVVSEVTEDSARLSWDDPWAF YESFLIQYQESEKVGEAIVLCVPGSERSYDL TGLKPGTEYTVSIYGVHNVYKDTNMRGLP LSAIFTT |
| 204 | PRT | Artificial | P54AR4-83v2-E54C with methionine | MLPAPKNLVVSEVTEDSARLSWDDPWAF YESFLIQYQESEKVGEAIVLTVPGSCRSYDL TGLKPGTEYTVSIYGVHNVYKDTNMRGLP LSAIFTT |
| 205 | PRT | Artificial | P54AR4-83v2-R55C with methionine | MLPAPKNLVVSEVTEDSARLSWDDPWAF YESFLIQYQESEKVGEAIVLTVPGSECSYDL TGLKPGTEYTVSIYGVHNVYKDTNMRGLP LSAIFTT |
| 206 | PRT | Artificial | P54AR4-83v2-T60C with methionine | MLPAPKNLVVSEVTEDSARLSWDDPWAF YESFLIQYQESEKVGEAIVLTVPGSERSYDL CGLKPGTEYTVSIYGVHNVYKDTNMRGLP LSAIFTT |
| 207 | PRT | Artificial | P54AR4-83v2-G61C with methionine | MLPAPKNLVVSEVTEDSARLSWDDPWAF YESFLIQYQESEKVGEAIVLTVPGSERSYDL TCLKPGTEYTVSIYGVHNVYKDTNMRGLP LSAIFTT |
| 208 | PRT | Artificial | P54AR4-83v2-K63C with methionine | MLPAPKNLVVSEVTEDSARLSWDDPWAF YESFLIQYQESEKVGEAIVLTVPGSERSYDL TGLCPGTEYTVSIYGVHNVYKDTNMRGLP LSAIFTT |
| 209 | PRT | Artificial | P54AR4-83v2-G65C with methionine | MLPAPKNLVVSEVTEDSARLSWDDPWAF YESFLIQYQESEKVGEAIVLTVPGSERSYDL TGLKPCTEYTVSIYGVHNVYKDTNMRGLP LSAIFTT |
| 210 | PRT | Artificial | P54AR4-83v2-N7C with methionine | MLPAPKCLVVSEVTEDSARLSWDDPWAF YESFLIQYQESEKVGEAIVLTVPGSERSYDL TGLKPGTEYTVSIYGVHNVYKDTNMRGLP LSAIFTT |
| 211 | PRT | Artificial | P54AR4-83v2-S71C with methionine | MLPAPKNLVVSEVTEDSARLSWDDPWAF YESFLIQYQESEKVGEAIVLTVPGSERSYDL TGLKPGTEYTVCIYGVHNVYKDTNMRGLP LSAIFTT |
| 212 | PRT | Artificial | P54AR4-83v2-L89C with methionine | MLPAPKNLVVSEVTEDSARLSWDDPWAF YESFLIQYQESEKVGEAIVLTVPGSERSYDL TGLKPGTEYTVSIYGVHNVYKDTNMRGLP CSAIFTT |
| 213 | PRT | Artificial | P54AR4-83v2-S90C with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LCAIFTT |
| 214 | PRT | Artificial | P54AR4-83v2A91C with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSCIFTT |
| 215 | PRT | Artificial | P54AR4-83v2-I92C with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSACFTT |

SEQUENCE LISTING

| SEQ ID NO: | Type | Species | Description | Sequence |
|---|---|---|---|---|
| 216 | PRT | Artificial | P54AR4-83v2-T94C with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSAIFCT |
| 217 | PRT | Artificial | P54AR4-83v2-cys with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSAIFTTGGHHHHHHC |
| 218 | PRT | Artificial | ECB147 with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSAIFTTAPAPAPAPAPLPAPKNLVVSRVTE DSARLSWTAPDAAFDSFWIRYFEFLGSGEA IVLTVPGSERSYDLTGLKPGTEYVVNIMSV KGGSISPPLSAIFTTAPSPAPAPAPLAEAKV LANRELDKYGVSDYYKNLINNAKTVEGV KALLDEILAALP |
| 219 | PRT | Artificial | ECB147v1 with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSAIFTTAPCPAPAPAPLPAPKNLVVSRVTE DSARLSWTAPDAAFDSFWIRYFEFLGSGEA IVLTVPGSERSYDLTGLKPGTEYVVNIMSV KGGSISPPLSAIFTTAPSPAPAPAPLAEAKV LANRELDKYGVSDYYKNLINNAKTVEGV KALLDEILAALP |
| 220 | PRT | Artificial | ECB147v2 with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSAIFTTAPAPAPAPAPLPAPKNLVVSRVTE DSARLSWTAPDAAFDSFWIRYFEFLGSGEA IVLTVPGSERSYDLTGLCPGTEYVVNIMSV KGGSISPPLSAIFTTAPAPAPAPAPLAEAKV LANRELDKYGVSDYYKNLINNAKTVEGV KALLDEILAALP |
| 221 | PRT | Artificial | ECB147v3 with methionine | MLPAPKNLVVSEVTEDSARLSWDDPWAF YESFLIQYQESEKVGEAIVLTVPGSERSYDL TGLCPGTEYTVSIYGVHNVYKDTNMRGLP LSAIFTTAPCPAPAPAPLPAPKNLVVSRVTE DSARLSWTAPDAAFDSFWIRYFEFLGSGEA IVLTVPGSERSYDLTGLCPGTEYVVNIMSV KGGSISPPLSAIFTTAPCPAPAPAPLAEAKV LANRELDKYGVSDYYKNLINNAKTVEGV KALLDEILAALP |
| 222 | PRT | Artificial | ECB147v4 with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSAIFTTAPAPAPAPAPLPAPKNLVVSRVTE DSARLSWTAPDAAFDSFWIRYFEFLGSGEA IVLTVPGSERSYDLTGLKPGTEYVVNIMSV KGGSISPPLSAIFTTAPCPAPAPAPLAEAKV LANRELDKYGVSDYYKNLINNAKTVEGV KALLDEILAALP |
| 223 | PRT | Artificial | ECB147v5 with methionine | MLPAPKNLVVSEVTEDSARLSWDDPWAF YESFLIQYQESEKVGEAIVLTVPGSERSYDL TGLCPGTEYTVSIYGVHNVYKDTNMRGLP LSAIFTTAPAPAPAPAPLPAPKNLVVSRVTE DSARLSWTAPDAAFDSFWIRYFEFLGSGEA IVLTVPGSERSYDLTGLCPGTEYVVNIMSV KGGSISPPLSAIFTTAPAPAPAPAPLAEAKV LANRELDKYGVSDYYKNLINNAKTVEGV KALLDEILAALP |
| 224 | PRT | Artificial | ECB147v6 with methionine | MLPAPKNLVVSEVTEDSARLSWDDPWAF YESFLIQYQESEKVGEAIVLTVPGSERSYDL TGLCPGTEYTVSIYGVHNVYKDTNMRGLP |

SEQUENCE LISTING

| SEQ ID NO: | Type | Species | Description | Sequence |
|---|---|---|---|---|
| | | | | LSAIFTTAPAPAPAPAPLPAPKNLVVSRVTE DSARLSWTAPDAAFDSFWIRYFEFLGSGEA IVLTVPGSERSYDLTGLKPGTEYVVNIMSV KGGSISPPLSAIFTTAPAPAPAPAPLAEAKV LANRELDKYGVSDYYKNLINNAKTVEGV KALLDEILAALP |
| 225 | PRT | Artificial | ECB147v7 with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSAIFTTAPCPAPAPAPLPAPKNLVVSRVTE DSARLSWTAPDAAFDSFWIRYFEFLGSGEA IVLTVPGSERSYDLTGLKPGTEYVVNIMSV KGGSISPPLSAIFTTAPCPAPAPAPLAEAKV LANRELDKYGVSDYYKNLINNAKTVEGV KALLDEILAALP |
| 226 | PRT | Artificial | ECB82-cys with methionine | MLPAPKNLVVSEVTEDSARLSWDDPWAF YESFLIQYQESEKVGEAIVLTVPGSERSYDL TGLKPGTEYTVSIYGVHNVYKDTNMRGLP LSAIFTTAPAPAPAPAPLPAPKNLVVSRVTE DSARLSWTAPDAAFDSFWIRYFEFLGSGEA IVLTVPGSERSYDLTGLKPGTEYVVNIMGV KGGKISPPLSAIFTTAPAPAPAPAPTIDEWL LKEAKEKAIEELKKAGITSDYYFDLINKAK TVEGVNALKDEILKAGGHHHHHC |
| 227 | PRT | Artificial | P54AR4-83v2-V8C without methionine | LPAPKNLCVSEVTEDSARLSWDDPWAFYE SFLIQYQESEKVGEAIVLTVPGSERSYDLTG LKPGTEYTVSIYGVHNVYKDTNMRGLPLS AIFTT |
| 228 | PRT | Artificial | P54AR4-83v2-S10C without methionine | LPAPKNLVVCEVTEDSARLSWDDPWAFYE SFLIQYQESEKVGEAIVLTVPGSERSYDLTG LKPGTEYTVSIYGVHNVYKDTNMRGLPLS AIFTT |
| 229 | PRT | Artificial | P54AR4-83v2-E11C without methionine | LPAPKNLVVSCVTEDSARLSWDDPWAFYE SFLIQYQESEKVGEAIVLTVPGSERSYDLTG LKPGTEYTVSIYGVHNVYKDTNMRGLPLS AIFTT |
| 230 | PRT | Artificial | P54AR4-83v2-E14C without methionine | LPAPKNLVVSEVTCDSARLSWDDPWAFYE SFLIQYQESEKVGEAIVLTVPGSERSYDLTG LKPGTEYTVSIYGVHNVYKDTNMRGLPLS AIFTT |
| 231 | PRT | Artificial | P54AR4-83v2-D15C without methionine | LPAPKNLVVSEVTECSARLSWDDPWAFYE SFLIQYQESEKVGEAIVLTVPGSERSYDLTG LKPGTEYTVSIYGVHNVYKDTNMRGLPLS AIFTT |
| 232 | PRT | Artificial | P54AR4-83v2-S16C without methionine | LPAPKNLVVSEVTEDCARLSWDDPWAFYE SFLIQYQESEKVGEAIVLTVPGSERSYDLTG LKPGTEYTVSIYGVHNVYKDTNMRGLPLS AIFTT |
| 233 | PRT | Artificial | P54AR4-83v2-S20C without methionine | LPAPKNLVVSEVTEDSARLCWDDPWAFYE SFLIQYQESEKVGEAIVLTVPGSERSYDLTG LKPGTEYTVSIYGVHNVYKDTNMRGLPLS AIFTT |
| 234 | PRT | Artificial | P54AR4-83v2-S30C without methionine | LPAPKNLVVSEVTEDSARLSWDDPWAFYE CFLIQYQESEKVGEAIVLTVPGSERSYDLTG LKPGTEYTVSIYGVHNVYKDTNMRGLPLS AIFTT |
| 235 | PRT | Artificial | P54AR4-83v2-Q34C without methionine | LPAPKNLVVSEVTEDSARLSWDDPWAFYE SFLICYQESEKVGEAIVLTVPGSERSYDLTG LKPGTEYTVSIYGVHNVYKDTNMRGLPLS AIFTT |

| SEQ ID NO: | Type | Species | Description | Sequence |
|---|---|---|---|---|
| 236 | PRT | Artificial | P54AR4-83v2-S38C without methionine | LPAPKNLVVSEVTEDSARLSWDDPWAFYE SFLIQYQECEKVGEAIVLTVPGSERSYDLTG LKPGTEYTVSIYGVHNVYKDTNMRGLPLS AIFTT |
| 237 | PRT | Artificial | P54AR4-83v2-K40C without methionine | LPAPKNLVVSEVTEDSARLSWDDPWAFYE SFLIQYQESECVGEAIVLTVPGSERSYDLTG LKPGTEYTVSIYGVHNVYKDTNMRGLPLS AIFTT |
| 238 | PRT | Artificial | P54AR4-83v2-V41C without methionine | LPAPKNLVVSEVTEDSARLSWDDPWAFYE SFLIQYQESEKCGEAIVLTVPGSERSYDLTG LKPGTEYTVSIYGVHNVYKDTNMRGLPLS AIFTT |
| 239 | PRT | Artificial | P54AR4-83v2-I45C without methionine | LPAPKNLVVSEVTEDSARLSWDDPWAFYE SFLIQYQESEKVGEACVLTVPGSERSYDLTG LKPGTEYTVSIYGVHNVYKDTNMRGLPLS AIFTT |
| 240 | PRT | Artificial | P54AR4-83v2-L47C without methionine | LPAPKNLVVSEVTEDSARLSWDDPWAFYE SFLIQYQESEKVGEAIVCTVPGSERSYDLT GLKPGTEYTVSIYGVHNVYKDTNMRGLPL SAIFTT |
| 241 | PRT | Artificial | P54AR4-83v2-T48C without methionine | LPAPKNLVVSEVTEDSARLSWDDPWAFYE SFLIQYQESEKVGEAIVLCVPGSERSYDLT GLKPGTEYTVSIYGVHNVYKDTNMRGLPL SAIFTT |
| 242 | PRT | Artificial | P54AR4-83v2-E53C without methionine | LPAPKNLVVSEVTEDSARLSWDDPWAFYE SFLIQYQESEKVGEAIVLTVPGSCRSYDLT GLKPGTEYTVSIYGVHNVYKDTNMRGLPL SAIFTT |
| 243 | PRT | Artificial | P54AR4-83v2-R54C without methionine | LPAPKNLVVSEVTEDSARLSWDDPWAFYE SFLIQYQESEKVGEAIVLTVPGSECSYDLTG LKPGTEYTVSIYGVHNVYKDTNMRGLPLS AIFTT |
| 244 | PRT | Artificial | P54AR4-83v2-T59C without methionine | LPAPKNLVVSEVTEDSARLSWDDPWAFYE SFLIQYQESEKVGEAIVLTVPGSERSYDLC GLKPGTEYTVSIYGVHNVYKDTNMRGLPL SAIFTT |
| 245 | PRT | Artificial | P54AR4-83v2-G60C without methionine | LPAPKNLVVSEVTEDSARLSWDDPWAFYE SFLIQYQESEKVGEAIVLTVPGSERSYDLTC LKPGTEYTVSIYGVHNVYKDTNMRGLPLS AIFTT |
| 246 | PRT | Artificial | P54AR4-83v2-K62C without methionine | LPAPKNLVVSEVTEDSARLSWDDPWAFYE SFLIQYQESEKVGEAIVLTVPGSERSYDLTG LCPGTEYTVSIYGVHNVYKDTNMRGLPLS AIFTT |
| 247 | PRT | Artificial | P54AR4-83v2-G64C without methionine | LPAPKNLVVSEVTEDSARLSWDDPWAFYE SFLIQYQESEKVGEAIVLTVPGSERSYDLTG LKPCTEYTVSIYGVHNVYKDTNMRGLPLS AIFTT |
| 248 | PRT | Artificial | P54AR4-83v2-N6C without methionine | LPAPKCLVVSEVTEDSARLSWDDPWAFYE SFLIQYQESEKVGEAIVLTVPGSERSYDLTG LKPGTEYTVSIYGVHNVYKDTNMRGLPLS AIFTT |
| 249 | PRT | Artificial | P54AR4-83v2-S70C without methionine | LPAPKNLVVSEVTEDSARLSWDDPWAFYE SFLIQYQESEKVGEAIVLTVPGSERSYDLTG LKPGTEYTVCIYGVHNVYKDTNMRGLPLS AIFTT |

SEQUENCE LISTING

| SEQ ID NO: | Type | Species | Description | Sequence |
|---|---|---|---|---|
| 250 | PRT | Artificial | P54AR4-83v2-L88C without methionine | LPAPKNLVVSEVTEDSARLSWDDPWAFYE SFLIQYQESEKVGEAIVLTVPGSERSYDLTG LKPGTEYTVSIYGVHNVYKDTNMRGLPCS AIFTT |
| 251 | PRT | Artificial | P54AR4-83v2-S89C without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLC AIFTT |
| 252 | PRT | Artificial | P54AR4-83v2A90C without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS CIFTT |
| 253 | PRT | Artificial | P54AR4-83v2-I91C without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS ACFTT |
| 254 | PRT | Artificial | P54AR4-83v2-T93C without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS AIFCT |
| 255 | PRT | Artificial | P54AR4-83v2-cys without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS AIFTTGGHHHHHHC |
| 256 | PRT | Artificial | ECB147 without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS AIFTTAPAPAPAPAPLPAPKNLVVSRVTED SARLSWTAPDAAFDSFWIRYFEFLGSGEAI VLTVPGSERSYDLTGLKPGTEYVVNIMSV KGGSISPPLSAIFTTAPSPAPAPAPLAEAKV LANRELDKYGVSDYYKNLINNAKTVEGV KALLDEILAALP |
| 257 | PRT | Artificial | ECB147v1 without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS AIFTTAPCPAPAPAPLPAPKNLVVSRVTEDS ARLSWTAPDAAFDSFWIRYFEFLGSGEAIV LTVPGSERSYDLTGLKPGTEYVVNIMSVK GGSISPPLSAIFTTAPSPAPAPAPLAEAKVL ANRELDKYGVSDYYKNLINNAKTVEGVK ALLDEILAALP |
| 258 | PRT | Artificial | ECB147v2 without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS AIFTTAPAPAPAPAPLPAPKNLVVSRVTED SARLSWTAPDAAFDSFWIRYFEFLGSGEAI VLTVPGSERSYDLTGLCPGTEYVVNIMSV KGGSISPPLSAIFTTAPAPAPAPAPLAEAKV LANRELDKYGVSDYYKNLINNAKTVEGV KALLDEILAALP |
| 259 | PRT | Artificial | ECB147v3 without methionine | LPAPKNLVVSEVTEDSARLSWDDPWAFYE SFLIQYQESEKVGEAIVLTVPGSERSYDLTG LCPGTEYTVSIYGVHNVYKDTNMRGLPLS AIFTTAPCPAPAPAPLPAPKNLVVSRVTEDS ARLSWTAPDAAFDSFWIRYFEFLGSGEAIV LTVPGSERSYDLTGLCPGTEYVVNIMSVK GGSISPPLSAIFTTAPCPAPAPAPLAEAKVL ANRELDKYGVSDYYKNLINNAKTVEGVK ALLDEILAALP |
| 260 | PRT | Artificial | ECB147v4 without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS |

SEQUENCE LISTING

| SEQ ID NO: | Type | Species | Description | Sequence |
|---|---|---|---|---|
| | | | | AIFTTAPAPAPAPAPLPAPKNLVVSRVTED SARLSWTAPDAAFDSFWIRYFEFLGSGEAI VLTVPGSERSYDLTGLKPGTEYVVNIMSV KGGSISPPLSAIFTTAPCPAPAPAPLAEAKV LANRELDKYGVSDYYKNLINNAKTVEGV KALLDEILAALP |
| 261 | PRT | Artificial | ECB147v5 without methionine | LPAPKNLVVSEVTEDSARLSWDDPWAFYE SFLIQYQESEKVGEAIVLTVPGSERSYDLTG LCPGTEYTVSIYGVHNVYKDTNMRGLPLS AIFTTAPAPAPAPAPLPAPKNLVVSRVTED SARLSWTAPDAAFDSFWIRYFEFLGSGEAI VLTVPGSERSYDLTGLCPGTEYVVNIMSV KGGSISPPLSAIFTTAPAPAPAPAPLAEAKV LANRELDKYGVSDYYKNLINNAKTVEGV KALLDEILAALP |
| 262 | PRT | Artificial | ECB147v6 without methionine | LPAPKNLVVSEVTEDSARLSWDDPWAFYE SFLIQYQESEKVGEAIVLTVPGSERSYDLTG LCPGTEYTVSIYGVHNVYKDTNMRGLPLS AIFTTAPAPAPAPAPLPAPKNLVVSRVTED SARLSWTAPDAAFDSFWIRYFEFLGSGEAI VLTVPGSERSYDLTGLKPGTEYVVNIMSV KGGSISPPLSAIFTTAPAPAPAPAPLAEAKV LANRELDKYGVSDYYKNLINNAKTVEGV KALLDEILAALP |
| 263 | PRT | Artificial | ECB147v7 without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS AIFTTAPCPAPAPAPLPAPKNLVVSRVTEDS ARLSWTAPDAAFDSFWIRYFEFLGSGEAIV LTVPGSERSYDLTGLKPGTEYVVNIMSVK GGSISPPLSAIFTTAPCPAPAPAPLAEAKVL ANRELDKYGVSDYYKNLINNAKTVEGVK ALLDEILAALP |
| 264 | PRT | Artificial | ECB82-cys without methionine | LPAPKNLVVSEVTEDSARLSWDDPWAFYE SFLIQYQESEKVGEAIVLTVPGSERSYDLTG LKPGTEYTVSIYGVHNVYKDTNMRGLPLS AIFTTAPAPAPAPAPLPAPKNLVVSRVTED SARLSWTAPDAAFDSFWIRYFEFLGSGEAI VLTVPGSERSYDLTGLKPGTEYVVNIMGV KGGKISPPLSAIFTTAPAPAPAPAPTIDEWL LKEAKEKAIEELKKAGITSDYYFDLINKAK TVEGVNALKDEILKAGGHHHHHC |
| 265 | PRT | Artificial | Tencon-cys | LPAPKNLVVSEVTEDSLRLSWTAPDAAFD SFLIQYQESEKVGEAINLTVPGSERSYDLTG LKPGTEYTVSIYGVKGGHRSNPLSAEFTTG GHHHHHHC |

What is claimed:

1. An engineered fibronectin type III (FN3) domain peptide comprising an amino acid residue substituted with a cysteine residue at an amino acid position selected from the group consisting of residues 6, 8, 10, 14, 15, 20, 45, 48, 53, 54, 59, 64, and 88 of the FN3 domain, wherein the amino acid positions of the residues of the FN3 domain correspond to the amino acid positions of SEQ ID NO: 1, and wherein the FN3 domain peptide comprises a peptide having at least 87% identity to a peptide comprising the amino acid sequence of SEQ ID NO: 27.

2. The engineered FN3 domain peptide of claim 1, further comprising a half-life extending moiety.

3. The engineered FN3 domain peptide of claim 2, wherein the half-life extending moiety is an albumin binding molecule, a polyethylene glycol (PEG), or at least a portion of an Fc region of an immunoglobulin.

4. The engineered FN3 domain peptide of claim 1, wherein the engineered FN3 domain peptide has an amino acid sequence selected from the group consisting of the amino acid sequence of SEQ ID NO: 189, SEQ ID NO: 227, SEQ ID NO: 190, SEQ ID NO: 228, SEQ ID NO: 192, SEQ ID NO: 230, SEQ ID NO: 193, SEQ ID NO: 231, SEQ ID NO: 195, SEQ ID NO: 233, SEQ ID NO: 201, SEQ ID NO: 239, SEQ ID NO: 203, SEQ ID NO: 241, SEQ ID NO: 205, SEQ ID NO: 243, SEQ ID NO: 206, SEQ ID NO: 244, SEQ ID NO: 209, and SEQ ID NO: 247.

5. An engineered fibronectin type III (FN3) domain peptide comprising an amino acid residue substituted with a cysteine residue at an amino acid position selected from the group consisting of residues 11, 16, 30, 34, 38, 40, 41, 47, 60, 62, 70, 83, 84, and 85 of the FN3 domain, wherein the amino acid positions of the residues of the FN3 domain correspond to the amino acid positions of SEQ ID NO: 1, and wherein the FN3 domain peptide comprises a peptide having at least 87% identity to a peptide comprising the amino acid sequence of SEQ ID NO: 27.

6. The engineered FN3 domain peptide of claim 5, further comprising a half-life extending moiety.

7. The engineered FN3 domain peptide of claim 6, wherein the half-life extending moiety is an albumin binding molecule, a polyethylene glycol (PEG), or at least a portion of an Fc region of an immunoglobulin.

8. The engineered FN3 domain peptide of claim 5, wherein the engineered FN3 domain peptide has an amino acid sequence selected from the group consisting of the amino acid sequence of SEQ ID NO: 191, SEQ ID NO: 229, SEQ ID NO: 194, SEQ ID NO:232, SEQ ID NO:196, SEQ ID NO: 234, SEQ ID NO: 197, SEQ ID NO: 235, SEQ ID NO: 198, SEQ ID NO: 236, SEQ ID NO: 199, SEQ ID NO: 237, SEQ ID NO: 200, SEQ ID NO: 238, SEQ ID NO: 202, SEQ ID NO: 240, SEQ ID NO: 207, SEQ ID NO: 245, SEQ ID NO: 208, SEQ ID NO: 246, SEQ ID NO: 211, SEQ ID NO: 249, SEQ ID NO: 212, SEQ ID NO: 250, SEQ ID NO: 213, SEQ ID NO: 251, SEQ ID NO: 214, and SEQ ID NO: 252.

* * * * *

SEQUENCE LISTING

<160> NUMBER OF SEQ ID NOS: 265

<210> SEQ ID NO 1
<211> LENGTH: 89
<212> TYPE: PRT
<213> ORGANISM: Artificial Sequence
<220> FEATURE:
<223> OTHER INFORMATION: Tencon FN3 scaffold

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu

```
                    20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Lys Gly Gly His Arg Ser
 65                  70                  75                  80

Asn Pro Leu Ser Ala Glu Phe Thr Thr
                85

<210> SEQ ID NO 2
<211> LENGTH: 58
<212> TYPE: DNA
<213> ORGANISM: Artificial Sequence
<220> FEATURE:
<223> OTHER INFORMATION: primer

<400> SEQUENCE: 2
ggaaacagga tctaccatgc tgccggcgcc gaaaaacctg gttgtttctg aagttacc          58

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
aacaccgtag atagaaacgg t                                                  21

<210> SEQ ID NO 4
<211> LENGTH: 131
<212> TYPE: DNA
<213> ORGANISM: Artificial Sequence
<220> FEATURE:
<223> OTHER INFORMATION: primer

<400> SEQUENCE: 4
cggcggttag aacgcggcta caattaatac ataaccccat cccctgttg acaattaatc         60 atcggctcgt ataatgtgtg gaattgtgag cggataacaa tttcacacag gaaacaggat      120
ctaccatgct g                                                           131

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
cggcggttag aacgcggcta c                                                  21

<210> SEQ ID NO 6
<211> LENGTH: 66
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
```

```
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 6
ggtggtgaat tccgcagaca gcggsnnsnn snnsnnsnns nnsnnaacac cgtagataga      60
aacggt                                                                66

<210> SEQ ID NO 7
<211> LENGTH: 69
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 7
ggtggtgaat tccgcagaca gcggsnnsnn snnsnnsnns nnsnnsnnaa caccgtagat      60
agaaacggt                                                             69

<210> SEQ ID NO 8
<211> LENGTH: 72
<212> TYPE: DNA
```

```
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

<400> SEQUENCE: 8
ggtggtgaat tccgcagaca gcggsnnsnn snnsnnsnns nnsnnsnnsn naacaccgta    60
gatagaaacg gt                                                        72

<210> SEQ ID NO 9
<211> LENGTH: 75
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
```

```
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 9
ggtggtgaat tccgcagaca gcggsnnsnn snnsnnsnns nnsnnsnnsn nsnnaacacc      60
gtagatagaa acggt                                                      75

<210> SEQ ID NO 10
<211> LENGTH: 80
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 10
rmggtggtga attccgcaga cagcggsnns nnsnnsnnsn nsnnsnnsnn snnsnnsnna      60
acaccgtaga tagaaacggt                                                 80
```

```
<210> SEQ ID NO 11
<211> LENGTH: 81
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 11
ggtggtgaat tccgcagaca gcggsnnsnn snnsnnsnns nnsnnsnnsn nsnnsnnsnn      60
aacaccgtag atagaaacgg t                                               81

<210> SEQ ID NO 12
<211> LENGTH: 81
<212> TYPE: DNA
<213> ORGANISM: Artificial Sequence
<220> FEATURE:
<223> OTHER INFORMATION: primer

<400> SEQUENCE: 12
aagatcagtt gcggccgcta gactagaacc gctgccatgg tgatggtgat ggtgaccgcc      60
ggtggtgaat tccgcagaca g                                               81

<210> SEQ ID NO 13
<211> LENGTH: 30
```

```
<212> TYPE: DNA
<213> ORGANISM: Artificial Sequence
<220> FEATURE:
<223> OTHER INFORMATION: primer

<400> SEQUENCE: 13
cggcggttag aacgcggcta caattaatac                                    30

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
catgattacg ccaagctcag aa                                            22

<210> SEQ ID NO 15
<211> LENGTH: 65
<212> TYPE: DNA
<213> ORGANISM: Artificial Sequence
<220> FEATURE:
<223> OTHER INFORMATION: primer

<400> SEQUENCE: 15
gagccgccgc caccggttta atggtgatgg tgatggtgac caccggtggt gaattccgca   60
gacag                                                               65

<210> SEQ ID NO 16
<211> LENGTH: 37
<212> TYPE: DNA
<213> ORGANISM: Artificial Sequence
<220> FEATURE:
<223> OTHER INFORMATION: primer

<400> SEQUENCE: 16
aagaaggaga accggtatgc tgccggcgcc gaaaaac                             37

<210> SEQ ID NO 17
<211> LENGTH: 89
<212> TYPE: DNA
<213> ORGANISM: Artificial Sequence
<220> FEATURE:
<223> OTHER INFORMATION: primer

<400> SEQUENCE: 17
tttgggaagc ttctaggtct cggcggtcac catcaccatc accatggcag cggttctagt   60
ctagcggccc caactgatct tcaccaaac                                     89

<210> SEQ ID NO 18
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 18

Leu Pro Ala Pro Lys Asn Leu Val Val Ser Glu Val Thr Glu Asp Ser
1               5                   10                  15

Leu Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Asn Leu Thr
        35                  40                  45
```

```
Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 19
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 19

Leu Pro Ala Pro Lys Asn Leu Val Val Ser Glu Val Thr Glu Asp Ser
1               5                   10                  15

Leu Arg Leu Ser Trp Thr Tyr Asp Arg Asp Gly Tyr Asp Ser Phe Leu
                20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 20
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 20

Leu Pro Ala Pro Lys Asn Leu Val Val Ser Glu Val Thr Glu Asp Ser
1               5                   10                  15

Leu Arg Leu Ser Trp Gly Tyr Asn Gly Asp His Phe Asp Ser Phe Leu
                20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 21
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 21

Leu Pro Ala Pro Lys Asn Leu Val Val Ser Glu Val Thr Glu Asp Ser
1               5                   10                  15
```

```
Leu Arg Leu Ser Trp Asp Asp Pro Arg Gly Phe Tyr Glu Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 22
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 22

Leu Pro Ala Pro Lys Asn Leu Val Val Ser Glu Val Thr Glu Asp Ser
1               5                   10                  15

Leu Arg Leu Ser Trp Thr Trp Pro Tyr Ala Asp Leu Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 23
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 23

Leu Pro Ala Pro Lys Asn Leu Val Val Ser Glu Val Thr Glu Asp Ser
1               5                   10                  15

Leu Arg Leu Ser Trp Gly Tyr Asn Gly Asp His Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 24
<211> LENGTH: 95
<212> TYPE: PRT
<213> ORGANISM: Artificial Sequence
<220> FEATURE:
<223> OTHER INFORMATION: EGFR binding FN3 domain
```

<400> SEQUENCE: 24

Leu Pro Ala Pro Lys Asn Leu Val Val Ser Glu Val Thr Glu Asp Ser
1               5                   10                  15

Leu Arg Leu Ser Trp Asp Tyr Asp Leu Gly Val Tyr Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 25
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 25

Leu Pro Ala Pro Lys Asn Leu Val Val Ser Glu Val Thr Glu Asp Ser
1               5                   10                  15

Leu Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 26
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 26

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Leu Gly Ser Tyr Val Phe
65                  70                  75                  80

Glu His Asp Val Met Leu Pro Leu Ser Ala Glu Phe Thr Thr
                85                  90

<210> SEQ ID NO 27
<211> LENGTH: 94

```
<212> TYPE: PRT
<213> ORGANISM: Artificial Sequence
<220> FEATURE:
<223> OTHER INFORMATION: EGFR binding FN3 domain

<400> SEQUENCE: 27

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 28
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 28

Leu Pro Ala Pro Lys Asn Leu Val Val Ser Glu Val Thr Glu Asp Ser
1               5                   10                  15

Ala Arg Leu Ser Trp Thr Ala Pro Asp Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Leu Gly Ser Tyr Val Phe
65                  70                  75                  80

Glu His Asp Val Met Leu Pro Leu Ser Ala Ile Phe Thr Thr
                85                  90

<210> SEQ ID NO 29
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 29

Leu Pro Ala Pro Lys Asn Leu Val Val Ser Glu Val Thr Glu Asp Ser
1               5                   10                  15

Leu Arg Leu Ser Trp Thr Trp Pro Tyr Ala Asp Leu Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
```

-continued

```
                    85                  90

<210> SEQ ID NO 30
<211> LENGTH: 37
<212> TYPE: PRT
<213> ORGANISM: Artificial Sequence
<220> FEATURE:
<223> OTHER INFORMATION: primer

<400> SEQUENCE: 30

Ala Ala Gly Ala Ala Gly Gly Ala Gly Ala Ala Cys Cys Gly Gly Thr
1               5                   10                  15

Ala Thr Gly Cys Thr Gly Cys Cys Gly Gly Cys Gly Cys Cys Gly Ala
            20                  25                  30

Ala Ala Ala Ala Cys
        35

<210> SEQ ID NO 31
<211> LENGTH: 65
<212> TYPE: PRT
<213> ORGANISM: Artificial Sequence
<220> FEATURE:
<223> OTHER INFORMATION: primer

<400> SEQUENCE: 31

Gly Ala Gly Cys Cys Gly Cys Cys Gly Cys Ala Cys Cys Gly Gly Gly
1               5                   10                  15

Thr Thr Thr Ala Ala Thr Gly Gly Thr Gly Ala Thr Gly Gly Thr Gly
            20                  25                  30

Ala Thr Gly Gly Thr Gly Ala Cys Cys Ala Cys Cys Gly Gly Thr Gly
        35                  40                  45

Gly Thr Gly Ala Ala Gly Ala Thr Cys Gly Cys Ala Gly Ala Cys Ala
    50                  55                  60

Gly
65

<210> SEQ ID NO 32
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 32

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Asp Glu Val Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Asn Ile Leu Gly Val Lys Gly Gly Ser Ile Ser
65                  70                  75                  80

Val Pro Leu Ser Ala Ile Phe Thr Thr
                85

<210> SEQ ID NO 33
<211> LENGTH: 89
<212> TYPE: PRT
<213> ORGANISM: Artificial Sequence
```

```
<220> FEATURE:
<223> OTHER INFORMATION: c-Met binding FN3 domain

<400> SEQUENCE: 33

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
            20                  25                  30

Ile Arg Tyr Asp Glu Phe Leu Arg Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Thr Ile Leu Gly Val Lys Gly Leu Val Ser
65                  70                  75                  80

Thr Pro Leu Ser Ala Ile Phe Thr Thr
                85

<210> SEQ ID NO 34
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 34

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ile Val Asn Ile Met Gly Val Lys Gly Gly Ser Ile Ser
65                  70                  75                  80

His Pro Leu Ser Ala Ile Phe Thr Thr
                85

<210> SEQ ID NO 35
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 35

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Leu Gly Val Lys Gly Gly Gly Leu Ser
65                  70                  75                  80

Val Pro Leu Ser Ala Ile Phe Thr Thr
                85
```

<210> SEQ ID NO 36
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 36

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
                20                  25                  30

Ile Arg Tyr Phe Glu Phe Leu Gly Ser Gly Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Gln Ile Leu Gly Val Lys Gly Gly Tyr Ile Ser
65                  70                  75                  80

Ile Pro Leu Ser Ala Ile Phe Thr Thr
                85
```

<210> SEQ ID NO 37
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 37

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Arg Tyr Leu Glu Phe Leu Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Gln Ile Met Gly Val Lys Gly Gly Thr Val Ser
65                  70                  75                  80

Pro Pro Leu Ser Ala Ile Phe Thr Thr
                85
```

<210> SEQ ID NO 38
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 38

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Gly Ile Asn Gly Val Lys Gly Gly Tyr Ile Ser
```

```
                 65                  70                  75                  80

Tyr Pro Leu Ser Ala Ile Phe Thr Thr
                85

<210> SEQ ID NO 39
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 39

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Asp Leu Lys Pro Gly
    50                  55                  60

Thr Glu Tyr Gly Val Thr Ile Asn Gly Val Lys Gly Arg Val Ser
65                  70                  75                  80

Thr Pro Leu Ser Ala Ile Phe Thr Thr
                85

<210> SEQ ID NO 40
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 40

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Gln Ile Ile Gly Val Lys Gly Gly His Ile Ser
65                  70                  75                  80

Leu Pro Leu Ser Ala Ile Phe Thr Thr
                85

<210> SEQ ID NO 41
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 41

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45
```

```
Val Pro Gly Ser Glu Arg Ser Tyr Asp Leu Thr Gly Leu Lys Pro Gly
         50                  55                  60

Thr Glu Tyr Val Val Asn Ile Met Gly Val Lys Gly Gly Lys Ile Ser
 65                  70                  75                  80

Pro Pro Leu Ser Ala Ile Phe Thr Thr
                 85

<210> SEQ ID NO 42
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 42

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
         50                  55                  60

Thr Glu Tyr Ala Val Asn Ile Met Gly Val Lys Gly Gly Arg Val Ser
 65                  70                  75                  80

Val Pro Leu Ser Ala Ile Phe Thr Thr
                 85

<210> SEQ ID NO 43
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 43

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
         50                  55                  60

Thr Glu Tyr Val Val Gln Ile Leu Gly Val Lys Gly Gly Ser Ile Ser
 65                  70                  75                  80

Val Pro Leu Ser Ala Ile Phe Thr Thr
                 85

<210> SEQ ID NO 44
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 44

Leu Pro Ala Pro Lys Asn Leu Val Val Ser Arg Val Thr Glu Asp Ser
 1               5                  10                  15
```

```
Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Val Val Asn Ile Met Gly Val Lys Gly Ser Ile Ser
 65                  70                  75                  80

Tyr Pro Leu Ser Ala Ile Phe Thr Thr
                85

<210> SEQ ID NO 45
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 45

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Val Val Gln Ile Leu Gly Val Lys Gly Tyr Ile Ser
 65                  70                  75                  80

Ile Pro Leu Ser Ala Ile Phe Thr Thr
                85

<210> SEQ ID NO 46
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 46

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Val Val Gln Ile Met Gly Val Lys Gly Gly Thr Val Ser
 65                  70                  75                  80

Pro Pro Leu Ser Ala Ile Phe Thr Thr
                85

<210> SEQ ID NO 47
<211> LENGTH: 89
<212> TYPE: PRT
<213> ORGANISM: Artificial Sequence
<220> FEATURE:
<223> OTHER INFORMATION: c-Met binding FN3 domain
```

```
<400> SEQUENCE: 47

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Thr Thr Ala Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Ser Ile Ser
65                  70                  75                  80

Pro Pro Leu Ser Ala Ile Phe Thr Thr
                85

<210> SEQ ID NO 48
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 48

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Leu Leu Ser Thr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Ser Ile Ser
65                  70                  75                  80

Pro Pro Leu Ser Ala Ile Phe Thr Thr
                85

<210> SEQ ID NO 49
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 49

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Val Ser Lys Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Ser Ile Ser
65                  70                  75                  80

Pro Pro Leu Ser Ala Ile Phe Thr Thr
                85

<210> SEQ ID NO 50
<211> LENGTH: 205
```

<212> TYPE: PRT
<213> ORGANISM: Artificial Sequence
<220> FEATURE:
<223> OTHER INFORMATION: bispecific EGFR/cMet binding molecule

<400> SEQUENCE: 50

```
Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
            20                  25                  30
Leu Ile Gln Tyr Gln Glu Ser Glu Lys Val Gly Glu Ala Ile Val Leu
        35                  40                  45
Thr Val Pro Gly Ser Glu Arg Ser Tyr Asp Leu Thr Gly Leu Lys Pro
    50                  55                  60
Gly Thr Glu Tyr Thr Val Ser Ile Tyr Gly Val His Asn Val Tyr Lys
65                  70                  75                  80
Asp Thr Asn Met Arg Gly Leu Pro Leu Ser Ala Ile Phe Thr Thr Gly
                85                  90                  95
Gly Gly Gly Ser Gly Gly Gly Gly Ser Gly Gly Gly Gly Ser Gly Gly
            100                 105                 110
Gly Gly Ser Met Leu Pro Ala Pro Lys Asn Leu Val Val Ser Arg Val
        115                 120                 125
Thr Glu Asp Ser Ala Arg Leu Ser Trp Thr Ala Pro Asp Ala Ala Phe
    130                 135                 140
Asp Ser Phe Trp Ile Arg Tyr Asp Glu Val Val Val Gly Gly Glu Ala
145                 150                 155                 160
Ile Val Leu Thr Val Pro Gly Ser Glu Arg Ser Tyr Asp Leu Thr Gly
                165                 170                 175
Leu Lys Pro Gly Thr Glu Tyr Tyr Val Asn Ile Leu Gly Val Lys Gly
            180                 185                 190
Gly Ser Ile Ser Val Pro Leu Ser Ala Ile Phe Thr Thr
        195                 200                 205
```

<210> SEQ ID NO 51
<211> LENGTH: 204
<212> TYPE: PRT
<213> ORGANISM: Artificial Sequence
<220> FEATURE:
<223> OTHER INFORMATION: bispecific EGFR/cMet binding molecule

<400> SEQUENCE: 51

```
Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
            20                  25                  30
Leu Ile Gln Tyr Gln Glu Ser Glu Lys Val Gly Glu Ala Ile Val Leu
        35                  40                  45
Thr Val Pro Gly Ser Glu Arg Ser Tyr Asp Leu Thr Gly Leu Lys Pro
    50                  55                  60
Gly Thr Glu Tyr Thr Val Ser Ile Tyr Gly Val His Asn Val Tyr Lys
65                  70                  75                  80
Asp Thr Asn Met Arg Gly Leu Pro Leu Ser Ala Ile Phe Thr Thr Gly
                85                  90                  95
Gly Gly Gly Ser Gly Gly Gly Gly Ser Gly Gly Gly Gly Ser Gly Gly
            100                 105                 110
Gly Gly Ser Leu Pro Ala Pro Lys Asn Leu Val Val Ser Arg Val Thr
        115                 120                 125
```

```
Glu Asp Ser Ala Arg Leu Ser Trp Thr Ala Pro Asp Ala Ala Phe Asp
    130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Asn Ile Met Gly Val Lys Gly Gly
                180                 185                 190

Lys Ile Ser Pro Pro Leu Ser Ala Ile Phe Thr Thr
                195                 200
```

<210> SEQ ID NO 52
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 52

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
                35                  40                  45

Thr Val Pro Gly Ser Glu Arg Ser Tyr Asp Leu Thr Gly Leu Lys Pro
50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Ser Gly Gly
                100                 105                 110

Gly Gly Ser Met Leu Pro Ala Pro Lys Asn Leu Val Val Ser Arg Val
                115                 120                 125

Thr Glu Asp Ser Ala Arg Leu Ser Trp Thr Ala Pro Asp Ala Ala Phe
    130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Gln Ile Ile Gly Val Lys Gly
                180                 185                 190

Gly His Ile Ser Leu Pro Leu Ser Ala Ile Phe Thr Thr
                195                 200                 205
```

<210> SEQ ID NO 53
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 53

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
```

```
                20                  25                  30
Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Ser Gly Gly
                100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
        130                 135                 140

Asp Ser Phe Phe Ile Arg Tyr Asp Glu Phe Leu Arg Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Trp Val Thr Ile Leu Gly Val Lys Gly
            180                 185                 190

Gly Leu Val Ser Thr Pro Leu Ser Ala Ile Phe Thr Thr
        195                 200                 205

<210> SEQ ID NO 54
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 54

Met Leu Pro Ala Pro Lys Asn Leu Val Val Ser Glu Val Thr Glu Asp
 1               5                  10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Ser Gly Gly
                100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
        130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Asn Ile Met Gly Val Lys Gly
```

```
                    180                 185                 190

Gly Lys Ile Ser Pro Leu Ser Ala Ile Phe Thr Thr
            195                 200                 205

<210> SEQ ID NO 55
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 55

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Gly Ser Gly Gly Gly Gly Ser Gly Gly
            100                 105                 110

Gly Gly Ser Met Leu Pro Ala Pro Lys Asn Leu Val Val Ser Arg Val
        115                 120                 125

Thr Glu Asp Ser Ala Arg Leu Ser Trp Thr Ala Pro Asp Ala Ala Phe
    130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Gln Ile Ile Gly Val Lys Gly
            180                 185                 190

Gly His Ile Ser Leu Pro Leu Ser Ala Ile Phe Thr Thr
        195                 200                 205

<210> SEQ ID NO 56
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 56

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80
```

Asp Thr Asn Met Arg Gly Leu Pro Leu Ser Ala Ile Phe Thr Thr Gly
                85                  90                  95

Gly Gly Gly Ser Gly Gly Gly Gly Ser Gly Gly Gly Ser Gly Gly
            100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Gln Ile Ile Gly Val Lys Gly
            180                 185                 190

Gly His Ile Ser Leu Pro Leu Ser Ala Ile Phe Thr Thr
            195                 200                 205

<210> SEQ ID NO 57
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 57

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Gly Lys Ile Ser Pro Pro Leu Ser Ala Ile Phe
            180                 185                 190

Thr Thr

<210> SEQ ID NO 58
<211> LENGTH: 194
<212> TYPE: PRT
<213> ORGANISM: Artificial Sequence
<220> FEATURE:
<223> OTHER INFORMATION: bispecific EGFR/cMet binding molecule

```
<400> SEQUENCE: 58

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Asp Glu Val Val
    130                 135                 140

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
                165                 170                 175

Leu Gly Val Lys Gly Gly Ser Ile Ser Val Pro Leu Ser Ala Ile Phe
            180                 185                 190

Thr Thr

<210> SEQ ID NO 59
<211> LENGTH: 195
<212> TYPE: PRT
<213> ORGANISM: Artificial Sequence
<220> FEATURE:
<223> OTHER INFORMATION: bispecific EGFR/cMet binding molecule

<400> SEQUENCE: 59

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Met Leu Pro Ala Pro Lys Asn
            100                 105                 110

Leu Val Val Ser Arg Val Thr Glu Asp Ser Ala Arg Leu Ser Trp Thr
        115                 120                 125

Ala Pro Asp Ala Ala Phe Asp Ser Phe Trp Ile Arg Tyr Phe Glu Phe
    130                 135                 140

Leu Gly Ser Gly Glu Ala Ile Val Leu Thr Val Pro Gly Ser Glu Arg
```

```
                145                 150                 155                 160
Ser Tyr Asp Leu Thr Gly Leu Lys Pro Gly Thr Glu Tyr Val Val Asn
                    165                 170                 175

Ile Met Gly Val Lys Gly Gly Lys Ile Ser Pro Pro Leu Ser Ala Ile
                    180                 185                 190

Phe Thr Thr
        195

<210> SEQ ID NO 60
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 60

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Asp Glu Val Val
        130                 135                 140

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
                165                 170                 175

Leu Gly Val Lys Gly Gly Ser Ile Ser Val Pro Leu Ser Ala Ile Phe
                180                 185                 190

Thr Thr

<210> SEQ ID NO 61
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 61

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
```

```
            50                  55                  60
Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Leu
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
                180                 185                 190

Thr Thr

<210> SEQ ID NO 62
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 62

Met Leu Pro Ala Pro Lys Asn Leu Val Val Ser Glu Val Thr Glu Asp
  1               5                  10                  15

Ser Ala Arg Leu Ser Trp Asp Asp Pro Trp Ala Phe Tyr Glu Ser Phe
                 20                  25                  30

Leu Ile Gln Tyr Gln Glu Ser Glu Lys Val Gly Glu Ala Ile Val Leu
             35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Val
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
                180                 185                 190

Thr Thr

<210> SEQ ID NO 63
<211> LENGTH: 194
```

```
<212> TYPE: PRT
<213> ORGANISM: Artificial Sequence
<220> FEATURE:
<223> OTHER INFORMATION: bispecific EGFR/cMet binding molecule

<400> SEQUENCE: 63

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Val
    130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr

<210> SEQ ID NO 64
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 64

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125
```

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
                180                 185                 190

Thr Thr

<210> SEQ ID NO 65
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 65

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
                180                 185                 190

Thr Thr

<210> SEQ ID NO 66
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 66

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu

```
                    35                  40                  45
Thr Val Pro Gly Ser Glu Arg Ser Tyr Asp Leu Thr Gly Leu Lys Pro
     50                  55                  60
Gly Thr Glu Tyr Thr Val Ser Ile Tyr Gly Val His Asn Val Tyr Lys
 65                  70                  75                  80
Asp Thr Asn Ile Arg Gly Leu Pro Leu Ser Ala Ile Phe Thr Thr Ala
                 85                  90                  95
Pro Ala Pro Ala Pro Ala Pro Ala Pro Leu Pro Ala Pro Lys Asn Leu
                100                 105                 110
Val Val Ser Arg Val Thr Glu Asp Ser Ala Arg Leu Ser Trp Thr Ala
            115                 120                 125
Pro Asp Ala Ala Phe Asp Ser Phe Trp Ile Arg Tyr Phe Glu Phe Val
            130                 135                 140
Gly Ser Gly Glu Ala Ile Val Leu Thr Val Pro Gly Ser Glu Arg Ser
145                 150                 155                 160
Tyr Asp Leu Thr Gly Leu Lys Pro Gly Thr Glu Tyr Val Val Asn Ile
                165                 170                 175
Leu Gly Val Lys Gly Gly Ser Ile Ser Pro Pro Leu Ser Ala Ile Phe
                180                 185                 190
Thr Thr

<210> SEQ ID NO 67
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 67

Met Leu Pro Ala Pro Lys Asn Leu Val Val Ser Glu Val Thr Glu Asp
  1               5                  10                  15
Ser Ala Arg Leu Ser Trp Asp Asp Pro His Ala Phe Tyr Glu Ser Phe
                 20                  25                  30
Leu Ile Gln Tyr Gln Glu Ser Glu Lys Val Gly Glu Ala Ile Val Leu
                 35                  40                  45
Thr Val Pro Gly Ser Glu Arg Ser Tyr Asp Leu Thr Gly Leu Lys Pro
     50                  55                  60
Gly Thr Glu Tyr Thr Val Ser Ile Tyr Gly Val His Asn Val Tyr Lys
 65                  70                  75                  80
Asp Thr Asn Ile Arg Gly Leu Pro Leu Ser Ala Ile Phe Thr Thr Ala
                 85                  90                  95
Pro Ala Pro Ala Pro Ala Pro Ala Pro Leu Pro Ala Pro Lys Asn Leu
                100                 105                 110
Val Val Ser Arg Val Thr Glu Asp Ser Ala Arg Leu Ser Trp Thr Ala
            115                 120                 125
Pro Asp Ala Ala Phe Asp Ser Phe Trp Ile Arg Tyr Phe Glu Phe Val
            130                 135                 140
Ser Lys Gly Asp Ala Ile Val Leu Thr Val Pro Gly Ser Glu Arg Ser
145                 150                 155                 160
Tyr Asp Leu Thr Gly Leu Lys Pro Gly Thr Glu Tyr Val Val Asn Ile
                165                 170                 175
Leu Gly Val Lys Gly Gly Ser Ile Ser Pro Pro Leu Ser Ala Ile Phe
                180                 185                 190
Thr Thr
```

<210> SEQ ID NO 68
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 68

```
Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
            180                 185                 190

Thr Thr
```

<210> SEQ ID NO 69
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 69

```
Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110
```

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
            180                 185                 190

Thr Thr

<210> SEQ ID NO 70
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 70

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr

<210> SEQ ID NO 71
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 71

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe

```
            20                  25                  30
Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Val
    130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr
```

<210> SEQ ID NO 72
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 72

```
Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
            180                 185                 190
```

Thr Thr

<210> SEQ ID NO 73
<211> LENGTH: 1210
<212> TYPE: PRT
<213> ORGANISM: HOMO SAPIENS

<400> SEQUENCE: 73

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

```
Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780
```

```
Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
```

Ser Ser Glu Phe Ile Gly Ala
    1205                1210

<210> SEQ ID NO 74
<211> LENGTH: 53
<212> TYPE: PRT
<213> ORGANISM: HOMO SAPIENS

<400> SEQUENCE: 74

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 75
<211> LENGTH: 2201
<212> TYPE: PRT
<213> ORGANISM: Homo sapiens

<400> SEQUENCE: 75

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
    130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175

Glu Pro Gly Trp Lys Gly Pro Asn Cys Ser Glu Pro Cys Pro Gly
            180                 185                 190

Asn Cys His Leu Arg Gly Arg Cys Ile Asp Gly Gln Cys Ile Cys Asp
        195                 200                 205

Asp Gly Phe Thr Gly Glu Asp Cys Ser Gln Leu Ala Cys Pro Ser Asp
    210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys

```
                    245                 250                 255
Ser Glu Glu His Gly Thr Cys Val Asp Gly Leu Cys Val Cys His Asp
                260                 265                 270
Gly Phe Ala Gly Asp Cys Asn Lys Pro Leu Cys Leu Asn Asn Cys
            275                 280                 285
Tyr Asn Arg Gly Arg Cys Val Glu Asn Glu Cys Val Cys Asp Glu Gly
        290                 295                 300
Phe Thr Gly Glu Asp Cys Ser Glu Leu Ile Cys Pro Asn Asp Cys Phe
305                 310                 315                 320
Asp Arg Gly Arg Cys Ile Asn Gly Thr Cys Tyr Cys Glu Glu Gly Phe
                325                 330                 335
Thr Gly Glu Asp Cys Gly Lys Pro Thr Cys Pro His Ala Cys His Thr
                340                 345                 350
Gln Gly Arg Cys Glu Glu Gly Gln Cys Val Cys Asp Glu Gly Phe Ala
                355                 360                 365
Gly Val Asp Cys Ser Glu Lys Arg Cys Pro Ala Asp Cys His Asn Arg
            370                 375                 380
Gly Arg Cys Val Asp Gly Arg Cys Glu Cys Asp Asp Gly Phe Thr Gly
385                 390                 395                 400
Ala Asp Cys Gly Glu Leu Lys Cys Pro Asn Gly Cys Ser Gly His Gly
                405                 410                 415
Arg Cys Val Asn Gly Gln Cys Val Cys Asp Glu Gly Tyr Thr Gly Glu
                420                 425                 430
Asp Cys Ser Gln Leu Arg Cys Pro Asn Asp Cys His Ser Arg Gly Arg
            435                 440                 445
Cys Val Glu Gly Lys Cys Val Cys Glu Gln Gly Phe Lys Gly Tyr Asp
        450                 455                 460
Cys Ser Asp Met Ser Cys Pro Asn Asp Cys His Gln His Gly Arg Cys
465                 470                 475                 480
Val Asn Gly Met Cys Val Cys Asp Asp Gly Tyr Thr Gly Glu Asp Cys
                485                 490                 495
Arg Asp Arg Gln Cys Pro Arg Asp Cys Ser Asn Arg Gly Leu Cys Val
                500                 505                 510
Asp Gly Gln Cys Val Cys Glu Asp Gly Phe Thr Gly Pro Asp Cys Ala
            515                 520                 525
Glu Leu Ser Cys Pro Asn Asp Cys His Gly Gln Gly Arg Cys Val Asn
        530                 535                 540
Gly Gln Cys Val Cys His Glu Gly Phe Met Gly Lys Asp Cys Lys Glu
545                 550                 555                 560
Gln Arg Cys Pro Ser Asp Cys His Gly Gln Gly Arg Cys Val Asp Gly
                565                 570                 575
Gln Cys Ile Cys His Glu Gly Phe Thr Gly Leu Asp Cys Gly Gln His
                580                 585                 590
Ser Cys Pro Ser Asp Cys Asn Asn Leu Gly Gln Cys Val Ser Gly Arg
            595                 600                 605
Cys Ile Cys Asn Glu Gly Tyr Ser Gly Glu Asp Cys Ser Glu Val Ser
        610                 615                 620
Pro Pro Lys Asp Leu Val Val Thr Glu Val Thr Glu Thr Val Asn
625                 630                 635                 640
Leu Ala Trp Asp Asn Glu Met Arg Val Thr Glu Tyr Leu Val Val Tyr
                645                 650                 655
Thr Pro Thr His Glu Gly Gly Leu Glu Met Gln Phe Arg Val Pro Gly
                660                 665                 670
```

-continued

```
Asp Gln Thr Ser Thr Ile Ile Gln Glu Leu Glu Pro Gly Val Glu Tyr
            675                 680                 685

Phe Ile Arg Val Phe Ala Ile Leu Glu Asn Lys Lys Ser Ile Pro Val
690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Glu Thr Ser Tyr
                755                 760                 765

Arg Gln Thr Gly Leu Ala Pro Gly Gln Glu Tyr Glu Ile Ser Leu His
770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
                835                 840                 845

Ile Asp Leu Thr Glu Asp Glu Asn Gln Tyr Ser Ile Gly Asn Leu Lys
            850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                885                 890                 895

Arg Asn Leu Arg Arg Val Ser Gln Thr Asp Asn Ser Ile Thr Leu Glu
                900                 905                 910

Trp Arg Asn Gly Lys Ala Ala Ile Asp Ser Tyr Arg Ile Lys Tyr Ala
            915                 920                 925

Pro Ile Ser Gly Gly Asp His Ala Glu Val Asp Val Pro Lys Ser Gln
            930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
                965                 970                 975

Ala Thr Ile Asn Ala Ala Thr Glu Leu Asp Thr Pro Lys Asp Leu Gln
            980                 985                 990

Val Ser Glu Thr Ala Glu Thr Ser  Leu Thr Leu Leu Trp  Lys Thr Pro
            995                 1000                 1005

Leu Ala Lys Phe Asp Arg Tyr  Arg Leu Asn Tyr Ser  Leu Pro Thr
        1010                1015                1020

Gly Gln Trp Val Gly Val Gln  Leu Pro Arg Asn Thr  Thr Ser Tyr
        1025                1030                1035

Val Leu Arg Gly Leu Glu Pro  Gly Gln Glu Tyr Asn  Val Leu Leu
        1040                1045                1050

Thr Ala Glu Lys Gly Arg His  Lys Ser Lys Pro Ala  Arg Val Lys
        1055                1060                1065

Ala Ser Thr Glu Gln Ala Pro  Glu Leu Glu Asn Leu  Thr Val Thr
        1070                1075                1080
```

```
Glu Val Gly Trp Asp Gly Leu Arg Leu Asn Trp Thr Ala Ala Asp
    1085                1090                1095
Gln Ala Tyr Glu His Phe Ile Ile Gln Val Gln Glu Ala Asn Lys
    1100                1105                1110
Val Glu Ala Ala Arg Asn Leu Thr Val Pro Gly Ser Leu Arg Ala
    1115                1120                1125
Val Asp Ile Pro Gly Leu Lys Ala Ala Thr Pro Tyr Thr Val Ser
    1130                1135                1140
Ile Tyr Gly Val Ile Gln Gly Tyr Arg Thr Pro Val Leu Ser Ala
    1145                1150                1155
Glu Ala Ser Thr Gly Glu Thr Pro Asn Leu Gly Glu Val Val Val
    1160                1165                1170
Ala Glu Val Gly Trp Asp Ala Leu Lys Leu Asn Trp Thr Ala Pro
    1175                1180                1185
Glu Gly Ala Tyr Glu Tyr Phe Phe Ile Gln Val Gln Glu Ala Asp
    1190                1195                1200
Thr Val Glu Ala Ala Gln Asn Leu Thr Val Pro Gly Gly Leu Arg
    1205                1210                1215
Ser Thr Asp Leu Pro Gly Leu Lys Ala Ala Thr His Tyr Thr Ile
    1220                1225                1230
Thr Ile Arg Gly Val Thr Gln Asp Phe Ser Thr Pro Leu Ser
    1235                1240                1245
Val Glu Val Leu Thr Glu Glu Val Pro Asp Met Gly Asn Leu Thr
    1250                1255                1260
Val Thr Glu Val Ser Trp Asp Ala Leu Arg Leu Asn Trp Thr Thr
    1265                1270                1275
Pro Asp Gly Thr Tyr Asp Gln Phe Thr Ile Gln Val Gln Glu Ala
    1280                1285                1290
Asp Gln Val Glu Glu Ala His Asn Leu Thr Val Pro Gly Ser Leu
    1295                1300                1305
Arg Ser Met Glu Ile Pro Gly Leu Arg Ala Gly Thr Pro Tyr Thr
    1310                1315                1320
Val Thr Leu His Gly Glu Val Arg Gly His Ser Thr Arg Pro Leu
    1325                1330                1335
Ala Val Glu Val Val Thr Glu Asp Leu Pro Gln Leu Gly Asp Leu
    1340                1345                1350
Ala Val Ser Glu Val Gly Trp Asp Gly Leu Arg Leu Asn Trp Thr
    1355                1360                1365
Ala Ala Asp Asn Ala Tyr Glu His Phe Val Ile Gln Val Gln Glu
    1370                1375                1380
Val Asn Lys Val Glu Ala Ala Gln Asn Leu Thr Leu Pro Gly Ser
    1385                1390                1395
Leu Arg Ala Val Asp Ile Pro Gly Leu Glu Ala Ala Thr Pro Tyr
    1400                1405                1410
Arg Val Ser Ile Tyr Gly Val Ile Arg Gly Tyr Arg Thr Pro Val
    1415                1420                1425
Leu Ser Ala Glu Ala Ser Thr Ala Lys Glu Pro Glu Ile Gly Asn
    1430                1435                1440
Leu Asn Val Ser Asp Ile Thr Pro Glu Ser Phe Asn Leu Ser Trp
    1445                1450                1455
Met Ala Thr Asp Gly Ile Phe Glu Thr Phe Thr Ile Glu Ile Ile
    1460                1465                1470
Asp Ser Asn Arg Leu Leu Glu Thr Val Glu Tyr Asn Ile Ser Gly
```

```
            1475                1480                1485

Ala Glu Arg Thr Ala His Ile Ser Gly Leu Pro Pro Ser Thr Asp
    1490                1495                1500

Phe Ile Val Tyr Leu Ser Gly Leu Ala Pro Ser Ile Arg Thr Lys
    1505                1510                1515

Thr Ile Ser Ala Thr Ala Thr Thr Glu Ala Leu Pro Leu Leu Glu
    1520                1525                1530

Asn Leu Thr Ile Ser Asp Ile Asn Pro Tyr Gly Phe Thr Val Ser
    1535                1540                1545

Trp Met Ala Ser Glu Asn Ala Phe Asp Ser Phe Leu Val Thr Val
    1550                1555                1560

Val Asp Ser Gly Lys Leu Leu Asp Pro Gln Glu Phe Thr Leu Ser
    1565                1570                1575

Gly Thr Gln Arg Lys Leu Glu Leu Arg Gly Leu Ile Thr Gly Ile
    1580                1585                1590

Gly Tyr Glu Val Met Val Ser Gly Phe Thr Gln Gly His Gln Thr
    1595                1600                1605

Lys Pro Leu Arg Ala Glu Ile Val Thr Glu Ala Glu Pro Glu Val
    1610                1615                1620

Asp Asn Leu Leu Val Ser Asp Ala Thr Pro Asp Gly Phe Arg Leu
    1625                1630                1635

Ser Trp Thr Ala Asp Glu Gly Val Phe Asp Asn Phe Val Leu Lys
    1640                1645                1650

Ile Arg Asp Thr Lys Lys Gln Ser Glu Pro Leu Glu Ile Thr Leu
    1655                1660                1665

Leu Ala Pro Glu Arg Thr Arg Asp Ile Thr Gly Leu Arg Glu Ala
    1670                1675                1680

Thr Glu Tyr Glu Ile Glu Leu Tyr Gly Ile Ser Lys Gly Arg Arg
    1685                1690                1695

Ser Gln Thr Val Ser Ala Ile Ala Thr Thr Ala Met Gly Ser Pro
    1700                1705                1710

Lys Glu Val Ile Phe Ser Asp Ile Thr Glu Asn Ser Ala Thr Val
    1715                1720                1725

Ser Trp Arg Ala Pro Thr Ala Gln Val Glu Ser Phe Arg Ile Thr
    1730                1735                1740

Tyr Val Pro Ile Thr Gly Gly Thr Pro Ser Met Val Thr Val Asp
    1745                1750                1755

Gly Thr Lys Thr Gln Thr Arg Leu Val Lys Leu Ile Pro Gly Val
    1760                1765                1770

Glu Tyr Leu Val Ser Ile Ile Ala Met Lys Gly Phe Glu Glu Ser
    1775                1780                1785

Glu Pro Val Ser Gly Ser Phe Thr Thr Ala Leu Asp Gly Pro Ser
    1790                1795                1800

Gly Leu Val Thr Ala Asn Ile Thr Asp Ser Glu Ala Leu Ala Arg
    1805                1810                1815

Trp Gln Pro Ala Ile Ala Thr Val Asp Ser Tyr Val Ile Ser Tyr
    1820                1825                1830

Thr Gly Glu Lys Val Pro Glu Ile Thr Arg Thr Val Ser Gly Asn
    1835                1840                1845

Thr Val Glu Tyr Ala Leu Thr Asp Leu Glu Pro Ala Thr Glu Tyr
    1850                1855                1860

Thr Leu Arg Ile Phe Ala Glu Lys Gly Pro Gln Lys Ser Ser Thr
    1865                1870                1875
```

```
Ile Thr Ala Lys Phe Thr Asp Leu Asp Ser Pro Arg Asp Leu
1880            1885                1890

Thr Ala Thr Glu Val Gln Ser Glu Thr Ala Leu Leu Thr Trp Arg
1895            1900                1905

Pro Pro Arg Ala Ser Val Thr Gly Tyr Leu Leu Val Tyr Glu Ser
1910            1915                1920

Val Asp Gly Thr Val Lys Glu Val Ile Val Gly Pro Asp Thr Thr
1925            1930                1935

Ser Tyr Ser Leu Ala Asp Leu Ser Pro Ser Thr His Tyr Thr Ala
1940            1945                1950

Lys Ile Gln Ala Leu Asn Gly Pro Leu Arg Ser Asn Met Ile Gln
1955            1960                1965

Thr Ile Phe Thr Thr Ile Gly Leu Leu Tyr Pro Phe Pro Lys Asp
1970            1975                1980

Cys Ser Gln Ala Met Leu Asn Gly Asp Thr Thr Ser Gly Leu Tyr
1985            1990                1995

Thr Ile Tyr Leu Asn Gly Asp Lys Ala Glu Ala Leu Glu Val Phe
2000            2005                2010

Cys Asp Met Thr Ser Asp Gly Gly Gly Trp Ile Val Phe Leu Arg
2015            2020                2025

Arg Lys Asn Gly Arg Glu Asn Phe Tyr Gln Asn Trp Lys Ala Tyr
2030            2035                2040

Ala Ala Gly Phe Gly Asp Arg Arg Glu Glu Phe Trp Leu Gly Leu
2045            2050                2055

Asp Asn Leu Asn Lys Ile Thr Ala Gln Gly Gln Tyr Glu Leu Arg
2060            2065                2070

Val Asp Leu Arg Asp His Gly Glu Thr Ala Phe Ala Val Tyr Asp
2075            2080                2085

Lys Phe Ser Val Gly Asp Ala Lys Thr Arg Tyr Lys Leu Lys Val
2090            2095                2100

Glu Gly Tyr Ser Gly Thr Ala Gly Asp Ser Met Ala Tyr His Asn
2105            2110                2115

Gly Arg Ser Phe Ser Thr Phe Asp Lys Asp Thr Asp Ser Ala Ile
2120            2125                2130

Thr Asn Cys Ala Leu Ser Tyr Lys Gly Ala Phe Trp Tyr Arg Asn
2135            2140                2145

Cys His Arg Val Asn Leu Met Gly Arg Tyr Gly Asp Asn Asn His
2150            2155                2160

Ser Gln Gly Val Asn Trp Phe His Trp Lys Gly His Glu His Ser
2165            2170                2175

Ile Gln Phe Ala Glu Met Lys Leu Arg Pro Ser Asn Phe Arg Asn
2180            2185                2190

Leu Glu Gly Arg Arg Lys Arg Ala
2195            2200

<210> SEQ ID NO 76
<211> LENGTH: 89
<212> TYPE: PRT
<213> ORGANISM: Artificial Sequence
<220> FEATURE:
<223> OTHER INFORMATION: Fibcon FN3 domain

<400> SEQUENCE: 76

Leu Asp Ala Pro Thr Asp Leu Gln Val Thr Asn Val Thr Asp Thr Ser
1               5                   10                  15
```

```
Ile Thr Val Ser Trp Thr Pro Pro Ser Ala Thr Ile Thr Gly Tyr Arg
                20                  25                  30

Ile Thr Tyr Thr Pro Ser Asn Gly Pro Gly Glu Pro Lys Glu Leu Thr
            35                  40                  45

Val Pro Pro Ser Ser Thr Ser Val Thr Ile Thr Gly Leu Thr Pro Gly
 50                  55                  60

Val Glu Tyr Val Val Ser Leu Tyr Ala Leu Lys Asp Asn Gln Glu Ser
 65                  70                  75                  80

Pro Pro Leu Val Gly Thr Gln Thr Thr
                85
```

```
<210> SEQ ID NO 77
<211> LENGTH: 94
<212> TYPE: PRT
<213> ORGANISM: Homo sapiens

<400> SEQUENCE: 77
```

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr
                85                  90
```

```
<210> SEQ ID NO 78
<211> LENGTH: 4
<212> TYPE: PRT
<213> ORGANISM: Artificial Sequence
<220> FEATURE:
<223> OTHER INFORMATION: linker

<400> SEQUENCE: 78

Gly Ser Gly Ser
 1
```

```
<210> SEQ ID NO 79
<211> LENGTH: 25
<212> TYPE: PRT
<213> ORGANISM: Artificial Sequence
<220> FEATURE:
<223> OTHER INFORMATION: linker

<400> SEQUENCE: 79
```

```
Gly Gly Gly Gly Ser Gly Gly Gly Ser Gly Gly Gly Ser Gly
 1               5                  10                  15

Gly Gly Gly Ser Gly Gly Gly Gly Ser
                20                  25
```

```
<210> SEQ ID NO 80
<211> LENGTH: 4
<212> TYPE: PRT
<213> ORGANISM: Artificial Sequence
<220> FEATURE:
<223> OTHER INFORMATION: linker
```

```
<400> SEQUENCE: 80

Ala Pro Ala Pro
1

<210> SEQ ID NO 81
<211> LENGTH: 10
<212> TYPE: PRT
<213> ORGANISM: Artificial Sequence
<220> FEATURE:
<223> OTHER INFORMATION: linker

<400> SEQUENCE: 81

Ala Pro Ala Pro Ala Pro Ala Pro Ala Pro
1               5                   10

<210> SEQ ID NO 82
<211> LENGTH: 20
<212> TYPE: PRT
<213> ORGANISM: Artificial Sequence
<220> FEATURE:
<223> OTHER INFORMATION: linker

<400> SEQUENCE: 82

Ala Pro Ala Pro Ala Pro Ala Pro Ala Pro Ala Pro Ala Pro Ala Pro
1               5                   10                  15

Ala Pro Ala Pro
            20

<210> SEQ ID NO 83
<211> LENGTH: 40
<212> TYPE: PRT
<213> ORGANISM: Artificial Sequence
<220> FEATURE:
<223> OTHER INFORMATION: linker

<400> SEQUENCE: 83

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
            35                  40

<210> SEQ ID NO 84
<211> LENGTH: 29
<212> TYPE: PRT
<213> ORGANISM: Artificial Sequence
<220> FEATURE:
<223> OTHER INFORMATION: linker

<400> SEQUENCE: 84

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
            20                  25

<210> SEQ ID NO 85
<211> LENGTH: 8
<212> TYPE: PRT
<213> ORGANISM: Artificial Sequence
<220> FEATURE:
<223> OTHER INFORMATION: tencon BC loop

<400> SEQUENCE: 85
```

Thr Ala Pro Asp Ala Ala Phe Asp
1               5

<210> SEQ ID NO 86
<211> LENGTH: 7
<212> TYPE: PRT
<213> ORGANISM: Artificial Sequence
<220> FEATURE:
<223> OTHER INFORMATION: tencon FG loop

<400> SEQUENCE: 86

Lys Gly Gly His Arg Ser Asn
1               5

<210> SEQ ID NO 87
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 87

Ala Asp Pro His Gly Phe Tyr Asp
1               5

<210> SEQ ID NO 88
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 88

Thr Tyr Asp Arg Asp Gly Tyr Asp
1               5

<210> SEQ ID NO 89
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 89

Trp Asp Pro Phe Ser Phe Tyr Asp
1               5

<210> SEQ ID NO 90
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 90

Asp Asp Pro Arg Gly Phe Tyr Glu
1               5

<210> SEQ ID NO 91
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 91

Thr Trp Pro Tyr Ala Asp Leu Asp

```
<210> SEQ ID NO 92
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 92

Gly Tyr Asn Gly Asp His Phe Asp
1               5

<210> SEQ ID NO 93
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 93

Asp Tyr Asp Leu Gly Val Tyr Asp
1               5

<210> SEQ ID NO 94
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 94

Asp Asp Pro Trp Asp Phe Tyr Glu
1               5

<210> SEQ ID NO 95
<211> LENGTH: 12
<212> TYPE: PRT
<213> ORGANISM: Artificial Sequence
<220> FEATURE:
<223> OTHER INFORMATION: EGFR binding FN3 domain FG loop

<400> SEQUENCE: 95

His Asn Val Tyr Lys Asp Thr Asn Met Arg Gly Leu
1               5                   10

<210> SEQ ID NO 96
<211> LENGTH: 11
<212> TYPE: PRT
<213> ORGANISM: Artificial Sequence
<220> FEATURE:
<223> OTHER INFORMATION: EGFR binding FN3 domain FG loop

<400> SEQUENCE: 96

Leu Gly Ser Tyr Val Phe Glu His Asp Val Met
1               5                   10

<210> SEQ ID NO 97
<211> LENGTH: 285
<212> TYPE: DNA
<213> ORGANISM: Artificial Sequence
<220> FEATURE:
<223> OTHER INFORMATION: EGFR binding FN3 domain from ECB97; P54AR4-
      83V22

<400> SEQUENCE: 97
atgttgccag cgccgaagaa cctggtagtt agcgaggtta ctgaggacag cgcgcgtctg      60
```

```
agctgggacg atccgtgggc gttctacgag agctttctga tccagtatca agagagcgag    120
aaagtcggtg aagcgattgt gctgaccgtc ccgggctccg agcgttccta cgacctgacc    180
ggtttgaagc cgggtaccga gtatacggtg agcatctacg gtgttcacaa tgtctataag    240
gacactaata tccgcggtct gcctctgagc gccattttca ccacc                    285
```

```
<210> SEQ ID NO 98
<211> LENGTH: 285
<212> TYPE: DNA
<213> ORGANISM: Artificial Sequence
<220> FEATURE:
<223> OTHER INFORMATION: EGFR binding FN3 domain from ECB15; P54AR4-
      83V2

<400> SEQUENCE: 98
```

```
atgctgccag ccctaagaa tctggtcgtg agcgaagtaa ccgaggacag cgcccgcctg     60
agctgggacg acccgtgggc gttctatgag tctttcctga ttcagtatca agaaagcgaa    120
aaagttggcg aagcgatcgt cctgaccgtc ccgggtagcg agcgctccta cgatctgacc    180
ggcctgaaac cgggtacgga gtacacggtg tccatttacg gtgttcacaa tgtgtataaa    240
gacaccaaca tgcgtggcct gccgctgtcg gcgattttca ccacc                    285
```

```
<210> SEQ ID NO 99
<211> LENGTH: 89
<212> TYPE: PRT
<213> ORGANISM: Artificial Sequence
<220> FEATURE:
<223> OTHER INFORMATION: tencon27 FN3 domain

<400> SEQUENCE: 99
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly His Arg Ser
65                  70                  75                  80

Asn Pro Leu Ser Ala Ile Phe Thr Thr
                85

```
<210> SEQ ID NO 100
<211> LENGTH: 89
<212> TYPE: PRT
<213> ORGANISM: Artificial Sequence
<220> FEATURE:
<223> OTHER INFORMATION: TCL14 library
<220> FEATURE:
<221> NAME/KEY: MISC_FEATURE
<222> LOCATION: (32)..(32)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is any amino acid
<220> FEATURE:
<221> NAME/KEY: MISC_FEATURE
<222> LOCATION: (36)..(36)
<223> OTHER INFORMATION: Xaa is any amino acid
<220> FEATURE:
<221> NAME/KEY: MISC_FEATURE
```

<222> LOCATION: (38)..(38)
<223> OTHER INFORMATION: Xaa is any amino acid
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
<222> LOCATION: (40)..(40)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa is any amino acid
<220> FEATURE:
<221> NAME/KEY: MISC_FEATURE
<222> LOCATION: (68)..(68)
<223> OTHER INFORMATION: Xaa is any amino acid
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (72)..(72)
<223> OTHER INFORMATION: Xaa is any amino acid
<220> FEATURE:
<221> NAME/KEY: MISC_FEATURE
<222> LOCATION: (78)..(78)
<223> OTHER INFORMATION: Xaa is any amino acid
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (81)..(81)
<223> OTHER INFORMATION: Xaa is any amino acid

<400> SEQUENCE: 100

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Ser Ala Ile Phe Thr Thr
                85

<210> SEQ ID NO 101
<211> LENGTH: 1408
<212> TYPE: PRT
<213> ORGANISM: HOMO SAPIENS

<400> SEQUENCE: 101

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

```
Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
        130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
        290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
```

```
                485                 490                 495
Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
                530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
                610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Thr Trp Trp Lys Glu Pro Leu Asn Ile Val Ser Phe Leu
                755                 760                 765

Phe Cys Phe Ala Ser Gly Gly Ser Thr Ile Thr Gly Val Gly Lys Asn
                770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
                805                 810                 815

Ile Cys Cys Thr Thr Pro Ser Leu Gln Gln Leu Asn Leu Gln Leu Pro
                820                 825                 830

Leu Lys Thr Lys Ala Phe Phe Met Leu Asp Gly Ile Leu Ser Lys Tyr
                835                 840                 845

Phe Asp Leu Ile Tyr Val His Asn Pro Val Phe Lys Pro Phe Glu Lys
                850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
                900                 905                 910
```

```
Thr Val Pro Asn Asp Leu Leu Lys Leu Asn Ser Glu Leu Asn Ile Glu
         915                 920                 925

Trp Lys Gln Ala Ile Ser Ser Thr Val Leu Gly Lys Val Ile Val Gln
    930                 935                 940

Pro Asp Gln Asn Phe Thr Gly Leu Ile Ala Gly Val Ser Ile Ser
945                 950                 955                 960

Thr Ala Leu Leu Leu Leu Leu Gly Phe Phe Leu Trp Leu Lys Lys Arg
                965                 970                 975

Lys Gln Ile Lys Asp Leu Gly Ser Glu Leu Val Arg Tyr Asp Ala Arg
            980                 985                 990

Val His Thr Pro His Leu Asp Arg Leu Val Ser Ala Arg Ser Val Ser
        995                 1000                1005

Pro Thr Thr Glu Met Val Ser Asn Glu Ser Val Asp Tyr Arg Ala
    1010                1015                1020

Thr Phe Pro Glu Asp Gln Phe Pro Asn Ser Ser Gln Asn Gly Ser
    1025                1030                1035

Cys Arg Gln Val Gln Tyr Pro Leu Thr Asp Met Ser Pro Ile Leu
    1040                1045                1050

Thr Ser Gly Asp Ser Asp Ile Ser Ser Pro Leu Leu Gln Asn Thr
    1055                1060                1065

Val His Ile Asp Leu Ser Ala Leu Asn Pro Glu Leu Val Gln Ala
    1070                1075                1080

Val Gln His Val Val Ile Gly Pro Ser Ser Leu Ile Val His Phe
    1085                1090                1095

Asn Glu Val Ile Gly Arg Gly His Phe Gly Cys Val Tyr His Gly
    1100                1105                1110

Thr Leu Leu Asp Asn Asp Gly Lys Lys Ile His Cys Ala Val Lys
    1115                1120                1125

Ser Leu Asn Arg Ile Thr Asp Ile Gly Glu Val Ser Gln Phe Leu
    1130                1135                1140

Thr Glu Gly Ile Ile Met Lys Asp Phe Ser His Pro Asn Val Leu
    1145                1150                1155

Ser Leu Leu Gly Ile Cys Leu Arg Ser Glu Gly Ser Pro Leu Val
    1160                1165                1170

Val Leu Pro Tyr Met Lys His Gly Asp Leu Arg Asn Phe Ile Arg
    1175                1180                1185

Asn Glu Thr His Asn Pro Thr Val Lys Asp Leu Ile Gly Phe Gly
    1190                1195                1200

Leu Gln Val Ala Lys Gly Met Lys Tyr Leu Ala Ser Lys Lys Phe
    1205                1210                1215

Val His Arg Asp Leu Ala Ala Arg Asn Cys Met Leu Asp Glu Lys
    1220                1225                1230

Phe Thr Val Lys Val Ala Asp Phe Gly Leu Ala Arg Asp Met Tyr
    1235                1240                1245

Asp Lys Glu Tyr Tyr Ser Val His Asn Lys Thr Gly Ala Lys Leu
    1250                1255                1260

Pro Val Lys Trp Met Ala Leu Glu Ser Leu Gln Thr Gln Lys Phe
    1265                1270                1275

Thr Thr Lys Ser Asp Val Trp Ser Phe Gly Val Leu Leu Trp Glu
    1280                1285                1290

Leu Met Thr Arg Gly Ala Pro Pro Tyr Pro Asp Val Asn Thr Phe
    1295                1300                1305
```

```
Asp Ile Thr Val Tyr Leu Leu Gln Gly Arg Arg Leu Leu Gln Pro
    1310                1315                1320

Glu Tyr Cys Pro Asp Pro Leu Tyr Glu Val Met Leu Lys Cys Trp
    1325                1330                1335

His Pro Lys Ala Glu Met Arg Pro Ser Phe Ser Glu Leu Val Ser
    1340                1345                1350

Arg Ile Ser Ala Ile Phe Ser Thr Phe Ile Gly Glu His Tyr Val
    1355                1360                1365

His Val Asn Ala Thr Tyr Val Asn Val Lys Cys Val Ala Pro Tyr
    1370                1375                1380

Pro Ser Leu Leu Ser Ser Glu Asp Asn Ala Asp Asp Glu Val Asp
    1385                1390                1395

Thr Arg Pro Ala Ser Phe Trp Glu Thr Ser
    1400                1405

<210> SEQ ID NO 102
<211> LENGTH: 697
<212> TYPE: PRT
<213> ORGANISM: HOMO SAPIENS

<400> SEQUENCE: 102

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
                35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
    130                 135                 140

Tyr Cys Arg Asn Pro Arg Gly Glu Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
            180                 185                 190

Asp His Thr Glu Ser Gly Lys Ile Cys Gln Arg Trp Asp His Gln Thr
        195                 200                 205

Pro His Arg His Lys Phe Leu Pro Glu Arg Tyr Pro Asp Lys Gly Phe
    210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
            260                 265                 270
```

```
Glu Cys Ile Gln Gly Gln Gly Glu Gly Tyr Arg Gly Thr Val Asn Thr
        275                 280                 285

Ile Trp Asn Gly Ile Pro Cys Gln Arg Trp Asp Ser Gln Tyr Pro His
290                 295                 300

Glu His Asp Met Thr Pro Glu Asn Phe Lys Cys Lys Asp Leu Arg Glu
305                 310                 315                 320

Asn Tyr Cys Arg Asn Pro Asp Gly Ser Glu Ser Pro Trp Cys Phe Thr
                325                 330                 335

Thr Asp Pro Asn Ile Arg Val Gly Tyr Cys Ser Gln Ile Pro Asn Cys
            340                 345                 350

Asp Met Ser His Gly Gln Asp Cys Tyr Arg Gly Asn Gly Lys Asn Tyr
        355                 360                 365

Met Gly Asn Leu Ser Gln Thr Arg Ser Gly Leu Thr Cys Ser Met Trp
370                 375                 380

Asp Lys Asn Met Glu Asp Leu His Arg His Ile Phe Trp Glu Pro Asp
385                 390                 395                 400

Ala Ser Lys Leu Asn Glu Asn Tyr Cys Arg Asn Pro Asp Asp Asp Ala
                405                 410                 415

His Gly Pro Trp Cys Tyr Thr Gly Asn Pro Leu Ile Pro Trp Asp Tyr
            420                 425                 430

Cys Pro Ile Ser Arg Cys Glu Gly Asp Thr Thr Pro Thr Ile Val Asn
        435                 440                 445

Leu Asp His Pro Val Ile Ser Cys Ala Lys Thr Lys Gln Leu Arg Val
450                 455                 460

Val Asn Gly Ile Pro Thr Arg Thr Asn Ile Gly Trp Met Val Ser Leu
465                 470                 475                 480

Arg Tyr Arg Asn Lys His Ile Cys Gly Gly Ser Leu Ile Lys Glu Ser
                485                 490                 495

Trp Val Leu Thr Ala Arg Gln Cys Phe Pro Ser Arg Asp Leu Lys Asp
            500                 505                 510

Tyr Glu Ala Trp Leu Gly Ile His Asp Val His Gly Arg Gly Asp Glu
        515                 520                 525

Lys Cys Lys Gln Val Leu Asn Val Ser Gln Leu Val Tyr Gly Pro Glu
530                 535                 540

Gly Ser Asp Leu Val Leu Met Lys Leu Ala Arg Pro Ala Val Leu Asp
545                 550                 555                 560

Asp Phe Val Ser Thr Ile Asp Leu Pro Asn Tyr Gly Cys Thr Ile Pro
                565                 570                 575

Glu Lys Thr Ser Cys Ser Val Tyr Gly Trp Gly Tyr Thr Gly Leu Ile
            580                 585                 590

Asn Tyr Asp Gly Leu Leu Arg Val Ala His Leu Tyr Ile Met Gly Asn
        595                 600                 605

Glu Lys Cys Ser Gln His His Arg Gly Lys Val Thr Leu Asn Glu Ser
610                 615                 620

Glu Ile Cys Ala Gly Ala Glu Lys Ile Gly Ser Gly Pro Cys Glu Gly
625                 630                 635                 640

Asp Tyr Gly Gly Pro Leu Val Cys Glu Gln His Lys Met Arg Met Val
                645                 650                 655

Leu Gly Val Ile Val Pro Gly Arg Gly Cys Ala Ile Pro Asn Arg Pro
            660                 665                 670

Gly Ile Phe Val Arg Val Ala Tyr Tyr Ala Lys Trp Ile His Lys Ile
        675                 680                 685
```

Ile Leu Thr Tyr Lys Val Pro Gln Ser
    690             695

<210> SEQ ID NO 103
<211> LENGTH: 276
<212> TYPE: DNA
<213> ORGANISM: Artificial Sequence
<220> FEATURE:
<223> OTHER INFORMATION: c-Met binding FN3 domain

<400> SEQUENCE: 103

```
ctgccggctc cgaagaactt ggtggtgagc cgtgttaccg aagatagcgc acgcctgagc      60
tggacggcac cggatgcggc gttcgatagc ttctggattc gctatttttga gtttctgggt    120
agcggtgagg caattgttct gacggtgccg ggctctgaac gctcctacga tttgaccggt    180
ctgaaaccgg caccgagta tgtggtgaac attctgagcg ttaagggcgg tagcatcagc     240
ccaccgctga gcgcgatctt cacgactggt ggttgc                              276
```

<210> SEQ ID NO 104
<211> LENGTH: 267
<212> TYPE: DNA
<213> ORGANISM: Artificial Sequence
<220> FEATURE:
<223> OTHER INFORMATION: c-Met binding FN3 domain

<400> SEQUENCE: 104

```
ctgccggcac cgaagaacct ggttgtcagc cgtgtgaccg aggatagcgc acgttttgagc    60
tggaccgctc cggatgcagc ctttgacagc ttctggattc gttactttga atttctgggt   120
agcggtgagg cgatcgttct gacggtgccg ggctctgaac gcagctatga tttgacgggc   180
ctgaagccgg gtactgagta cgtggttaac atcatgggcg ttaagggtgg taaaatcagc   240
ccgccattgt ccgcgatctt taccacg                                        267
```

<210> SEQ ID NO 105
<211> LENGTH: 5
<212> TYPE: PRT
<213> ORGANISM: Artificial Sequence
<220> FEATURE:
<223> OTHER INFORMATION: linker

<400> SEQUENCE: 105

Gly Gly Gly Gly Ser
1               5

<210> SEQ ID NO 106
<211> LENGTH: 194
<212> TYPE: PRT
<213> ORGANISM: Artificial Sequence
<220> FEATURE:
<223> OTHER INFORMATION: Bispecific EGFR/c-Met binding molecule

<400> SEQUENCE: 106

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys

```
                65                  70                  75                  80
Asp Thr Asn Ile Arg Gly Leu Pro Leu Ser Ala Ile Phe Thr Thr Ala
                    85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
                180                 185                 190

Thr Thr

<210> SEQ ID NO 107
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 107

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 108
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 108

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
```

```
                85                  90

<210> SEQ ID NO 109
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 109

Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 110
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 110

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 111
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 111

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60
```

```
Thr Glu Tyr Val Val Asn Ile Leu Gly Val Lys Gly Gly Lys Ile Ser
 65                  70                  75                  80

Pro Pro Leu Ser Ala Ile Phe Thr Thr
                85

<210> SEQ ID NO 112
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 112

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30

Ile Arg Tyr Phe Glu Phe Val Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Asn Ile Leu Gly Val Lys Gly Gly Ser Ile Ser
 65                  70                  75                  80

Pro Pro Leu Ser Ala Ile Phe Thr Thr
                85

<210> SEQ ID NO 113
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 113

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30

Ile Arg Tyr Phe Glu Phe Val Ser Lys Gly Asp Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Asn Ile Leu Gly Val Lys Gly Gly Ser Ile Ser
 65                  70                  75                  80

Pro Pro Leu Ser Ala Ile Phe Thr Thr
                85

<210> SEQ ID NO 114
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 114

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30
```

Ile Arg Tyr Phe Glu Phe Leu Gly Ser Gly Glu Ala Ile Val Leu Thr
             35                  40                  45

Val Pro Gly Ser Glu Arg Ser Tyr Asp Leu Thr Gly Leu Lys Pro Gly
 50                  55                  60

Thr Glu Tyr Val Val Asn Ile Leu Ser Val Lys Gly Gly Ser Ile Ser
 65                  70                  75                  80

Pro Pro Leu Ser Ala Ile Phe Thr Thr
                 85

<210> SEQ ID NO 115
<211> LENGTH: 591
<212> TYPE: DNA
<213> ORGANISM: Artificial Sequence
<220> FEATURE:
<223> OTHER INFORMATION: Bispecific EGFR/c-Met binding molecule

<400> SEQUENCE: 115

| | |
|---|---|
| atgttgccag cgccgaagaa cctggtagtt agcgaggtta ctgaggacag cgcgcgtctg | 60 |
| agctgggacg atccgtgggc gttctacgag agctttctga tccagtatca agagagcgag | 120 |
| aaagtcggtg aagcgattgt gctgaccgtc ccgggctccg agcgttccta cgacctgacc | 180 |
| ggtttgaagc cggtaccgga gtatacggtg agcatctacg tgttcacaa tgtctataag | 240 |
| gacactaata tccgcggtct gcctctgagc gccattttca ccaccgcacc ggcaccggct | 300 |
| ccggctcctg ccccgctgcc ggctccgaag aacttggtgg tgagccgtgt taccgaagat | 360 |
| agcgcacgcc tgagctggac ggcaccggat gcggcgttcg atagcttctg gattcgctat | 420 |
| tttgagtttc tgggtagcgg tgaggcaatt gttctgacgg tgccgggctc tgaacgctcc | 480 |
| tacgatttga ccggtctgaa accgggcacc gagtatgtgg tgaacattct gagcgttaag | 540 |
| ggcggtagca tcagcccacc gctgagcgcg atcttcacga ctggtggttg c | 591 |

<210> SEQ ID NO 116
<211> LENGTH: 582
<212> TYPE: DNA
<213> ORGANISM: Artificial Sequence
<220> FEATURE:
<223> OTHER INFORMATION: Bispecific EGFR/c-Met binding molecule

<400> SEQUENCE: 116

| | |
|---|---|
| atgctgccag cccctaagaa tctggtcgtg agcgaagtaa ccgaggacag cgcccgcctg | 60 |
| agctgggacg accgtgggc gttctatgag tctttcctga ttcagtatca agaaagcgaa | 120 |
| aaagttggcg aagcgatcgt cctgaccgtc ccgggtagcg agcgctccta cgatctgacc | 180 |
| ggcctgaaac cgggtacgga gtacacggtg tccatttacg tgttcacaa tgtgtataaa | 240 |
| gacaccaaca tgcgtggcct gccgctgtcg gcgattttca ccaccgcgcc tgcgccagcg | 300 |
| cctgcaccgg ctccgctgcc ggcaccgaag aacctggttg tcagccgtgt gaccgaggat | 360 |
| agcgcacgtt tgagctggac cgctccggat gcagcctttg acagcttctg gattcgttac | 420 |
| tttgaatttc tgggtagcgg tgaggcgatc gttctgacgg tgccgggctc tgaacgcagc | 480 |
| tatgatttga cgggcctgaa gccgggtact gagtacgtgg ttaacatcat gggcgttaag | 540 |
| ggtggtaaaa tcagcccgcc attgtccgcg atctttacca cg | 582 |

<210> SEQ ID NO 117
<211> LENGTH: 51
<212> TYPE: PRT
<213> ORGANISM: Artificial Sequence
<220> FEATURE:
<223> OTHER INFORMATION: albumin binding domain

<400> SEQUENCE: 117

Thr Ile Asp Glu Trp Leu Leu Lys Glu Ala Lys Glu Lys Ala Ile Glu
1               5                   10                  15

Glu Leu Lys Lys Ala Gly Ile Thr Ser Asp Tyr Tyr Phe Asp Leu Ile
            20                  25                  30

Asn Lys Ala Lys Thr Val Glu Gly Val Asn Ala Leu Lys Asp Glu Ile
        35                  40                  45

Leu Lys Ala
    50

<210> SEQ ID NO 118
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 118

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Asp Glu Val Val
    130                 135                 140

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
                165                 170                 175

Leu Gly Val Lys Gly Gly Ser Ile Ser Val Pro Leu Ser Ala Ile Phe
            180                 185                 190

Thr Thr Ala Pro Ala Pro Ala Pro Ala Pro Ala Pro Leu Ala Glu Ala
        195                 200                 205

Lys Val Leu Ala Asn Arg Glu Leu Asp Lys Tyr Gly Val Ser Asp Tyr
    210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 119
<211> LENGTH: 250
<212> TYPE: PRT
<213> ORGANISM: Artificial Sequence
<220> FEATURE:

<223> OTHER INFORMATION: Bispecific EGFR/c-Met binding molecule

<400> SEQUENCE: 119

Met Leu Pro Ala Pro Lys Asn Leu Val Val Ser Glu Val Thr Glu Asp
1               5                   10                  15
Ser Ala Arg Leu Ser Trp Ala Asp Pro His Gly Phe Tyr Asp Ser Phe
            20                  25                  30
Leu Ile Gln Tyr Gln Glu Ser Glu Lys Val Gly Glu Ala Ile Val Leu
        35                  40                  45
Thr Val Pro Gly Ser Glu Arg Ser Tyr Asp Leu Thr Gly Leu Lys Pro
    50                  55                  60
Gly Thr Glu Tyr Thr Val Ser Ile Tyr Gly Val His Asn Val Tyr Lys
65                  70                  75                  80
Asp Thr Asn Met Arg Gly Leu Pro Leu Ser Ala Ile Phe Thr Thr Ala
                85                  90                  95
Pro Ala Pro Ala Pro Ala Pro Ala Pro Leu Pro Ala Pro Lys Asn Leu
            100                 105                 110
Val Val Ser Arg Val Thr Glu Asp Ser Ala Arg Leu Ser Trp Thr Ala
        115                 120                 125
Pro Asp Ala Ala Phe Asp Ser Phe Trp Ile Arg Tyr Asp Glu Val Val
    130                 135                 140
Val Gly Gly Glu Ala Ile Val Leu Thr Val Pro Gly Ser Glu Arg Ser
145                 150                 155                 160
Tyr Asp Leu Thr Gly Leu Lys Pro Gly Thr Glu Tyr Tyr Val Asn Ile
                165                 170                 175
Leu Gly Val Lys Gly Gly Ser Ile Ser Val Pro Leu Ser Ala Ile Phe
            180                 185                 190
Thr Thr Ala Pro Ala Pro Ala Pro Ala Pro Ala Pro Leu Ala Glu Ala
        195                 200                 205
Lys Val Leu Ala Asn Arg Glu Leu Asp Lys Tyr Gly Val Ser Asp Tyr
    210                 215                 220
Tyr Lys Asn Leu Ile Asn Asn Ala Lys Thr Val Glu Gly Val Lys Ala
225                 230                 235                 240
Leu Leu Asp Glu Ile Leu Ala Ala Leu Pro
                245                 250

<210> SEQ ID NO 120
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 120

Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
            20                  25                  30
Leu Ile Gln Tyr Gln Glu Ser Glu Lys Val Gly Glu Ala Ile Val Leu
        35                  40                  45
Thr Val Pro Gly Ser Glu Arg Ser Tyr Asp Leu Thr Gly Leu Lys Pro
    50                  55                  60
Gly Thr Glu Tyr Thr Val Ser Ile Tyr Gly Val His Asn Val Tyr Lys
65                  70                  75                  80
Asp Thr Asn Met Arg Gly Leu Pro Leu Ser Ala Ile Phe Thr Thr Ala
                85                  90                  95

```
Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Lys Ile Ser Pro Leu Ser Ala Ile Phe
            180                 185                 190

Thr Thr Ala Pro Ala Pro Ala Pro Ala Pro Leu Ala Glu Ala
            195                 200                 205

Lys Val Leu Ala Asn Arg Glu Leu Asp Lys Tyr Gly Val Ser Asp Tyr
            210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 121
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 121

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Lys Ile Ser Pro Leu Ser Ala Ile Phe
            180                 185                 190

Thr Thr Ala Pro Ala Pro Ala Pro Ala Pro Leu Ala Glu Ala
            195                 200                 205
```

```
Lys Val Leu Ala Asn Arg Glu Leu Asp Lys Tyr Gly Val Ser Asp Tyr
            210                 215                 220

Tyr Lys Asn Leu Ile Asn Ala Lys Thr Val Glu Gly Val Lys Ala
225                 230                 235                 240

Leu Leu Asp Glu Ile Leu Ala Ala Leu Pro
                245                 250

<210> SEQ ID NO 122
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 122

Met Leu Pro Ala Pro Lys Asn Leu Val Val Ser Glu Val Thr Glu Asp
1               5                   10                  15

Ser Leu Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 123
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 123

Met Leu Pro Ala Pro Lys Asn Leu Val Val Ser Glu Val Thr Glu Asp
1               5                   10                  15

Ser Leu Arg Leu Ser Trp Thr Tyr Asp Arg Asp Gly Tyr Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 124
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 124

Met Leu Pro Ala Pro Lys Asn Leu Val Val Ser Glu Val Thr Glu Asp
1               5                   10                  15
```

Ser Leu Arg Leu Ser Trp Gly Tyr Asn Gly Asp His Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 125
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 125

Met Leu Pro Ala Pro Lys Asn Leu Val Val Ser Glu Val Thr Glu Asp
1               5                   10                  15

Ser Leu Arg Leu Ser Trp Asp Asp Pro Arg Gly Phe Tyr Glu Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 126
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 126

Met Leu Pro Ala Pro Lys Asn Leu Val Val Ser Glu Val Thr Glu Asp
1               5                   10                  15

Ser Leu Arg Leu Ser Trp Thr Trp Pro Tyr Ala Asp Leu Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 127
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 127

Met Leu Pro Ala Pro Lys Asn Leu Val Val Ser Glu Val Thr Glu Asp
1               5                   10                  15

Ser Leu Arg Leu Ser Trp Gly Tyr Asn Gly Asp His Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 128
<211> LENGTH: 96
<212> TYPE: PRT
<213> ORGANISM: Artificial Sequence
<220> FEATURE:
<223> OTHER INFORMATION: EGFR binding FN3 domain

<400> SEQUENCE: 128

Met Leu Pro Ala Pro Lys Asn Leu Val Val Ser Glu Val Thr Glu Asp
1               5                   10                  15

Ser Leu Arg Leu Ser Trp Asp Tyr Asp Leu Gly Val Tyr Phe Asp Ser
            20                  25                  30

Phe Leu Ile Gln Tyr Gln Glu Ser Glu Lys Val Gly Glu Ala Ile Asn
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val His Asn Val Tyr
65                  70                  75                  80

Lys Asp Thr Asn Met Arg Gly Leu Pro Leu Ser Ala Glu Phe Thr Thr
                85                  90                  95

<210> SEQ ID NO 129
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 129

Met Leu Pro Ala Pro Lys Asn Leu Val Val Ser Glu Val Thr Glu Asp
1               5                   10                  15

Ser Leu Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 130
<211> LENGTH: 95

```
<212> TYPE: PRT
<213> ORGANISM: Artificial Sequence
<220> FEATURE:
<223> OTHER INFORMATION: EGFR binding FN3 domain

<400> SEQUENCE: 130

Met Leu Pro Ala Pro Lys Asn Leu Val Val Ser Glu Val Thr Glu Asp
1               5                   10                  15

Ser Leu Arg Leu Ser Trp Thr Ala Pro Asp Ala Ala Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Leu Gly Ser Tyr Val
65                  70                  75                  80

Phe Glu His Asp Val Met Leu Pro Leu Ser Ala Glu Phe Thr Thr
                85                  90                  95

<210> SEQ ID NO 131
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 131

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 132
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 132

Met Leu Pro Ala Pro Lys Asn Leu Val Val Ser Glu Val Thr Glu Asp
1               5                   10                  15

Ser Ala Arg Leu Ser Trp Thr Ala Pro Asp Ala Ala Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Leu Gly Ser Tyr Val
65                  70                  75                  80

Phe Glu His Asp Val Met Leu Pro Leu Ser Ala Ile Phe Thr Thr
```

<210> SEQ ID NO 133
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 133

```
Met Leu Pro Ala Pro Lys Asn Leu Val Val Ser Glu Val Thr Glu Asp
1               5                   10                  15

Ser Leu Arg Leu Ser Trp Thr Trp Pro Tyr Ala Asp Leu Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95
```

<210> SEQ ID NO 134
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 134

```
Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95
```

<210> SEQ ID NO 135
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 135

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60
```

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 136
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 136

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 137
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 137

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 138
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 138

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
         35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr Gly Gly
                 85                  90                  95

Gly Gly Ser Gly Gly Gly Gly Ser Gly Gly Gly Ser Gly Gly Gly Gly
                100                 105                 110

Gly Ser Met Leu Pro Ala Pro Lys Asn Leu Val Val Ser Arg Val Thr
         115                 120                 125

Glu Asp Ser Ala Arg Leu Ser Trp Thr Ala Pro Asp Ala Ala Phe Asp
130                 135                 140

Ser Phe Trp Ile Arg Tyr Asp Glu Val Val Gly Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Tyr Val Asn Ile Leu Gly Val Lys Gly Gly
                180                 185                 190

Ser Ile Ser Val Pro Leu Ser Ala Ile Phe Thr Thr
         195                 200

<210> SEQ ID NO 139
<211> LENGTH: 203
<212> TYPE: PRT
<213> ORGANISM: Artificial Sequence
<220> FEATURE:
<223> OTHER INFORMATION: Bispecific EGFR/c-Met binding domain

<400> SEQUENCE: 139

Leu Pro Ala Pro Lys Asn Leu Val Val Ser Glu Val Thr Glu Asp Ser
 1               5                  10                  15

Ala Arg Leu Ser Trp Asp Asp Pro Trp Ala Phe Tyr Glu Ser Phe Leu
                 20                  25                  30

Ile Gln Tyr Gln Glu Ser Glu Lys Val Gly Glu Ala Ile Val Leu Thr
         35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr Gly Gly
                 85                  90                  95

Gly Gly Ser Gly Gly Gly Gly Ser Gly Gly Gly Ser Gly Gly Gly Gly
                100                 105                 110

Gly Ser Leu Pro Ala Pro Lys Asn Leu Val Val Ser Arg Val Thr Glu
         115                 120                 125

Asp Ser Ala Arg Leu Ser Trp Thr Ala Pro Asp Ala Ala Phe Asp Ser
130                 135                 140

Phe Trp Ile Arg Tyr Phe Glu Phe Leu Gly Ser Gly Glu Ala Ile Val
145                 150                 155                 160

Leu Thr Val Pro Gly Ser Glu Arg Ser Tyr Asp Leu Thr Gly Leu Lys
                165                 170                 175

Pro Gly Thr Glu Tyr Val Val Asn Ile Met Gly Val Lys Gly Gly Lys
                180                 185                 190

Ile Ser Pro Pro Leu Ser Ala Ile Phe Thr Thr
        195                 200

<210> SEQ ID NO 140
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 140

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Gly Ser Gly Gly Gly
            100                 105                 110

Gly Ser Met Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
        130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Gln Ile Ile Gly Val Lys Gly Gly
            180                 185                 190

His Ile Ser Leu Pro Leu Ser Ala Ile Phe Thr Thr
            195                 200

<210> SEQ ID NO 141
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 141

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

```
Gly Gly Ser Gly Gly Gly Ser Gly Gly Gly Ser Gly Gly Gly
            100                 105                 110

Gly Ser Met Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
130                 135                 140

Ser Phe Phe Ile Arg Tyr Asp Glu Phe Leu Arg Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Trp Val Thr Ile Leu Gly Val Lys Gly Gly
            180                 185                 190

Leu Val Ser Thr Pro Leu Ser Ala Ile Phe Thr Thr
            195                 200
```

<210> SEQ ID NO 142
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 142

```
Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
            85                  90                  95

Gly Gly Ser Gly Gly Gly Ser Gly Gly Gly Ser Gly Gly Gly
            100                 105                 110

Gly Ser Met Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Asn Ile Met Gly Val Lys Gly Gly
            180                 185                 190

Lys Ile Ser Pro Pro Leu Ser Ala Ile Phe Thr Thr
            195                 200
```

<210> SEQ ID NO 143
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 143

```
Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Gly Ser Gly Gly Gly
            100                 105                 110

Gly Ser Met Leu Pro Ala Pro Lys Asn Leu Val Val Ser Arg Val Thr
        115                 120                 125

Glu Asp Ser Ala Arg Leu Ser Trp Thr Ala Pro Asp Ala Ala Phe Asp
    130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Gln Ile Ile Gly Val Lys Gly Gly
            180                 185                 190

His Ile Ser Leu Pro Leu Ser Ala Ile Phe Thr Thr
            195                 200
```

<210> SEQ ID NO 144
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 144

```
Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Gly Ser Gly Gly Gly
            100                 105                 110

Gly Ser Met Leu Pro Ala Pro Lys Asn Leu Val Val Ser Arg Val Thr
        115                 120                 125

Glu Asp Ser Ala Arg Leu Ser Trp Thr Ala Pro Asp Ala Ala Phe Asp
    130                 135                 140

Ser Phe Trp Ile Arg Tyr Phe Glu Phe Leu Gly Ser Gly Glu Ala Ile
```

```
                145                 150                 155                 160
Val Leu Thr Val Pro Gly Ser Glu Arg Ser Tyr Asp Leu Thr Gly Leu
                    165                 170                 175

Lys Pro Gly Thr Glu Tyr Val Val Gln Ile Ile Gly Val Lys Gly Gly
                    180                 185                 190

His Ile Ser Leu Pro Leu Ser Ala Ile Phe Thr Thr
                    195                 200

<210> SEQ ID NO 145
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 145

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Gly Val Lys Gly Gly Lys Ile Ser Pro Leu Ser Ala Ile Phe Thr
                180                 185                 190

Thr

<210> SEQ ID NO 146
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 146

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
```

```
                 50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr Ala Pro
                     85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Asp Glu Val Val Val
            130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
                180                 185                 190

Thr
```

<210> SEQ ID NO 147
<211> LENGTH: 194
<212> TYPE: PRT
<213> ORGANISM: Artificial Sequence
<220> FEATURE:
<223> OTHER INFORMATION: Bispecific EGFR/c-Met binding domain

<400> SEQUENCE: 147

```
Leu Pro Ala Pro Lys Asn Leu Val Val Ser Glu Val Thr Glu Asp Ser
  1               5                  10                  15

Ala Arg Leu Ser Trp Ala Asp Pro His Gly Phe Tyr Asp Ser Phe Leu
             20                  25                  30

Ile Gln Tyr Gln Glu Ser Glu Lys Val Gly Glu Ala Ile Val Leu Thr
         35                  40                  45

Val Pro Gly Ser Glu Arg Ser Tyr Asp Leu Thr Gly Leu Lys Pro Gly
     50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr Ala Pro
                     85                  90                  95

Ala Pro Ala Pro Ala Pro Ala Pro Met Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Gly Lys Ile Ser Pro Pro Leu Ser Ala Ile Phe
                180                 185                 190

Thr Thr
```

<210> SEQ ID NO 148
<211> LENGTH: 193

```
<212> TYPE: PRT
<213> ORGANISM: Artificial Sequence
<220> FEATURE:
<223> OTHER INFORMATION: Bispecific EGFR/c-Met binding domain

<400> SEQUENCE: 148

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Asp Glu Val Val Val
    130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
            180                 185                 190

Thr

<210> SEQ ID NO 149
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 149

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125
```

```
Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Lys Ile Ser Pro Pro Leu Ser Ala Ile Phe Thr
            180                 185                 190

Thr
```

<210> SEQ ID NO 150
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 150

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Val Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
            180                 185                 190

Thr
```

<210> SEQ ID NO 151
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 151

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
```

```
                35                  40                  45
Val Pro Gly Ser Glu Arg Ser Tyr Asp Leu Thr Gly Leu Lys Pro Gly
         50                  55                  60

Thr Glu Tyr Thr Val Ser Ile Tyr Gly Val His Asn Val Tyr Lys Asp
 65                  70                  75                  80

Thr Asn Ile Arg Gly Leu Pro Leu Ser Ala Ile Phe Thr Thr Ala Pro
                 85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Val Ser
            130                 135                 140

Lys Gly Asp Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
                180                 185                 190

Thr

<210> SEQ ID NO 152
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 152

Leu Pro Ala Pro Lys Asn Leu Val Val Ser Glu Val Thr Glu Asp Ser
  1               5                  10                  15

Ala Arg Leu Ser Trp Asp Asp Pro Trp Ala Phe Tyr Glu Ser Phe Leu
             20                  25                  30

Ile Gln Tyr Gln Glu Ser Glu Lys Val Gly Glu Ala Ile Val Leu Thr
         35                  40                  45

Val Pro Gly Ser Glu Arg Ser Tyr Asp Leu Thr Gly Leu Lys Pro Gly
         50                  55                  60

Thr Glu Tyr Thr Val Ser Ile Tyr Gly Val His Asn Val Tyr Lys Asp
 65                  70                  75                  80

Thr Asn Ile Arg Gly Leu Pro Leu Ser Ala Ile Phe Thr Thr Ala Pro
                 85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
                180                 185                 190

Thr
```

<210> SEQ ID NO 153
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 153

```
Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Lys Ile Ser Pro Pro Leu Ser Ala Ile Phe Thr
                180                 185                 190

Thr
```

<210> SEQ ID NO 154
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 154

```
Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110
```

```
Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Val Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
                180                 185                 190

Thr

<210> SEQ ID NO 155
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 155

Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Val Ser
        130                 135                 140

Lys Gly Asp Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
                180                 185                 190

Thr

<210> SEQ ID NO 156
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 156

Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
```

```
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
            180                 185                 190

Thr
```

<210> SEQ ID NO 157
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 157

```
Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Lys Ile Ser Pro Pro Leu Ser Ala Ile Phe Thr
            180                 185                 190
```

Thr

<210> SEQ ID NO 158
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 158

```
Leu Pro Ala Pro Lys Asn Leu Val Val Ser Glu Val Thr Glu Asp Ser
1               5                   10                  15
Ala Arg Leu Ser Trp Ala Asp Pro His Gly Phe Tyr Asp Ser Phe Leu
            20                  25                  30
Ile Gln Tyr Gln Glu Ser Glu Lys Val Gly Glu Ala Ile Val Leu Thr
        35                  40                  45
Val Pro Gly Ser Glu Arg Ser Tyr Asp Leu Thr Gly Leu Lys Pro Gly
    50                  55                  60
Thr Glu Tyr Thr Val Ser Ile Tyr Gly Val His Asn Val Tyr Lys Asp
65                  70                  75                  80
Thr Asn Ile Arg Gly Leu Pro Leu Ser Ala Ile Phe Thr Thr Ala Pro
                85                  90                  95
Ala Pro Ala Pro Ala Pro Leu Pro Ala Pro Lys Asn Leu Val
            100                 105                 110
Val Ser Arg Val Thr Glu Asp Ser Ala Arg Leu Ser Trp Thr Ala Pro
        115                 120                 125
Asp Ala Ala Phe Asp Ser Phe Trp Ile Arg Tyr Phe Glu Phe Val Gly
    130                 135                 140
Ser Gly Glu Ala Ile Val Leu Thr Val Pro Gly Ser Glu Arg Ser Tyr
145                 150                 155                 160
Asp Leu Thr Gly Leu Lys Pro Gly Thr Glu Tyr Val Val Asn Ile Leu
                165                 170                 175
Gly Val Lys Gly Gly Ser Ile Ser Pro Pro Leu Ser Ala Ile Phe Thr
            180                 185                 190
Thr
```

<210> SEQ ID NO 159
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 159

```
Leu Pro Ala Pro Lys Asn Leu Val Val Ser Glu Val Thr Glu Asp Ser
1               5                   10                  15
Ala Arg Leu Ser Trp Ala Asp Pro His Gly Phe Tyr Asp Ser Phe Leu
            20                  25                  30
Ile Gln Tyr Gln Glu Ser Glu Lys Val Gly Glu Ala Ile Val Leu Thr
        35                  40                  45
Val Pro Gly Ser Glu Arg Ser Tyr Asp Leu Thr Gly Leu Lys Pro Gly
    50                  55                  60
Thr Glu Tyr Thr Val Ser Ile Tyr Gly Val His Asn Val Tyr Lys Asp
65                  70                  75                  80
Thr Asn Ile Arg Gly Leu Pro Leu Ser Ala Ile Phe Thr Thr Ala Pro
                85                  90                  95
```

```
Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Val Ser
    130                 135                 140

Lys Gly Asp Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
            180                 185                 190

Thr

<210> SEQ ID NO 160
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 160

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
            180                 185                 190

Thr

<210> SEQ ID NO 161
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 161

Leu Pro Ala Pro Lys Asn Leu Val Val Ser Glu Val Thr Glu Asp Ser
```

```
1               5                   10                  15
Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
            180                 185                 190

Thr
```

<210> SEQ ID NO 162
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 162

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Asp Glu Val Val Val
            130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175
```

```
Gly Val Lys Gly Gly Ser Ile Ser Val Pro Leu Ser Ala Ile Phe Thr
            180                 185                 190

Thr Ala Pro Ala Pro Ala Pro Ala Pro Leu Ala Glu Ala Lys
        195                 200                 205

Val Leu Ala Asn Arg Glu Leu Asp Lys Tyr Gly Val Ser Asp Tyr Tyr
210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 163
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 163

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Asp Glu Val Val Val
    130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
            180                 185                 190

Thr Ala Pro Ala Pro Ala Pro Ala Pro Leu Ala Glu Ala Lys
        195                 200                 205

Val Leu Ala Asn Arg Glu Leu Asp Lys Tyr Gly Val Ser Asp Tyr Tyr
210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 164
<211> LENGTH: 249
<212> TYPE: PRT
<213> ORGANISM: Artificial Sequence
```

```
<220> FEATURE:
<223> OTHER INFORMATION: Bispecific EGFR/c-Met binding domain

<400> SEQUENCE: 164

Leu Pro Ala Pro Lys Asn Leu Val Val Ser Glu Val Thr Glu Asp Ser
1               5                   10                  15

Ala Arg Leu Ser Trp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Gly Val Lys Gly Gly Lys Ile Ser Pro Pro Leu Ser Ala Ile Phe Thr
                180                 185                 190

Thr Ala Pro Ala Pro Ala Pro Ala Pro Ala Pro Leu Ala Glu Ala Lys
            195                 200                 205

Val Leu Ala Asn Arg Glu Leu Asp Lys Tyr Gly Val Ser Asp Tyr Tyr
        210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 165
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 165

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
```

```
                85                  90                  95
Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
            165                 170                 175

Gly Val Lys Gly Gly Lys Ile Ser Pro Pro Leu Ser Ala Ile Phe Thr
        180                 185                 190

Thr Ala Pro Ala Pro Ala Pro Ala Pro Leu Ala Glu Ala Lys
    195                 200                 205

Val Leu Ala Asn Arg Glu Leu Asp Lys Tyr Gly Val Ser Asp Tyr Tyr
        210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
            245

<210> SEQ ID NO 166
<211> LENGTH: 588
<212> TYPE: DNA
<213> ORGANISM: Artificial Sequence
<220> FEATURE:
<223> OTHER INFORMATION: Bispecific EGFR/c-Met binding domain

<400> SEQUENCE: 166
ttgccagcgc cgaagaacct ggtagttagc gaggttactg aggacagcgc gcgtctgagc      60
tgggacgatc cgtgggcgtt ctacgagagc tttctgatcc agtatcaaga gagcgagaaa     120
gtcggtgaag cgattgtgct gaccgtcccg ggctccgagc gttcctacga cctgaccggt     180
ttgaagccgg gtaccgagta tacggtgagc atctacggtg ttcacaatgt ctataaggac     240
actaatatcc gcggtctgcc tctgagcgcc attttcacca ccgcaccggc accggctccg     300
gctcctgccc cgctgccggc tccgaagaac ttggtggtga ccgtgttac gaagatagc      360 gcacgcctga gctggacggc accggatgcg gcgttcgata gcttctggat cgctattttt     420
gagtttctgg gtagcggtga ggcaattgtt ctgacggtgc cgggctctga cgctcctac      480 gatttgaccg gtctgaaacc gggcaccgag tatgtggtga acattctgag cgttaagggc     540
ggtagcatca gcccaccgct gagcgcgatc ttcacgactg gtggttgc                  588

<210> SEQ ID NO 167
<211> LENGTH: 579
<212> TYPE: DNA
<213> ORGANISM: Artificial Sequence
<220> FEATURE:
<223> OTHER INFORMATION: Bispecific EGFR/c-Met binding domain

<400> SEQUENCE: 167
ctgccagccc ctaagaatct ggtcgtgagc gaagtaaccg aggacagcgc ccgcctgagc      60
tgggacgacc cgtgggcgtt ctatgagtct ttcctgattc agtatcaaga aagcgaaaaa     120
gttggcgaag cgatcgtcct gaccgtcccg ggtagcgagc gctcctacga tctgaccggc     180
ctgaaaccgg gtacggagta cacggtgtcc atttacggtg ttcacaatgt gtataaagac     240
```

```
accaacatgc gtggcctgcc gctgtcggcg attttcacca ccgcgcctgc gccagcgcct    300
gcaccggctc cgctgccggc accgaagaac ctggttgtca gccgtgtgac cgaggatagc    360
gcacgtttga gctggaccgc tccggatgca gcctttgaca gcttctggat tcgttacttt    420
gaatttctgg gtagcggtga ggcgatcgtt ctgacggtgc cgggctctga acgcagctat    480
gatttgacgg gcctgaagcc gggtactgag tacgtggtta acatcatggg cgttaagggt    540
ggtaaaatca gcccgccatt gtccgcgatc tttaccacg                           579
```

<210> SEQ ID NO 168
<211> LENGTH: 282
<212> TYPE: DNA
<213> ORGANISM: Artificial Sequence
<220> FEATURE:
<223> OTHER INFORMATION: EGFR binding FN3 domain from ECB97

<400> SEQUENCE: 168

```
ttgccagcgc cgaagaacct ggtagttagc gaggttactg aggacagcgc gcgtctgagc     60
tgggacgatc cgtgggcgtt ctacgagagc tttctgatcc agtatcaaga gagcgagaaa    120
gtcggtgaag cgattgtgct gaccgtcccg ggctccgagc gttcctacga cctgaccggt    180
ttgaagccgg gtaccgagta tacggtgagc atctacggtg ttcacaatgt ctataaggac    240
actaatatcc gcggtctgcc tctgagcgcc attttcacca cc                       282
```

<210> SEQ ID NO 169
<211> LENGTH: 282
<212> TYPE: DNA
<213> ORGANISM: Artificial Sequence
<220> FEATURE:
<223> OTHER INFORMATION: EGFR binding FN3 domain from ECB15

<400> SEQUENCE: 169

```
ctgccagccc ctaagaatct ggtcgtgagc gaagtaaccg aggacagcgc ccgcctgagc     60
tgggacgacc cgtgggcgtt ctatgagtct ttcctgattc agtatcaaga aagcgaaaaa    120
gttggcgaag cgatcgtcct gaccgtcccg ggtagcgagc gctcctacga tctgaccggc    180
ctgaaaccgg gtacggagta cacggtgtcc atttacggtg ttcacaatgt gtataaagac    240
accaacatgc gtggcctgcc gctgtcggcg attttcacca cc                       282
```

<210> SEQ ID NO 170
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 170

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
```

```
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
            165                 170                 175

Leu Gly Val Lys Gly Gly Lys Ile Ser Pro Pro Leu Ser Ala Ile Phe
            180                 185                 190

Thr Thr Cys
        195

<210> SEQ ID NO 171
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 171

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
            85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
            165                 170                 175

Leu Gly Val Lys Gly Gly Ser Ile Ser Pro Pro Leu Ser Ala Ile Phe
            180                 185                 190

Thr Thr Cys
        195

<210> SEQ ID NO 172
<211> LENGTH: 195
<212> TYPE: PRT
<213> ORGANISM: Artificial Sequence
<220> FEATURE:
<223> OTHER INFORMATION: Bispecific EGFR/c-Met binding molecule
```

<400> SEQUENCE: 172

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr Cys
        195

<210> SEQ ID NO 173
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 173

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
130                 135                 140

```
Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
            180                 185                 190

Thr Thr Cys
        195

<210> SEQ ID NO 174
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 174

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
            180                 185                 190

Thr Thr Cys
        195

<210> SEQ ID NO 175
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 175

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu
            35                  40                  45
```

```
Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
                180                 185                 190

Thr Thr Cys
        195

<210> SEQ ID NO 176
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 176

Met Leu Pro Ala Pro Lys Asn Leu Val Val Ser Glu Val Thr Glu Asp
 1               5                  10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
        130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
                180                 185                 190

Thr Thr Cys
        195
```

<210> SEQ ID NO 177
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 177

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
            180                 185                 190

Thr Thr Cys
        195

<210> SEQ ID NO 178
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 178

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu

```
                100                 105                 110
Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
            180                 185                 190

Thr Thr Cys
        195

<210> SEQ ID NO 179
<211> LENGTH: 12
<212> TYPE: PRT
<213> ORGANISM: Artificial Sequence
<220> FEATURE:
<223> OTHER INFORMATION: Consensus FG loop of EGFR bindiing FN3 domain
<220> FEATURE:
<221> NAME/KEY: VARIANT
<222> LOCATION: (9)..(9)
<223> OTHER INFORMATION: Xaa may be Met or Ile

<400> SEQUENCE: 179

His Asn Val Tyr Lys Asp Thr Asn Xaa Arg Gly Leu
1               5                   10

<210> SEQ ID NO 180
<211> LENGTH: 12
<212> TYPE: PRT
<213> ORGANISM: Artificial Sequence
<220> FEATURE:
<223> OTHER INFORMATION: GF loop of EGFR binding FN3 domain

<400> SEQUENCE: 180

Leu Gly Ser Tyr Val Phe Glu His Asp Val Met Leu
1               5                   10

<210> SEQ ID NO 181
<211> LENGTH: 8
<212> TYPE: PRT
<213> ORGANISM: Artificial Sequence
<220> FEATURE:
<223> OTHER INFORMATION: Consensus BC loop of EGFR binding FN3 domain
<220> FEATURE:
<221> NAME/KEY: VARIANT
<222> LOCATION: (1)..(1)
<223> OTHER INFORMATION: Xaa may be Ala, Thr, Gly or Asp
<220> FEATURE:
<221> NAME/KEY: VARIANT
<222> LOCATION: (2)..(2)
<223> OTHER INFORMATION: Xaa may be Ala, Asp, Tyr or Trp
<220> FEATURE:
<221> NAME/KEY: VARIANT
<222> LOCATION: (3)..(3)
<223> OTHER INFORMATION: Xaa may be Pro, Asp or Asn
<220> FEATURE:
<221> NAME/KEY: VARIANT
<222> LOCATION: (4)..(4)
<223> OTHER INFORMATION: Xaa may be Leu or absent
<220> FEATURE:
<221> NAME/KEY: VARIANT
<222> LOCATION: (5)..(5)
<223> OTHER INFORMATION: Xaa may be Asp, His, Arg, Gly, Tyr or Trp
<220> FEATURE:
<221> NAME/KEY: VARIANT
```

```
<222> LOCATION: (6)..(6)
<223> OTHER INFORMATION: Xaa may be Glu, Asp or Ala
<220> FEATURE:
<221> NAME/KEY: VARIANT
<222> LOCATION: (7)..(7)
<223> OTHER INFORMATION: Xaa may be Ala, Phe, Gly, His or Asp
<220> FEATURE:
<221> NAME/KEY: VARIANT
<222> LOCATION: (8)..(8)
<223> OTHER INFORMATION: Xaa may be Tyr, Phe or Leu

<400> SEQUENCE: 181

Xaa Xaa Xaa Xaa Xaa Xaa Xaa Xaa
1               5

<210> SEQ ID NO 182
<211> LENGTH: 95
<212> TYPE: PRT
<213> ORGANISM: Artificial Sequence
<220> FEATURE:
<223> OTHER INFORMATION: EGFR binding FN3 domain consensus sequence
<220> FEATURE:
<221> NAME/KEY: VARIANT
<222> LOCATION: (22)..(22)
<223> OTHER INFORMATION: Xaa may be Ala, Thr, Gly or Asp
<220> FEATURE:
<221> NAME/KEY: VARIANT
<222> LOCATION: (23)..(23)
<223> OTHER INFORMATION: Xaa may be Ala, Asp, Tyr or Trp
<220> FEATURE:
<221> NAME/KEY: VARIANT
<222> LOCATION: (24)..(24)
<223> OTHER INFORMATION: Xaa may be Pro, Asp or Asn
<220> FEATURE:
<221> NAME/KEY: VARIANT
<222> LOCATION: (25)..(25)
<223> OTHER INFORMATION: Xaa may be Leu or absent
<220> FEATURE:
<221> NAME/KEY: VARIANT
<222> LOCATION: (26)..(26)
<223> OTHER INFORMATION: Xaa may be Asp, His, Arg, Gly, Tyr or Trp
<220> FEATURE:
<221> NAME/KEY: VARIANT
<222> LOCATION: (27)..(27)
<223> OTHER INFORMATION: Xaa may be Gly, Asp or Ala
<220> FEATURE:
<221> NAME/KEY: VARIANT
<222> LOCATION: (28)..(28)
<223> OTHER INFORMATION: Xaa may be Ala, Phe, Gly, His or Asp
<220> FEATURE:
<221> NAME/KEY: VARIANT
<222> LOCATION: (29)..(29)
<223> OTHER INFORMATION: Xaa may be Tyr, Phe or Leu
<220> FEATURE:
<221> NAME/KEY: VARIANT
<222> LOCATION: (84)..(84)
<223> OTHER INFORMATION: Xaa may be Met or Ile

<400> SEQUENCE: 182

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Xaa Asp Ser Phe
                20                  25                  30

Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
50                  55                  60

Gly Thr Glu Tyr Thr Val Ser Ile Tyr Gly Val His Asn Val Tyr Lys
65                  70                  75                  80

Asp Thr Asn Xaa Arg Gly Leu Pro Leu Ser Ala Glu Phe Thr Thr
                85                  90                  95
```

```
<210> SEQ ID NO 183
<211> LENGTH: 95
<212> TYPE: PRT
<213> ORGANISM: Artificial Sequence
<220> FEATURE:
<223> OTHER INFORMATION: EGFR binding FN3 domain consensus sequence
<220> FEATURE:
<221> NAME/KEY: VARIANT
<222> LOCATION: (22)..(22)
<223> OTHER INFORMATION: Xaa may be Ala, Thr, Gly or Asp
<220> FEATURE:
<221> NAME/KEY: VARIANT
<222> LOCATION: (23)..(23)
<223> OTHER INFORMATION: Xaa may be Ala, Asp, Tyr or Trp
<220> FEATURE:
<221> NAME/KEY: VARIANT
<222> LOCATION: (24)..(24)
<223> OTHER INFORMATION: Xaa may be Pro, Asp or Asn
<220> FEATURE:
<221> NAME/KEY: VARIANT
<222> LOCATION: (25)..(25)
<223> OTHER INFORMATION: Xaa may be Leu or absent
<220> FEATURE:
<221> NAME/KEY: VARIANT
<222> LOCATION: (26)..(26)
<223> OTHER INFORMATION: Xaa may be Asp, His, Arg, Gly, Tyr or Trp
<220> FEATURE:
<221> NAME/KEY: VARIANT
<222> LOCATION: (27)..(27)
<223> OTHER INFORMATION: Xaa may be Gly, Asp or Ala
<220> FEATURE:
<221> NAME/KEY: VARIANT
<222> LOCATION: (28)..(28)
<223> OTHER INFORMATION: Xaa may be Ala, Phe, Gly, His or Asp
<220> FEATURE:
<221> NAME/KEY: VARIANT
<222> LOCATION: (29)..(29)
<223> OTHER INFORMATION: Xaa may be Tyr, Phe or Leu

<400> SEQUENCE: 183

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Xaa Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Leu Gly Ser Tyr Val
65                  70                  75                  80

Phe Glu His Asp Val Met Leu Pro Leu Ser Ala Glu Phe Thr Thr
                85                  90                  95

<210> SEQ ID NO 184
<211> LENGTH: 15
<212> TYPE: PRT
<213> ORGANISM: Artificial Sequence
<220> FEATURE:
<223> OTHER INFORMATION: c-Met binding FN3 domain C strand and CD loop
      consensus sequence
<220> FEATURE:
<221> NAME/KEY: VARIANT
<222> LOCATION: (4)..(4)
<223> OTHER INFORMATION: Xaa is Trp, Phe or Val
<220> FEATURE:
<221> NAME/KEY: VARIANT
<222> LOCATION: (8)..(8)
<223> OTHER INFORMATION: Xaa is Asp, Phe or Leu
<220> FEATURE:
<221> NAME/KEY: VARIANT
```

<222> LOCATION: (10)..(10)
<223> OTHER INFORMATION: Xaa is Val, Phe or Leu
<220> FEATURE:
<221> NAME/KEY: VARIANT
<222> LOCATION: (11)..(11)
<223> OTHER INFORMATION: Xaa is Val, Leu or Thr
<220> FEATURE:
<221> NAME/KEY: VARIANT
<222> LOCATION: (12)..(12)
<223> OTHER INFORMATION: Xaa is Val, Arg, Gly, Leu, Thr or Ser
<220> FEATURE:
<221> NAME/KEY: VARIANT
<222> LOCATION: (13)..(13)
<223> OTHER INFORMATION: Xaa is Gly, Ser, Ala, Thr or Lys
<220> FEATURE:
<221> NAME/KEY: VARIANT
<222> LOCATION: (15)..(15)
<223> OTHER INFORMATION: Xaa is Glu or Asp

<400> SEQUENCE: 184

Asp Ser Phe Xaa Ile Arg Tyr Xaa Glu Xaa Xaa Xaa Xaa Gly Xaa
1               5                   10                  15

<210> SEQ ID NO 185
<211> LENGTH: 17
<212> TYPE: PRT
<213> ORGANISM: Artificial Sequence
<220> FEATURE:
<223> OTHER INFORMATION: c-Met binding FN3 domain F strand and FG loop
      consensus sequence
<220> FEATURE:
<221> NAME/KEY: VARIANT
<222> LOCATION: (4)..(4)
<223> OTHER INFORMATION: Xaa is Tyr, Trp, Ile, Val, Gly or Ala
<220> FEATURE:
<221> NAME/KEY: VARIANT
<222> LOCATION: (6)..(6)
<223> OTHER INFORMATION: Xaa is Asn, Thr, Qln or Gly
<220> FEATURE:
<221> NAME/KEY: VARIANT
<222> LOCATION: (8)..(8)
<223> OTHER INFORMATION: Xaa is Leu, Met, Asn or Ile
<220> FEATURE:
<221> NAME/KEY: VARIANT
<222> LOCATION: (9)..(9)
<223> OTHER INFORMATION: Xaa is Gly or Ser
<220> FEATURE:
<221> NAME/KEY: VARIANT
<222> LOCATION: (14)..(14)
<223> OTHER INFORMATION: Xaa is Ser, Leu, Gly, Tyr, Thr, Arg, His or Lys
<220> FEATURE:
<221> NAME/KEY: VARIANT
<222> LOCATION: (15)..(15)
<223> OTHER INFORMATION: Xaa is Ile, Val or Leu
<220> FEATURE:
<221> NAME/KEY: VARIANT
<222> LOCATION: (17)..(17)
<223> OTHER INFORMATION: Xaa is Val, Thr, His, Ile, Pro, Tyr or Leu

<400> SEQUENCE: 185

Thr Glu Tyr Xaa Val Xaa Ile Xaa Xaa Val Lys Gly Gly Xaa Xaa Ser
1               5                   10                  15

Xaa

<210> SEQ ID NO 186
<211> LENGTH: 89
<212> TYPE: PRT
<213> ORGANISM: Artificial Sequence
<220> FEATURE:
<223> OTHER INFORMATION: c-Met binding FN3 domain consensus sequence
<220> FEATURE:
<221> NAME/KEY: VARIANT
<222> LOCATION: (32)..(32)
<223> OTHER INFORMATION: Xaa is Trp, Phe or Val

```
<220> FEATURE:
<221> NAME/KEY: VARIANT
<222> LOCATION: (36)..(36)
<223> OTHER INFORMATION: Xaa is Asp, Phe or Leu
<220> FEATURE:
<221> NAME/KEY: VARIANT
<222> LOCATION: (38)..(38)
<223> OTHER INFORMATION: Xaa is Val, Phe or Leu
<220> FEATURE:
<221> NAME/KEY: VARIANT
<222> LOCATION: (39)..(39)
<223> OTHER INFORMATION: Xaa is Val, Leu or Thr
<220> FEATURE:
<221> NAME/KEY: VARIANT
<222> LOCATION: (40)..(40)
<223> OTHER INFORMATION: Xaa is Val, Arg, Gly, Leu, Thr or Ser
<220> FEATURE:
<221> NAME/KEY: VARIANT
<222> LOCATION: (41)..(41)
<223> OTHER INFORMATION: Xaa is Gly, Ser, Ala, Thr or Lys
<220> FEATURE:
<221> NAME/KEY: VARIANT
<222> LOCATION: (43)..(43)
<223> OTHER INFORMATION: Xaa is Glu or Asp
<220> FEATURE:
<221> NAME/KEY: VARIANT
<222> LOCATION: (68)..(68)
<223> OTHER INFORMATION: Xaa is Tyr, Trp, Ile, Val, Gly or Ala
<220> FEATURE:
<221> NAME/KEY: VARIANT
<222> LOCATION: (70)..(70)
<223> OTHER INFORMATION: Xaa is Asn, Thr, Qln or Gly
<220> FEATURE:
<221> NAME/KEY: VARIANT
<222> LOCATION: (72)..(72)
<223> OTHER INFORMATION: Xaa is Leu, Met, Asn or Ile
<220> FEATURE:
<221> NAME/KEY: VARIANT
<222> LOCATION: (73)..(73)
<223> OTHER INFORMATION: Xaa is Gly or Ser
<220> FEATURE:
<221> NAME/KEY: VARIANT
<222> LOCATION: (78)..(78)
<223> OTHER INFORMATION: Xaa is Ser, Leu, Gly, Tyr, Thr, Arg, His or Lys
<220> FEATURE:
<221> NAME/KEY: VARIANT
<222> LOCATION: (79)..(79)
<223> OTHER INFORMATION: Xaa is Ile, Val or Leu
<220> FEATURE:
<221> NAME/KEY: VARIANT
<222> LOCATION: (81)..(81)
<223> OTHER INFORMATION: Xaa is Val, Thr, His, Ile, Pro, Tyr or Leu

<400> SEQUENCE: 186

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
                20                  25                  30

Ile Arg Tyr Xaa Glu Xaa Xaa Xaa Xaa Gly Xaa Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Xaa Val Xaa Ile Xaa Xaa Val Lys Gly Gly Xaa Xaa Ser
65                  70                  75                  80

Xaa Pro Leu Ser Ala Glu Phe Thr Thr
                85

<210> SEQ ID NO 187
<211> LENGTH: 94
<212> TYPE: PRT
<213> ORGANISM: Artificial Sequence
<220> FEATURE:
```

<223> OTHER INFORMATION: EGFR consensus FN3 domain of bispecific EGFR/
      c-Met molecule
<220> FEATURE:
<221> NAME/KEY: VARIANT
<222> LOCATION: (11)..(11)
<223> OTHER INFORMATION: Xaa is Glu, Asn or Arg
<220> FEATURE:
<221> NAME/KEY: VARIANT
<222> LOCATION: (14)..(14)
<223> OTHER INFORMATION: Xaa is Glu or Pro
<220> FEATURE:
<221> NAME/KEY: VARIANT
<222> LOCATION: (17)..(17)
<223> OTHER INFORMATION: Xaa is Leu or Ala
<220> FEATURE:
<221> NAME/KEY: VARIANT
<222> LOCATION: (25)..(25)
<223> OTHER INFORMATION: Xaa is His or Trp
<220> FEATURE:
<221> NAME/KEY: VARIANT
<222> LOCATION: (29)..(29)
<223> OTHER INFORMATION: Xaa is Glu or Asp
<220> FEATURE:
<221> NAME/KEY: VARIANT
<222> LOCATION: (37)..(37)
<223> OTHER INFORMATION: Xaa is Glu or Pro
<220> FEATURE:
<221> NAME/KEY: VARIANT
<222> LOCATION: (46)..(46)
<223> OTHER INFORMATION: Xaa is Asn or Val
<220> FEATURE:
<221> NAME/KEY: VARIANT
<222> LOCATION: (73)..(73)
<223> OTHER INFORMATION: Xaa is Gly or Tyr
<220> FEATURE:
<221> NAME/KEY: VARIANT
<222> LOCATION: (83)..(83)
<223> OTHER INFORMATION: Xaa is Met or Ile
<220> FEATURE:
<221> NAME/KEY: VARIANT
<222> LOCATION: (91)..(91)
<223> OTHER INFORMATION: Xaa is Glu or Ile

<400> SEQUENCE: 187

Leu Pro Ala Pro Lys Asn Leu Val Val Ser Xaa Val Thr Xaa Asp Ser
1               5                   10                  15

Xaa Arg Leu Ser Trp Asp Asp Pro Xaa Ala Phe Tyr Xaa Ser Phe Leu
                20                  25                  30

Ile Gln Tyr Gln Xaa Ser Glu Lys Val Gly Glu Ala Ile Xaa Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Xaa Val His Asn Val Tyr Lys Asp
65                  70                  75                  80

Thr Asn Xaa Arg Gly Leu Pro Leu Ser Ala Xaa Phe Thr Thr
                85                  90

<210> SEQ ID NO 188
<211> LENGTH: 89
<212> TYPE: PRT
<213> ORGANISM: Artificial Sequence
<220> FEATURE:
<223> OTHER INFORMATION: c-Met consensus FN3 domain of bispecific EGFR/
      c-Met molecule
<220> FEATURE:
<221> NAME/KEY: VARIANT
<222> LOCATION: (11)..(11)
<223> OTHER INFORMATION: Xaa is Glu, Asn or Arg
<220> FEATURE:
<221> NAME/KEY: VARIANT
<222> LOCATION: (14)..(14)
<223> OTHER INFORMATION: Xaa is Glu or Pro

```
<220> FEATURE:
<221> NAME/KEY: VARIANT
<222> LOCATION: (17)..(17)
<223> OTHER INFORMATION: Xaa is Leu or Ala
<220> FEATURE:
<221> NAME/KEY: VARIANT
<222> LOCATION: (37)..(37)
<223> OTHER INFORMATION: Xaa is Glu or Pro
<220> FEATURE:
<221> NAME/KEY: VARIANT
<222> LOCATION: (39)..(39)
<223> OTHER INFORMATION: Xaa is Val or Leu
<220> FEATURE:
<221> NAME/KEY: VARIANT
<222> LOCATION: (40)..(40)
<223> OTHER INFORMATION: Xaa is Gly or Ser
<220> FEATURE:
<221> NAME/KEY: VARIANT
<222> LOCATION: (41)..(41)
<223> OTHER INFORMATION: Xaa is Ser or Lys
<220> FEATURE:
<221> NAME/KEY: VARIANT
<222> LOCATION: (43)..(43)
<223> OTHER INFORMATION: Xaa is Glu or Asp
<220> FEATURE:
<221> NAME/KEY: VARIANT
<222> LOCATION: (46)..(46)
<223> OTHER INFORMATION: Xaa is Asn or Val
<220> FEATURE:
<221> NAME/KEY: VARIANT
<222> LOCATION: (72)..(72)
<223> OTHER INFORMATION: Xaa is Leu or Met
<220> FEATURE:
<221> NAME/KEY: VARIANT
<222> LOCATION: (73)..(73)
<223> OTHER INFORMATION: Xaa is Gly or Ser
<220> FEATURE:
<221> NAME/KEY: VARIANT
<222> LOCATION: (78)..(78)
<223> OTHER INFORMATION: Xaa is Ser or Lys
<220> FEATURE:
<221> NAME/KEY: VARIANT
<222> LOCATION: (86)..(86)
<223> OTHER INFORMATION: Xaa is Glu or Ile

<400> SEQUENCE: 188

Leu Pro Ala Pro Lys Asn Leu Val Val Ser Xaa Val Thr Xaa Asp Ser
1               5                   10                  15

Xaa Arg Leu Ser Trp Thr Ala Pro Asp Ala Ala Phe Asp Ser Phe Trp
                20                  25                  30

Ile Arg Tyr Phe Xaa Phe Xaa Xaa Xaa Gly Xaa Ala Ile Xaa Leu Thr
                35                  40                  45

Val Pro Gly Ser Glu Arg Ser Tyr Asp Leu Thr Gly Leu Lys Pro Gly
            50                  55                  60

Thr Glu Tyr Val Val Asn Ile Xaa Xaa Val Lys Gly Gly Xaa Ile Ser
65                  70                  75                  80

Pro Pro Leu Ser Ala Xaa Phe Thr Thr
                85

<210> SEQ ID NO 189
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 189

Met Leu Pro Ala Pro Lys Asn Leu Cys Val Ser Glu Val Thr Glu Asp
1               5                   10                  15

Ser Ala Arg Leu Ser Trp Asp Asp Pro Trp Ala Phe Tyr Glu Ser Phe
```

20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 190
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 190

Met Leu Pro Ala Pro Lys Asn Leu Val Val Cys Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 191
<211> LENGTH: 95
<212> TYPE: PRT
<213> ORGANISM: Artificial sequence
<220> FEATURE:
<223> OTHER INFORMATION: EGFR binding FN3 domain

<400> SEQUENCE: 191

Met Leu Pro Ala Pro Lys Asn Leu Val Val Ser Cys Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 192
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 192

-continued

```
Met Leu Pro Ala Pro Lys Asn Leu Val Val Ser Glu Val Thr Cys Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95
```

<210> SEQ ID NO 193
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 193

```
Met Leu Pro Ala Pro Lys Asn Leu Val Val Ser Glu Val Thr Glu Cys
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95
```

<210> SEQ ID NO 194
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 194

```
Met Leu Pro Ala Pro Lys Asn Leu Val Val Ser Glu Val Thr Glu Asp
1               5                   10                  15

Cys Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95
```

<210> SEQ ID NO 195
<211> LENGTH: 95
<212> TYPE: PRT

```
<213> ORGANISM: Artificial Sequence
<220> FEATURE:
<223> OTHER INFORMATION: EGFR binding FN3 domain

<400> SEQUENCE: 195

Met Leu Pro Ala Pro Lys Asn Leu Val Val Ser Glu Val Thr Glu Asp
1               5                   10                  15

Ser Ala Arg Leu Cys Trp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 196
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 196

Met Leu Pro Ala Pro Lys Asn Leu Val Val Ser Glu Val Thr Glu Asp
1               5                   10                  15

Ser Ala Arg Leu Ser Trp Asp Pro Trp Ala Phe Tyr Glu Cys Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 197
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 197

Met Leu Pro Ala Pro Lys Asn Leu Val Val Ser Glu Val Thr Glu Asp
1               5                   10                  15

Ser Ala Arg Leu Ser Trp Asp Pro Trp Ala Phe Tyr Glu Ser Phe
            20                  25                  30

Leu Ile Cys Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95
```

<210> SEQ ID NO 198
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 198

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Cys Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 199
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 199

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Cys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 200
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 200

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Lys Cys Gly Glu Ala Ile Val Leu
        35                  40                  45

Thr Val Pro Gly Ser Glu Arg Ser Tyr Asp Leu Thr Gly Leu Lys Pro
    50                  55                  60

-continued

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 201
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 201

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Cys Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 202
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 202

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Cys
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 203
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 203

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu

```
            35                  40                  45

Cys Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr
                 85                  90                  95

<210> SEQ ID NO 204
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 204

Met Leu Pro Ala Pro Lys Asn Leu Val Val Ser Glu Val Thr Glu Asp
 1               5                  10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Cys Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr
                 85                  90                  95

<210> SEQ ID NO 205
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 205

Met Leu Pro Ala Pro Lys Asn Leu Val Val Ser Glu Val Thr Glu Asp
 1               5                  10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Cys Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr
                 85                  90                  95

<210> SEQ ID NO 206
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 206

Met Leu Pro Ala Pro Lys Asn Leu Val Val Ser Glu Val Thr Glu Asp
 1               5                  10                  15
```

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Cys Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 207
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 207

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Cys Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 208
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 208

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Cys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 209
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 209

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Cys Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 210
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 210

Met Leu Pro Ala Pro Lys Cys Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 211
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 211

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Cys Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 212

```
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 212

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Cys Ser Ala Ile Phe Thr Thr
                85                  90                  95

<210> SEQ ID NO 213
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 213

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Cys Ala Ile Phe Thr Thr
                85                  90                  95

<210> SEQ ID NO 214
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 214

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80
```

Asp Thr Asn Met Arg Gly Leu Pro Leu Ser Cys Ile Phe Thr Thr
            85                  90                  95

<210> SEQ ID NO 215
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 215

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Cys Phe Thr Thr
            85                  90                  95

<210> SEQ ID NO 216
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 216

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Cys Thr
            85                  90                  95

<210> SEQ ID NO 217
<211> LENGTH: 104
<212> TYPE: PRT
<213> ORGANISM: Artificial Sequence
<220> FEATURE:
<223> OTHER INFORMATION: EGFR binding FN3 domain

<400> SEQUENCE: 217

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro

```
            50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Gly
                 85                  90                  95

Gly His His His His His Cys
                100

<210> SEQ ID NO 218
<211> LENGTH: 250
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 218

Met Leu Pro Ala Pro Lys Asn Leu Val Val Ser Glu Val Thr Glu Asp
  1               5                  10                  15

Ser Ala Arg Leu Ser Trp Asp Asp Pro Trp Ala Phe Tyr Glu Ser Phe
                 20                  25                  30

Leu Ile Gln Tyr Gln Glu Ser Glu Lys Val Gly Glu Ala Ile Val Leu
             35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Leu
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Ser Val Lys Gly Gly Ser Ile Ser Pro Pro Leu Ser Ala Ile Phe
                180                 185                 190

Thr Thr Ala Pro Ser Pro Ala Pro Ala Pro Ala Pro Leu Ala Glu Ala
            195                 200                 205

Lys Val Leu Ala Asn Arg Glu Leu Asp Lys Tyr Gly Val Ser Asp Tyr
        210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 219
<211> LENGTH: 250
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 219
```

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Cys Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Ser Val Lys Gly Gly Ser Ile Ser Pro Pro Leu Ser Ala Ile Phe
            180                 185                 190

Thr Thr Ala Pro Ser Pro Ala Pro Ala Pro Leu Ala Glu Ala
        195                 200                 205

Lys Val Leu Ala Asn Arg Glu Leu Asp Lys Tyr Gly Val Ser Asp Tyr
    210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250
```

<210> SEQ ID NO 220
<211> LENGTH: 250
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 220

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110
```

```
Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Cys Pro Gly Thr Glu Tyr Val Val Asn Ile
                165                 170                 175

Met Ser Val Lys Gly Gly Ser Ile Ser Pro Pro Leu Ser Ala Ile Phe
            180                 185                 190

Thr Thr Ala Pro Ala Pro Ala Pro Ala Pro Leu Ala Glu Ala
        195                 200                 205

Lys Val Leu Ala Asn Arg Glu Leu Asp Lys Tyr Gly Val Ser Asp Tyr
    210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 221
<211> LENGTH: 250
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 221

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Cys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Cys Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Cys Pro Gly Thr Glu Tyr Val Val Asn Ile
                165                 170                 175

Met Ser Val Lys Gly Gly Ser Ile Ser Pro Pro Leu Ser Ala Ile Phe
            180                 185                 190

Thr Thr Ala Pro Cys Pro Ala Pro Ala Pro Leu Ala Glu Ala
        195                 200                 205

Lys Val Leu Ala Asn Arg Glu Leu Asp Lys Tyr Gly Val Ser Asp Tyr
    210                 215                 220
```

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
            245                 250

<210> SEQ ID NO 222
<211> LENGTH: 250
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 222

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Ser Val Lys Gly Gly Ser Ile Ser Pro Pro Leu Ser Ala Ile Phe
            180                 185                 190

Thr Thr Ala Pro Cys Pro Ala Pro Ala Pro Leu Ala Glu Ala
        195                 200                 205

Lys Val Leu Ala Asn Arg Glu Leu Asp Lys Tyr Gly Val Ser Asp Tyr
    210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
            245                 250

<210> SEQ ID NO 223
<211> LENGTH: 250
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 223

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Cys Pro
         50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Cys Pro Gly Thr Glu Tyr Val Val Asn Ile
                165                 170                 175

Met Ser Val Lys Gly Gly Ser Ile Ser Pro Pro Leu Ser Ala Ile Phe
            180                 185                 190

Thr Thr Ala Pro Ala Pro Ala Pro Ala Pro Leu Ala Glu Ala
        195                 200                 205

Lys Val Leu Ala Asn Arg Glu Leu Asp Lys Tyr Gly Val Ser Asp Tyr
        210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 224
<211> LENGTH: 250
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 224

Met Leu Pro Ala Pro Lys Asn Leu Val Val Ser Glu Val Thr Glu Asp
 1               5                  10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Cys Pro
         50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Ser Val Lys Gly Gly Ser Ile Ser Pro Pro Leu Ser Ala Ile Phe
            180                 185                 190

Thr Thr Ala Pro Ala Pro Ala Pro Ala Pro Leu Ala Glu Ala
            195                 200                 205

Lys Val Leu Ala Asn Arg Glu Leu Asp Lys Tyr Gly Val Ser Asp Tyr
210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 225
<211> LENGTH: 250
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 225

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Cys Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Ser Val Lys Gly Gly Ser Ile Ser Pro Pro Leu Ser Ala Ile Phe
            180                 185                 190

Thr Thr Ala Pro Cys Pro Ala Pro Ala Pro Leu Ala Glu Ala
            195                 200                 205

Lys Val Leu Ala Asn Arg Glu Leu Asp Lys Tyr Gly Val Ser Asp Tyr
210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 226
<211> LENGTH: 264
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 226

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Gly Lys Ile Ser Pro Pro Leu Ser Ala Ile Phe
            180                 185                 190

Thr Thr Ala Pro Ala Pro Ala Pro Ala Pro Thr Ile Asp Glu
        195                 200                 205

Trp Leu Leu Lys Glu Ala Lys Glu Lys Ala Ile Glu Glu Leu Lys Lys
    210                 215                 220

Ala Gly Ile Thr Ser Asp Tyr Tyr Phe Asp Leu Ile Asn Lys Ala Lys
225                 230                 235                 240

Thr Val Glu Gly Val Asn Ala Leu Lys Asp Glu Ile Leu Lys Ala Gly
                245                 250                 255

Gly His His His His His His Cys
            260
```

<210> SEQ ID NO 227
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 227

```
Leu Pro Ala Pro Lys Asn Leu Cys Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
```

```
               35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 228
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 228

Leu Pro Ala Pro Lys Asn Leu Val Val Cys Glu Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 229
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 229

Leu Pro Ala Pro Lys Asn Leu Val Val Ser Cys Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 230
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 230

Leu Pro Ala Pro Lys Asn Leu Val Val Ser Glu Val Thr Cys Asp Ser
1               5                   10                  15
```

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 231
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 231

Leu Pro Ala Pro Lys Asn Leu Val Val Ser Glu Val Thr Glu Cys Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 232
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 232

Leu Pro Ala Pro Lys Asn Leu Val Val Ser Glu Val Thr Glu Asp Cys
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 233
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 233

Leu Pro Ala Pro Lys Asn Leu Val Val Ser Glu Val Thr Glu Asp Ser
1               5                   10                  15

Ala Arg Leu Cys Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 234
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 234

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Cys Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 235
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 235

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Cys Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 236

```
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 236

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Cys Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 237
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 237

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Cys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 238
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 238

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Cys Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80
```

Thr Asn Met Arg Gly Leu Pro Leu Ser Ala Ile Phe Thr Thr
            85                  90

<210> SEQ ID NO 239
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 239

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Cys Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
            85                  90

<210> SEQ ID NO 240
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 240

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Cys Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
            85                  90

<210> SEQ ID NO 241
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 241

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Cys
        35                  40                  45

Val Pro Gly Ser Glu Arg Ser Tyr Asp Leu Thr Gly Leu Lys Pro Gly

```
                    50                  55                  60
Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr
                 85                  90

<210> SEQ ID NO 242
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 242

Leu Pro Ala Pro Lys Asn Leu Val Val Ser Glu Val Thr Glu Asp Ser
  1               5                  10                  15

Ala Arg Leu Ser Trp Asp Asp Pro Trp Ala Phe Tyr Glu Ser Phe Leu
                 20                  25                  30

Ile Gln Tyr Gln Glu Ser Glu Lys Val Gly Glu Ala Ile Val Leu Thr
             35                  40                  45

Val Pro Gly Ser Cys Arg Ser Tyr Asp Leu Thr Gly Leu Lys Pro Gly
         50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr
                 85                  90

<210> SEQ ID NO 243
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 243

Leu Pro Ala Pro Lys Asn Leu Val Val Ser Glu Val Thr Glu Asp Ser
  1               5                  10                  15

Ala Arg Leu Ser Trp Asp Asp Pro Trp Ala Phe Tyr Glu Ser Phe Leu
                 20                  25                  30

Ile Gln Tyr Gln Glu Ser Glu Lys Val Gly Glu Ala Ile Val Leu Thr
             35                  40                  45

Val Pro Gly Ser Glu Cys Ser Tyr Asp Leu Thr Gly Leu Lys Pro Gly
         50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr
                 85                  90

<210> SEQ ID NO 244
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 244

Leu Pro Ala Pro Lys Asn Leu Val Val Ser Glu Val Thr Glu Asp Ser
  1               5                  10                  15

Ala Arg Leu Ser Trp Asp Asp Pro Trp Ala Phe Tyr Glu Ser Phe Leu
                 20                  25                  30
```

```
Ile Gln Tyr Gln Glu Ser Glu Lys Val Gly Glu Ala Ile Val Leu Thr
            35                  40                  45

Val Pro Gly Ser Glu Arg Ser Tyr Asp Leu Cys Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr
                85                  90

<210> SEQ ID NO 245
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 245

Leu Pro Ala Pro Lys Asn Leu Val Val Ser Glu Val Thr Glu Asp Ser
 1               5                  10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Cys Leu Lys Pro Gly
 50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr
                85                  90

<210> SEQ ID NO 246
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 246

Leu Pro Ala Pro Lys Asn Leu Val Val Ser Glu Val Thr Glu Asp Ser
 1               5                  10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Cys Pro Gly
 50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr
                85                  90

<210> SEQ ID NO 247
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 247
```

-continued

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Cys
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 248
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 248

Leu Pro Ala Pro Lys Cys Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 249
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 249

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Cys Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 250
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 250

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Cys Ser Ala Ile Phe Thr Thr
                85                  90

<210> SEQ ID NO 251
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 251

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Cys Ala Ile Phe Thr Thr
                85                  90

<210> SEQ ID NO 252
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 252

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Cys Ile Phe Thr Thr
                85                  90

<210> SEQ ID NO 253
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 253

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Cys Phe Thr Thr
                85                  90

<210> SEQ ID NO 254
<211> LENGTH: 94
<212> TYPE: PRT
<213> ORGANISM: Artificial Sequence
<220> FEATURE:
<223> OTHER INFORMATION: EGFR-binding FN3 domain

<400> SEQUENCE: 254

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Cys Thr
                85                  90

<210> SEQ ID NO 255
<211> LENGTH: 103
<212> TYPE: PRT
<213> ORGANISM: Artificial Sequence
<220> FEATURE:
<223> OTHER INFORMATION: EGFR-binding FN3 domain

<400> SEQUENCE: 255

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp

```
Thr Asn Met Arg Gly Leu Pro Leu Ser Ala Ile Phe Thr Thr Gly Gly
                85                  90                  95

His His His His His His Cys
                100

<210> SEQ ID NO 256
<211> LENGTH: 249
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 256

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Ser Val Lys Gly Gly Ser Ile Ser Pro Pro Leu Ser Ala Ile Phe Thr
                180                 185                 190

Thr Ala Pro Ser Pro Ala Pro Ala Pro Leu Ala Glu Ala Lys
            195                 200                 205

Val Leu Ala Asn Arg Glu Leu Asp Lys Tyr Gly Val Ser Asp Tyr Tyr
        210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 257
<211> LENGTH: 249
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 257

Leu Pro Ala Pro Lys Asn Leu Val Val Ser Glu Val Thr Glu Asp Ser
1               5                   10                  15
```

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
50                      55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Cys Pro Ala Pro Ala Pro Leu Pro Ala Pro Lys Asn Leu Val
                    100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Ser Val Lys Gly Gly Ser Ile Ser Pro Pro Leu Ser Ala Ile Phe Thr
                180                 185                 190

Thr Ala Pro Ser Pro Ala Pro Ala Pro Leu Ala Glu Ala Lys
            195                 200                 205

Val Leu Ala Asn Arg Glu Leu Asp Lys Tyr Gly Val Ser Asp Tyr Tyr
210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 258
<211> LENGTH: 249
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 258

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
50                      55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

```
Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Cys Pro Gly Thr Glu Tyr Val Val Asn Ile Met
                165                 170                 175

Ser Val Lys Gly Gly Ser Ile Ser Pro Leu Ser Ala Ile Phe Thr
            180                 185                 190

Thr Ala Pro Ala Pro Ala Pro Ala Pro Leu Ala Glu Ala Lys
                195                 200                 205

Val Leu Ala Asn Arg Glu Leu Asp Lys Tyr Gly Val Ser Asp Tyr Tyr
    210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245
```

<210> SEQ ID NO 259
<211> LENGTH: 249
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 259

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Cys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Cys Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Cys Pro Gly Thr Glu Tyr Val Val Asn Ile Met
                165                 170                 175

Ser Val Lys Gly Gly Ser Ile Ser Pro Leu Ser Ala Ile Phe Thr
            180                 185                 190

Thr Ala Pro Cys Pro Ala Pro Ala Pro Leu Ala Glu Ala Lys
                195                 200                 205

Val Leu Ala Asn Arg Glu Leu Asp Lys Tyr Gly Val Ser Asp Tyr Tyr
    210                 215                 220

Lys Asn Leu Ile Asn Asn Ala Lys Thr Val Glu Gly Val Lys Ala Leu
225                 230                 235                 240
```

Leu Asp Glu Ile Leu Ala Ala Leu Pro
                245

<210> SEQ ID NO 260
<211> LENGTH: 249
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 260

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Ser Val Lys Gly Gly Ser Ile Ser Pro Pro Leu Ser Ala Ile Phe Thr
            180                 185                 190

Thr Ala Pro Cys Pro Ala Pro Ala Pro Ala Pro Leu Ala Glu Ala Lys
        195                 200                 205

Val Leu Ala Asn Arg Glu Leu Asp Lys Tyr Gly Val Ser Asp Tyr Tyr
    210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 261
<211> LENGTH: 249
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 261

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

```
Val Pro Gly Ser Glu Arg Ser Tyr Asp Leu Thr Gly Leu Cys Pro Gly
        50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr Ala Pro
                 85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Cys Pro Gly Thr Glu Tyr Val Val Asn Ile Met
                165                 170                 175

Ser Val Lys Gly Gly Ser Ile Ser Pro Pro Leu Ser Ala Ile Phe Thr
                180                 185                 190

Thr Ala Pro Ala Pro Ala Pro Ala Pro Ala Pro Leu Ala Glu Ala Lys
            195                 200                 205

Val Leu Ala Asn Arg Glu Leu Asp Lys Tyr Gly Val Ser Asp Tyr Tyr
            210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 262
<211> LENGTH: 249
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 262

Leu Pro Ala Pro Lys Asn Leu Val Val Ser Glu Val Thr Glu Asp Ser
 1               5                  10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Cys Pro Gly
    50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr Ala Pro
                 85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160
```

```
Asp Leu Thr Gly Leu Lys Pro Gly Thr Glu Tyr Val Val Asn Ile Met
            165                 170                 175

Ser Val Lys Gly Gly Ser Ile Ser Pro Leu Ser Ala Ile Phe Thr
        180                 185                 190

Thr Ala Pro Ala Pro Ala Pro Ala Pro Leu Ala Glu Ala Lys
        195                 200                 205

Val Leu Ala Asn Arg Glu Leu Asp Lys Tyr Gly Val Ser Asp Tyr Tyr
    210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 263
<211> LENGTH: 249
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 263

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Cys Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
            165                 170                 175

Ser Val Lys Gly Gly Ser Ile Ser Pro Leu Ser Ala Ile Phe Thr
        180                 185                 190

Thr Ala Pro Cys Pro Ala Pro Ala Pro Leu Ala Glu Ala Lys
        195                 200                 205

Val Leu Ala Asn Arg Glu Leu Asp Lys Tyr Gly Val Ser Asp Tyr Tyr
    210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 264
```

<211> LENGTH: 263
<212> TYPE: PRT
<213> ORGANISM: Artificial Sequence
<220> FEATURE:
<223> OTHER INFORMATION: bispecific anti-EGFR/c-Met binding FN3 domain

<400> SEQUENCE: 264

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Gly Val Lys Gly Gly Lys Ile Ser Pro Pro Leu Ser Ala Ile Phe Thr
            180                 185                 190

Thr Ala Pro Ala Pro Ala Pro Ala Pro Thr Ile Asp Glu Trp
        195                 200                 205

Leu Leu Lys Glu Ala Lys Glu Lys Ala Ile Glu Glu Leu Lys Lys Ala
    210                 215                 220

Gly Ile Thr Ser Asp Tyr Tyr Phe Asp Leu Ile Asn Lys Ala Lys Thr
225                 230                 235                 240

Val Glu Gly Val Asn Ala Leu Lys Asp Glu Ile Leu Lys Ala Gly Gly
                245                 250                 255

His His His His His His Cys
            260

<210> SEQ ID NO 265
<211> LENGTH: 98
<212> TYPE: PRT
<213> ORGANISM: Artificial Sequence
<220> FEATURE:
<223> OTHER INFORMATION: Tencon FN3 scaffold

<400> SEQUENCE: 265

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly

```
            50                  55                  60
Thr Glu Tyr Thr Val Ser Ile Tyr Gly Val Lys Gly Gly His Arg Ser
65                  70                  75                  80

Asn Pro Leu Ser Ala Glu Phe Thr Thr Gly Gly His His His His
                85                  90                  95

His Cys
```